(12) United States Patent
O'Shannessy et al.

(10) Patent No.: US 10,822,410 B2
(45) Date of Patent: Nov. 3, 2020

(54) ANTI-FOLATE RECEPTOR ALPHA ANTIBODIES AND USES THEREOF

(71) Applicant: Eisai R&D Management Co., Ltd., Bunkyo-Ku, Tokyo (JP)

(72) Inventors: Daniel John O'Shannessy, Schwenksville, PA (US); Elizabeth B. Somers, West Grove, PA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 380 days.

(21) Appl. No.: 15/821,296

(22) Filed: Nov. 22, 2017

(65) Prior Publication Data

US 2018/0148504 A1     May 31, 2018

Related U.S. Application Data

(60) Provisional application No. 62/425,752, filed on Nov. 23, 2016.

(51) Int. Cl.
| | |
|---|---|
| A61K 39/395 | (2006.01) |
| C07K 16/28 | (2006.01) |
| G01N 33/82 | (2006.01) |
| A61P 35/00 | (2006.01) |
| G01N 33/574 | (2006.01) |

(52) U.S. Cl.
CPC .............. *C07K 16/28* (2013.01); *A61P 35/00* (2018.01); *G01N 33/57492* (2013.01); *G01N 33/82* (2013.01); *C07K 2317/14* (2013.01); *C07K 2317/24* (2013.01); *C07K 2317/56* (2013.01); *C07K 2317/565* (2013.01); *G01N 2333/705* (2013.01); *G01N 2800/7028* (2013.01)

(58) Field of Classification Search
None
See application file for complete search history.

(56) References Cited

U.S. PATENT DOCUMENTS

| | | |
|---|---|---|
| 7,754,698 B2 | 7/2010 | Freier |
| 8,475,795 B2 | 7/2013 | O'Shannessy |
| 2005/0232919 A1 | 10/2005 | Grasso et al. |
| 2012/0207771 A1 | 8/2012 | O'Shannessy et al. |
| 2013/0017195 A1 | 1/2013 | O'Shannessy |

FOREIGN PATENT DOCUMENTS

| | | | |
|---|---|---|---|
| EP | 2199796 | A1 | 6/2010 |
| WO | WO 2009/132081 | A2 | 10/2009 |
| WO | WO 2012/061759 | A2 | 5/2012 |
| WO | WO 2012/061759 | A3 | 5/2012 |
| WO | WO 2014/036495 | A2 | 3/2014 |
| WO | WO 2014/036495 | A3 | 3/2014 |
| WO | WO 2014/036495 | A4 | 3/2014 |
| WO | WO 2016/168440 | A1 | 10/2016 |

OTHER PUBLICATIONS

Almagro & Fransson, Frontiers in Bioscience 2008 (Year: 2008).*
De Genst et al., Dev Comp Immunol 2006; 30:187-98 (Year: 2006).*
Yoshinaga et al., J. Biochem 2008; 143:593-601 (Year: 2008).*
Basal et al., "Functional Folate Receptor Alpha is Elevated in the Blood of Ovarian Cancer Patients", PloS ONE, 2009, 4(7), e6292, 7 pages.
Bueno et al., "The α Folate Receptor is Highley Activated in Malignant Plural Mesothelioma", Journal of Thoracic and Cardiovacular Surgery, 2001, 121(2), 225-233.
Cline, "Perspectives for Gene Therapy: Inserting New Genetic Information into Mammalian Cells by Physical Techniques and Viral Vectors", Pharmac. Ther. 1985, 29, 69-92.
Despierre et al., "Folate receptor Alpha (FRA) expression remains unchange in epithelial ovarian and endometrial cancer after chemotherapy", Gynecologic Oncology, 2013, 130(1), 192-199.
Elnakat et al., "Role of folate receptor genes in reproduction and related cancers", Frontiers in Bioscience, 2006, 11, 506-519.
Fisher, "Exploratory Study of $^{99m}$Tc-EC20 Imagining for Identifying Patients with Folate Receptor-Positive Solid Tumors", The Journal of Nuclear Medicine, 2008, 49(6), 899-906.
Franklin et al., "New Anti-Lung-Cancer Antibody Cluster 12 Reacts With Human Folate Receptors Present on Adenocarcinoma", Int J Cancer, 1994, Supp 8, 89-95.
Gadi et al., "In vivo sensitization of ovarian tumors to chemotherapy by expression of E. coli purine nucloside phosphorylas in a small fraction of cells", Gene Therapy, 2000, 7, 1738-1743.
Hartmann et al., "Folate receptor overexpression is associated with poor outcome in brease cancer", Int J Cancer, 2007, 121, 938-942.
Iwakiri et al., "Expression Status of Folate Receptor α Is Significantly Correlated with Prognosis in Non-Small-Cell Lung Cancers", Annals of Surgical Oncology, 2008, 15(3), 889-899.
Karlin et al., "Methods for accessing the statistical significance of molecular sequence features by using general scoring schemes", Proc. Natl. Acad. Sci. USA, 1990, 87, 2264-2268.
Karlin et al., "Applications and statistics for multiple high-scoring segments in molecuar sequences", Proc Natl Acad Sci USA, 1993, 90, 5873-5877.

(Continued)

*Primary Examiner* — Meera Natarajan
(74) *Attorney, Agent, or Firm* — BakerHostetler

(57) ABSTRACT

Described herein are antibodies, and antigen-binding fragments thereof, that are specific for folate receptor alpha, related polynucleotides, expression vectors, and cells that express the described antibodies. Also provided are methods of using the described antibodies, and antigen-binding fragments thereof, and related kits to detect folate receptor alpha. Provided herein are also methods for diagnosing folate receptor alpha-expressing cancers using the described antibodies, and antigen-binding fragments thereof. The methods involve determining the amount of folate receptor alpha in a sample derived from a subject and comparing this level with the level of folate receptor alpha in a control sample or reference sample.

63 Claims, 17 Drawing Sheets
Specification includes a Sequence Listing.

(56) References Cited

OTHER PUBLICATIONS

Kurosaki et al., "Serum folate receptor alpha as a biomarker for ovarian cancer: Implications for diagnosis, prognosis and predicting its local tumor expression", International Journal of Cancer, 1966, 138(8), 1994-2002.
Okayama et al., "A cDNA Cloning Vector That Permits Expression of cDNA Inserts in Mammalian Cells", Molecular and Cellular Biology, 1983, 280-289.
O'Shannessy et al., "Characterization of the Human Folate Receptor Alpha via Novel Antibody-Based Probes", Oncotarget, 2011, 2(12), 1227-1243.
Parker et al., "Folate receptor expression in cardinomas and normal tissues determined by a quantitative radioligand binding assay", Analytical Biochemistry, 2005, 338, 284-293.
Saba et al., "Examining expression of folate receptor in squamous cell cardinoma of the head and neck as a target for a novel nanotherapeutic drug", Head Neck, 2009, 31(4), 475-481.
Weitman et al., "Distribution of the Folate Receptor GP38 in the normal and malignant Cell Lines and Tissues", Cancer Research, Jun. 1992, 52, 3396-3401.
Weitman et al., "Cellular Localization of the Folate Receptor: Potential Role in Drug Toxicity and Folate Homeostasis", Cancer Research, Dec. 1992, 52, 6708-6711.
Yang et al., "The Folate Receptor α is Frequently Overexpressed in Osteosarcome Samples and Plays a Role in the Uptake of the Physiologic Substrate 5-Methyltetrahydrofolate", Clinical Cancer Research, 2007, 13, 2557-2567.

* cited by examiner

| Specific signal at 500 pg/mL | Detection Antibody | | | | | | | | | | | | | |
|---|---|---|---|---|---|---|---|---|---|---|---|---|---|---|
| Capture antibody | 19D4.B7 | 30G6.G6.G4.E9 | 6A2.G7 | 24H8.D3 | 24H8.F3 | 1A8.G11.E7 | 19D2.G9 | 1D2.G8.G10 | 2F11.F8 | 1C6.E12.G8 | 5C12.H8 | 26A9.C4 | 28H12.G9 | +CONT |
| +CONT | --- | --- | --- | --- | --- | --- | --- | --- | --- | --- | --- | --- | --- | 60367 |
| 19D2.G9 | 65534 | 40728 | 11679 | 110 | 242 | 106 | 163 | 67 | 71 | 80 | 77 | 79 | 150 | --- |
| 1A8.G11.E7 | 58694 | 52459 | 5996 | 71 | 139 | 67 | 74 | 57 | 65 | 54 | 66 | 62 | 151 | --- |
| 24H8.D3 | 49088 | 46090 | 6616 | 69 | 158 | 84 | 73 | 79 | 59 | 74 | 71 | 59 | 155 | --- |
| 24H8.F3 | 19129 | 22607 | 3892 | 88 | 104 | 87 | 67 | 67 | 54 | 75 | 60 | 56 | 67 | --- |
| 30G6.G6.G4.E9 | 81 | 213 | 2406 | 20321 | 28334 | 17947 | 26895 | 7910 | 6792 | 10908 | 5294 | 6713 | 2490 | --- |
| 19D4.B7 | 87 | 65 | 10758 | 40460 | 33555 | 41409 | 34109 | 21839 | 26527 | 37479 | 18443 | 16532 | 10796 | --- |
| 6A2.G7 | 4958 | 3119 | 92 | 1934 | 1868 | 1837 | 2596 | 1689 | 1183 | 967 | 596 | 361 | 371 | --- |
| 1C6.E12.G8 | 2017 | 1267 | 217 | 59 | 64 | 75 | 67 | 74 | 56 | 86 | 58 | 58 | 77 | --- |
| 1D2.G8.G10 | 1973 | 1119 | 347 | 52 | 64 | 64 | 57 | 87 | 60 | 53 | 57 | 64 | 55 | --- |
| 26A9.C4 | 2626 | 2326 | 347 | 81 | 72 | 80 | 70 | 86 | 69 | 73 | 78 | 79 | 57 | --- |
| 28H12.G9 | 1217 | 769 | 432 | 97 | 85 | 83 | 83 | 78 | 73 | 92 | 68 | 62 | 71 | --- |
| 2F11.F8 | 1258 | 626 | 283 | 64 | 61 | 60 | 74 | 62 | 179 | 67 | 123 | 61 | 66 | --- |
| 5C12.H8 | 320 | 169 | 100 | 69 | 70 | 76 | 64 | 73 | 53 | 70 | 100 | 68 | 64 | --- |

FIG. 2A

| Average of S/B | Detection Antibody | | | | | | | | | | | | | |
|---|---|---|---|---|---|---|---|---|---|---|---|---|---|---|
| Capture antibody | 19D4.B7 | 30G6.G6.G4.E9 | 6A2.G7 | 24H8.D3 | 24H8.F3 | 1A8.G11.E7 | 19D2.G9 | 1D2.G8.G10 | 2F11.F8 | 1C6.E12.G8 | 5C12.H8 | 26A9.C4 | 28H12.G9 | +CONT |
| +CONT | --- | --- | --- | --- | --- | --- | --- | --- | --- | --- | --- | --- | --- | 341 |
| 19D2.G9 | 560 | 450 | 205 | 2 | 4 | 2 | 2 | 1 | 1 | 1 | 1 | 1 | 2 | --- |
| 1A8.G11.E7 | 405 | 504 | 89 | 1 | 2 | 1 | 1 | 1 | 1 | 1 | 1 | 1 | 2 | --- |
| 24H8.D3 | 361 | 450 | 109 | 1 | 2 | 1 | 1 | 1 | 1 | 1 | 1 | 1 | 3 | --- |
| 24H8.F3 | 207 | 318 | 63 | 1 | 1 | 1 | 1 | 1 | 1 | 1 | 1 | 1 | 1 | --- |
| 30G6.G6.G4.E9 | 1 | 1 | 31 | 273 | 501 | 244 | 347 | 75 | 81 | 144 | 61 | 114 | 31 | --- |
| 19D4.B7 | 1 | 1 | 145 | 332 | 327 | 310 | 371 | 218 | 338 | 449 | 253 | 250 | 202 | --- |
| 6A2.G7 | 82 | 33 | 1 | 38 | 27 | 27 | 35 | 26 | 23 | 19 | 9 | 6 | 5 | --- |
| 1C6.E12.G8 | 28 | 11 | 3 | 1 | 1 | 1 | 1 | 1 | 1 | 1 | 1 | 1 | 1 | --- |
| 1D2.G8.G10 | 29 | 14 | 5 | 1 | 1 | 1 | 1 | 1 | 1 | 1 | 1 | 1 | 1 | --- |
| 26A9.C4 | 34 | 29 | 4 | 1 | 2 | 1 | 2 | 1 | 1 | 1 | 1 | 1 | 1 | --- |
| 28H12.G9 | 17 | 9 | 7 | 1 | 1 | 1 | 2 | 1 | 1 | 1 | 1 | 1 | 1 | --- |
| 2F11.F8 | 17 | 8 | 5 | 1 | 2 | 1 | 2 | 1 | 1 | 1 | 1 | 1 | 1 | --- |
| 5C12.H8 | 5 | 2 | 1 | 1 | 2 | 1 | 1 | 1 | 1 | 1 | 1 | 1 | 1 | --- |

| Drug Suppression of Cal Signal at 500 pg/mL | Detection Antibody | | | | | | | | | | | | | |
|---|---|---|---|---|---|---|---|---|---|---|---|---|---|---|
| Capture antibody | 19D4.B7 | 30G6.G6.G4.E9 | 6A2.G7 | 24H8.D3 | 24H8.F3 | 1A8.G11.E7 | 19D2.G9 | 1D2.G8.G10 | 2F11.F8 | 1C6.E12.G8 | 5C12.H8 | 26A9.C4 | 28H12.G9 | +CONT |
| +CONT | --- | --- | --- | --- | --- | --- | --- | --- | --- | --- | --- | --- | --- | -5% |
| 19D2.G9 | 2% | -4% | -4% | --- | --- | --- | --- | --- | --- | --- | --- | --- | --- | --- |
| 1A8.G11.E7 | -16% | -6% | 16% | --- | --- | --- | --- | --- | --- | --- | --- | --- | --- | --- |
| 24H8.D3 | -3% | 0% | -15% | --- | --- | --- | --- | --- | --- | --- | --- | --- | --- | --- |
| 24H8.F3 | 9% | -6% | 7% | --- | --- | --- | --- | --- | --- | --- | --- | --- | --- | --- |
| 30G6.G6.G4.E9 | --- | --- | -5% | -2% | -8% | 2% | -5% | 8% | -1% | -7% | -7% | -11% | -15% | --- |
| 19D4.B7 | --- | --- | -9% | -6% | -14% | -2% | -19% | 2% | -4% | -18% | -10% | -14% | -21% | --- |
| 6A2.G7 | -13% | -1% | --- | -9% | -5% | 2% | -7% | -7% | -4% | 6% | --- | --- | --- | --- |
| 1C6.E12.G8 | -11% | -9% | --- | --- | --- | --- | --- | --- | --- | --- | --- | --- | --- | --- |
| 1D2.G8.G10 | -12% | -11% | --- | --- | --- | --- | --- | --- | --- | --- | --- | --- | --- | --- |
| 26A9.C4 | 72% | -28% | --- | --- | --- | --- | --- | --- | --- | --- | --- | --- | --- | --- |
| 28H12.G9 | -17% | --- | --- | --- | --- | --- | --- | --- | --- | --- | --- | --- | --- | --- |
| 2F11.F8 | -2% | --- | --- | --- | --- | --- | --- | --- | --- | --- | --- | --- | --- | --- |
| 5C12.H8 | --- | --- | --- | --- | --- | --- | --- | --- | --- | --- | --- | --- | --- | --- |

FIG. 3B

| Drug suppression of serum | Detection Antibody | | | | | | | | | | | | | |
|---|---|---|---|---|---|---|---|---|---|---|---|---|---|---|
| Capture antibody | 19D4.B7 | 30G6.G6.G4.E9 | 6A2.G7 | 24H8.D3 | 24H8.F3 | 1A8.G11.E7 | 19D2.G9 | 1D2.G8.G10 | 2F11.F8 | 1C6.E12.G8 | 5C12.H8 | 26A9.C4 | 28H12.G9 | +CONT |
| +CONT | --- | --- | --- | --- | --- | --- | --- | --- | --- | --- | --- | --- | --- | 12.05% |
| 19D2.G9 | 4.68% | --- | --- | --- | --- | --- | --- | --- | --- | --- | --- | -55.56% | --- | --- |
| 1A8.G11.E7 | -4.78% | --- | --- | --- | -61.3% | --- | --- | --- | --- | --- | --- | --- | --- | --- |
| 24H8.D3 | -2.80% | --- | --- | --- | --- | --- | --- | --- | --- | --- | --- | --- | --- | --- |
| 24H8.F3 | -12.98% | -0.93% | --- | --- | --- | --- | --- | --- | --- | --- | --- | --- | --- | --- |
| 30G6.G6.G4.E9 | --- | --- | --- | --- | --- | --- | --- | --- | --- | --- | --- | --- | --- | --- |
| 19D4.B7 | --- | --- | -45.83 | 4.49% | -10.6% | -4.92% | -3.38% | -2.12% | 0.82% | -6.01% | --- | -3.77% | --- | --- |
| 6A2.G7 | -52.0% | --- | --- | --- | --- | --- | --- | --- | --- | -22.2% | --- | --- | --- | --- |
| 1C6.E12.G8 | 84.62% | --- | --- | --- | --- | --- | --- | --- | --- | --- | --- | --- | --- | --- |
| 1D2.G8.G10 | -59.67% | --- | --- | --- | --- | --- | --- | --- | --- | --- | --- | --- | --- | --- |
| 26A9.C4 | -73.17% | --- | --- | --- | --- | --- | --- | --- | --- | --- | --- | --- | --- | --- |
| 28H12.G9 | --- | --- | --- | --- | --- | --- | --- | --- | --- | --- | --- | --- | --- | --- |
| 2F11.F8 | --- | --- | --- | --- | --- | --- | --- | --- | --- | --- | --- | --- | --- | --- |
| 5C12.H8 | --- | --- | --- | --- | --- | --- | --- | --- | --- | --- | --- | --- | --- | --- |

|  |  | 1A8.G11.E7 | 24H8.D3 | 19D2.G9 | 19D4.B7 |
|---|---|---|---|---|---|
| 19D4.B7 | S1 1:5 | 113% | 104% | 106% |  |
|  | S1 1:10 | 99% | 93% | 108% |  |
|  | S1 1:20 | 100% | 100% | 100% |  |
|  | S1 1:40 | 96% | 89% | 97% |  |
|  | S2 1:5 | 96% | 105% | 100% |  |
|  | S2 1:10 | 102% | 103% | 96% |  |
|  | S2 1:20 | 100% | 100% | 100% |  |
|  | S2 1:40 | 93% | 105% | 77% |  |

|  |  | 1A8.G11.E7 | 24H8.D3 | 19D2.G9 | 19D4.B7 |
|---|---|---|---|---|---|
| 1A8.G11.E7 | S1 1:5 |  |  |  | 87% |
|  | S1 1:10 |  |  |  | 106% |
|  | S1 1:20 |  |  |  | 100% |
|  | S1 1:40 |  |  |  | 103% |
|  | S2 1:5 |  |  |  | 107% |
|  | S2 1:10 |  |  |  | 74% |
|  | S2 1:20 |  |  |  | 100% |
|  | S2 1:40 |  |  |  | 91% |

|  |  | 1A8.G11.E7 | 24H8.D3 | 19D2.G9 | 19D4.B7 |
|---|---|---|---|---|---|
| 24H8.D3 | S1 1:5 |  |  |  | 97% |
|  | S1 1:10 |  |  |  | 95% |
|  | S1 1:20 |  |  |  | 100% |
|  | S1 1:40 |  |  |  | 90% |
|  | S2 1:5 |  |  |  | 104% |
|  | S2 1:10 |  |  |  | 103% |
|  | S2 1:20 |  |  |  | 100% |
|  | S2 1:40 |  |  |  | 102% |

|  |  | 1A8.G11.E7 | 24H8.D3 | 19D2.G9 | 19D4.B7 |
|---|---|---|---|---|---|
| 9F3 | S1 1:5 | 103% | 101% | 99% | 92% |
|  | S1 1:10 | 95% | 96% | 96% | 92% |
|  | S1 1:20 | 100% | 100% | 100% | 100% |
|  | S1 1:40 | 120% | 93% | 99% | 106% |
|  | S2 1:5 | 87% | 102% | 94% | 83% |
|  | S2 1:10 | 92% | 102% | 97% | 83% |
|  | S2 1:20 | 100% | 100% | 100% | 100% |
|  | S2 1:40 | 97% | 100% | 113% | 84% |

FIG. 4

| LLOD | 1A8.G11.E7 | 24H8.D3 | 19D2.G9 | 19D4.B7 | Reference |
|---|---|---|---|---|---|
| 19D4.B7 | 0.848 | 0.784 | 1.23 | | |
| 1A8.G11.E7 | 5108 | 5241 | 2705 | 255 | |
| 24H8.D3 | NA | NA | 2852 | 0.57 | |
| 9F3 | 0.739 | 1.57 | 1.09 | 0.61 | |
| Reference | | | | 1.01 | 0.23 |

| HILL SLOPE | 1A8.G11.E7 | 24H8.D3 | 19D2.G9 | 19D4.B7 | Reference |
|---|---|---|---|---|---|
| 19D4.B7 | 1.07 | 1.06 | 1.08 | | |
| 1A8.G11.E7 | | | | 1.09 | |
| 24H8.D3 | | | | 1.09 | |
| 9F3 | 1.02 | 1.02 | 1.07 | 1.11 | |
| Reference | | | | | 1.02 |

*FIG. 5B*

| Antibody | Clone | CR LOT # | Final Conc. (mg/mL) | % Yield | % Incorporation | Final B/P |
|---|---|---|---|---|---|---|
| FOLR-1 | 24H8 D3 | 140910-02-SAB-11646 Prebictin | 2.129 | 79 | 43 | 4.3 |

| Characterization Method | | Metric | Measured |
|---|---|---|---|
| Experion | Non-Reducing | Ab% Total Mass | 99% |
| | Reducing | % Total Mass H+L | 100% |
| | | H/L Ratio | 2.1 |
| DLS | Cumulant Fit | Radius (nm) | 8.2 |
| | | Ab% Polydispersity | Multimodal |
| | | Ab% Intensity | 100% |
| | | Ab% Mass | 100% |
| | Regularization Fit | Radius of Ab peak (nm) | 5.3 |
| | | Ab% Polydispersity | 18% |
| | | Ab% intensity | 65% |
| | | Ab% mass | 98% |
| cIEF | | pI of main peak | 6.2 |
| | | pI range | 5.9-6.4 |
| | | Profile Shape | Monoclonal |

FIG. 12A

| Antibody | Clone | CR LOT # | Final Conc. (mg/mL) | % Yield | % Incorporation | Final B/P |
|---|---|---|---|---|---|---|
| FOLR-1 | 19D4B7 | 140415-01-SAB-11536 Prestag | 1.591 | 98 | 57 | 11.4 |

| Characterization Method | | Metric | Measured |
|---|---|---|---|
| Experion | Non-Reducing | Ab% Total Mass | 97% |
| | Reducing | % Total Mass H+L | 100% |
| | | H/L Ratio | 1.6 |
| DLS | Cumulant Fit | Radius (nm) | 5.8 |
| | | Ab% Polydispersity | 17.9% |
| | | Ab% Intensity | 100% |
| | | Ab% Mass | 100% |
| | Regularization Fit | Radius of Ab peak (nm) | 5.6 |
| | | Ab% Polydispersity | 15% |
| | | Ab% Intensity | 94% |
| | | Ab% Mass | 100% |
| cIEF | | pI of main peak | 6.1 |
| | | pI range | 5.9-6.3 |
| | | Profile Shape | Monoclonal |

FIG. 12B

ANTI-FOLATE RECEPTOR ALPHA ANTIBODIES AND USES THEREOF

CROSS REFERENCE TO RELATED APPLICATIONS

This application claims the benefit of U.S. Provisional Patent Application No. 62/425,752, filed Nov. 23, 2016, the entirety of which is incorporated by reference.

SEQUENCE LISTING

The instant application contains a Sequence Listing which has been submitted electronically in ASCII format and is hereby incorporated by reference in its entirety. Said ASCII copy, created on Dec. 13, 2017, is named 104018_001018_SL.txt and is 143,203 bytes in size.

TECHNICAL FIELD

The subject matter provided herein relates to folate receptor alpha (FRα)-specific antibodies as well as methods of using the antibodies to detect FRα and methods to diagnose, monitor, or treat FRα-expressing cancers.

BACKGROUND

In humans, the high affinity receptor for folate comes in four isoforms: alpha, beta, gamma, and delta. The alpha, beta and delta forms are typically bound to the membranes of cells by a glycosyl phosphatidylinositol (GPI) anchor. They recycle between extracellular and endocytic compartments and are capable of transporting folate into the cell. Soluble forms of folate receptor may be derived by the action of proteases or phospholipase on membrane anchored folate receptors.

Folate receptor alpha (also referred to as FRα, FR-alpha, FOLR-1 or FOLR1) is expressed in a variety of epithelial tissues, including those of the choroid plexus, lung, thyroid, kidney, uterus, breast, Fallopian tube, epididymis, and salivary glands. Weitman, S D et al., Cancer Res 52: 3396-3401 (1992); Weitman S D et al., Cancer Res 52: 6708-6711 (1992). Overexpression of FRα has been observed in various cancers, including lung cancer (e.g., carcinoid tumors, and non-small cell lung cancers, such as adenocarcinomas); mesothelioma; ovarian cancer; renal cancer; brain cancer (e.g., anaplastic ependymoma, cerebellar juvenile pilocytic astrocytoma, and brain metastases); cervical cancer; nasopharyngeal cancer; mesodermally derived tumor; squamous cell carcinoma of the head and neck; endometrial cancer; papillary serous and endometrioid adenocarcinomas of the ovary, serous cystadenocarcinomas of the ovary, breast cancer; bladder cancer; pancreatic cancer; bone cancer (e.g., high-grade osteosarcoma); pituitary cancer (e.g., pituitary adenomas); colorectal cancer and medullary thyroid cancer. See e.g., U.S. Pat. No. 7,754,698; U.S. Patent Application No. 2005/0232919; Intl. Publ. No. WO 2009/132081; Bueno R et al., J of Thoracic and Cardiovascular Surgery, 121(2): 225-233 (2001); Elkanat H & Ratnam M. Frontiers in Bioscience, 11, 506-519 (2006); Basal et al., PLoS ONE, 4(7):6292 (2009); Fisher R E J Nucl Med, 49: 899-906 (2008); Franklin, W A et al., Int J Cancer, Suppl 8: 89-95 (1994); Hartmann L C et al., ht J Cancer 121: 938-942 (2007); Iwakiri S et al., Annals of Surgical Oncology, 15(3): 889-899 (2008); European patent publication EP 2199796, Parker N. et al., Analytical Biochemistry, 338: 284-293 (2005); Weitman, S D et al., Cancer Res 52: 3396-3401 (1992); Saba N F et al., Head Neck, 31(4): 475-481 (2009); Yang R et al., Clin Cancer Res 13: 2557-2567 (2007). In some types of cancers (e.g., squamous cell carcinoma of the head and neck), a high level of FRα expression is associated with a poor prognosis, whereas in other types of cancers (e.g., non-small-cell lung cancers), a higher level of FRα expression is associated with a more favorable prognosis. See, e.g., Iwakiri S et al., Annals of Surgical Oncology, 15(3): 889-899; Saba N F et al., Head Neck, 31(4): 475-481 (2009).

Earlier detection of cancer improves survival rates and quality of life. To improve the likelihood of early detection and treatment, a pressing need exists for non-invasive methods for diagnosing FRα-expressing cancers and for monitoring existing FRα-expressing cancers.

SUMMARY

Provided herein are antibodies that specifically bind to FRα. Also described are related polynucleotides capable of encoding the provided antibodies, cells expressing the provided antibodies, as well as associated vectors and detectable antibody labels. In addition, methods of using the provided antibodies to detect FRα and to diagnose, monitor, or treat ovarian cancer are described. For example, the provided antibodies may be used to diagnose, monitor or treat a folate receptor alpha-expressing cancer in a subject.

Folate Receptor Alpha (FRα)-Specific Antibodies

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method. In some embodiments, the antibodies or antigen-binding fragments include a light chain CDR1 amino acid sequence substantially the same as, or identical to, SEQ ID NO: 1. In some embodiments, the antibodies or antigen-binding fragments include a light chain CDR2 amino acid sequence substantially the same as, or identical to, SEQ ID NO: 2, wherein the CDR is defined according to the IMGT method. In some embodiments, the antibodies or antigen-binding fragments include a light chain CDR3 amino acid sequence substantially the same as, or identical to, SEQ ID NO: 3, wherein the CDR is defined according to the IMGT method. In some embodiments, the antibodies or antigen-binding fragments include a heavy chain CDR1 amino acid sequence substantially the same as, or identical to, SEQ ID NO: 8, wherein the CDR is defined according to the IMGT method. In some embodiments, the antibodies or antigen-binding fragments include a heavy chain CDR2 substantially the same as, or identical to, amino acid sequence of SEQ ID NO: 9, wherein the CDR is defined according to the IMGT method. In some embodiments, the antibodies or antigen-binding fragments include a heavy chain CDR3 amino acid sequence substantially the same as, or identical to SEQ ID NO: 10, wherein the CDR is defined according to the IMGT method.

In some embodiments, the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method. In some embodiments, the antibodies or antigen-binding fragments include a light chain CDR1 amino acid sequence substantially the same as, or identical to, SEQ ID NO: 4, wherein the CDR is defined according to the KABAT method. In some embodiments, the antibodies or antigen-binding fragments include a light chain CDR2 amino acid sequence substantially the same as, or identical to, SEQ ID NO: 5, wherein the CDR is defined according to the KABAT method. In some embodiments, the antibodies or antigen-binding fragments include a light chain CDR3 amino acid sequence substantially the same as, or identical to, SEQ ID NO: 3, wherein the CDR is defined according to the KABAT method. In some embodiments, the antibodies or antigen-binding fragments include a heavy chain CDR1 amino acid sequence substantially the same as, or identical to, SEQ ID NO: 11, wherein the CDR is defined according to the KABAT method. In some embodiments, the antibodies or antigen-binding fragments include a heavy chain CDR2 substantially the same as, or identical to, amino acid sequence of SEQ ID NO: 12, wherein the CDR is defined according to the KABAT method. In some embodiments, the antibodies or antigen-binding fragments include a heavy chain CDR3 amino acid sequence substantially the same as, or identical to SEQ ID NO: 13, wherein the CDR is defined according to the KABAT method.

In some embodiments, the antibodies or antigen-binding fragments are murine, IgG, chimeric or humanized.

In some embodiments, the antibodies or antigen-binding fragments include a light chain variable region amino acid sequence that is at least 90% identical to the amino acid sequence of SEQ ID NO: 6 and a heavy chain variable region amino acid sequence that is at least 90% identical to the amino acid sequence of SEQ ID NO: 14 where the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method.

Also disclosed are antibodies or antigen-binding fragments comprising a light chain variable region amino acid sequence that is at least 90% identical to the amino acid sequence of SEQ ID NO: 6, and a heavy chain variable region amino acid sequence that is at least 90% identical to the amino acid sequence of SEQ ID NO: 14 where the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method.

Also disclosed are isolated antibodies or antigen-binding fragments specific for FRα which include a light chain variable region amino acid sequence substantially the same as, or identical to, SEQ ID NO: 6. In some embodiments, the isolated antibody or antigen-binding fragment includes a heavy chain variable region amino acid sequence substantially the same as, or identical to, SEQ ID NO: 14. In some embodiments, the isolated antibody or antigen-binding fragment includes a light chain variable region amino acid sequence substantially the same as, or identical to, SEQ ID NO: 6 and a heavy chain variable region amino acid sequence substantially the same as, or identical to, SEQ ID NO: 14.

Also disclosed are isolated antibodies or antigen-binding fragments specific for FRα which include a light chain amino acid sequence substantially the same as, or identical to, SEQ ID NO: 7. In some embodiments, the isolated antibody or antigen-binding fragment includes a heavy chain amino acid sequence substantially the same as, or identical to, SEQ ID NO: 15. In some embodiments, the isolated antibody or antigen-binding fragment includes a light chain amino acid sequence substantially the same as, or identical to, SEQ ID NO: 7 and a heavy chain amino acid sequence substantially the same as, or identical to, SEQ ID NO: 15.

In some embodiments, the FRα antibody is produced by antibody-producing cells deposited with the American Type Culture Collection (10801 University Blvd., Manassas, Va. 20110-2209) on May 5, 2016 and assigned Accession No. PTA-123090.

Also disclosed are isolated polynucleotides which have a nucleotide sequence substantially the same as, or identical to, SEQ ID NO: 21. In some embodiments, the isolated polynucleotides have a nucleotide sequence substantially the same as, or identical to, SEQ ID NO: 29. In some embodiments, the isolated polynucleotides have a nucleotide sequence substantially the same as, or identical to, SEQ ID NO: 21 and a nucleotide sequence substantially the same as, or identical to, SEQ ID NO: 29.

Also disclosed are isolated polynucleotides which have a nucleotide sequence substantially the same as, or identical to, SEQ ID NO: 22. In some embodiments, the isolated polynucleotides have a nucleotide sequence substantially the same as, or identical to, SEQ ID NO: 30. In some embodiments, the isolated polynucleotides have a nucleotide sequence substantially the same as, or identical to, SEQ ID NO: 22 and a nucleotide sequence substantially the same as, or identical to, SEQ ID NO: 30.

Also disclosed are isolated polynucleotides that encode an antibody or antigen-binding fragment comprising a light chain variable region, wherein the light chain variable region amino acid sequence is substantially the same as, or identical to, SEQ ID NO: 6. In some embodiments, the isolated polynucleotides encode an antibody or antigen-binding fragment comprising a heavy chain variable region, wherein the heavy chain variable region amino acid sequence is substantially the same as, or identical to, SEQ ID NO: 14. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 6 and the heavy chain variable region amino acid sequence is substantially the same as, or identical to, SEQ ID NO: 14.

Also disclosed are isolated polynucleotides that encode an antibody or antigen-binding fragment comprising a light chain, wherein the light chain amino acid sequence is substantially the same as, or identical to, SEQ ID NO: 7. In some embodiments, the isolated polynucleotides encode an antibody or antigen-binding fragment comprising a heavy chain, wherein the heavy chain amino acid sequence is substantially the same as, or identical to, SEQ ID NO: 15. In some embodiments, the isolated polynucleotides encode an antibody or antigen-binding fragment comprising a light chain and a heavy chain, wherein the light chain amino acid sequence is substantially the same as, or identical to, SEQ ID NO: 7 and the heavy chain amino acid sequence is substantially the same as, or identical to, SEQ ID NO: 15.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 1, a light chain CDR2 of the encoded antibody is substantially the same as, or identical to, the amino acid sequence of SEQ ID NO: 2, a light chain CDR3 of the encoded antibody is substantially the same as, or identical to, the amino acid sequence of SEQ ID NO: 3, a heavy chain CDR1 of the encoded antibody is substantially the same as, or identical to, the amino acid sequence of SEQ ID NO: 8, a heavy chain CDR2 of the encoded antibody is substantially the same as, or identical to, the amino acid sequence of SEQ ID NO: 9, and a heavy chain CDR3 of the encoded antibody is substantially the same as, or identical to, the amino acid sequence of SEQ ID NO: 10, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 1, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 9, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 10, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 4, a light chain CDR2 of the encoded antibody is substantially the same as, or identical to, the amino acid sequence of SEQ ID NO: 5, a light chain CDR3 of the encoded antibody is substantially the same as, or identical to, the amino acid sequence of SEQ ID NO: 3, a heavy chain CDR1 of the encoded antibody is substantially the same as, or identical to, the amino acid sequence of SEQ ID NO: 11, a heavy chain CDR2 of the encoded antibody is substantially the same as, or identical to, the amino acid sequence of SEQ ID NO: 12, and a heavy chain CDR3 of the encoded antibody is substantially the same as, or identical to, the amino acid sequence of SEQ ID NO: 13, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 4, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 5, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 11, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 12, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 13, wherein the CDR is defined according to the KABAT method.

Described herein are isolated polynucleotide nucleotide sequences substantially similar to, or the same as, SEQ ID NO: 16, SEQ ID NO: 17, SEQ ID NO: 18, SEQ ID NO: 23, SEQ ID NO: 24, and SEQ ID NO 25. In other embodiments, the isolated polynucleotides are substantially similar to, or the same as, SEQ ID NO: 19, SEQ ID NO: 20, SEQ ID NO: 18, SEQ ID NO: 26, SEQ ID NO: 27, and SEQ ID NO 28.

Also described herein are isolated polynucleotides that encode an antibody or antigen-binding fragment specific for folate receptor alpha (FRα) wherein the light chain CDR1 of the encoded antibody is substantially the same as, or identical to, the amino acid sequence of SEQ ID NO: 1, the light chain CDR2 of the encoded antibody is substantially the same as, or identical to, the amino acid sequence of SEQ ID NO: 2, and the light chain CDR3 of the encoded antibody is substantially the same as, or identical to, the amino acid sequence SEQ ID NO: 3, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 1, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the IMGT method.

Also described herein are isolated polynucleotides that encode an antibody or antigen-binding fragment specific for folate receptor alpha (FRα) wherein the light chain CDR1 of the encoded antibody is substantially the same as, or identical to, the amino acid sequence of SEQ ID NO: 4, the light chain CDR2 of the encoded antibody is substantially the same as, or identical to, the amino acid sequence of SEQ ID NO: 5, and the light chain CDR3 of the encoded antibody is substantially the same as, or identical to, the amino acid sequence SEQ ID NO: 3, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 4, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 5, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the KABAT method.

Also described herein are isolated polynucleotides that encode an antibody or antigen-binding fragment specific for folate receptor alpha (FRα) wherein the heavy chain CDR1 of the encoded antibody is substantially the same as, or identical to, the amino acid sequence of SEQ ID NO: 8, the heavy chain CDR2 of the encoded antibody is substantially the same as, or identical to, the amino acid sequence of SEQ ID NO: 9, and the heavy chain CDR3 of the encoded antibody is substantially the same as, or identical to, the amino acid sequence SEQ ID NO: 10, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 9, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 10, wherein the CDR is defined according to the IMGT method.

Also described herein are isolated polynucleotides that encode an antibody or antigen-binding fragment specific for folate receptor alpha (FRα) wherein the heavy chain CDR1 of the encoded antibody is substantially the same as, or identical to, the amino acid sequence of SEQ ID NO: 11, the heavy chain CDR2 of the encoded antibody is substantially the same as, or identical to, the amino acid sequence of SEQ ID NO: 12, and the heavy chain CDR3 of the encoded antibody is substantially the same as, or identical to, the amino acid sequence SEQ ID NO: 13, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 11, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 12, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 13, wherein the CDR is defined according to the KABAT method.

In some embodiments the isolated polynucleotides capable of encoding the domains provided herein may be included on the same, or different, vectors to produce an antibody or antigen-binding fragment. Also provided are cells capable of expressing the described vectors. The cells may be eukaryotic cells, yeast cells, plant cells or bacteria. In preferred embodiments, the eukaryotic cell is a CHO cell.

Methods for Detecting Folate Receptor Alpha (FRα) in a Biological Sample

Provided herein are methods for detecting folate receptor alpha (FRα) in a biological sample. In some embodiments, the method involves exposing the sample to any one of the antibodies or antigen-binding fragments described herein and detecting FRα. In some embodiments, the biological sample is derived from urine, blood, serum, plasma, saliva, ascites, circulating cells, circulating tumor cells, cells that are not tissue associated, tissues, surgically resected tumor tissue, biopsies, fine needle aspiration samples, or histological preparations. In some embodiments, the biological sample is derived from a human or nonhuman primate. In some embodiments, the antibody is labeled. In some embodiments, the label is a radiolabel, an epitope tag, biotin, a chromophore label, a fluorophore label, an electrochemiluminescence (ECL) label, or an enzyme. In preferred embodiments, the electrochemiluminescence (ECL) label is a sulfo-tag. In some embodiments, the method further involves exposing the sample to a second antibody or antigen-binding fragment of any one of the described antibodies. In some embodiments, the second antibody or antigen-binding fragment is immobilized to a solid support. In preferred embodiments, the second antibody or antigen-binding fragment is biotinylated and the solid support is coated with streptavidin, and the isolated antibody or antigen-binding fragment is immobilized to the solid support by the binding of biotin to streptavidin. In some embodiments, the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA. In some embodiments, the sample is diluted prior to detecting folate receptor alpha (FRα) in the sample. In some embodiments, the sample is centrifuged, vortexed, or both, prior to detecting folate receptor alpha (FRα) in the sample. In some embodiments, the level of folate receptor alpha (FRα) in the sample is quantified. In some embodiments, the sample is exposed to MORAb-003 prior to detecting folate receptor alpha (FRα) in the sample.

Also provided herein are methods for detecting folate receptor alpha (FRα) in a biological sample. In some embodiments, the method involves exposing the sample to a first isolated antibody or antigen-binding fragment comprising a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a first isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 5, 2016 that has been assigned Accession No. PTA-123090 and a second isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or a second isolated antibody that is produced by antibody-producing cells deposited with the American Type Culture Collection (10801 University Blvd., Manassas, Va. 20110-2209) on May 19, 2011 that has been assigned Accession No. PTA-11884, wherein the first isolated antibody or antigen-binding fragment is immobilized to a solid support and the second isolated antibody or antigen-binding fragment is labeled.

In other embodiments, the method involves exposing the sample to a first isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or the isolated antibody that is produced by antibody-producing cells deposited with the American Type Culture Collection (10801 University Blvd., Manassas, Va. 20110-2209) on May 19, 2011 that has been assigned Accession No. PTA-11884 and a second isolated antibody or antigen-binding fragment comprising a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a second isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or a second isolated antibody that is produced by antibody-producing cells deposited with the American Type Culture Collection (10801 University Blvd., Manassas, Va. 20110-2209) on May 5, 2016 that has been assigned Accession No. PTA-123090, wherein the first isolated antibody or antigen-binding fragment is immobilized to a solid support and the second isolated antibody or antigen-binding fragment is labeled.

In some embodiments, the biological sample is derived from urine, blood, serum, plasma, saliva, ascites, circulating cells, circulating tumor cells, cells that are not tissue associated, tissues, surgically resected tumor tissue, biopsies, fine needle aspiration samples, or histological preparations. In some embodiments, the biological sample is derived from a human or nonhuman primate. In some embodiments, the antibody is labeled. In some embodiments, the label is a radiolabel, an epitope tag, biotin, a chromophore label, a fluorophore label, an electrochemiluminescence (ECL) label, or an enzyme. In preferred embodiments, the electrochemiluminescence (ECL) label is a sulfo-tag. In some embodiments, the first isolated antibody or antigen-binding fragment is biotinylated and the solid support is coated with streptavidin, and the isolated antibody or antigen-binding fragment is immobilized to the solid support by the binding of biotin to streptavidin. In some embodiments, the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA. In some embodiments, the level of FRα in the sample is quantified. In some embodiments, the sample is exposed to MORAb-003 prior to detecting folate receptor alpha (FRα) in the sample.

Methods for Diagnosing, Monitoring and Treating Folate Receptor Alpha (FRα)-Expressing Cancer Provided herein are methods for diagnosing a folate receptor alpha (FRα)-expressing cancer in a subject. In some embodiments, the described methods involve exposing the biological sample of the subject to any one of the antibodies or antigen-binding fragments described herein. In some embodiments, the described methods involve exposing the biological sample of the subject to an antibody or antigen-binding fragment capable of binding the epitope of FRα that is bound by any one of the antibodies or antigen binding fragments described herein. In some embodiments, the described methods involve quantifying the amount of FRα present in the sample that is bound by the antibody or antigen-binding fragment. In some embodiments, the described methods involve comparing the amount of FRα present in the sample to a known standard. In some embodiments, the described methods involve determining whether the subject's FRα levels fall within the levels of FRα associated with cancer.

Also described herein are methods for monitoring a folate receptor alpha (FRα)-expressing cancer in a subject. In some embodiments, the described methods involve exposing the biological sample of the subject to any one of the antibodies or antigen-binding fragments described herein. In some embodiments, the described methods involve exposing the biological sample of the subject to an antibody or antigen-binding fragment capable of binding the epitope of FRα that is bound by the antibody or antigen binding fragment of any one of the antibodies or antigen-binding fragments described herein. In some embodiments, the described methods involve quantifying the amount of FRα present in the sample that is bound by the antibody or antigen-binding fragment. In some embodiments, the described methods involve comparing the amount of FRα present in the sample to a known standard. In some embodiments, the described methods involve comparing the amount of FRα present in the sample to a biological sample obtained from the subject at an earlier point in time. In some embodiments, the described methods involve determining whether the subject's FRα levels are indicative of cancer progression, regression or stable disease.

Also provided herein are methods for treating a folate receptor alpha (FRα)-expressing cancer in a subject. In some embodiments, the described methods involve exposing the biological sample of the subject to any one of the antibodies or antigen-binding fragments described herein. In some embodiments, the described methods involve exposing the biological sample of the subject to an antibody or antigen-binding fragment capable of binding the epitope of FRα that is bound by any one of the antibodies or antigen-binding fragments described herein. In some embodiments, the described methods involve quantifying the amount of FRα present in the sample that is bound by the antibody or antigen-binding fragment. In some embodiments, the described methods involve comparing the amount of FRα present in the sample to a known standard. In some embodiments, the described methods involve determining whether the subject's FRα levels fall within the levels of FRα associated with cancer. In some embodiments, the described methods involve administering to the subject, or prescribing, a treatment for the cancer.

In some embodiments of the methods described herein, the antibody or antigen-binding fragment of any one of the antibodies or antigen-binding fragments described herein is labeled. In some embodiments, the label is a radiolabel, an epitope tag, biotin, a chromophore label, a fluorophore label, an electrochemiluminescence (ECL) label, or an enzyme. In preferred embodiments, the electrochemiluminescence (ECL) label is a sulfo-tag.

In some embodiments of the methods described herein, the antibody or antigen-binding fragment is the isolated antibody or antigen-binding fragment which includes a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method. In some embodiments of the methods described herein, the antibody or antigen-binding fragment is the isolated antibody or antigen-binding fragment which includes a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method. In some embodiments, the FRα antibody is produced by antibody-producing cells deposited with the American Type Culture Collection (10801 University Blvd., Manassas, Va. 20110-2209) on May 5, 2016 and assigned Accession No. PTA-123090. In some embodiments, the antibody or antigen-binding fragment is the isolated antibody or antigen-binding fragment with a light chain CDR1 amino acid sequence substantially the same as, or identical to, SEQ ID NO: 31, a light chain CDR2 amino acid sequence substantially the same as, or identical to, SEQ ID NO: 32, a light chain CDR3 amino acid sequence substantially the same as, or identical to, SEQ ID NO: 33, a heavy chain CDR1 amino acid sequence substantially the same as, or identical to SEQ ID NO: 35, a heavy chain CDR2 amino acid sequence substantially the same as, or identical to, SEQ ID NO: 36, and a heavy chain CDR3 amino acid sequence substantially the same as, or identical to, SEQ ID NO: 37 or the isolated antibody or antigen-binding fragment produced by antibody-producing cells deposited with the American Type Culture Collection (10801 University Blvd., Manassas, Va. 20110-2209) on May 19, 2011 that has been assigned Accession No. PTA-11884.

In some embodiments of the methods described herein, the step of exposing a biological sample of the subject to the antibody or antigen-binding fragment of any one of the antibodies or antigen-binding fragments described herein or an antibody or antigen-binding fragment capable of binding the epitope of folate receptor alpha (FRα) that is bound by the antibody or antigen binding fragment of any one of the antibodies or antigen-binding fragments described herein further comprises exposing the biological sample of the subject to a second antibody or antigen-binding fragment capable of binding FRα.

In some embodiments of the methods described herein, the second antibody or antigen-binding fragment includes a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method. In some embodiments of the methods described herein, the second antibody or antigen-binding fragment includes a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method. In some embodiments of the methods described herein, the second antibody or antigen-binding fragment is the isolated antibody or antigen-binding fragment that is produced by antibody-producing cells deposited with the American Type Culture Collection (10801 University Blvd., Manassas, Va. 20110-2209) on May 5, 2016 that has been assigned Accession No. PTA-123090. In some embodiments, the second antibody or antigen-binding fragment is the isolated antibody or antigen-binding fragment with a light chain CDR1 amino acid sequence substantially the same as, or identical to, SEQ ID NO: 31, a light chain CDR2 amino acid sequence substantially the same as, or identical to, SEQ ID NO: 32, a light chain CDR3 amino acid sequence substantially the same as, or identical to, SEQ ID NO: 33, a heavy chain CDR1 amino acid sequence substantially the same as, or identical to SEQ ID NO: 35, a heavy chain CDR2 amino acid sequence substantially the same as, or identical to, SEQ ID NO: 36, and a heavy chain CDR3 amino acid sequence substantially the same as, or identical to, SEQ ID NO: 37 or the isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884.

In some embodiments, the antibody or antigen-binding fragment is the isolated antibody or antigen-binding fragment with a light chain CDR1 amino acid sequence substantially the same as, or identical to, SEQ ID NO: 31, a light chain CDR2 amino acid sequence substantially the same as, or identical to, SEQ ID NO: 32, a light chain CDR3 amino acid sequence substantially the same as, or identical to, SEQ ID NO: 33, a heavy chain CDR1 amino acid sequence substantially the same as, or identical to SEQ ID NO: 35, a heavy chain CDR2 amino acid sequence substantially the same as, or identical to, SEQ ID NO: 36, and a heavy chain CDR3 amino acid sequence substantially the same as, or identical to, SEQ ID NO: 37 or the isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884 and the second antibody or antigen-binding fragment is the isolated antibody or antigen-binding fragment with a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method; the isolated antibody or antigen-binding fragment with a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method; or the antigen-binding fragment is the isolated antibody or antigen-binding fragment that is produced by antibody-producing cells deposited with the American Type Culture Collection (10801 University Blvd., Manassas, Va. 20110-2209) on May 5, 2016 that has been assigned Accession No. PTA-123090.

In some embodiments, the second antibody or antigen-binding fragment is immobilized to a solid support. In some embodiments, the second antibody or antigen-binding fragment is biotinylated and the solid support is coated with streptavidin, and the isolated antibody or antigen-binding fragment is immobilized to the solid support by the binding of biotin to streptavidin. In some embodiments, the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA. In some embodiments, the FRα-expressing cancer is ovarian cancer. In some embodiments, the method is conducted following treatment of the subject for cancer with MORAb-003.

Kits of the Invention

Provided herein are kits for detecting the presence of folate receptor alpha (FRα) in a biological sample. In some embodiments, the kit may contain any one of the antibodies or antigen-binding fragments described herein. In some embodiments, the kit may contain an antibody or antigen-binding fragment capable of binding the epitope of FRα that is bound by any one of the antibodies or antigen-binding fragments described herein. In some embodiments, the kit may contain an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884. In some embodiments, the kit may contain a vessel for containing the antibody, when not in use, and instructions for use of the antibody.

Also provided herein are kits for detecting the presence of folate receptor alpha (FRα) in a biological sample. In some embodiments, the kit may contain the antibody or antigen-binding fragment of any one of the antibodies or antigen-binding fragments described herein, wherein the antibody or antigen-binding fragment is affixed to a solid support. In some embodiments, the kit may contain an antibody or antigen-binding fragment capable of binding the epitope of FRα that is bound by the antibody or antigen binding fragment of any one of the antibodies or antigen-binding fragments described herein wherein the antibody or antigen-binding fragment is affixed to a solid support. In some embodiments, the kit may contain an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884, wherein the antibody or antigen-binding fragment is affixed to a solid support.

Also described herein are kits for detecting the presence of folate receptor alpha (FRα) in a biological sample. In some embodiments, the kit may contain the antibody or antigen-binding fragment of any one of the antibodies or antigen-binding fragments described herein, wherein the antibody or antigen-binding fragment is detectably labeled. In some embodiments, the kit may contain an antibody or antigen-binding fragment capable of binding the epitope of FRα that is bound by the antibody or antigen binding fragment of any one of the antibodies or antigen-binding fragments described herein, wherein the antibody or antigen-binding fragment is detectably labeled. In some embodiments, the kit may contain an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884, wherein the antibody or antigen-binding fragment is detectably labeled.

BRIEF DESCRIPTION OF THE DRAWINGS

FIG. 2A shows the light intensity count resulting from pairwise combinations of thirteen capture antibodies and thirteen detection antibodies. FIG. 2B shows the average signal to background (S/B) values resulting from pairwise combinations of thirteen capture antibodies and thirteen detection antibodies.

FIG. 3A shows percent interference/drug suppression after adding 10 μg/mL MORAb-003 for the pairwise combinations of thirteen capture antibodies and thirteen detection antibodies in a control calibrator solution containing untagged recombinant purified FRα at a concentration of 500 pg/mL. FIG. 3B shows percent interference/drug suppression after adding 10 μg/mL MORAb-003 for the pairwise combinations of thirteen capture antibodies and thirteen detection antibodies in serum samples. The positive control is located in the upper right corner for comparison. Percent interference=(Signal with MORAb-003—Blank)/(Signal without MORAb-003—Blank).

FIG. 4 shows examples of dilution linearity when using 24H8.D3 and 19D4.B7 as both the capture and detection antibody as compared to other antibody pairs. Dilution adjusted concentrations were normalized to the concentration at 1:20 dilution and the grayed sections represent antibody combinations not considered during the screening.

FIGS. 5A and 5B show the FRα standard curves and hillslopes. FIG. 5A depicts graphs of signal plotted against concentration for a defined capture antibody and paired with one of four detection antibodies. FIG. 5B shows the standard curve and hill slope data for the tested antibody pairs.

FIG. 7A shows a graph of the light intensity counts (y-axis) of eight standard FRα samples and five serum samples (x-axis) at 10, 20, 40, 80, 160 and 320-fold dilutions. FIG. 7B shows a graph of the percent normalized recovery (y-axis) plotted against the fold dilution for all five serum samples (x-axis). FIG. 7C shows a graph of the light intensity counts (y-axis) of eight standard FRα samples and five urine samples (x-axis) at 10, 20, 40, 80, 160 and 320-fold dilutions. FIG. 7D shows a graph of the % normalized recovery (y-axis) plotted against the fold dilution for all five urine samples (x-axis).

FIG. 8A shows the results from the five serum samples and FIG. 8B shows the results from the five urine samples.

FIGS. 12A and 12B show the antibody characterization profiles for 24H8.D3 (FIG. 12A) and 19D4.B7 (FIG. 12B), along with the results from capillary isoelectric focusing (cIEF), dynamic light scattering (DLS), and experion automated electrophoresis characterization tests.

DETAILED DESCRIPTION OF ILLUSTRATIVE EMBODIMENTS

Figure 1:
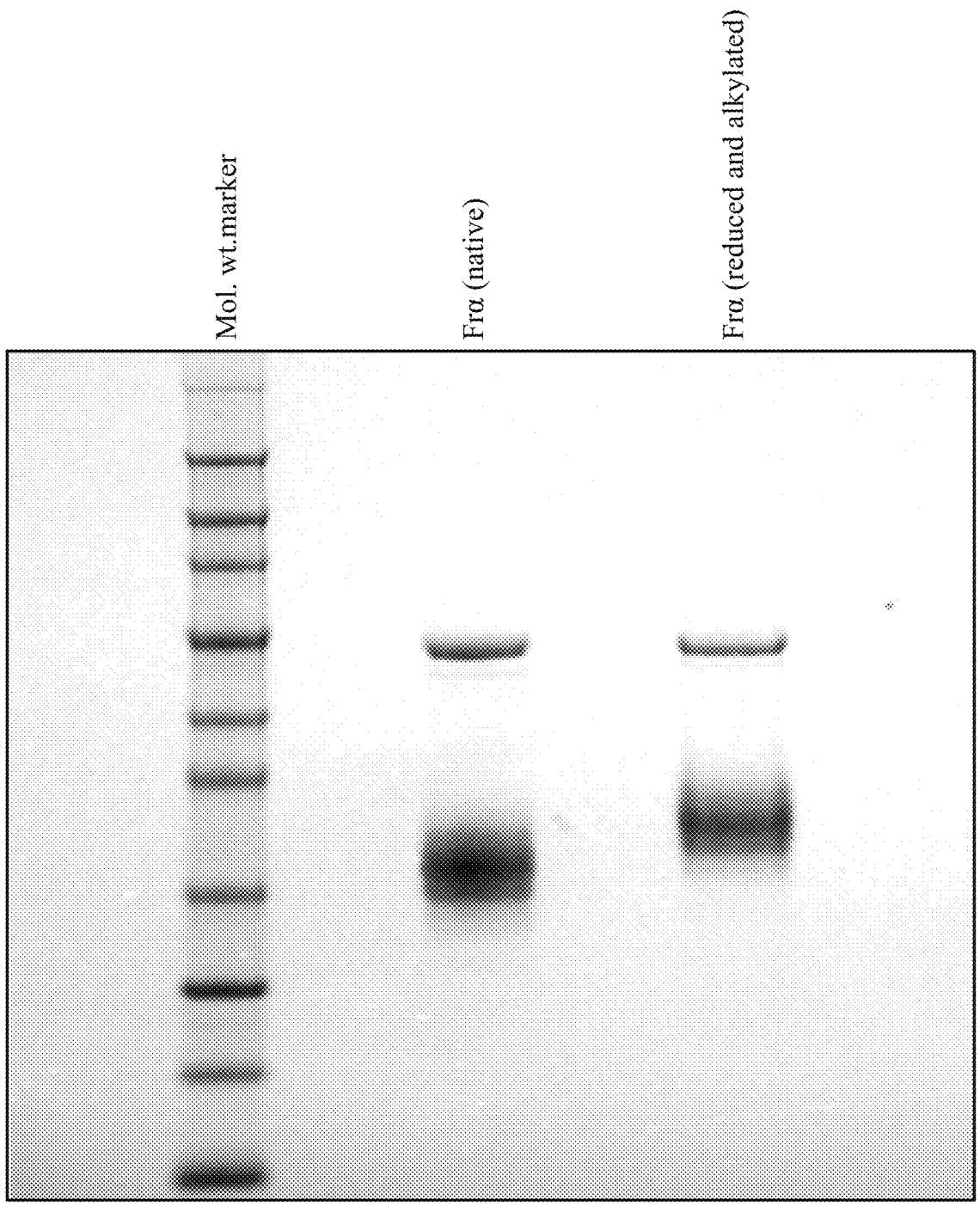
FIG. 1 depicts the migratory patterns of folate receptor alpha (FRα or FOLR1) by SDS-PAGE under nonreducing conditions. FRα was assessed in either native (lane 2) or reduced and alkylated (lane 3) form.

The following description characterizes antibodies that specifically bind to FRα. Also described are related polynucleotides capable of encoding the provided antibodies, cells expressing the provided antibodies, as well as associated vectors and detectable antibody labels. In addition, methods of using the provided antibodies to detect FRα and to diagnose, monitor, or treat ovarian cancer are described. For example, the provided antibodies may be used to diagnose, monitor or treat a folate receptor alpha-expressing cancer in a subject.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value; as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins that can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. Such identity may be determined using nBLAST algorithm (Altschul et al., (1990) *Proc. Natl. Acad. Sci. USA* 87:2264-8; Karlin and Altschul (1993) *Proc. Natl. Acad. Sci. USA* 90:5873-7).

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include FRα specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

A "vector" is a replicon, such as plasmid, phage, cosmid, or virus in which another nucleic acid segment may be operably inserted so as to bring about the replication or expression of the segment.

A cell has been "transformed" when exogenous or heterologous nucleic acids such as DNA have been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

"Antibody" refers to all isotypes of immunoglobulins (IgG, IgA, IgE, IgM, IgD, and IgY) including various monomeric and polymeric forms of each isotype, unless otherwise specified.

Antigen-binding fragments are any proteinaceous structure that may exhibit binding affinity for a particular antigen. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase. The CDR sequences of this invention are defined using the KABAT method (Kabat, E. A. et al., Sequences of Proteins of Immunological Interest, Fifth Edition, U.S. Department of Health and Human Services, U.S. Government Printing Office (1991)) or the international ImMunoGeneTics (IMGT) method (Lefranc, M.-P., et al. (2005). IMGT, the international ImMunoGeneTics information System®. *Nucl. Acids Res.* 33, D593-D597).

"Specific binding" when used in the context of antibodies, or antibody fragments, represents binding via domains encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds to a cognate antigen with a Kd of less than about $1 \times 10^{-8}$ M, as measured by a surface plasmon resonance assay or a cell binding assay.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

As used herein, the term "folate receptor alpha" (also referred to as FRα, FR-alpha, FOLR-1 or FOLR1) refers to the alpha isoform of the high affinity receptor for folate. Membrane bound FRα is attached to the cell surface by a glycosyl phosphatidylinositol (GPI) anchor. Soluble forms of FRα may be derived by the action of proteases or phospholipase on membrane anchored folate receptors. The amino acid sequence for human FRα is set forth herein as SEQ ID NO: 293. Variants, for example, naturally occurring allelic variants or sequences containing at least one amino acid substitution, are encompassed by the terms as used herein. As will be appreciated by those skilled in the art, cell associated and non-cell associated forms of human FRα may encompass variant forms of SEQ ID NO: 293.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like.

Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

The term "progression," as used in the context of progression of a FRα-expressing cancer, includes the change of a cancer from a less severe to a more severe state. This could include an increase in the number or severity of tumors, the degree of metastasis, the speed with which the cancer is growing or spreading, and the like. For example, "the progression of ovarian cancer" includes the progression of such a cancer from a less severe to a more severe state, such as the progression from stage I to stage II, from stage II to stage III, etc.

The term "regression," as used in the context of regression of a FRα-expressing cancer, includes the change of a cancer from a more severe to a less severe state. This could include a decrease in the number or severity of tumors, the degree of metastasis, the speed with which the cancer is growing or spreading, and the like. For example, "the regression of ovarian cancer" includes the regression of such a cancer from a more severe to a less severe state, such as the progression from stage III to stage II, from stage II to stage I, etc.

The term "stable" as used in the context of stable FRα-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

FRα-Specific Antibodies and Antigen-Binding Fragments

Described herein are isolated monoclonal antibodies or antigen-binding fragments that specifically bind FRα. The general structure of an antibody molecule comprises an antigen binding domain, which includes heavy and light chains, and the Fc domain, which serves a variety of functions, including complement fixation and binding antibody receptors.

The described antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The antibodies or antigen-binding fragments described herein can occur in a variety of forms, but will include one or more of the antibody variable domain segments or CDRs shown in Table 1.

TABLE 1

Antibody segments of the described anti-FRα antibodies and antigen-binding fragments thereof ("Lc" denotes light chain and "Hc" denotes heavy chain)

| Antibody Segment | SEQ ID NO. | Sequence |
| --- | --- | --- |
| Monoclonal antibody 24H8.D3 (murine IgG constant region) Amino Acid Sequences | | |
| Lc CDR1 (IMGT) | 1 | QDISNH |
| Lc CDR2 (IMGT) | 2 | YTS |
| Lc CDR3 (IMGT) | 3 | QQGNTLWT |
| Lc CDR1 (KABAT) | 4 | RASQDISNHLN |
| Lc CDR2 (KABAT) | 5 | YTSKLHS |
| Lc CDR3 (KABAT) | 3 | QQGNTLWT |
| Lc variable domain segment | 6 | DIQMTQTTSSLSASLGDRVTISCRASQDISNHLNWYQQKPDGTIKLLIYYTSKLHSG VPSRFSGSGSGTDYSLTISNLEQEDIATYFCQQGNTLWTFGGGTKLEIK |
| Lc | 7 | DIQMTQTTSSLSASLGDRVTISCRASQDISNHLNWYQQKPDGTIKLLIYYTSKLHSG VPSRFSGSGSGTDYSLTISNLEQEDIATYFCQQGNTLWTFGGGTKLEIKRADAAPT |
| Hc CDR1 (IMGT) | 8 | GFSLTSYG |
| Hc CDR2 (IMGT) | 9 | IWGDGST |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Hc CDR3 (IMGT) | 10 | AKPHPAATGAMDY |
| Hc CDR1 (KABAT) | 11 | SYGVS |
| Hc CDR2 (KABAT) | 12 | VIWGDGSTNYHSTLIS |
| Hc CDR3 (KABAT) | 13 | PHPAATGAMDY |
| Hc variable domain segment | 14 | QVQLKESGPGLVAPSQSLSITCTVSGFSLTSYGVSWVRQPPGKGLEWLGVIWGDGSTNYHSTLISRLSISKDNSKSQVFLKLNSLQTDDTATYYCAKPHPAATGAMDYWGQGTSVTVSS |
| Hc | 15 | QVQLKESGPGLVAPSQSLSITCTVSGFSLTSYGVSWYRQPPGKGLEWLGVIWGDGSTNYHSTLISRLSISKDNSKSQVFLKLNSLQTDDTATYYCAKPHPAATGAMDYWGQGTSVTVSSAKTTPPSVYPLAPGSAAQTNSMVTLGCLVKGYFPEPVTVTWNSGSLSSGVHTF |

Monoclonal antibody 24H8.03 (murine IgG constant region)
Nucleic Acid Sequences

| Antibody Segment | SEQ ID NO. | Sequence |
|---|---|---|
| Lc CDR1 (IMGT) | 16 | CAGGACATTAGCAATCAT |
| Lc CDR2 (IMGT) | 17 | TACACATCA |
| Lc CDR3 (IMGT) | 18 | CAACAGGGTAATACGCTTTGGACG |
| Lc CDR1 (KABAT) | 19 | AGGGCAAGTCAGGACATTAGCAATCATTTAAAC |
| Lc CDR2 (KABAT) | 20 | TACACATCAAAATTACACTCA |
| Lc CDR3 (KABAT) | 18 | CAACAGGGTAATACGCTTTGGACG |
| Lc variable domain segment | 21 | GATATCCAGATGACACAGACTACATCCTCCCTGTCTGCCTCTCTGGGAGACAGAGTCACCATCAGTTGCAGGGCAAGTCAGGACATTAGCAATCATTTAAACTGGTATCAACAGAAACCAGATGGAACTATTAAACTCCTGATCTACTACACATCAAAATTACACTCAGGAGTCCCATCAAGGTTCAGTGGCAGTGGGTCTGGAACAGATTATTCTCTCACCATTAGCAACCTGGAACAAGAAGATATTGCCACTTACTTTTGCCAACAGGGTAATACGCTTTGGACGTTCGGTGGAGGCACCAAGCTGGAAATCAAA |
| Lc | 22 | GATATCCAGATGACACAGACTACATCCTCCCTGTCTGCCTCTCTGGGAGACAGAGTCACCATCAGTTGCAGGGCAAGTCAGGACATTAGCAATCATTTAAACTGGTATCAACAGAAACCAGATGGAACTATTAAACTCCTGATCTACTACACATCAAAATTACACTCAGGAGTCCCATCAAGGTTCAGTGGCAGTGGGTCTGGAACAGATTATTCTCTCACCATTAGCAACCTGGAACAAGAAGATATTGCCACTTACTTTTGCCAACAGGGTAATACGCTTTGGACGTTCGGTGGAGGCACCAAGCTGGAAATCAAACGGGCTGATGCTGCACCAACT |
| Hc CDR1 (IMGT) | 23 | GGGTTCTCATTAACCAGTTATGGT |
| Hc CDR2 (IMGT) | 24 | ATATGGGGTGACGGGAGCACA |
| Hc CDR3 (IMGT) | 25 | GCCAAACCTCATCCTGCGGCTACTGGCGCTATGGACTAC |
| Hc CDR1 (KABAT) | 26 | AGTTATGGTGTAAGC |
| Hc CDR2 (KABAT) | 27 | GTAATATGGGGTGACGGGAGCACAAATTATCATTCAACTCTCATATCC |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Hc CDR3 (KABAT) | 28 | CCTCATCCTGCGGCTACTGGCGCTATGGACTAC |
| Hc variable domain segment | 29 | CAGGTGCAGCTGAAGGAGTCAGGACCTGGCCTGGTGGCGCCCTCACAGAGCCT GTCCATCACATGCACTGTCTCAGGGTTCTCATTAACCAGTTATGGTGTAAGCTG GGTTCGCCAGCCTCCAGGAAAGGGTCTGGAGTGGCTGGGAGTAATATGGGGTG ACGGGAGCACAAATTATCATTCAACTCTCATATCCAGACTGAGCATCAGCAAG GATAACTCCAAGAGCCAAGTTTTCTTAAAACTGAACAGTCTGCAAACTGATGA CACAGCCACGTACTACTGTGCCAAACCTCATCCTGCGGCTACTGGCGCTATGG ACTACTGGGGTCAAGGAACCTCAGTCACCGTCTCCTCA |
| Hc | 30 | CAGGTGCAGCTGAAGGAGTCAGGACCTGGCCTGGTGGCGCCCTCACAGAGCCT GTCCATCACATGCACTGTCTCAGGGTTCTCATTAACCAGTTATGGTGTAAGCTG GGTTCGCCAGCCTCCAGGAAAGGGTCTGGAGTGGCTGGGAGTAATATGGGGTG ACGGGAGCACAAATTATCATTCAACTCTCATATCCAGACTGAGCATCAGCAAG GATAACTCCAAGAGCCAAGTTTTCTTAAAACTGAACAGTCTGCAAACTGATGA CACAGCCACGTACTACTGTGCCAAACCTCATCCTGCGGCTACTGGCGCTATGG ACTACTGGGGTCAAGGAACCTCAGTCACCGTCTCCTCAGCCAAAACGACACCC CCATCTGTCTATCCACTGGCCCCTGGATCTGCTGCCCAAACTAACTCCATGGTG ACCCTGGGATGCCTGGTCAAGGGCTATTTCCCTGAGCCAGTGACAGTGACCTG GAACTCTGGATCCCTGTCCAGCGGTGTGCACACCTTC |

Monoclonal antibody 19D4.B7 (murine IgG2a constant region)
Amino Acid Sequences

| Antibody Segment | SEQ ID NO. | Sequence |
|---|---|---|
| Lc CDR1 (IMGT) | 31 | RASESVDTYGNNFIH |
| Lc CDR2 (IMGT) | 32 | LASNLES |
| Lc CDR3 (IMGT) | 33 | QQNNGDPWT |
| Lc variable domain segment | 34 | PASLAVSLGQRATISCRASESVDTYGNNFIHWYQQKPGQPPKLLIYLASNLESGVP ARFSGSGSRTDFTLTIDPVEADDAATYYCQQNNGDPWTFGGGTKLEIKRADAAP |
| Hc CDR1 (IMGT) | 35 | HPYMH |
| Hc CDR2 (IMGT) | 36 | RIDRANGNTKYDPKFQG |
| Hc CDR3 (IMGT) | 37 | EEVADYTMDY |
| Hc variable domain segment | 38 | GARELVKPGASVKLSCTASGFNIKHPYMHWVKQRPDQGLEWIGRIDPANGNTKY DPKFQGKATITADTSSNTAYLQLSSLTSEDTAVYYCGREEVADYTMDYWGQGTS VTVSSAK TTAPSVYPLAPV |

Monoclonal antibody 19D4.B7 (murine IgG2a constant region)
Nucleic Acid Sequences

| Antibody Segment | SEQ ID NO. | Sequence |
|---|---|---|
| Lc CDR1 (IMGT) | 39 | AGAGCCAGTGAAAGTGTTGATACTTATGGCAATAATTTTATACAC |
| Lc CDR2 (IMGT) | 40 | CTTGCATCCAACCTAGAATCT |
| Lc CDR3 (IMGT) | 41 | CAGCAAAATAATGGGGATCCGTGGACG |
| Lc variable domain segment | 42 | CCAGCTTCTTTGGCTGTGTCTCTAGGGCAGAGGGCCACCATATCCTGCAGAGCC AGTGAAAGTGTTGATACTTATGGCAATAATTTTATACACTGGTACCAGCAGAA ACCAGGACAGCCACCCAAACTCCTCATTTATCTTGCATCCAACCTAGAATCTGG GGTCCCTGCCAGGTTCAGTGGCAGTGGGTCTAGGACAGACTTCACCCTCACCA TTGATCCTGTGGAGGCTGATGATGCTGCAACCTATTACTGTCAGCAAAATAATG GGGATCCGTGGACGTTCGGTGGAGGCACCAAGCTGG AGATCAAACGGGCTGATGCTGCACCAA |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
| --- | --- | --- |
| Hc CDR1 (IMGT) | 43 | CACCCCTATATGCAC |
| Hc CDR2 (IMGT) | 44 | AGGATTGATCCTGCGAATGGTAATACTAAATATGACCCGAAGTTCCAGGGC |
| Hc CDR3 (IMGT) | 45 | GAGGAGGTGGCGGACTATACTATGGACTAC |
| Hc variable domain segment | 46 | GGGGCAGAGCTTGTGAAGCCAGGGGCCTCAGTCAAGTTGTCCTGCACAGCTTC TGGCTTCAACATTAAACACCCCTATATGCACTGGGTGAAGCAGAGGCCTGACC AGGGCCTGGAGTGGATTGGAAGGATTGATCCTGCGAATGGTAATACTAAATAT GACCCGAAGTTCCAGGGCAAGGCCACTATAACAGCAGACACATCCTCCAACAC AGCCTACCTACAGCTCAGCAGCCTGACATCTGAGGACACTGCCGTCTATTACTG TGGTAGAGAGGAGGTGGCGGACTATACTATGGACTACTGGGGTCAAGGAACCT CAGTCACCGTCTCCTCAGCCAAAACAACAGCCCCATCGGTCTATCCACTGGCCC CTGTGTG |

Monoclonal antibody 24H8.F3 (murine IgG1 constant region)
Amino Acid Sequences

| Antibody Segment | SEQ ID NO. | Sequence |
| --- | --- | --- |
| Lc CDR1 (IMGT) | 1 | QDISNH |
| Lc CDR2 (IMGT) | 2 | YTS |
| Lc CDR3 (IMGT) | 3 | QQGNTLWT |
| Lc CDR1 (KABAT) | 4 | RASQDISNHLN |
| Lc CDR2 (KABAT) | 5 | YTSKLHS |
| Lc CDR3 (KABAT) | 3 | QQGNTLWT |
| Lc variable domain segment | 47 | TTSSLSASLGDRVTISCRASQDISNHLNWYQQKPDGTIKLLIYYTSKLHSGVPSRFS GSGSGTDYSLTISNLEQEDIATYFCQQGNTLWTFGGGTKLEIK |
| Lc | 48 | TTSSLSASLGDRVTISCRASQDISNHLNWYQQKPDGTIKLLIYYTSKLHSGVPSRFS GSGSGTDYSLTISNLEQEDIATYFCQQGNTLWTFGGGTKLEIKRADAAPTVSIFPPS SEQL |
| Hc CDR1 (IMGT) | 8 | GFSLTSYG |
| Hc CDR2 (IMGT) | 9 | IWGDGST |
| Hc CDR3 (IMGT) | 10 | AKPHPAATGAMDY |
| Hc CDR1 (KABAT) | 11 | SYGVS |
| Hc CDR2 (KABAT) | 12 | VIWGDGSTNYHSTLIS |
| Hc CDR3 (KABAT) | 13 | PHPAATGAMDY |
| Hc variable domain segment | 49 | GPGLVAPSQSLSITCTVSGFSLTSYGVSWVRQPPGKGLEWLGVIWGDGSTNYHSTL ISRLSISKDNSKSQVFLKLNSLQTDDTATYYCAKPHPAATGAMDYWGQGTSVTVS S |
| Hc | 50 | GPGLVAPSQSLSITCTVSGFSLTSYGVSWVRQPPGKGLEWLGVIWGDGSTNYHSTL ISRLSISKDNSKSQVFLKLNSLQTDDTATYYCAKPHPAATGAMDYWGQGTSVTVS SAKTTPPSVYPLAPGSAAQTNSMVTLGCLVKGYFPEPVTVTWNSGSLSSGVHTF |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
| --- | --- | --- |
| | | Monoclonal antibody 24H8.F3 (murine IgG1 constant region) Nucleic Acid Sequences |
| Lc CDR1 (IMGT) | 16 | CAGGACATTAGCAATCAT |
| Lc CDR2 (IMGT) | 17 | TACACATCA |
| Lc CDR3 (IMGT) | 18 | CAACAGGGTAATACGCTTTGGACG |
| Lc CDR1 (KABAT) | 19 | AGGGCAAGTCAGGACATTAGCAATCATTTAAAC |
| Lc CDR2 (KABAT) | 20 | TACACATCAAAATTACACTCA |
| Lc CDR3 (KABAT) | 18 | CAACAGGGTAATACGCTTTGGACG |
| Lc variable domain segment | 51 | ACTACATCCTCCCTGTCTGCCTCTCTGGGAGACAGAGTCACCATCAGTTGCAGG<br>GCAAGTCAGGACATTAGCAATCATTTAAACTGGTATCAACAGAAACCAGATGG<br>AACTATTAAACTCCTGATCTACTACACATCAAAATTACACTCAGGAGTCCCATC<br>AAGGTTCAGTGGCAGTGGGTCTGGAACAGATTATTCTCTCACCATTAGCAACCT<br>GGAACAAGAAGATATTGCCACTTACTTTTGCCAACAGGGTAATACGCTTTGGA<br>CGTTCGGTGGAGGCACCAAGCTGGAAATMAAA |
| Lc | 52 | CTACATCCTCCCTGTCTGCCTCTCTGGGAGACAGAGTCACCATCAGTTGCAGGG<br>CAAGTCAGGACATTAGCAATCATTTAAACTGGTATCAACAGAAACCAGATGGA<br>ACTATTAAACTCCTGATCTACTACACATCAAAATTACACTCAGGAGTCCCATCA<br>AGGTTCAGTGGCAGTGGGTCTGGAACAGATTATTCTCTCACCATTAGCAACCTG<br>GAACAAGAAGATATTGCCACTTACTTTTGCCAACAGGGTAATACGCTTTGGAC<br>GTTCGGTGGAGGCACCAAGCTGGAAATMAAACGGGCTGATGCTGCACCAACT<br>GTATCCATCTTCCCACCATCCAGTGAGCAGTTA |
| Hc CDR1 (IMGT) | 23 | GGGTTCTCATTAACCAGTTATGGT |
| Hc CDR2 (IMGT) | 24 | ATATGGGGTGACGGGAGCACA |
| Hc CDR3 (IMGT) | 25 | GCCAAACCTCATCCTGCGGCTACTGGCGCTATGGACTAC |
| Hc CDR1 (KABAT) | 26 | AGTTATGGTGTAAGC |
| Hc CDR2 (KABAT) | 27 | GTAATATGGGGTGACGGGAGCACAAATTATCATTCAACTCTCATATCC |
| Hc CDR3 (KABAT) | 28 | CCTCATCCTGCGGCTACTGGCGCTATGGACTAC |
| Hc variable domain segment | 53 | GGACCTGGCCTGGTGGCGCCCTCACAGAGCCTGTCCATCACATGCACTGTCTCA<br>GGGTTCTCATTAACCAGTTATGGTGTAAGCTGGGTTCGCCAGCCTCCAGGAAA<br>GGGTCTGGAGTGGCTGGGAGTAATATGGGGTGACGGGAGCACAAATTATCATT<br>CAACTCTCTATATCCAGACTGAGCATCAGCAAGGATAACTCCAAGAGCCAAGTT<br>TTCTTAAAACTGAACAGTCTGCAAACTGATGACACAGCCACGTACTACTGTGC<br>CAAACCTCATCCTGCGGCTACTGGCGCTATGGACTACTGGGGTCAAGGAACCT<br>CAGTCACCGTCTCCTCA |
| Hc | 54 | GGACCTGGCCTGGTGGCGCCCTCACAGAGCCTGTCCATCACATGCACTGTCTCA<br>GGGTTCTCATTAACCAGTTATGGTGTAAGCTGGGTTCGCCAGCCTCCAGGAAA<br>GGGTCTGGAGTGGCTGGGAGTAATATGGGGTGACGGGAGCACAAATTATCATT<br>CAACTCTCTATATCCAGACTGAGCATCAGCAAGGATAACTCCAAGAGCCAAGTT<br>TTCTTAAAACTGAACAGTCTGCAAACTGATGACACAGCCACGTACTACTGTGC<br>CAAACCTCATCCTGCGGCTACTGGCGCTATGGACTACTGGGGTCAAGGAACCT<br>CAGTCACCGTCTCCTCAGCCAAAACGACACCCCCATCTGTCTATCCACTGGCCC<br>CTGGATCTGCTGCCCAAACTAACTCCATGGTGACCCTGGGATGCCTGGTCAAG<br>GGCTATTTCCCTGAGCCAGTGACAGTGACCTGGAACTCTGGATCCCTGTCCAGC |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| | | GGTGTGCACACCTTCC |

Monoclonal antibody 1C6.E12.G8 (murine IgG1 constant region)
Amino Acid Sequences

| Antibody Segment | SEQ ID NO. | Sequence |
|---|---|---|
| Lc CDR1 (IMGT) | 55 | GNIHNY |
| Lc CDR2 (IMGT) | 56 | NAK |
| Lc CDR3 (IMGT) | 57 | QHFWSTPYT |
| Lc CDR1 (KABAT) | 58 | RASGNIHNYLA |
| Lc CDR2 (KABAT) | 59 | NAKTLAD |
| Lc CDR3 (KABAT) | 57 | QHFWSTPYT |
| Lc variable domain segment | 60 | QSPASLSASVGETVTITCRASGNIHNYLAWYQQKQGKSPQLLVYNAKTLADGVPSRFSGSGSGTQYSLKINSLQPEDFGSYYCQHFWSTPYTFGGGTKLEIK |
| Lc | 61 | QSPASLSASVGETVTITCRASGNIHNYLAWYQQKQGKSPQLLVYNAKTLADGVPSRFSGSGSGTQYSLKINSLQPEDFGSYYCQHFWSTPYTFGGGTKLEIKRADAAPTVSIFPPSSEQL |
| Hc CDR1 (IMGT) | 62 | GFTFNSSY |
| Hc CDR2 (IMGT) | 63 | IYAGNGGT |
| Hc CDR3 (IMGT) | 64 | ETYTNYWYFDV |
| Hc CDR1 (KABAT) | 65 | SSYIT |
| Hc CDR2 (KABAT) | 66 | WIYAGNGGTTYNQKFTG |
| Hc CDR3 (KABAT) | 64 | ETYTNYWYFDV |
| Hc variable domain segment | 67 | SGARELVKPGASVKLSCKTSGFTNSSYITWLKQKPGQSLEWIAWIYAGNGGTTYNQKFTGKAQLTVDTSSSTAYMQFSSLTTEDSAIYYCASETYTNYWYFDVWGSGTTVTVSS |
| Hc | 68 | SGARELVKPGASVKLSCKTSGFTFNSSYITWLKQKPGQSLEWIAWIYAGNGGTTYNQKFTGKAQLTVDTSSSTAYMQFSSLTTEDSAIYYCASETYTNYWYFDVWGSGTTVTVSSAKTTPPSVYPLAPGSAAQTNSMVTLGCLVKGYFPEPVTVTWNSGSLSSGVHTF |

Monoclonal antibody 1C6.E12.G8 (murine IgG1 constant region)
Nucleic Acid Sequences

| Antibody Segment | SEQ ID NO. | Sequence |
|---|---|---|
| Lc CDR1 (IMGT) | 69 | GGGAATATTCACAATTAT |
| Lc CDR2 (IMGT) | 70 | AATGCAAAA |
| Lc CDR3 (IMGT) | 71 | CAACATTTTTGAGTACTCCGTACACG |
| Lc CDR1 (KABAT) | 72 | CGAGCAAGTGGGAATATTCACAATTATTTAGCA |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Lc CDR2 (KABAT) | 73 | AATGCAAAAACCTTAGCAGAT |
| Lc CDR3 (KABAT) | 71 | CAACATTTTTGGAGTACTCCGTACACG |
| Lc variable domain segment | 74 | CAGTCTCCAGCCTCCCTATCTGCATCTGTGGGAGAAACTGTCACCATCACATGT CGAGCAAGTGGGAATATTCACAATTATTTAGCATGGTATCAGCAGAAACAGGG AAAATCTCCTCAGCTCCTGGTCTATAATGCAAAAACCTTAGCAGATGGTGTGCC ATCAAGGTTCAGTGGCAGTGGATCAGGAACACAATATTCTCTCAAGATCAACA GCCTGCAGCCTGAAGATTTTGGGAGTTATTACTGTCAACATTTTTGGAGTACTC CGTACACGTTCGGAGGGGGGACCAAGCTGGAAATAAAA |
| Lc | 75 | CAGTCTCCAGCCTCCCTATCTGCATCTGTGGGAGAAACTGTCACCATCACATGT CGAGCAAGTGGGAATATTCACAATTATTTAGCATGGTATCAGCAGAAACAGGG AAAATCTCCTCAGCTCCTGGTCTATAATGCAAAAACCTTAGCAGATGGTGTGCC ATCAAGGTTCAGTGGCAGTGGATCAGGAACACAATATTCTCTCAAGATCAACA GCCTGCAGCCTGAAGATTTTGGGAGTTATTACTGTCAACATTTTTGGAGTACTC CGTACACGTTCGGAGGGGGGACCAAGCTGGAAATAAAACGGGCTGATGCTGC ACCAACTGTATCCATCTTCCCACCATCCAGTGAGCAGTTA |
| Hc CDR1 (IMGT) | 76 | GGCTTCACCTTCAACAGTAGCTAT |
| Hc CDR2 (IMGT) | 77 | ATTTATGCTGGAAATGGTGGTACT |
| Hc CDR3 (IMGT) | 78 | GCAAGCGAGACGTATACTAACTACTGGTACTTCGATGTC |
| Hc CDR1 (KABAT) | 79 | AGTAGCTATATAACT |
| Hc CDR2 (KABAT) | 80 | TGGATTTATGCTGGAAATGGTGGTACTACCTATAATCAGAAATTCACAGGC |
| Hc CDR3 (KABAT) | 81 | GAGACGTATACTAACTACTGGTACTTCGATGTC |
| Hc variable domain segment | 82 | TCTGGAGCTGAGCTGGTGAAGCCTGGGGCTTCAGTGAAGCTGTCCTGCAAGAC TTCTGGCTTCACCTTCAACAGTAGCTATATAACTTGGTTGAAGCAAAAGCCTGG ACAGAGTCTTGAGTGGATTGCATGGATTTATGCTGGAAATGGTGGTACTACCTA TAATCAGAAATTCACAGGCAAGGCCCAATTGACTGTCGACACATCCTCCAGCA CAGCCTACATGCAGTTCAGCAGCCTGACAACTGAGGACTCTGCCATCTATTACT GTGCAAGCGAGACGTATACTAACTACTGGTACTTCGATGTCTGGGGCTCAGGG ACCACGGTCACCGTCTCCTCA |
| Hc | 83 | TCTGGAGCTGAGCTGGTGAAGCCTGGGGCTTCAGTGAAGCTGTCCTGCAAGAC TTCTGGCTTCACCTTCAACAGTAGCTATATAACTTGGTTGAAGCAAAAGCCTGG ACAGAGTCTTGAGTGGATTGCATGGATTTATGCTGGAAATGGTGGTACTACCTA TAATCAGAAATTCACAGGCAAGGCCCAATTGACTGTCGACACATCCTCCAGCA CAGCCTACATGCAGTTCAGCAGCCTGACAACTGAGGACTCTGCCATCTATTACT GTGCAAGCGAGACGTATACTAACTACTGGTACTTCGATGTCTGGGGCTCAGGG ACCACGGTCACCGTCTCCTCAGCCAAAACGACACCCCCATCTGTCTATCCACTG GCCCCTGGATCTGCTGCCCAAACTAACTCCATGGTGACCCTGGGATGCCTGGTC AAGGGCTATTTCCCTGAGCCAGTGACAGTGACCTGGAACTCTGGATCCCTGTCC AGCGGTGTGCACACCTTCC |

Monoclonal antibody 1D2.D8.G10 (murine IgG1 constant region)
Amino Acid Sequences

| Lc CDR1 (IMGT) | 84 | KSVSTSGYSY |
| Lc CDR2 (IMGT) | 85 | LAS |
| Lc CDR3 (IMGT) | 86 | QQSRELPPT |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Lc CDR1 (KABAT) | 87 | RASKSVSTSGYSYMY |
| Lc CDR2 (KABAT) | 32 | LASNLES |
| Lc CDR3 (KABAT) | 86 | QQSRELPPT |
| Lc variable domain segment | 88 | QSPASLVVSLGQRATISCRASKSVSTSGYSYMYWYQQKSGQPPKLLIYLASNLESG VPARFSGGGSGTDFTLNIHPVEEEDAATYYCQQSRELPPTFGGGTKLEIK |
| Lc | 89 | QSPASLVVSLGQRATISCRASKSVSTSGYSYMYWYQQKSGQPPKLLIYLASNLESG VPARFSGGGSGTDFTLNIHPVEEEDAATYYCQQSRELPPTFGGGTKLEIKRADAAP TVSIFPPSSEQL |
| Hc CDR1 (IMGT) | 90 | GYSFTSNW |
| Hc CDR2 (IMGT) | 91 | IYPGNSDT |
| Hc CDR3 (IMGT) | 92 | TRGDGSSFWYFDV |
| Hc CDR1 (KABAT) | 93 | SNWMH |
| Hc CDR2 (KABAT) | 94 | AIYPGNSDTSYNQKFKG |
| Hc CDR3 (KABAT) | 95 | GDGSSFWYFDV |
| Hc variable domain segment | 96 | QSGTVLARPGASVKMSCKASGYSFTSNWMHWIKQRPGQGLEWIGAIYPGNSDTS YNQKFKGKAKLTAVTSASTAYMELSSLTNEDSAVYHCTRGDGSSFWYFDVWGA GTTVTVSS |
| Hc | 97 | QSGTVLARPGASVKMSCKASGYSFTSNWMHWIKQRPGQGLEWIGAIYPGNSDTS YNQKFKGKAKLTAVTSASTAYMELSSLTNEDSAVYHCTRGDGSSFWYFDVWGA GTTVTVSSAKTTPPSVYPLAPGSAAQTNSMVTLGCLVKGYFPEPVTVTWNSGSLSS GVHTF |

Monoclonal antibody 1D2.D8.G10 (murine IgG1 constant region)
Nucleic Acid Sequences

| Antibody Segment | SEQ ID NO. | Sequence |
|---|---|---|
| Lc CDR1 (IMGT) | 98 | AAAAGTGTCAGTACATCTGGCTATAGTTAT |
| Lc CDR2 (IMGT) | 99 | CTTGCATCC |
| Lc CDR3 (IMGT) | 100 | CAGCAAAGTAGGGAGCTTCCTCCCACG |
| Lc CDR1 (KABAT) | 101 | AGGGCCAGTAAAAGTGTCAGTACATCTGGCTATAGTTATATGTAC |
| Lc CDR2 (KABAT) | 40 | CTTGCATCCAACCTAGAATCT |
| Lc CDR3 (KABAT) | 100 | CAGCAAAGTAGGGAGCTTCCTCCCACG |
| Lc variable domain segment | 102 | CAGTCTCCTGCTTCCTTAGTTGTATCTCTGGGGCAGAGGGCCACCATCTCATGC AGGGCCAGTAAAAGTGTCAGTACATCTGGCTATAGTTATATGTACTGGTACCA ACAGAAATCAGGACAGCCACCCAAACTCCTCATCTATCTTGCATCCAACCTAG AATCTGGGGTCCCTGCCAGGTTCAGTGGCGGTGGGTCTGGGACAGACTTCACC CTCAACATCCATCCTGTGGAGGAGGAGGATGCTGCAACCTATTACTGTCAGCA AAGTAGGGAGCTTCCTCCCACGTTCGGAGGGGGGACCAAGCTGGAAATAAAA |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Lc | 103 | CAGTCTCCTGCTTCCTTAGTTGTATCTCTGGGGCAGAGGGCCACCATCTCATGC AGGGCCAGTAAAAGTGTCAGTACATCTGGCTATAGTTATATGTACTGGTACCA ACAGAAATCAGGACAGCCACCCAAACTCCTCATCTATCTTGCATCCAACCTAG AATCTGGGGTCCCTGCCAGGTTCAGTGGCGGTGGGTCTGGGACAGACTTCACC CTCAACATCATCCTGTGGAGGAGGAGGATGCTGCAACCTATTACTGTCACCA AAGTAGGGAGCTTCCTCCCACGTTCGGAGGGGGGACCAAGCTGGAAATAAAA CGGGCTGATGCTGCACCAACTGTATCCATCTTCCCACCATCCAGTGAGCAGTTA |
| Hc CDR1 (IMGT) | 104 | GGCTACAGCTTTACCAGCAACTGG |
| Hc CDR2 (IMGT) | 105 | ATTTATCCTGGAAATAGTGATACT |
| Hc CDR3 (IMGT) | 106 | ACAAGAGGGGACGGTAGTAGTTTCTGGTACTTCGATGTC |
| Hc CDR1 (KABAT) | 107 | AGCAACTGGATGCAC |
| Hc CDR2 (KABAT) | 108 | GCTATTTATCCTGGAAATAGTGATACTAGTTACAACCAGAAGTTCAAGGGC |
| Hc CDR3 (KABAT) | 109 | GGGGACGGTAGTAGTTTCTGGTACTTCGATGTC |
| Hc variable domain segment | 110 | CAGTCTGGGACTGTGCTGGCAAGGCCTGGGGCTTCCGTGAAGATGTCCTGCAA GGCTTCTGGCTACAGCTTTACCAGCAACTGGATGCACTGGATAAAACAGAGGC CTGGACAGGGTCTAGAGTGGATTGGTGCTATTTATCCTGGAAATAGTGATACTA GTTACAACCAGAAGTTCAAGGGCAAGGCCAAACTGACTGCAGTCACATCCGCC AGCACTGCCTACATGGAGCTCAGCAGCCTGACAAATGAGGACTCTGCGGTCTA TCACTGTACAAGAGGGGACGGTAGTAGTTTCTGGTACTTCGATGTCTGGGGCG CAGGGACCACGGTCACCGTCTCCTCA |
| Hc | 111 | CAGTCTGGGACTGTGCTGGCAAGGCCTGGGGCTTCCGTGAAGATGTCCTGCAA GGCTTCTGGCTACAGCTTTACCAGCAACTGGATGCACTGGATAAAACAGAGGC CTGGACAGGGTCTAGAGTGGATTGGTGCTATTTATCCTGGAAATAGTGATACTA GTTACAACCAGAAGTTCAAGGGCAAGGCCAAACTGACTGCAGTCACATCCGCC AGCACTGCCTACATGGAGCTCAGCAGCCTGACAAATGAGGACTCTGCGGTCTA TCACTGTACAAGAGGGGACGGTAGTAGTTTCTGGTACTTCGATGTCTGGGGCG CAGGGACCACGGTCACCGTCTCCTCAGCCAAAACGACACCCCCATCTGTCTAT CCACTGGCCCCTGGATCTGCTGCCCAAACTAACTCCATGGTGACCCTGGGATGC CTGGTCAAGGGCTATTTCCCTGAGCCAGTGACAGTGACCTGGAACTCTGGATC CCTGTCCAGCGGTGTGCACACCTTCC |

Monoclonal antibody 6A2.G7 (murine IgG1 constant region)
Amino Acid Sequences

| Lc CDR1 (IMGT) | 112 | QDISNY |
| Lc CDR2 (IMGT) | 2 | YTS |
| Lc CDR3 (IMGT) | 113 | QQGNTLPYT |
| Lc CDR1 (KABAT) | 114 | RASQDISNYLN |
| Lc CDR2 (KABAT) | 115 | YTSRLHS |
| Lc CDR3 (KABAT) | 113 | QQGNTLPYT |
| Lc variable domain segment | 116 | SSLSASLGDRVTISCRASQDISNYLNWYQQKPDGTVKLLIYYTSRLHSGVPSRFSGS GSGTDYSLTISNLEQEDIATYFCQQGNTLPYTFGGGTKLEIK |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Lc | 117 | SSLSASLGDRVTISCRASQDISNYLNWYQQKPDGTVKLLIYYTSRLHSGVPSRFSGSGSGTDYSLTISNLEQEDIATYFCQQGNTLPYTFGGGTKLEIKRADAAPTVSIFPPSSEQL |
| Hc CDR1 (IMGT) | 118 | GYTFSRYN |
| Hc CDR2 (IMGT) | 119 | IYPGNGDT |
| Hc CDR3 (IMGT) | 120 | ARDYGSRYALDY |
| Hc CDR1 (KABAT) | 121 | RYNMH |
| Hc CDR2 (KABAT) | 122 | TIYPGNGDTSYNEKFKG |
| Hc CDR3 (KABAT) | 123 | DYGSRYALDY |
| Hc variable domain segment | 124 | GADLVKPGASVKMSCKASGYTFSRYNMHWVKQTPGQGLEWIGTIYPGNGDTSYNEKFKGKATLTADKSSSIVYMQVSSLTSEASAVYYCARDYGSRYALDYWGQGTSVTVSS |
| Hc | 125 | GADLVKPGASVKMSCKASGYTFSRYNMHWVKQTPGQGLEWIGTIYPGNGDTSYNEKFKGKATLTADKSSSIVYMQVSSLTSEASAVYYCARDYGSRYALDYWGQGTSVTVSSAKTTPPSVYPLAPGSAAQTNSMVTLGCLVKGYFPEPVTVTWNSGSLSSGVHTF |

Monoclonal antibody 6A2.G7 (murine IgG1 constant region)
Nucleic Acid Sequences

| Antibody Segment | SEQ ID NO. | Sequence |
|---|---|---|
| Lc CDR1 (IMGT) | 126 | CAGGACATTAGCAATTAT |
| Lc CDR2 (IMGT) | 17 | TACACATCA |
| Lc CDR3 (IMGT) | 127 | CAACAGGGTAATACGCTTCCGTACACG |
| Lc CDR1 (KABAT) | 128 | AGGGCAAGTCAGGACATTAGCAATTATTTAAAC |
| Lc CDR2 (KABAT) | 129 | TACACATCAAGATTACACTCA |
| Lc CDR3 (KABAT) | 127 | CAACAGGGTAATACGCTTCCGTACACG |
| Lc variable domain segment | 130 | TCCTCCCTGTCTGCCTCTCTGGGAGACAGAGTCACCATCAGTTGCAGGGCAAGTCAGGACATTAGCAATTATTTAAACTGGTATCAGCAGAAACCAGATGGAACTGTTAAACTCCTGATCTACTACACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCGTACACGTTCGGAGGGGGGACCAAGCTGGAAATAAAA |
| Lc | 131 | TCCTCCCTGTCTGCCTCTCTGGGAGACAGAGTCACCATCAGTTGCAGGGCAAGTCAGGACATTAGCAATTATTTAAACTGGTATCAGCAGAAACCAGATGGAACTGTTAAACTCCTGATCTACTACACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCGTACACGTTCGGAGGGGGGACCAAGCTGGAAATAAAACGGGCTGATGCTGCACCAACTGTATCCATCTTCCCACCATCCAGTGAGCAGTTA |
| Hc CDR1 (IMGT) | 132 | GGCTACACATTTAGCCGTTACAAT |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Hc CDR2 (IMGT) | 133 | ATTTATCCAGGAAAATGGTGATACT |
| Hc CDR3 (IMGT) | 134 | GCAAGAGACTACGGTAGTCGGTATGCTTTGGACTAC |
| Hc CDR1 (KABAT) | 135 | CGTTACAATATGCAC |
| Hc CDR2 (KABAT) | 136 | ACTATTTATCCAGGAAAATGGTGATACTTCCTACAATGAGAAGTTCAAAGGC |
| Hc CDR3 (KABAT) | 137 | GACTACGGTAGTCGGTATGCTTTGGACTAC |
| Hc variable domain segment | 138 | GGGGCTGACCTGGTGAAGCCTGGGGCCTCAGTGAAGATGTCCTGCAAGGCTTC TGGCTACACATTTAGCCGTTACAATATGCACTGGGTAAAACAGACACCTGGAC AGGGCCTGGAATGGATTGGAACTATTTATCCAGGAAAATGGTGATACTTCCTAC AATGAGAAGTTCAAAGGCAAGGCCACATTGACTGCAGACAAATCCTCCAGTAT AGTCTACATGCAGGTCAGCAGCCTGACATCTGAGGCCTCTGCGGTCTATTACTG TGCAAGAGACTACGGTAGTCGGTATGCTTTGGACTACTGGGGTCAAGGAACCT CAGTCACCGTCTCCTCA |
| Hc | 139 | GGGGCTGACCTGGTGAAGCCTGGGGCCTCAGTGAAGATGTCCTGCAAGGCTTC TGGCTACACATTTAGCCGTTACAATATGCACTGGGTAAAACAGACACCTGGAC AGGGCCTGGAATGGATTGGAACTATTTATCCAGGAAAATGGTGATACTTCCTAC AATGAGAAGTTCAAAGGCAAGGCCACATTGACTGCAGACAAATCCTCCAGTAT AGTCTACATGCAGGTCAGCAGCCTGACATCTGAGGCCTCTGCGGTCTATTACTG TGCAAGAGACTACGGTAGTCGGTATGCTTTGGACTACTGGGGTCAAGGAACCT CAGTCACCGTCTCCTCAGCCAAAACGACACCCCCATCTGTCTATCCACTGGCCC CTGGATCTGCTGCCCAAACTAACTCCATGGTGACCCTGGGATGCCTGGTCAAG GGCTATTTCCCTGAGCCAGTGACAGTGACCTGGAACTCTGGATCCCTGTCCAGC GGTGTGCACACCTTCC |

Monoclonal antibody 19D2.G9 (murine IgG1 constant region)
Amino Acid Sequences

| Antibody Segment | SEQ ID NO. | Sequence |
|---|---|---|
| Lc CDR1 (IMGT) | 55 | GNIHNY |
| Lc CDR2 (IMGT) | 140 | HAK |
| Lc CDR3 (IMGT) | 141 | QHFWSTPPWT |
| Lc CDR1 (KABAT) | 58 | RASGNIHNYLA |
| Lc CDR2 (KABAT) | 142 | HAKTLARE |
| Lc CDR3 (KABAT) | 141 | QHFWSTPPWT |
| Lc variable domain segment | 143 | QSPASLSASVGETVTITCRASGNIHNYLAWYQQKQGKSPQLLVNHAKTLAREGVP SRFSGSGSKTQYSLKITSLQPEDFGSYYCQHFWSTPPWTFGGGTKVEIR |
| Lc | 144 | QSPASLSASVGETVTITCRASGNIHNYLAWYQQKQGKSPQLLVNHAKTLAREGVP SRFSGSGSKTQYSLKITSLQPEDFGSYYCQHFWSTPPWTFGGGTKVEIRRADAAPT VSIFPPSSEQL |
| Hc CDR1 (IMGT) | 145 | GFSLTTYG |
| Hc CDR2 (IMGT) | 146 | IWSGGST |
| Hc CDR3 (IMGT) | 147 | VRYRYDEGFTY |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Hc CDR1 (KABAT) | 148 | TVGVH |
| Hc CDR2 (KABAT) | 149 | VIWSGGSTEYNAVFIS |
| Hc CDR3 (KABAT) | 150 | YRYDEGFTY |
| Hc variable domain segment | 151 | GPGLVQPSQSLSITCTVSGFSLTTYGVHWVRQSPGKGLEWLGVIWSGGSTEYNAVFISRMSITKDNSKSQVFFKMNSLEANDTAIYYCVRYRYDEGFTYWGQGSLVTVSA |
| Hc | 152 | GPGLVQPSQSLSITCTVSGFSLTTYGVHWVRQSPGKGLEWLGVIWSGGSTEYNAVFISRMSITKDNSKSQVFFKMNSLEANDTAIYYCVRYRYDEGFTYWGQGSLVTVSAAKTTPPSVYPLAPGSAAQTNSMVTLGCLVKGYFPEPVTVTWNSGSLSSGVHTF |

Monoclonal antibody 19D2.G9 (murine IgG1 constant region) Nucleic Acid Sequences

| Antibody Segment | SEQ ID NO. | Sequence |
|---|---|---|
| Lc CDR1 (IMGT) | 69 | GGGAATATTCACAATTAT |
| Lc CDR2 (IMGT) | 153 | CATGCAAAA |
| Lc CDR3 (IMGT) | 154 | CAACATTTTTGGAGTACTCCTCCGTGGACG |
| Lc CDR1 (KABAT) | 72 | CGAGCAAGTGGGAATATTCACAATTATTTAGCA |
| Lc CDR2 (KABAT) | 155 | CATGCAAAAACCTTAGCAGAA |
| Lc CDR3 (KABAT) | 154 | CAACATTTTTGGAGTACTCCTCCGTGGACG |
| Lc variable domain segment | 156 | CAGTCTCCAGCCTCCCTATCTGCATCTGTGGGAGAAACTGTCACCATCACATGTCGAGCAAGTGGGAATATTCACAATTATTTAGCATGGTATCAGCAGAAACAGGGAAAATCTCCTCAGCTCCTGGTCAATCATGCAAAAACCTTAGCAGAAGGTGTGCCATCAAGGTTCAGTGGCAGTGGATCAAAAACACAATATTCTCTCAAGATCACCAGCCTGCAGCCTGAAGATTTTGGGAGTTATTACTGTCAACATTTTTGGAGTACTCCTCCGTGGACGTTCGGTGGAGGCACCAAGGTGGAAATCAGA |
| Lc | 157 | CAGTCTCCAGCCTCCCTATCTGCATCTGTGGGAGAAACTGTCACCATCACATGTCGAGCAAGTGGGAATATTCACAATTATTTAGCATGGTATCAGCAGAAACAGGGAAAATCTCCTCAGCTCCTGGTCAATCATGCAAAAACCTTAGCAGAAGGTGTGCCATCAAGGTTCAGTGGCAGTGGATCAAAAACACAATATTCTCTCAAGATCACCAGCCTGCAGCCTGAAGATTTTGGGAGTTATTACTGTCAACATTTTTGGAGTACTCCTCCGTGGACGTTCGGTGGAGGCACCAAGGTGGAAATCAGACGGGCTGATGCTGCACCAACTGTATCCATCTTCCCACCATCCAGTGAGCAGTTA |
| Hc CDR1 (IMGT) | 158 | GGTTTCTCATTAACTACCTATGGT |
| Hc CDR2 (IMGT) | 159 | ATATGGAGTGGTGGAAGCACA |
| Hc CDR3 (IMGT) | 160 | GTCAGGTATAGGTACGACGAGGGATTCACTTAT |
| Hc CDR1 (KABAT) | 161 | ACCTATGGTGTACAC |
| Hc CDR2 (KABAT) | 162 | GTGATATGGAGTGGTGGAAGCACAGAATATAATGCAGTTTTCATCTCC |
| Hc CDR3 (KABAT) | 163 | TATAGGTACGACGAGGGATTCACTTAT |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Hc variable domain segment | 164 | GGACCTGGCCTAGTGCAGCCCTCACAGAGCCTGTCCATCACCTGCACAGTCTCT<br>GGTTTCTCATTAACTACCTATGGTGTACACTGGGTTCGCCAGTCTCCAGGAAAG<br>GGTCTGGAGTGGCTGGGAGTGATATGGAGTGGTGGAAGCACAGAATATAATGC<br>AGTTTTCATCTCCAGAATGAGCATCACCAAGGACAATTCCAAGAGCCAAGTTT<br>TCTTTAAAATGAACAGTCTGGAAGCTAATGACACAGCCATATATTACTGTGTCA<br>GGTATAGGTACGACGAGGGATTCACTTATTGGGGCCAAGGGAGTCTGGTCACT<br>GTCTCTGCA |
| Hc | 165 | GGACCTGGCCTAGTGCAGCCCTCACAGAGCCTGTCCATCACCTGCACAGTCTCT<br>GGTTTCTCATTAACTACCTATGGTGTACACTGGGTTCGCCAGTCTCCAGGAAAG<br>GGTCTGGAGTGGCTGGGAGTGATATGGAGTGGTGGAAGCACAGAATATAATGC<br>AGTTTTCATCTCCAGAATGAGCATCACCAAGGACAATTCCAAGAGCCAAGTTT<br>TCTTTAAAATGAACAGTCTGGAAGCTAATGACACAGCCATATATTACTGTGTCA<br>GGTATAGGTACGACGAGGGATTCACTTATTGGGGCCAAGGGAGTCTGGTCACT<br>GTCTCTGCAGCCAAAACGACACCCCCATCTGTCTATCCACTGGCCCCTGGATCT<br>GCTGCCCAAACTAACTCCATGGTGACCCTGGGATGCCTGGTCAAGGGCTATTTC<br>CCTGAGCCAGTGACAGTGACCTGGAACTCTGGATCCCTGTCCAGCGGTGTGCA<br>CACCTTCC |

Monoclonal antibody 26A9.C4 (murine IgG1 constant region)
Amino Acid Sequences

| | | |
|---|---|---|
| Lc CDR1 (IMGT) | 55 | GNIHNY |
| Lc CDR2 (IMGT) | 56 | NAK |
| Lc CDR3 (IMGT) | 57 | QHFWSTPYT |
| Lc CDR1 (KABAT) | 58 | RASGNIHNYLA |
| Lc CDR2 (KABAT) | 59 | NAKTLAD |
| Lc CDR3 (KABAT) | 57 | QHFWSTPYT |
| Lc variable domain segment | 166 | QSPASLSASVGDTVTITCRASGNIHNYLAWYQQKQGKSPQLLVYNAKTLADGVPS<br>RFSGSGSGTQYSLKINSLQPEDFGNYYCQHFWSTPYTFGGGTKLEIK |
| Lc | 167 | QSPASLSASVGDTVTITCRASGNIHNYLAWYQQKQGKSPQLLVYNAKTLADGVPS<br>RFSGSGSGTQYSLKINSLQPEDFGNYYCQHFWSTPYTFGGGTKLEIKRADAAPTVSI<br>FPPSSEQL |
| Hc CDR1 (IMGT) | 168 | GFTFSSSF |
| Hc CDR2 (IMGT) | 169 | IYGGNGGT |
| Hc CDR3 (IMGT) | 170 | ASETYGNYWYFDV |
| Hc CDR1 (KABAT) | 171 | SSFIS |
| Hc CDR2 (KABAT) | 172 | WIYGGNGGISYNQNFTG |
| Hc CDR3 (KABAT) | 173 | ETYGNYWYFDV |
| Hc variable domain segment | 174 | SGAREVKPGASVKLSCKTSGFTFSSSFISWLKQKPGQSLEWIAWIYGGNGGTSYN<br>QNFTGKAQLTVDTSSSTAYMQFSSLTTEDSAVYYCASETYGNYWYFDVWGAGTT<br>VTVSS |
| Hc | 175 | SGARELVKPGASVKLSCKTSGFTFSSSFISWLKQKPGQSLEWIAWIYGGNGGTSYN<br>QNFTGKAQLTVDTSSSTAYMQFSSLTTEDSAVYYCASETYGNYWYFDVWGAGTT |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| | | VTVSSAKTTPPSVYPLAPGSAAQTNSMVTLGCLVKGYFPEPVTVTWNSGSLSSGV HTF |

Monoclonal antibody 26A9.C4 (murine IgG1 constant region)
Nucleic Acid Sequences

| Antibody Segment | SEQ ID NO. | Sequence |
|---|---|---|
| Lc CDR1 (IMGT) | 69 | GGGAATATTCACAATTAT |
| Lc CDR2 (IMGT) | 70 | AATGCAAAA |
| Lc CDR3 (IMGT) | 71 | CAACATTTTTGGAGTACTCCGTACACCG |
| Lc CDR1 (KABAT) | 72 | CGAGCAAGTGGGAATATTCACAATTATTTAGCA |
| Lc CDR2 (KABAT) | 73 | AATGCAAAAACCTTAGCAGAT |
| Lc CDR3 (KABAT) | 176 | AACATTTTTGGAGTACTCCGTACACG |
| Lc variable domain segment | 177 | CAGTCTCCAGCCTCCCTATCTGCATCTGTGGGAGACACTGTCACCATCACATGT CGAGCAAGTGGGAATATTCACAATTATTTAGCATGGTATCAGCAGAAACAGGG AAAATCTCCTCAGCTCCTGGTCTATAATGCAAAAACCTTAGCAGATGGTGTGCC ATCAAGGTTCAGTGGCAGTGGATCAGGAACACAATATTCTCTCAAGATCAACA GCCTGCAGCCTGAAGATTTTGGGAATTATTACTGTCAACATTTTTGGAGTACTC CGTACACGTTCGGAGGGGGGACCAAGCTGGAAATAAAA |
| Lc | 178 | CAGTCTCCAGCCTCCCTATCTGCATCTGTGGGAGACACTGTCACCATCACATGT CGAGCAAGTGGGAATATTCACAATTATTTAGCATGGTATCAGCAGAAACAGGG AAAATCTCCTCAGCTCCTGGTCTATAATGCAAAAACCTTAGCAGATGGTGTGCC ATCAAGGTTCAGTGGCAGTGGATCAGGAACACAATATTCTCTCAAGATCAACA GCCTGCAGCCTGAAGATTTTGGGAATTATTACTGTCAACATTTTTGGAGTACTC CGTACACGTTCGGAGGGGGGACCAAGCTGGAAATAAAACGGGCTGATGCTGC ACCAACTGTATCCATCTTCCCACCATCCAGTGAGCAGTTA |
| Hc CDR1 (IMGT) | 179 | GGCTTCACCTTCAGCAGTAGTTTT |
| Hc CDR2 (IMGT) | 180 | ATTTATGGTGGAAATGGTGGTACT |
| Hc CDR3 (IMGT) | 181 | GCAAGCGAGACGTATGGTAACTACTGGTACTTCGATGTC |
| Hc CDR1 (KABAT) | 182 | AGTAGTTTTATAAGT |
| Hc CDR2 (KABAT) | 183 | TGGATTTATGGTGGAAATGGTGGTACTAGCTATAATCAGAACTTCACAGGC |
| Hc CDR3 (KABAT) | 184 | GAGACGTATGGTAACTACTGGTACTTCGATGTC |
| Hc variable domain segment | 185 | TCTGGAGCTGAACTGGTGAAGCCTGGGGCTTCAGTGAAGCTGTCCTGCAAGAC TTCTGGCTTCACCTTCAGCAGTAGTTTTATAAGTTGGTTGAAGCAAAAGCCTGG ACAGAGTCTTGAGTGGATTGCATGGATTTATGGTGGAAATGGTGGTACTAGCT ATAATCAGAACTTCACAGGCAAGGCCCAACTGACTGTAGACACATCCTCCAGT ACAGCCTACATGCAATTCAGCAGCCTGACAACTGAGGACTCTGCCGTCTATTA CTGTGCAAGCGAGACGTATGGTAACTACTGGTACTTCGATGTCTGGGGCGCAG GGACCACGGTCACCGTCTCCTCA |
| Hc | 186 | TCTGGAGCTGAACTGGTGAAGCCTGGGGCTTCAGTGAAGCTGTCCTGCAAGAC TTCTGGCTTCACCTTCAGCAGTAGTTTTATAAGTTGGTTGAAGCAAAAGCCTGG ACAGAGTCTTGAGTGGATTGCATGGATTTATGGTGGAAATGGTGGTACTAGCT ATAATCAGAACTTCACAGGCAAGGCCCAACTGACTGTAGACACATCCTCCAGT ACAGCCTACATGCAATTCAGCAGCCTGACAACTGAGGACTCTGCCGTCTATTA CTGTGCAAGCGAGACGTATGGTAACTACTGGTACTTCGATGTCTGGGGCGCAG GGACCACGGTCACCGTCTCCTCAGCCAAAACGACACCCCCATCTGTCTATCCAC |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| | | TGGCCCCTGGATCTGCTGCCCAAACTAACTCCATGGTGACCCTGGGATGCCTGG TCAAGGGCTATTTCCCTGAGCCAGTGACAGTGACCTGGAACTCTGGATCCCTGT CCAGCGGTGTGCACACCTTCC |

Monoclonal antibody 2F11.F8 (murine IgG1 constant region)
Amino Acid Sequences

| Antibody Segment | SEQ ID NO. | Sequence |
|---|---|---|
| Lc CDR1 (IMGT) | 187 | ENVDNYGISF |
| Lc CDR2 (IMGT) | 188 | AAS |
| Lc CDR3 (IMGT) | 189 | QQSKEVPWT |
| Lc CDR1 (KABAT) | 190 | RASENVDNYGISFMN |
| Lc CDR2 (KABAT) | 191 | AASNQGS |
| Lc CDR3 (KABAT) | 189 | QQSKEVPWT |
| Lc variable domain segment | 192 | PASLAVSLGQRATISCRASENVDNYGISFMNWFQQKPGQPPKVLIYAASNQGSGVP ARFSGSGSGTDFSLNIHPMEEDDTAMYFCQQSKEVPWTFGGGTKLEIT |
| Lc | 193 | PASLAVSLGQRATISCRASENVDNYGISFMNWFQQKPGQPPKWLIYAASNQGSGVP ARFSGSGSGTDFSLNIHPMEEDDTAMYFCQQSKEVPWTFGGGTKLEITRADAAPT VSIFPPSSEQL |
| Hc CDR1 (IMGT) | 194 | GYSITSGYY |
| Hc CDR2 (IMGT) | 195 | INYDGSN |
| Hc CDR3 (IMGT) | 196 | ARGNYYAMDY |
| Hc CDR1 (KABAT) | 197 | SGYYWI |
| Hc CDR2 (KABAT) | 198 | YINYDGSNNYNPSLKN |
| Hc CDR (KABAT) | 199 | GNYYAMDY |
| Hc variable domain segment | 200 | ESGPGLVKPSQSLSLTCSVTGYSITSGYYWIWIRQFPGNKLEWMGYINYDGSNNYN PSLKNRISITRDTSKNQFFLKLNSVTTEDTATYYCARGNYYAMDYWGQGTSVTVS S |
| Hc | 201 | ESGPGLVKPSQSLSLTCSVTGYSITSGYYWIWIRQFPGNKLEWMGYINYDGSNNYN PSLKNRISITRDTSKNQFFLKLNSVTTEDTATYYCARGNYYAMDYWGQGTSVTVS SAKTTPPSVYPLAPGSAAQTNSMVTLGCLVKGYFPEPVTVTWNSGSLSSGVHTF |

Monoclonal antibody 2F11.F8 (murine IgG1 constant region)
Nucleic Acid Sequences

| Antibody Segment | SEQ ID NO. | Sequence |
|---|---|---|
| Lc CDR1 (IMGT) | 202 | GAAAATGTTGATAATTATGGCATTAGTTTT |
| Lc CDR2 (IMGT) | 203 | GCTGCATCC |
| Lc CDR3 (IMGT) | 204 | CAGCAAAGTAAGGAGGTTCCGTGGACG |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
| --- | --- | --- |
| Lc CDR1 (KABAT) | 205 | AGAGCCAGCGAAAATGTTGATAATTATGGCATTAGTTTTATGAAC |
| Lc CDR2 (KABAT) | 206 | GCTGCATCCAACCAAGGATCC |
| Lc CDR3 (KABAT) | 204 | CAGCAAAGTAAGGAGGTTCCGTGGACG |
| Lc variable domain segment | 207 | CCAGCTTCTTTGGCTGTGTCTCTAGGACAGAGGGCCACCATCTCCTGCAGAGCC<br>AGCGAAAATGTTGATAATTATGGCATTAGTTTTATGAACTGGTTCCAACAGAA<br>ACCAGGACAGCCACCCAAAGTCCTCATCTATGCTGCATCCAACCAAGGATCCG<br>GGGTCCCTGCCAGGTTTAGTGGCAGTGGGTCTGGGACAGACTTCAGCCTCAAC<br>ATCCATCCTATGGAGGAGGATGATACTGCAATGTATTTCTGTCAGCAAAGTAA<br>GGAGGTTCCGTGGACGTTCGGTGGAGGCACCAAGCTGGAAATCACT |
| Lc | 208 | CCAGCTTCTTTGGCTGTGTCTCTAGGACAGAGGGCCACCATCTCCTGCAGAGCC<br>AGCGAAAATGTTGATAATTATGGCATTAGTTTTATGAACTGGTTCCAACAGAA<br>ACCAGGACAGCCACCCAAAGTCCTCATCTATGCTGCATCCAACCAAGGATCCG<br>GGGTCCCTGCCAGGTTTAGTGGCAGTGGGTCTGGGACAGACTTCAGCCTCAAC<br>ATCCATCCTATGGAGGAGGATGATACTGCAATGTATTTCTGTCAGCAAAGTAA<br>GGAGGTTCCGTGGACGTTCGGTGGAGGCACCAAGCTGGAAATCACTCGGGCTG<br>ATGCTGCACCAACTGTATCCATCTTCCCACCATCCAGTGAGCAGTTA |
| Hc CDR1 (IMGT) | 209 | GGCTACTCCATCACCAGTGGTTATTAC |
| Hc CDR2 (IMGT) | 210 | ATAAACTACGACGGTAGCAAT |
| Hc CDR3 (IMGT) | 211 | GCAAGAGGGAATTACTATGCTATGGACTAC |
| Hc CDR1 (KABAT) | 212 | AGTGGTTATTACTGGATC |
| Hc CDR2 (KABAT) | 213 | TACATAAACTACGACGGTAGCAATAACTACAACCCATCTCTCAAAAAT |
| Hc CDR3 (KABAT) | 214 | GGGAATTACTATGCTATGGACTAC |
| Hc variable domain segment | 215 | GAGTCAGGACCTGGCCTCGTGAAACCTTCTCAGTCTCTGTCTCTCACCTGCTCT<br>GTCACTGGCTACTCCATCACCAGTGGTTATTACTGGATCTGGATCCGGCAGTTT<br>CCAGGAAACAAACTGGAATGGATGGGCTACATAAACTACGACGGTAGCAATA<br>ACTACAACCCATCTCTCAAAAATCGAATCTCCATCACTCGTGACACATCTAAGA<br>ACCAGTTTTTCCTGAAGTTGAATTCTGTGACTACTGAGGACACAGCTACATATT<br>ACTGTGCAAGAGGGAATTACTATGCTATGGACTACTGGGGTCAAGGAACCTCA<br>GTCACCGTCTCCTCA |
| Hc | 216 | GAGTCAGGACCTGGCCTCGTGAAACCTTCTCAGTCTCTGTCTCTCACCTGCTCT<br>GTCACTGGCTACTCCATCACCAGTGGTTATTACTGGATCTGGATCCGGCAGTTT<br>CCAGGAAACAAACTGGAATGGATGGGCTACATAAACTACGACGGTAGCAATA<br>ACTACAACCCATCTCTCAAAAATCGAATCTCCATCACTCGTGACACATCTAAGA<br>ACCAGTTTTTCCTGAAGTTGAATTCTGTGACTACTGAGGACACAGCTACATATT<br>ACTGTGCAAGAGGGAATTACTATGCTATGGACTACTGGGGTCAAGGAACCTCA<br>GTCACCGTCTCCTCAGCCAAAACGACACCCCCATCTGTCTATCCACTGGCCCCT<br>GGATCTGCTGCCCAAACTAACTCCATGGTGACCCTGGGATGCCTGGTCAAGGG<br>CTATTTCCCTGAGCCAGTGACAGTGACCTGGAACTCTGGATCCCTGTCCAGCGG<br>TGTGCACACCTTCC |

Monoclonal antibody 5C12.H8 (murine IgG2b constant region) Amino Acid Sequences

| Antibody Segment | SEQ ID NO. | Sequence |
| --- | --- | --- |
| Lc CDR1 (IMGT) | 217 | ESVDNYGISF |
| Lc CDR2 (IMGT) | 188 | AAS |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Lc CDR3 (IMGT) | 189 | QQSKEVPWT |
| Lc CDR1 (KABAT) | 218 | RASESVDNYGISFMN |
| Lc CDR2 (KABAT) | 191 | AASNQGS |
| Lc CDR3 (KABAT) | 189 | QQSKEVPWT |
| Lc variable domain segment | 219 | SPASLAVSLGQRATISCRASESVDNYGISFMNWFQQKPGQPPKVLIYAASNQGSGV PARFSGSGSGTDFSLNIHPMEEDDTAMYFCQQSKEVPWTFGGGTKLEIK |
| Lc | 220 | SPASLAVSLGQRATISCRASESVDNYGISFMNWFQQKPGQPPKVLIYAASNQGSGV PARFSGSGSGTDFSLNIHPMEEDDTAMYFCQQSKEVPWTFGGGTKLEIKRADAAPT VSIFTTSSEQL |
| Hc CDR1 (IMGT) | 194 | GYSITSGYY |
| Hc CDR2 (IMGT) | 221 | ISYDGSN |
| Hc CDR3 (IMGT) | 196 | ARGNYYAMDY |
| Hc CDR1 (KABAT) | 197 | SGYYWI |
| Hc CDR2 (KABAT) | 222 | YISYDGSNNYNPSLKN |
| Hc CDR3 (KABAT) | 199 | GNYYAMDY |
| Hc variable domain segment | 223 | GPGLVKPSQSLSLTCSVTGYSITSGYYWIWIRQFPGNKLEWMGYISYDGSNNYNPS LKNRISITRDTSKNQFFLKLNSVTTEDTATYYCARGNYYAMDYWGQGTSVTVSS |
| Hc | 224 | GPGLVKPSQSLSLTCSVTGYSITSGYYWIWIRQFPGNKLEWMGYISYDGSNNYNPS LKNRISITRDTSKNQFFLKLNSVTTEDTATYYCARGNYYAMDYWGQGTSVTVSSA KTTPPSVYPLAPGCGDTTGSSVTLGCLVKGYFPESVTVTWNSGSLSSGVHTF |

Monoclonal antibody 5C12.H8 (murine IgG2b constant region) Nucleic Acid Sequences

| Antibody Segment | SEQ ID NO. | Sequence |
|---|---|---|
| Lc CDR1 (IMGT) | 225 | GAAAGTGTTGATAATTATGGCATTAGTTTT |
| Lc CDR2 (IMGT) | 203 | GCTGCATCC |
| Lc CDR3 (IMGT) | 204 | CAGCAAAGTAAGGAGGTTCCGTGGACG |
| Lc CDR1 (KABAT) | 226 | AGAGCCAGCGAAAGTGTTGATAATTATGGCATTAGTTTTATGAAC |
| Lc CDR2 (KABAT) | 206 | GCTGCATCCAACCAAGGATCC |
| Lc CDR3 (KABAT) | 204 | CAGCAAAGTAAGGAGGTTCCGTGGACG |
| Lc variable domain segment | 227 | TCTCCAGCTTCTTTGGCTGTGTCTCTAGGGCAGAGGGCCACCATCTCCTGCAGA GCCAGCGAAAGTGTTGATAATTATGGCATTAGTTTTATGAACTGGTTCCAACAG AAACCAGGACAGCCACCCAAAGTCCTCATCTATGCTGCATCCAACCAAGGATC CGGGGTCCCTGCCAGGTTTAGTGGCAGTGGGTCTGGGACAGACTTCAGCCTCA |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| | | ACATCCATCCTATGGAGGAGGATGATACTGCAATGTATTTCTGTCAGCAAAGT<br>AAGGAGGTTCCGTGGACGTTCGGTGGAGGCACCAAGCTGGAAATCAAA |
| Lc | 228 | TCTCCAGCTTCTTTGGCTGTGTCTCTAGGGCAGAGGGCCACCATCTCCTGCAGA<br>GCCAGCGAAAGTGTTGATAATTATGGCATTAGTTTTATGAACTGGTTCCAACAG<br>AAACCAGGACAGCCACCCAAAGTCCTCATCTATGCTGCATCCAACCAAGGATC<br>CGGGGTCCCTGCCAGGTTTAGTGGCAGTGGGTCTGGGACAGACTTCAGCCTCA<br>ACATCCATCCTATGGAGGAGGATGATACTGCAATGTATTTCTGTCAGCAAAGT<br>AAGGAGGTTCCGTGGACGTTCGCTGGAGGCACCAAGCTGGAAATCAAACGGG<br>CTGATGCTGCACCAACTGTATCCATCTTCCCACCATCCAGTGAGCAGTTA |
| Hc CDR1 (IMGT) | 209 | GGCTACTCCATCACCAGTGGTTATTAC |
| Hc CDR2 (IMGT) | 229 | ATAAGCTACGACGGTAGCAAT |
| Hc CDR3 (IMGT) | 211 | GCAAGAGGGAATTACTATGCTATGGACTAC |
| Hc CDR1 (KABAT) | 212 | AGTGGTTATTACTGGATC |
| Hc CDR2 (KABAT) | 230 | TACATAAGCTACGACGGTAGCAATAACTACAACCCATCTCTCAAAAAT |
| Hc CDR3 (KABAT) | 214 | GGGAATTACTATGCTATGGACTAC |
| Hc variable domain segment | 231 | GGACCTGGCCTCGTGAAACCTTCTCAGTCTCTGTCTCTCACCTGCTCTGTCACT<br>GGCTACTCCATCACCAGTGGTTATTACTGGATCTGGATCCGGCAGTTTCCAGGA<br>AACAAACTGGAATGGATGGGCTACATAAGCTACGACGGTAGCAATAACTACA<br>ACCCATCTCTCAAAAATCGAATCTCCATCACTCGTGACACATCTAAGAACCAGT<br>TTTTCCTGAAGTTGAATTCTGTGACTACTGAGGACACAGCTACATATTACTGTG<br>CAAGAGGGAATTACTATGCTATGGACTACTGGGGTCAAGGAACCTCAGTCACC<br>GTCTCCTCA |
| Hc | 232 | GGACCTGGCCTCGTGAAACCTTCTCAGTCTCTGTCTCTCACCTGCTCTGTCACT<br>GGCTACTCCATCACCAGTGGTTATTACTGGATCTGGATCCGGCAGTTTCCAGGA<br>AACAAACTGGAATGGATGGGCTACATAAGCTACGACGGTAGCAATAACTACA<br>ACCCATCTCTCAAAAATCGAATCTCCATCACTCGTGACACATCTAAGAACCAGT<br>TTTTCCTGAAGTTGAATTCTGTGACTACTGAGGACACAGCTACATATTACTGTG<br>CAAGAGGGAATTACTATGCTATGGACTACTGGGGTCAAGGAACCTCAGTCACC<br>GTCTCCTCAGCCAAAACAACACCCCCATCAGTCTATCCACTGGCCCTGGGTGT<br>GGAGATACAACTGGTTCCTCCGTGACTCTGGGATGCCTGGTCAAGGGCTACTTC<br>CCTGAGTCAGTGACTGTGACTTGGAACTCTGGATCCCTGTCCAGCGGTGTGCAC<br>ACCTTCC |

Monoclonal antibody 28H12.G9 (murine IgG1 constant region)
Amino Acid Sequences

| Lc CDR1 (IMGT) | 233 | QDVSTA |
| Lc CDR2 (IMGT) | 234 | SAS |
| Lc CDR3 (IMGT) | 235 | QQHYSTPLT |
| Lc CDR1 (KABAT) | 236 | KASQDVSTAVA |
| Lc CDR2 (KABAT) | 237 | SASYRYT |
| Lc CDR3 (KABAT) | 235 | QQHYSTPLT |
| Lc variable domain segment | 238 | QSHKFMSTSVGDRVSVTCKASQDVSTAVAWYQQKPGQSPKLLIFSASYRYTGVPD<br>RFTGSGSGTDFTFTISSVQAREDLAVYYCQQHYSTPLTFGAGTKLELK |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Lc | 239 | QSHKFMSTSVGDRVSVTCKASQDVSTAVAWYQQKPGQSPKLLIFSASYRYTGVPD RFTGSGSGTDFTFTISSVQAREDLAVYYCQQHYSTPLTFGAGTKLELKRADAAPTV SIFPPSSEQL |
| Hc CDR1 (IMGT) | 194 | GYSITSGYY |
| Hc CDR2 (IMGT) | 195 | INYDGSN |
| Hc CDR3 (IMGT) | 240 | ARRNYYAVDY |
| Hc CDR1 (KABAT) | 241 | SGYYWN |
| Hc CDR2 (KABAT) | 198 | YINYDGSNNYNTSLKN |
| Hc CDR3 (KABAT) | 242 | RNYYAVDY |
| Hc variable domain segment | 243 | GPGLVKPSQSLSLTCSVTGYSITSGYYWNWIRQFPGNKLEWMGYINYDGSNNYNP SLKNRISITRDTSKNQFFLKLNSVTTEDTATYYCARRNYYAVDYWGQGTSVTVSS |
| Hc | 244 | GPGLVKPSQSLSLTCSVTGYSITSGYYWNWIRQFPGNKLEWMGYINYDGSNNYNP SLKNRISITRDTSKNQFFLKLNSVTTEDTATYYCARRNYYAVDYWGQGTSVTVSS AKTTPPSVYPLAPGSAAQTNSMVTLGCLVKGYFPEPVTVTWNSGSLSSGVHTF |

Monoclonal antibody 28H12.G9 (murine IgG1 constant region)
Nucleic Acid Sequences

| Antibody Segment | SEQ ID NO. | Sequence |
|---|---|---|
| Lc CDR1 (IMGT) | 245 | CAGGATGTGAGTACTGCT |
| Lc CDR2 (IMGT) | 246 | TCGGCATCC |
| Lc CDR3 (IMGT) | 247 | CAGCAACATTATAGTACTCCGCTCACG |
| Lc CDR1 (KABAT) | 248 | AAGGCCAGTCAGGATGTGAGTACTGCTGTAGCC |
| Lc CDR2 (KABAT) | 249 | TCGGCATCCTACCGGTACACT |
| Lc CDR3 (KABAT) | 247 | CAGCAACATTATAGTACTCCGCTCACG |
| Lc variable domain segment | 250 | CAGTCTCACAAATTCATGTCCACATCAGTGGGAGACAGGGTCAGCGTCACCTG CAAGGCCAGTCAGGATGTGAGTACTGCTGTAGCCTGGTATCAACAGAAACCAG GACAATCGTCCTAAACTGCTGATTTTCTCGGCATCCTACCGGTACACTGGAGTCC CTGATCGCTTCACTGGCAGTGGATCTGGGACGGATTTCACTTTCACCATCAGCA GTGTGCAGGCTGAAGACCTGGCAGTTTATTACTGTCAGCAACATTATAGTACTC CGCTCACGTTCGGTGCTGGGACCAAGCTGGAGCTGAAA |
| Lc | 251 | CAGTCTCACAAATTCATGTCCACATCAGTGGGAGACAGGGTCAGCGTCACCTG CAAGGCCAGTCAGGATGTGAGTACTGCTGTAGCCTGGTATCAACAGAAACCAG GACAATCTCCTAAACTGCTGATTTTCTCGGCATCCTACCGGTACACTGGAGTCC CTGATCGCTTCACTGGCAGTGGATCTGGGACGGATTTCACTTTCACCATCAGCA GTGTGCAGGCTGAAGACCTGGCAGTTTATTACTGTCACCAACATTATAGTACTC CGCTCACGTTCGGTGCTGGGACCAAGCTGGAGCTGAAACGGGCTGATGCTGCA CCAACTGTATCCATCTTCCCACCATCCAGTGAGCAGTTA |
| Hc CDR1 (IMGT) | 209 | GGCTACTCCATCACCAGTGGTTATTAC |
| Hc CDR2 (IMGT) | 210 | ATAAACTACGACGGTAGCAAT |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| Hc CDR3 (IMGT) | 252 | GCAAGAAGAAATTACTATGCTGTGGACTAC |
| Hc CDR1 (KABAT) | 253 | AGTGGTTATTACTGGAAC |
| Hc CDR2 (KABAT) | 213 | TACATAAACTACGACGGTAGCAATAACTACAACCCATCTCTCAAAAAT |
| Hc CDR3 (KABAT) | 254 | AGAAATTACTATGCTGTGGACTAC |
| Hc variable domain segment | 255 | GGACCTGGCCTCGTGAAACCTTCTCAGTCTCTGTCTCTCACCTGCTCTGTCACTGGCTACTCCATCACCAGTGGTTATTACTGGAACTGGATCCGGCAGTTTCCAGGAAACAAACTGGAATGGATGGGCTACATAAACTACGACGGTAGCAATAACTACACCCATCTCTCAAAAATCGAATCTCCATCACTCGTGACACATCTAAGAACCAGTTTTTCCTGAAGTTGAATTCTGTGACTACTGAGGACACAGCTACATATTACTGTGCAAGAAGAAATTACTATGCTGTGGACTACTGGGGTCAAGGAACCTCAGTCACCGTCTCCTCA |
| Hc | 256 | GGACCTGGCCTCGTGAAACCTTCTCAGTCTCTGTCTCTCACCTGCTCTGTCACTGGCTACTCCATCACCAGTGGTTATTACTGGAACTGGATCCGGCAGTTTCCAGGAAACAAACTGGAATGGATGGGCTACATAAACTACGACGGTAGCAATAACTACACCCATCTCTCAAAAATCGAATCTCCATCACTCGTGACACATCTAAGAACCAGTTTTTCCTGAAGTTGAATTCTGTGACTACTGAGGACACAGCTACATATTACTGTGCAAGAAGAAATTACTATGCTGTGGACTACTGGGGTCAAGGAACCTCAGTCACCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCCTGTCCAGCGGTGTGCACACCTTCC |

Monoclonal antibody 30G6.G6.G4.E9 (murine IgG1 constant region) Amino Acid Sequences

| Antibody Segment | SEQ ID NO. | Sequence |
|---|---|---|
| Lc CDR1 (IMGT) | 257 | ESVDIYGTSF |
| Lc CDR2 (IMGT) | 188 | AAS |
| Lc CDR3 (IMGT) | 258 | HQSKEVPWT |
| Lc CDR1 (KABAT) | 259 | RASESVDIYGTSFMN |
| Lc CDR2 (KABAT) | 191 | AASNQGS |
| Lc CDR3 (KABAT) | 258 | HQSKEVPWT |
| Lc variable domain segment | 260 | PASLAVSLGQRATISCRASESVDIYGTSFMNWFQQKPGQPPKLLIYAASNQGSGVPARFSGSGSGTEFSLNIHPMEEDDTAMYFCHQSKENPWTFGGGTKLEIK |
| Lc | 261 | PASLAVSLGQRATISCRASESVDIYGTSFMNWFQQKPGQPPKLLIYAASNQGSGVPARFSGSGSGTEFSLNIHPMEEDDTAMYFCHQSKEVPWTFGGGTKLEIKRADAAPTVSIFPPSSEQL |
| Hc CDR1 (IMGT) | 8 | GFSLTSYG |
| Hc CDR2 (IMGT) | 262 | IWAGGIT |
| Hc CDR3 (IMGT) | 263 | ARIYYDYDAWFAY |
| Hc CDR1 (KABAT) | 264 | SYGVH |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
| --- | --- | --- |
| Hc CDR2 (KABAT) | 265 | VIWAGGITNYNSALMS |
| Hc CDR3 (KABAT) | 266 | IYYDYDAWFAY |
| Hc variable domain segment | 267 | GPGLVAPSQSLSITCTVSGFSLTSYGVHWVRQPPGKGLEWLGVIWAGGITNYNSAL MSRLSISKDNSKSQVFLKMNSLQTDDTAMYYCARIYYDYDAWFAYWGQGTLVT VSA |
| Hc | 268 | GPGLVAPSQSLSITCTVSGFSLTSYGVHWVRQPPGKGLEWLGVIWAGGITNYNSAL MSRLSISKDNSKSQVFLKMNSLQTDDTAMYYCARIYYDYDAWFAYWGQGTLVT VSAAKTTPPSVYPLAPGSAAQTNSMVTLGCLVKGYFREPVINTWNSGSLSSGVHT F |

Monoclonal antibody 30G6.G6.G4.E9 (murine IgG1 constant region)
Nucleic Acid Sequences

| Antibody Segment | SEQ ID NO. | Sequence |
| --- | --- | --- |
| Lc CDR1 (IMGT) | 269 | GAAAGTGTTGATATTTATGGCACTAGTTTT |
| Lc CDR2 (IMGT) | 203 | GCTGCATCC |
| Lc CDR3 (IMGT) | 270 | CACCAAAGTAAGGAGGTTCCGTGGACG |
| Lc CDR1 (KABAT) | 271 | AGAGCCAGCGAAAGTGTTGATATTTATGGCACTAGTTTTATGAAC |
| Lc CDR2 (KABAT) | 206 | GCTGCATCCAACCAAGGATCC |
| Lc CDR3 (KABAT) | 270 | CACCAAAGTAAGGAGGTTCCGTGGACG |
| Lc variable domain segment | 272 | CCAGCTTCTTTGGCTGTGTCTCTAGGGCAGAGGGCCACCATCTCCTGCAGAGCC AGCGAAAGTGTTGATATTTATGGCACTAGTTTTATGAACTGGTTCCAACAGAAA CCAGGACAGCCACCCAAACTCCTCATCTATGCTGCATCCAACCAAGGATCCGG GGTCCCTGCCAGGTTTAGTGGCAGTGGGTCTGGGACAGAGTTCAGCCTCAACA TCCATCCTATGGAGGAGGATGATACTGCAATGTATTTCTGTCACCAAAGTAAG GAGGTTCCGTGGACGTTCGGTGGAGGCACCAAGCTGGAAATCAAA |
| Lc | 273 | CCAGCTTCTTTGGCTGTGTCTCTAGGGCAGAGGGCCACCATCTCCTGCAGAGCC AGCGAAAGTGTTGATATTTATGGCACTAGTTTTATGAACTGGTTCCAACAGAAA CCAGGACAGCCACCCAAACTCCTCATCTATGCTGCATCCAACCAAGGATCCGG GGTCCCTGCCAGGTTTAGTGGCAGTGGGTCTGGGACAGAGTTCAGCCTCAACA TCCATCCTATGGAGGAGGATGATACTGCAATGTATTTCTGTCACCAAAGTAAG GAGGTTCCGTGGACGTTCGGTGGAGGCACCAAGCTGGAAATCAAACGGGCTGA TGCTGCACCAACTGTATCCATCTTCCCACCATCCAGTGAGCAGTTA |
| Hc CDR1 (IMGT) | 274 | GGGTTTTCATTAACCAGCTATGGT |
| Hc CDR2 (IMGT) | 275 | ATATGGGCCGGTGGAATCACA |
| Hc CDR3 (IMGT) | 276 | GCCAGGATCTACTATGATTACGACGCCTGGTTTGCTTAC |
| Hc CDR1 (KABAT) | 277 | AGCTATGGTGTACAC |
| Hc CDR2 (KABAT) | 278 | GTAATATGGGCCGGTGGAATCACAAATTATAATTCGGCTCTCATGTCC |
| Hc CDR3 (KABAT) | 279 | ATCTACTATGATTACGACGCCTGGTTTGCTTAC |
| Hc variable domain | 280 | GGACCTGGCCTGGTGGCGCCCTCACAGAGCCTGTCCATCACTTGCACTGTCTCT GGGTTTTCATTAACCAGCTATGGTGTACACTGGGTTCGCCAGCCTCCAGGAA |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| segment | | GGGTCTGGAGTGGCTGGGAGTAATATGGGCCGGTGGAATCACAAATTATAATT<br>CGGCTCTCATGTCCAGACTGAGCATCAGCAAAGACAACTCCAAGAGCCAAGTT<br>TTCTTAAAAATGAACAGTCTGCAAACTGATGATACAGCCATGTACTACTGTGCC<br>AGGATCTACTATGATTACGACGCCTGGTTTGCTTACTGGGGCCAAGGGACTCTG<br>GTCACTGTCTCTGCA |
| Hc | 281 | GGACCTGGCCTGGTGGCGCCCTCACAGAGCCTGTCCATCACTTGCACTGTCTCT<br>GGGTTTTCATTAACCAGCTATGGTGTACACTGGGTTCGCCAGCCTCCAGGAAA<br>GGGTCTGGAGTGGCTGGGAGTAATATGGGCCGGTGGAATCACAAATTATAATT<br>CGGCTCTCATGTCCAGACTGAGCATCAGCAAAGACAACTCCAAGAGCCAAGTT<br>TTCTTAAAAATGAACAGTCTGCAAACTGATGATACAGCCATGTACTACTGTGCC<br>AGGATCTACTATGATTACGACGCCTGGTTTGCTTACTGGGGCCAAGGGACTCTG<br>GTCACTGTCTCTGCAGCCAAAACGACACCCCATCTGTCTATCCACTGGCCCCT<br>GGATCTGCTGCCCAAACTAACTCCATGGTGACCCTGGGATGCCTGGTCAAGGG<br>CTATTTCCCTGAGCCAGTGACAGTGACCTGGAACTCTGGATCCCTGTCCAGCGG<br>TGTGCACACCTTCC |

Monoclonal antibody 1A8.G11.E7 (murine IgG1 constant region)
Amino Acid Sequences

| Antibody Segment | SEQ ID NO. | Sequence |
|---|---|---|
| Lc CDR1 (IMGT) | 1 | QDISNH |
| Lc CDR2 (IMGT) | 2 | YTS |
| Lc CDR3 (IMGT) | 3 | QQGNTLWT |
| Lc CDR1 (KABAT) | 4 | RASQDISNHLN |
| Lc CDR2 (KABAT) | 115 | YTSRLHS |
| Lc CDR3 (KABAT) | 3 | QQGNTLWT |
| Lc variable domain segment | 282 | TQTTSSLSASLGDRVTISCRASQDISNHLNWYQQKPDGTVKLLIYYTSRLHSGVPSR<br>FSGSGSGTDYSLTISNLEQEDIATYFCQQGNTLWTFGGGTKLEIK |
| Lc | 283 | TQTTSSLSASLGDRVTISCRASQDISNHLNWYQQKPDGTVKLLIYYTSRLHSGVPSR<br>FSGSGSGTDYSLTISNLEQEDIATYFCQQGNTLWTFGGGTKLEIKRADAAPTVSIFP<br>PSSEQV |
| Hc CDR1 (IMGT) | 8 | GFSLTSYG |
| Hc CDR2 (IMGT) | 9 | IWGDGST |
| Hc CDR3 (IMGT) | 10 | AKPHPAATGAMDY |
| Hc CDR1 (KABAT) | 11 | SYGVS |
| Hc CDR2 (KABAT) | 12 | VIWGDGSTNYHSTLIS |
| Hc CDR3 (KABAT) | 13 | PHPAATGAMDY |
| Hc variable domain segment | 284 | ESGPGLVAPSQSLSITCTVSGFSLTSYGVSWVRQPPGKGLEWLGVIWGDGSTNYHS<br>TLISRLSISKDNSKSQVFLKLNSLQTDDTATYYCAKPHPAATGAMDYWGQGTSVT<br>VSS |
| Hc | 285 | ESGPGLVAPSQSLSITCTVSGFSLTSYGVSWVRQPPGKGLEWLGVIWGDGSTNYHS<br>TLISRLSISKDNSKSQVFLKLNSLQTDDTATYYCAKPHPAATGAMDYWGQGTSVT<br>VSSAKTTPPSVYPLAPGSAAQTNSMVTLGCLVKGYFPEPVTVTWNSGSLSSGVHTF |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
| --- | --- | --- |
| Monoclonal antibody 1A8.G11.E7 (murine IgG1 constant region) Nucleic Acid Sequences | | |
| Lc CDR1 (IMGT) | 16 | CAGGACATTAGCAATCAT |
| Lc CDR2 (IMGT) | 17 | TACACATCA |
| Lc CDR3 (IMGT) | 18 | CAACAGGGTAATACGCTTTCGACG |
| Lc CDR1 (KABAT) | 19 | AGGGCAAGTCAGGACATTAGCAATCATTTAAAC |
| Lc CDR2 (KABAT) | 129 | TACACATCAAGATTACACTCA |
| Lc CDR3 (KABAT) | 18 | CAACAGGGTAATACGCTTTGGACG |
| Lc variable domain segment | 286 | ACACAGACTACATCCTCCCTGTCTGCCTCTCTGGGAGACAGAGTCACCATCAGT<br>TGCAGGGCAAGTCAGGACATTAGCAATCATTTAAACTGGTATCAGCAGAAACC<br>AGATGGAACTGTTAAACTCCTGATCTACTACACATCAAGATTACACTCAGGAG<br>TCCCATCAAGGTTCAGTGGCAGTGGGTCTGGAACAGATTATTCTCTCACCATTA<br>GCAACCTGGAGCAAGAGGATATTGCCACTTACTTTTGCCAACAGGGTAATACG<br>CTTTGGACGTTCGGTGGAGGCACCAAGCTGGAAATCAAA |
| Lc | 287 | ACACAGACTACATCCTCCCTGTCTGCCTCTCTGGGAGACAGAGTCACCATCAGT<br>TGCAGGGCAAGTCAGGACATTAGCAATCATTTAAACTGGTATCAGCAGAAACC<br>AGATGGAACTGTTAAACTCCTGATCTACTACACATCAAGATTACACTCAGGAG<br>TCCCATCAAGGTTCAGTGGCAGTGGGTCTGGAACAGATTATTCTCTCACCATTA<br>GCAACCTGGAGCAAGAGGATATTGCCACTTACTTTTGCCAACAGGGTAATACG<br>CTTTGGACGTTCGGTGGAGGCACCAAGCTGGAAATCAAACGGGCTGATGCTGC<br>ACCAACTGTATCCATCTTCCCACCATCCAGTGAGCAGGTT |
| Hc CDR1 (IMGT) | 288 | GGGTTCTCATTAACCAGCTATGGT |
| Hc CDR2 (IMGT) | 24 | ATATGGGGTGACGGGAGCACA |
| Hc CDR3 (IMGT) | 25 | GCCAAACCTCATCCTGCGGCTACTGGCGCTATGGACTAC |
| Hc CDR1 (KABAT) | 289 | AGCTATGGTGTAAGC |
| Hc CDR2 (KABAT) | 290 | GTAATATCiGGGTGACGGGAGCACAAATTATCACTCAACTCTCATATCC |
| Hc CDR3 (KABAT) | 28 | CCTCATCCTGCGGCTACTGGCGCTATGGACTAC |
| Hc variable domain segment | 291 | GAGTCAGGACCTGGCCTGGTGGCGCCCTCACAGAGCCTGTCCATCACATGCAC<br>TGTCTCAGGGTTCTCATTAACCAGCTATGGTGTAAGCTGGGTTCGCCAGCCTCC<br>AGGAAAGGGTCTGGAGTGGCTGGGAGTAATATGGGGTGACGGGAGCACAAAT<br>TATCACTCAACTCTCATATCCAGACTGAGCATCAGCAAGGATAACTCCAAGAG<br>CCAAGTTTTCTTAAAACTGAACAGTCTGCAAACTGATGACACAGCCACGTACT<br>ACTGTGCCAAACCTCATCCTGCGGCTACTGGCGCTATGGACTACTGGGGTCAA<br>GGAACCTCAGTCACCGTCTCCTCA |
| Hc | 292 | GAGTCAGGACCTGGCCTGGTGGCGCCCTCACAGAGCCTGTCCATCACATGCAC<br>TGTCTCAGGGTTCTCATTAACCAGCTATGGTGTAAGCTGGGTTCGCCAGCCTCC<br>AGGAAAGGGTCTGGAGTGGCTGGGAGTAATATGGGGTGACGGGAGCACAAAT<br>TATCACTCAACTCTCATATCCAGACTGAGCATCAGCAAGGATAACTCCAAGAG<br>CCAAGTTTTCTTAAAACTGAACAGTCTGCAAACTGATGACACAGCCACGTACT<br>ACTGTGCCAAACCTCATCCTGCGGCTACTGGCGCTATGGACTACTGGGGTCAA<br>GGAACCTCAGTCACCGTCTCCTCAGCCAAAACGACACCCCCATCTGTCTATCCA<br>CTGGCCCCTGGATCTGCTGCCCAAACTAACTCCATGGTGACCCTGGGATGCCTG<br>GTCAAGGGCTATTTCCCTGAGCCAGTGACAGTGACCTGGAACTCTGGATCCCT<br>GTCCAGCGGTGTGCACACCTTCC |

TABLE 1-continued

Antibody segments of the described anti-FRα antibodies and antigen-binding fragments thereof ("Lc" denotes light chain and "Hc" denotes heavy chain)

| Antibody Segment | SEQ ID NO. | Sequence |
|---|---|---|
| | | FRα Amino Acid Sequence |
| Full length | 293 | MAQRMTTQLLLLLVWVAVVGEAQTRIAWARTELLNVCMNAKHHKEKPGPEDKL HEQCRPWRKNACCSTNTSQEAHKDVSYLYRFNWNHCGEMAPACKRHFIQDTCLY ECSPNLGPWIQQVDQSWRKERVLNVPLCKEDCEQWWEDCRTSYTCKSNWHKGW NWTSGFNKCAVGAAQPFHF YFPTPTVLCN EIWTHSYKVS NYSRGSGRCIQMWFDPAQGNPNEEVARFYAAAMSGAGPWAAWPFLLSLALMLL WLLS |

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method. In some embodiments, the antibodies or antigen-binding fragments include a light chain CDR1 amino acid sequence substantially the same as, or identical to, SEQ ID NO: 1, wherein the CDRs are defined according to the IMGT method. In some embodiments, the antibodies or antigen-binding fragments include a light chain CDR2 amino acid sequence substantially the same as, or identical to, SEQ ID NO: 2, wherein the CDR is defined according to the IMGT method. In some embodiments, the antibodies or antigen-binding fragments include a light chain CDR3 amino acid sequence substantially the same as, or identical to, SEQ ID NO: 3, wherein the CDR is defined according to the IMGT method. In some embodiments, the antibodies or antigen-binding fragments include a heavy chain CDR1 amino acid sequence substantially the same as, or identical to, SEQ ID NO: 8, wherein the CDR is defined according to the IMGT method. In some embodiments, the antibodies or antigen-binding fragments include a heavy chain CDR2 substantially the same as, or identical to, amino acid sequence of SEQ ID NO: 9, wherein the CDR is defined according to the IMGT method. In some embodiments, the antibodies or antigen-binding fragments include a heavy chain CDR3 amino acid sequence substantially the same as, or identical to SEQ ID NO: 10, wherein the CDR is defined according to the IMGT method.

In some embodiments, the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method. In some embodiments, the antibodies or antigen-binding fragments include a light chain CDR1 amino acid sequence substantially the same as, or identical to, SEQ ID NO: 4, wherein the CDR is defined according to the KABAT method. In some embodiments, the antibodies or antigen-binding fragments include a light chain CDR2 amino acid sequence substantially the same as, or identical to, SEQ ID NO: 5, wherein the CDR is defined according to the KABAT method. In some embodiments, the antibodies or antigen-binding fragments include a light chain CDR3 amino acid sequence substantially the same as, or identical to, SEQ ID NO: 3, wherein the CDR is defined according to the KABAT method. In some embodiments, the antibodies or antigen-binding fragments include a heavy chain CDR1 amino acid sequence substantially the same as, or identical to, SEQ ID NO: 11, wherein the CDR is defined according to the KABAT method. In some embodiments, the antibodies or antigen-binding fragments include a heavy chain CDR2 substantially the same as, or identical to, amino acid sequence of SEQ ID NO: 12, wherein the CDR is defined according to the KABAT method. In some embodiments, the antibodies or antigen-binding fragments include a heavy chain CDR3 amino acid sequence substantially the same as, or identical to SEQ ID NO: 13, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 62, a heavy chain CDR2 amino acid sequence substantially the same as, or identical to, SEQ ID NO: 63, and a heavy chain CDR3 amino acid sequence substantially the same as, or identical to, SEQ ID NO: 64, wherein the CDRs are defined according to the IMGT method. In some embodiments, the antibodies or antigen-binding fragments include a light chain CDR1 amino acid sequence substantially the same as, or identical to, SEQ ID NO: 55. In some embodiments, the antibodies or antigen-binding fragments include a light chain CDR2 amino acid sequence substantially the same as, or identical to, SEQ ID NO: 56, wherein the CDR is defined according to the IMGT method. In some embodiments, the antibodies or antigen-binding fragments include a light chain CDR3 amino acid sequence substantially the same as, or identical to, SEQ ID NO: 57, wherein the CDR is defined according to the IMGT method. In some embodiments, the antibodies or antigen-binding fragments include a heavy chain CDR1 amino acid sequence substantially the same as, or identical to, SEQ ID NO: 62, wherein the CDR is defined according to the IMGT method. In some embodiments, the antibodies or antigen-binding fragments include a heavy chain CDR2 substantially the same as, or identical to, amino acid sequence of SEQ ID NO: 63, wherein the CDR is defined according to the IMGT method. In some embodiments, the antibodies or antigen-binding fragments include a heavy chain CDR3 amino acid sequence substantially the same as, or identical to SEQ ID NO: 64, wherein the CDR is defined according to the IMGT method.

In some embodiments, the antibodies or antigen-binding fragments include a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 65, a heavy chain CDR2 amino acid sequence substantially the same as, or identical to, SEQ ID NO: 66, and a heavy chain CDR3 amino acid sequence substantially the same as, or identical to, SEQ ID NO: 64, wherein the CDRs are defined according to the KABAT method. In some embodiments, the antibodies or antigen-binding fragments include a light chain CDR1 amino acid sequence substantially the same as, or identical to, SEQ ID NO: 58, wherein the CDR is defined according to the KABAT method. In some embodiments, the antibodies or antigen-binding fragments include a light chain CDR2 amino acid sequence substantially the same as, or identical to, SEQ ID NO: 59, wherein the CDR is defined according to the KABAT method. In some embodiments, the antibodies or antigen-binding fragments include a light chain CDR3 amino acid sequence substantially the same as, or identical to, SEQ ID NO: 57, wherein the CDR is defined according to the KABAT method. In some embodiments, the antibodies or antigen-binding fragments include a heavy chain CDR1 amino acid sequence substantially the same as, or identical to, SEQ ID NO: 65, wherein the CDR is defined according to the KABAT method. In some embodiments, the antibodies or antigen-binding fragments include a heavy chain CDR2 substantially the same as, or identical to, amino acid sequence of SEQ ID NO: 66, wherein the CDR is defined according to the KABAT method. In some embodiments, the antibodies or antigen-binding fragments include a heavy chain CDR3 amino acid sequence substantially the same as, or identical to SEQ ID NO: 64, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 84, a light chain CDR2 amino acid sequence substantially the same as, or identical to, SEQ ID NO: 85, a light chain CDR3 amino acid sequence substantially the same as, or identical to, SEQ ID NO: 86, a heavy chain CDR1 amino acid sequence substantially the same as, or identical to, SEQ ID NO: 90, a heavy chain CDR2 amino acid sequence substantially the same as, or identical to, SEQ ID NO: 91, and a heavy chain CDR3 amino acid sequence substantially the same as, or identical to, SEQ ID NO: 92, wherein the CDRs are defined according to the IMGT method. In some embodiments, the antibodies or antigen-binding fragments include a light chain CDR1 amino acid sequence substantially the same as, or identical to, SEQ ID NO: 84. In some embodiments, the antibodies or antigen-binding fragments include a light chain CDR2 amino acid sequence substantially the same as, or identical to, SEQ ID NO: 85, wherein the CDR is defined according to the IMGT method. In some embodiments, the antibodies or antigen-binding fragments include a light chain CDR3 amino acid sequence substantially the same as, or identical to, SEQ ID NO: 86, wherein the CDR is defined according to the IMGT method. In some embodiments, the antibodies or antigen-binding fragments include a heavy chain CDR1 amino acid sequence substantially the same as, or identical to, SEQ ID NO: 90, wherein the CDR is defined according to the IMGT method. In some embodiments, the antibodies or antigen-binding fragments include a heavy chain CDR2 substantially the same as, or identical to, amino acid sequence of SEQ ID NO: 91, wherein the CDR is defined according to the IMGT method. In some embodiments, the antibodies or antigen-binding fragments include a heavy chain CDR3 amino acid sequence substantially the same as, or identical to SEQ ID NO: 92, wherein the CDR is defined according to the IMGT method.

In some embodiments, the antibodies or antigen-binding fragments include a light chain CDR1 amino acid sequence substantially the same as, or identical to, SEQ ID NO: 87, a light chain CDR2 amino acid sequence substantially the same as, or identical to, SEQ ID NO: 32, a light chain CDR3 amino acid sequence substantially the same as, or identical to, SEQ ID NO: 86, a heavy chain CDR1 amino acid sequence substantially the same as, or identical to, SEQ ID NO: 93, a heavy chain CDR2 amino acid sequence substantially the same as, or identical to, SEQ ID NO: 94, and a heavy chain CDR3 amino acid sequence substantially the same as, or identical to, SEQ ID NO: 95, wherein the CDRs are defined according to the KABAT method. In some embodiments, the antibodies or antigen-binding fragments include a light chain CDR1 amino acid sequence substantially the same as, or identical to, SEQ ID NO: 87, wherein the CDR is defined according to the KABAT method. In some embodiments, the antibodies or antigen-binding fragments include a light chain CDR2 amino acid sequence substantially the same as, or identical to, SEQ ID NO: 32, wherein the CDR is defined according to the KABAT method. In some embodiments, the antibodies or antigen-binding fragments include a light chain CDR3 amino acid sequence substantially the same as, or identical to, SEQ ID NO: 86, wherein the CDR is defined according to the KABAT method. In some embodiments, the antibodies or antigen-binding fragments include a heavy chain CDR1 amino acid sequence substantially the same as, or identical to, SEQ ID NO: 93, wherein the CDR is defined according to the KABAT method. In some embodiments, the antibodies or antigen-binding fragments include a heavy chain CDR2 substantially the same as, or identical to, amino acid sequence of SEQ ID NO: 94, wherein the CDR is defined according to the KABAT method. In some embodiments, the antibodies or antigen-binding fragments include a heavy chain CDR3 amino acid sequence substantially the same as, or identical to SEQ ID NO: 95, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 112, a light chain CDR2 amino acid sequence substantially the same as, or identical to, SEQ ID NO: 2, a light chain CDR3 amino acid sequence substantially the same as, or identical to, SEQ ID NO: 113, a heavy chain CDR1 amino acid sequence substantially the same as, or identical to, SEQ ID NO: 118, a heavy chain CDR2 amino acid sequence substantially the same as, or identical to, SEQ ID NO: 119, and a heavy chain CDR3 amino acid sequence substantially the same as, or identical to, SEQ ID NO: 120, wherein the CDRs are defined according to the IMGT method. In some embodiments, the antibodies or antigen-binding fragments include a light chain CDR1 amino acid sequence substantially the same as, or identical to, SEQ ID NO: 112. In some embodiments, the antibodies or antigen-binding fragments include a light chain CDR2 amino acid sequence substantially the same as, or identical to, SEQ ID NO: 2, wherein the CDR is defined according to the IMGT method. In some embodiments, the antibodies or antigen-binding fragments include a light chain CDR3 amino acid sequence substantially the same as, or identical to, SEQ ID NO: 113, wherein the CDR is defined according to the IMGT method. In some embodiments, the antibodies or antigen-binding fragments include a heavy chain CDR1 amino acid sequence substantially the same as, or identical to, SEQ ID NO: 118, wherein the CDR is defined according to the IMGT method. In some embodiments, the antibodies or antigen-binding fragments include a heavy chain CDR2 substantially the same as, or identical to, amino acid sequence of SEQ ID NO: 119, wherein the CDR is defined according to the IMGT method. In some embodiments, the antibodies or antigen-binding fragments include a heavy chain CDR3 amino acid sequence substantially the same as, or identical to SEQ ID NO: 120, wherein the CDR is defined according to the IMGT method.

In some embodiments, the antibodies or antigen-binding fragments include a light chain CDR1 amino acid sequence substantially the same as, or identical to, SEQ ID NO: 114, a light chain CDR2 amino acid sequence substantially the same as, or identical to, SEQ ID NO: 115, a light chain CDR3 amino acid sequence substantially the same as, or identical to, SEQ ID NO: 113, a heavy chain CDR1 amino acid sequence substantially the same as, or identical to, SEQ ID NO: 121, a heavy chain CDR2 amino acid sequence substantially the same as, or identical to, SEQ ID NO: 122, and a heavy chain CDR3 amino acid sequence substantially the same as, or identical to, SEQ ID NO: 123, wherein the CDRs are defined according to the KABAT method. In some embodiments, the antibodies or antigen-binding fragments include a light chain CDR1 amino acid sequence substantially the same as, or identical to, SEQ ID NO: 114, wherein the CDR is defined according to the KABAT method. In some embodiments, the antibodies or antigen-binding fragments include a light chain CDR2 amino acid sequence substantially the same as, or identical to, SEQ ID NO: 115, wherein the CDR is defined according to the KABAT method. In some embodiments, the antibodies or antigen-binding fragments include a light chain CDR3 amino acid sequence substantially the same as, or identical to, SEQ ID NO: 113, wherein the CDR is defined according to the KABAT method. In some embodiments, the antibodies or antigen-binding fragments include a heavy chain CDR1 amino acid sequence substantially the same as, or identical to, SEQ ID NO: 121, wherein the CDR is defined according to the KABAT method. In some embodiments, the antibodies or antigen-binding fragments include a heavy chain CDR2 substantially the same as, or identical to, amino acid sequence of SEQ ID NO: 122, wherein the CDR is defined according to the KABAT method. In some embodiments, the antibodies or antigen-binding fragments include a heavy chain CDR3 amino acid sequence substantially the same as, or identical to SEQ ID NO: 123, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 55, a light chain CDR2 amino acid sequence substantially the same as, or identical to, SEQ ID NO: 140, a light chain CDR3 amino acid sequence substantially the same as, or identical to, SEQ ID NO: 141, a heavy chain CDR1 amino acid sequence substantially the same as, or identical to, SEQ ID NO: 145, a heavy chain CDR2 amino acid sequence substantially the same as, or identical to, SEQ ID NO: 146, and a heavy chain CDR3 amino acid sequence substantially the same as, or identical to, SEQ ID NO: 147, wherein the CDRs are defined according to the IMGT method. In some embodiments, the antibodies or antigen-binding fragments include a light chain CDR1 amino acid sequence substantially the same as, or identical to, SEQ ID NO: 55. In some embodiments, the antibodies or antigen-binding fragments include a light chain CDR2 amino acid sequence substantially the same as, or identical to, SEQ ID NO: 140, wherein the CDR is defined according to the IMGT method. In some embodiments, the antibodies or antigen-binding fragments include a light chain CDR3 amino acid sequence substantially the same as, or identical to, SEQ ID NO: 141, wherein the CDR is defined according to the IMGT method. In some embodiments, the antibodies or antigen-binding fragments include a heavy chain CDR1 amino acid sequence substantially the same as, or identical to, SEQ ID NO: 145, wherein the CDR is defined according to the IMGT method. In some embodiments, the antibodies or antigen-binding fragments include a heavy chain CDR2 substantially the same as, or identical to, amino acid sequence of SEQ ID NO: 146, wherein the CDR is defined according to the IMGT method. In some embodiments, the antibodies or antigen-binding fragments include a heavy chain CDR3 amino acid sequence substantially the same as, or identical to SEQ ID NO: 147, wherein the CDR is defined according to the IMGT method.

In some embodiments, the antibodies or antigen-binding fragments include a light chain CDR1 amino acid sequence substantially the same as, or identical to, SEQ ID NO: 58, a light chain CDR2 amino acid sequence substantially the same as, or identical to, SEQ ID NO: 142, a light chain CDR3 amino acid sequence substantially the same as, or identical to, SEQ ID NO: 141, a heavy chain CDR1 amino acid sequence substantially the same as, or identical to, SEQ ID NO: 148, a heavy chain CDR2 amino acid sequence substantially the same as, or identical to, SEQ ID NO: 149, and a heavy chain CDR3 amino acid sequence substantially the same as, or identical to, SEQ ID NO: 150, wherein the CDRs are defined according to the KABAT method. In some embodiments, the antibodies or antigen-binding fragments include a light chain CDR1 amino acid sequence substantially the same as, or identical to, SEQ ID NO: 58, wherein the CDR is defined according to the KABAT method. In some embodiments, the antibodies or antigen-binding fragments include a light chain CDR2 amino acid sequence substantially the same as, or identical to, SEQ ID NO: 142, wherein the CDR is defined according to the KABAT method. In some embodiments, the antibodies or antigen-binding fragments include a light chain CDR3 amino acid sequence substantially the same as, or identical to, SEQ ID NO: 141, wherein the CDR is defined according to the KABAT method. In some embodiments, the antibodies or antigen-binding fragments include a heavy chain CDR1 amino acid sequence substantially the same as, or identical to, SEQ ID NO: 148, wherein the CDR is defined according to the KABAT method. In some embodiments, the antibodies or antigen-binding fragments include a heavy chain CDR2 substantially the same as, or identical to, amino acid sequence of SEQ ID NO: 149, wherein the CDR is defined according to the KABAT method. In some embodiments, the antibodies or antigen-binding fragments include a heavy chain CDR3 amino acid sequence substantially the same as, or identical to SEQ ID NO: 150, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 168, a heavy chain CDR2 amino acid sequence substantially the same as, or identical to, SEQ ID NO: 169, and a heavy chain CDR3 amino acid sequence substantially the same as, or identical to, SEQ ID NO: 170, wherein the CDRs are defined according to the IMGT method. In some embodiments, the antibodies or antigen-binding fragments include a light chain CDR1 amino acid sequence substantially the same as, or identical to, SEQ ID NO: 55. In some embodiments, the antibodies or antigen-binding fragments include a light chain CDR2 amino acid sequence substantially the same as, or identical to, SEQ ID NO: 56, wherein the CDR is defined according to the IMGT method. In some embodiments, the antibodies or antigen-binding fragments include a light chain CDR3 amino acid sequence substantially the same as, or identical to, SEQ ID NO: 57, wherein the CDR is defined according to the IMGT method. In some embodiments, the antibodies or antigen-binding fragments include a heavy chain CDR1 amino acid sequence substantially the same as, or identical to, SEQ ID NO: 168, wherein the CDR is defined according to the IMGT method. In some embodiments, the antibodies or antigen-binding fragments include a heavy chain CDR2 substantially the same as, or identical to, amino acid sequence of SEQ ID NO: 169, wherein the CDR is defined according to the IMGT method. In some embodiments, the antibodies or antigen-binding fragments include a heavy chain CDR3 amino acid sequence substantially the same as, or identical to SEQ ID NO: 170, wherein the CDR is defined according to the IMGT method.

In some embodiments, the antibodies or antigen-binding fragments include a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 171, a heavy chain CDR2 amino acid sequence substantially the same as, or identical to, SEQ ID NO: 172, and a heavy chain CDR3 amino acid sequence substantially the same as, or identical to, SEQ ID NO: 173, wherein the CDRs are defined according to the KABAT method. In some embodiments, the antibodies or antigen-binding fragments include a light chain CDR1 amino acid sequence substantially the same as, or identical to, SEQ ID NO: 58, wherein the CDR is defined according to the KABAT method. In some embodiments, the antibodies or antigen-binding fragments include a light chain CDR2 amino acid sequence substantially the same as, or identical to, SEQ ID NO: 59, wherein the CDR is defined according to the KABAT method. In some embodiments, the antibodies or antigen-binding fragments include a light chain CDR3 amino acid sequence substantially the same as, or identical to, SEQ ID NO: 57, wherein the CDR is defined according to the KABAT method. In some embodiments, the antibodies or antigen-binding fragments include a heavy chain CDR1 amino acid sequence substantially the same as, or identical to, SEQ ID NO: 171, wherein the CDR is defined according to the KABAT method. In some embodiments, the antibodies or antigen-binding fragments include a heavy chain CDR2 substantially the same as, or identical to, amino acid sequence of SEQ ID NO: 172, wherein the CDR is defined according to the KABAT method. In some embodiments, the antibodies or antigen-binding fragments include a heavy chain CDR3 amino acid sequence substantially the same as, or identical to SEQ ID NO: 173, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 187, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 196, wherein the CDRs are defined according to the IMGT method. In some embodiments, the antibodies or antigen-binding fragments include a light chain CDR1 amino acid sequence substantially the same as, or identical to, SEQ ID NO: 187. In some embodiments, the antibodies or antigen-binding fragments include a light chain CDR2 amino acid sequence substantially the same as, or identical to, SEQ ID NO: 188, wherein the CDR is defined according to the IMGT method. In some embodiments, the antibodies or antigen-binding fragments include a light chain CDR3 amino acid sequence substantially the same as, or identical to, SEQ ID NO: 189, wherein the CDR is defined according to the IMGT method. In some embodiments, the antibodies or antigen-binding fragments include a heavy chain CDR1 amino acid sequence substantially the same as, or identical to, SEQ ID NO: 194, wherein the CDR is defined according to the IMGT method. In some embodiments, the antibodies or antigen-binding fragments include a heavy chain CDR2 substantially the same as, or identical to, amino acid sequence of SEQ ID NO: 195, wherein the CDR is defined according to the IMGT method. In some embodiments, the antibodies or antigen-binding fragments include a heavy chain CDR3 amino acid sequence substantially the same as, or identical to SEQ ID NO: 196, wherein the CDR is defined according to the IMGT method.

In some embodiments, the antibodies or antigen-binding fragments include a light chain CDR1 amino acid sequence substantially the same as, or identical to, SEQ ID NO: 190, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 198, and a heavy chain CDR3 amino acid sequence substantially the same as, or identical to, SEQ ID NO: 199, wherein the CDRs are defined according to the KABAT method. In some embodiments, the antibodies or antigen-binding fragments include a light chain CDR1 amino acid sequence substantially the same as, or identical to, SEQ ID NO: 190, wherein the CDR is defined according to the KABAT method. In some embodiments, the antibodies or antigen-binding fragments include a light chain CDR2 amino acid sequence substantially the same as, or identical to, SEQ ID NO: 191, wherein the CDR is defined according to the KABAT method. In some embodiments, the antibodies or antigen-binding fragments include a light chain CDR3 amino acid sequence substantially the same as, or identical to, SEQ ID NO: 189, wherein the CDR is defined according to the KABAT method. In some embodiments, the antibodies or antigen-binding fragments include a heavy chain CDR1 amino acid sequence substantially the same as, or identical to, SEQ ID NO: 197, wherein the CDR is defined according to the KABAT method. In some embodiments, the antibodies or antigen-binding fragments include a heavy chain CDR2 substantially the same as, or identical to, amino acid sequence of SEQ ID NO: 198, wherein the CDR is defined according to the KABAT method. In some embodiments, the antibodies or antigen-binding fragments include a heavy chain CDR3 amino acid sequence substantially the same as, or identical to SEQ ID NO: 199, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 217, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 221, and a heavy chain CDR3 amino acid sequence substantially the same as, or identical to, SEQ ID NO: 196, wherein the CDRs are defined according to the IMGT method. In some embodiments, the antibodies or antigen-binding fragments include a light chain CDR1 amino acid sequence substantially the same as, or identical to, SEQ ID NO: 217. In some embodiments, the antibodies or antigen-binding fragments include a light chain CDR2 amino acid sequence substantially the same as, or identical to, SEQ ID NO: 188, wherein the CDR is defined according to the IMGT method. In some embodiments, the antibodies or antigen-binding fragments include a light chain CDR3 amino acid sequence substantially the same as, or identical to, SEQ ID NO: 189, wherein the CDR is defined according to the IMGT method. In some embodiments, the antibodies or antigen-binding fragments include a heavy chain CDR1 amino acid sequence substantially the same as, or identical to, SEQ ID NO: 194, wherein the CDR is defined according to the IMGT method. In some embodiments, the antibodies or antigen-binding fragments include a heavy chain CDR2 substantially the same as, or identical to, amino acid sequence of SEQ ID NO: 221, wherein the CDR is defined according to the IMGT method. In some embodiments, the antibodies or antigen-binding fragments include a heavy chain CDR3 amino acid sequence substantially the same as, or identical to SEQ ID NO: 196, wherein the CDR is defined according to the IMGT method.

In some embodiments, the antibodies or antigen-binding fragments include a light chain CDR1 amino acid sequence substantially the same as, or identical to, SEQ ID NO: 218, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 222, and a heavy chain CDR3 amino acid sequence substantially the same as, or identical to, SEQ ID NO: 199, wherein the CDRs are defined according to the KABAT method. In some embodiments, the antibodies or antigen-binding fragments include a light chain CDR1 amino acid sequence substantially the same as, or identical to, SEQ ID NO: 218, wherein the CDR is defined according to the KABAT method. In some embodiments, the antibodies or antigen-binding fragments include a light chain CDR2 amino acid sequence substantially the same as, or identical to, SEQ ID NO: 191, wherein the CDR is defined according to the KABAT method. In some embodiments, the antibodies or antigen-binding fragments include a light chain CDR3 amino acid sequence substantially the same as, or identical to, SEQ ID NO: 189, wherein the CDR is defined according to the KABAT method. In some embodiments, the antibodies or antigen-binding fragments include a heavy chain CDR1 amino acid sequence substantially the same as, or identical to, SEQ ID NO: 197, wherein the CDR is defined according to the KABAT method. In some embodiments, the antibodies or antigen-binding fragments include a heavy chain CDR2 substantially the same as, or identical to, amino acid sequence of SEQ ID NO: 222, wherein the CDR is defined according to the KABAT method. In some embodiments, the antibodies or antigen-binding fragments include a heavy chain CDR3 amino acid sequence substantially the same as, or identical to SEQ ID NO: 199, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 233, a light chain CDR2 amino acid sequence substantially the same as, or identical to, SEQ ID NO: 234, a light chain CDR3 amino acid sequence substantially the same as, or identical to, SEQ ID NO: 235, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 240, wherein the CDRs are defined according to the IMGT method. In some embodiments, the antibodies or antigen-binding fragments include a light chain CDR1 amino acid sequence substantially the same as, or identical to, SEQ ID NO: 233. In some embodiments, the antibodies or antigen-binding fragments include a light chain CDR2 amino acid sequence substantially the same as, or identical to, SEQ ID NO: 234, wherein the CDR is defined according to the IMGT method. In some embodiments, the antibodies or antigen-binding fragments include a light chain CDR3 amino acid sequence substantially the same as, or identical to, SEQ ID NO: 235, wherein the CDR is defined according to the IMGT method. In some embodiments, the antibodies or antigen-binding fragments include a heavy chain CDR1 amino acid sequence substantially the same as, or identical to, SEQ ID NO: 194, wherein the CDR is defined according to the IMGT method. In some embodiments, the antibodies or antigen-binding fragments include a heavy chain CDR2 substantially the same as, or identical to, amino acid sequence of SEQ ID NO: 195, wherein the CDR is defined according to the IMGT method. In some embodiments, the antibodies or antigen-binding fragments include a heavy chain CDR3 amino acid sequence substantially the same as, or identical to SEQ ID NO: 240, wherein the CDR is defined according to the IMGT method.

In some embodiments, the antibodies or antigen-binding fragments include a light chain CDR1 amino acid sequence substantially the same as, or identical to, SEQ ID NO: 236, a light chain CDR2 amino acid sequence substantially the same as, or identical to, SEQ ID NO: 237, a light chain CDR3 amino acid sequence substantially the same as, or identical to, SEQ ID NO: 235, a heavy chain CDR1 amino acid sequence substantially the same as, or identical to, SEQ ID NO: 241, a heavy chain CDR2 amino acid sequence substantially the same as, or identical to, SEQ ID NO: 198, and a heavy chain CDR3 amino acid sequence substantially the same as, or identical to, SEQ ID NO: 242, wherein the CDRs are defined according to the KABAT method. In some embodiments, the antibodies or antigen-binding fragments include a light chain CDR1 amino acid sequence substantially the same as, or identical to, SEQ ID NO: 236, wherein the CDR is defined according to the KABAT method. In some embodiments, the antibodies or antigen-binding fragments include a light chain CDR2 amino acid sequence substantially the same as, or identical to, SEQ ID NO: 237, wherein the CDR is defined according to the KABAT method. In some embodiments, the antibodies or antigen-binding fragments include a light chain CDR3 amino acid sequence substantially the same as, or identical to, SEQ ID NO: 235, wherein the CDR is defined according to the KABAT method. In some embodiments, the antibodies or antigen-binding fragments include a heavy chain CDR1 amino acid sequence substantially the same as, or identical to, SEQ ID NO: 241, wherein the CDR is defined according to the KABAT method. In some embodiments, the antibodies or antigen-binding fragments include a heavy chain CDR2 substantially the same as, or identical to, amino acid sequence of SEQ ID NO: 198, wherein the CDR is defined according to the KABAT method. In some embodiments, the antibodies or antigen-binding fragments include a heavy chain CDR3 amino acid sequence substantially the same as, or identical to SEQ ID NO: 242, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 257, a light chain CDR2 amino acid sequence substantially the same as, or identical to, SEQ ID NO: 188, a light chain CDR3 amino acid sequence substantially the same as, or identical to, SEQ ID NO: 258, a heavy chain CDR1 amino acid sequence substantially the same as, or identical to, SEQ ID NO: 8, a heavy chain CDR2 amino acid sequence substantially the same as, or identical to, SEQ ID NO: 262, and a heavy chain CDR3 amino acid sequence substantially the same as, or identical to, SEQ ID NO: 263, wherein the CDRs are defined according to the IMGT method. In some embodiments, the antibodies or antigen-binding fragments include a light chain CDR1 amino acid sequence substantially the same as, or identical to, SEQ ID NO: 257. In some embodiments, the antibodies or antigen-binding fragments include a light chain CDR2 amino acid sequence substantially the same as, or identical to, SEQ ID NO: 188, wherein the CDR is defined according to the IMGT method. In some embodiments, the antibodies or antigen-binding fragments include a light chain CDR3 amino acid sequence substantially the same as, or identical to, SEQ ID NO: 258, wherein the CDR is defined according to the IMGT method. In some embodiments, the antibodies or antigen-binding fragments include a heavy chain CDR1 amino acid sequence substantially the same as, or identical to, SEQ ID NO: 8, wherein the CDR is defined according to the IMGT method. In some embodiments, the antibodies or antigen-binding fragments include a heavy chain CDR2 substantially the same as, or identical to, amino acid sequence of SEQ ID NO: 262, wherein the CDR is defined according to the IMGT method. In some embodiments, the antibodies or antigen-binding fragments include a heavy chain CDR3 amino acid sequence substantially the same as, or identical to SEQ ID NO: 263, wherein the CDR is defined according to the IMGT method.

In some embodiments, the antibodies or antigen-binding fragments include a light chain CDR1 amino acid sequence substantially the same as, or identical to, SEQ ID NO: 259, a light chain CDR2 amino acid sequence substantially the same as, or identical to, SEQ ID NO: 191, a light chain CDR3 amino acid sequence substantially the same as, or identical to, SEQ ID NO: 258, a heavy chain CDR1 amino acid sequence substantially the same as, or identical to, SEQ ID NO: 264, a heavy chain CDR2 amino acid sequence substantially the same as, or identical to, SEQ ID NO: 265, and a heavy chain CDR3 amino acid sequence substantially the same as, or identical to, SEQ ID NO: 266, wherein the CDRs are defined according to the KABAT method. In some embodiments, the antibodies or antigen-binding fragments include a light chain CDR1 amino acid sequence substantially the same as, or identical to, SEQ ID NO: 259, wherein the CDR is defined according to the KABAT method. In some embodiments, the antibodies or antigen-binding fragments include a light chain CDR2 amino acid sequence substantially the same as, or identical to, SEQ ID NO: 191, wherein the CDR is defined according to the KABAT method. In some embodiments, the antibodies or antigen-binding fragments include a light chain CDR3 amino acid sequence substantially the same as, or identical to, SEQ ID NO: 258, wherein the CDR is defined according to the KABAT method. In some embodiments, the antibodies or antigen-binding fragments include a heavy chain CDR1 amino acid sequence substantially the same as, or identical to, SEQ ID NO: 264, wherein the CDR is defined according to the KABAT method. In some embodiments, the antibodies or antigen-binding fragments include a heavy chain CDR2 substantially the same as, or identical to, amino acid sequence of SEQ ID NO: 265, wherein the CDR is defined according to the KABAT method. In some embodiments, the antibodies or antigen-binding fragments include a heavy chain CDR3 amino acid sequence substantially the same as, or identical to SEQ ID NO: 266, wherein the CDR is defined according to the KABAT method.

Described herein are isolated antibodies and antigen-binding fragments that specifically bind to FRα. In some embodiments, the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method. In some embodiments, the antibodies or antigen-binding fragments include a light chain CDR1 amino acid sequence substantially the same as, or identical to, SEQ ID NO: 1, wherein the CDR is defined according to the IMGT method. In some embodiments, the antibodies or antigen-binding fragments include a light chain CDR2 amino acid sequence substantially the same as, or identical to, SEQ ID NO: 2, wherein the CDR is defined according to the IMGT method. In some embodiments, the antibodies or antigen-binding fragments include a light chain CDR3 amino acid sequence substantially the same as, or identical to, SEQ ID NO: 3, wherein the CDR is defined according to the IMGT method. In some embodiments, the antibodies or antigen-binding fragments include a heavy chain CDR1 amino acid sequence substantially the same as, or identical to, SEQ ID NO: 8, wherein the CDR is defined according to the IMGT method. In some embodiments, the antibodies or antigen-binding fragments include a heavy chain CDR2 substantially the same as, or identical to, amino acid sequence of SEQ ID NO: 9, wherein the CDR is defined according to the IMGT method. In some embodiments, the antibodies or antigen-binding fragments include a heavy chain CDR3 amino acid sequence substantially the same as, or identical to SEQ ID NO: 10, wherein the CDR is defined according to the IMGT method.

In some embodiments, the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 115, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method. In some embodiments, the antibodies or antigen-binding fragments include a light chain CDR1 amino acid sequence substantially the same as, or identical to, SEQ ID NO: 4, wherein the CDR is defined according to the KABAT method. In some embodiments, the antibodies or antigen-binding fragments include a light chain CDR2 amino acid sequence substantially the same as, or identical to, SEQ ID NO: 115, wherein the CDR is defined according to the KABAT method. In some embodiments, the antibodies or antigen-binding fragments include a light chain CDR3 amino acid sequence substantially the same as, or identical to, SEQ ID NO: 3, wherein the CDR is defined according to the KABAT method. In some embodiments, the antibodies or antigen-binding fragments include a heavy chain CDR1 amino acid sequence substantially the same as, or identical to, SEQ ID NO: 11, wherein the CDR is defined according to the KABAT method. In some embodiments, the antibodies or antigen-binding fragments include a heavy chain CDR2 substantially the same as, or identical to, amino acid sequence of SEQ ID NO: 12, wherein the CDR is defined according to the KABAT method. In some embodiments, the antibodies or antigen-binding fragments include a heavy chain CDR3 amino acid sequence substantially the same as, or identical to SEQ ID NO: 13, wherein the CDR is defined according to the KABAT method.

The antibodies or antigen-binding fragments disclosed in the examples section are derived from mice. Similar antibodies may be derived from any species by recombinant means. For example, the antibodies or antigen-binding fragments may be chimeric rat, goat, horse, swine, bovine, chicken, rabbit, camelid, donkey, human, and the like. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human. For example, a chimeric antibody may comprise a mouse antigen binding domain with a human Fc or other such structural domain.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

Also disclosed are antibodies or antigen-binding fragments comprising a light chain variable region amino acid sequence that is at least 90% identical to the amino acid sequence of SEQ ID NO: 6 and a heavy chain variable region amino acid sequence that is at least 90% identical to the amino acid sequence of SEQ ID NO: 14 where the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method.

Also disclosed are antibodies or antigen-binding fragments comprising a light chain variable region amino acid sequence that is at least 90% identical to the amino acid sequence of SEQ ID NO: 6, and a heavy chain variable region amino acid sequence that is at least 90% identical to the amino acid sequence of SEQ ID NO: 14 where the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method.

Also disclosed are antibodies or antigen-binding fragments comprising a light chain variable region amino acid sequence that is at least 90% identical to the amino acid sequence of SEQ ID NO: 47 and a heavy chain variable region amino acid sequence that is at least 90% identical to the amino acid sequence of SEQ ID NO: 49 where the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method.

Also disclosed are antibodies or antigen-binding fragments comprising a light chain variable region amino acid sequence that is at least 90% identical to the amino acid sequence of SEQ ID NO: 47, and a heavy chain variable region amino acid sequence that is at least 90% identical to the amino acid sequence of SEQ ID NO: 49 where the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method.

Also disclosed are antibodies or antigen-binding fragments comprising a light chain variable region amino acid sequence that is at least 90% identical to the amino acid sequence of SEQ ID NO: 60 and a heavy chain variable region amino acid sequence that is at least 90% identical to the amino acid sequence of SEQ ID NO: 67 where the antibodies or antigen-binding fragments include a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 62, a heavy chain CDR2 amino acid sequence substantially the same as, or identical to, SEQ ID NO: 63, and a heavy chain CDR3 amino acid sequence substantially the same as, or identical to, SEQ ID NO: 64, wherein the CDRs are defined according to the IMGT method.

Also disclosed are antibodies or antigen-binding fragments comprising a light chain variable region amino acid sequence that is at least 90% identical to the amino acid sequence of SEQ ID NO: 60, and a heavy chain variable region amino acid sequence that is at least 90% identical to the amino acid sequence of SEQ ID NO: 67 where the antibodies or antigen-binding fragments include a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 65, a heavy chain CDR2 amino acid sequence substantially the same as, or identical to, SEQ ID NO: 66, and a heavy chain CDR3 amino acid sequence substantially the same as, or identical to, SEQ ID NO: 64, wherein the CDRs are defined according to the KABAT method.

Also disclosed are antibodies or antigen-binding fragments comprising a light chain variable region amino acid sequence that is at least 90% identical to the amino acid sequence of SEQ ID NO: 88 and a heavy chain variable region amino acid sequence that is at least 90% identical to the amino acid sequence of SEQ ID NO: 96 where the antibodies or antigen-binding fragments include a light chain CDR1 amino acid sequence substantially the same as, or identical to, SEQ ID NO: 84, a light chain CDR2 amino acid sequence substantially the same as, or identical to, SEQ ID NO: 85, a light chain CDR3 amino acid sequence substantially the same as, or identical to, SEQ ID NO: 86, a heavy chain CDR1 amino acid sequence substantially the same as, or identical to, SEQ ID NO: 90, a heavy chain CDR2 amino acid sequence substantially the same as, or identical to, SEQ ID NO: 91, and a heavy chain CDR3 amino acid sequence substantially the same as, or identical to, SEQ ID NO: 92, wherein the CDRs are defined according to the IMGT method.

Also disclosed are antibodies or antigen-binding fragments comprising a light chain variable region amino acid sequence that is at least 90% identical to the amino acid sequence of SEQ ID NO: 88, and a heavy chain variable region amino acid sequence that is at least 90% identical to the amino acid sequence of SEQ ID NO: 96 where the antibodies or antigen-binding fragments include a light chain CDR1 amino acid sequence substantially the same as, or identical to, SEQ ID NO: 87, a light chain CDR2 amino acid sequence substantially the same as, or identical to, SEQ ID NO: 32, a light chain CDR3 amino acid sequence substantially the same as, or identical to, SEQ ID NO: 86, a heavy chain CDR1 amino acid sequence substantially the same as, or identical to, SEQ ID NO: 93, a heavy chain CDR2 amino acid sequence substantially the same as, or identical to, SEQ ID NO: 94, and a heavy chain CDR3 amino acid sequence substantially the same as, or identical to, SEQ ID NO: 95, wherein the CDRs are defined according to the KABAT method.

Also disclosed are antibodies or antigen-binding fragments comprising a light chain variable region amino acid sequence that is at least 90% identical to the amino acid sequence of SEQ ID NO: 116 and a heavy chain variable region amino acid sequence that is at least 90% identical to the amino acid sequence of SEQ ID NO: 124 where the antibodies or antigen-binding fragments include a light chain CDR1 amino acid sequence substantially the same as, or identical to, SEQ ID NO: 112, a light chain CDR2 amino acid sequence substantially the same as, or identical to, SEQ ID NO: 2, a light chain CDR3 amino acid sequence substantially the same as, or identical to, SEQ ID NO: 113, a heavy chain CDR1 amino acid sequence substantially the same as, or identical to, SEQ ID NO: 118, a heavy chain CDR2 amino acid sequence substantially the same as, or identical to, SEQ ID NO: 119, and a heavy chain CDR3 amino acid sequence substantially the same as, or identical to, SEQ ID NO: 120, wherein the CDRs are defined according to the IMGT method.

Also disclosed are antibodies or antigen-binding fragments comprising a light chain variable region amino acid sequence that is at least 90% identical to the amino acid sequence of SEQ ID NO: 116, and a heavy chain variable region amino acid sequence that is at least 90% identical to the amino acid sequence of SEQ ID NO: 124 where the antibodies or antigen-binding fragments include a light chain CDR1 amino acid sequence substantially the same as, or identical to, SEQ ID NO: 114, a light chain CDR2 amino acid sequence substantially the same as, or identical to, SEQ ID NO: 115, a light chain CDR3 amino acid sequence substantially the same as, or identical to, SEQ ID NO: 113, a heavy chain CDR1 amino acid sequence substantially the same as, or identical to, SEQ ID NO: 121, a heavy chain CDR2 amino acid sequence substantially the same as, or identical to, SEQ ID NO: 122, and a heavy chain CDR3 amino acid sequence substantially the same as, or identical to, SEQ ID NO: 123, wherein the CDRs are defined according to the KABAT method.

Also disclosed are antibodies or antigen-binding fragments comprising a light chain variable region amino acid sequence that is at least 90% identical to the amino acid sequence of SEQ ID NO: 143 and a heavy chain variable region amino acid sequence that is at least 90% identical to the amino acid sequence of SEQ ID NO: 151 where the antibodies or antigen-binding fragments include a light chain CDR1 amino acid sequence substantially the same as, or identical to, SEQ ID NO: 55, a light chain CDR2 amino acid sequence substantially the same as, or identical to, SEQ ID NO: 140, a light chain CDR3 amino acid sequence substantially the same as, or identical to, SEQ ID NO: 141, a heavy chain CDR1 amino acid sequence substantially the same as, or identical to, SEQ ID NO: 145, a heavy chain CDR2 amino acid sequence substantially the same as, or identical to, SEQ ID NO: 146, and a heavy chain CDR3 amino acid sequence substantially the same as, or identical to, SEQ ID NO: 147, wherein the CDRs are defined according to the IMGT method.

Also disclosed are antibodies or antigen-binding fragments comprising a light chain variable region amino acid sequence that is at least 90% identical to the amino acid sequence of SEQ ID NO: 143, and a heavy chain variable region amino acid sequence that is at least 90% identical to the amino acid sequence of SEQ ID NO: 151 where the antibodies or antigen-binding fragments include a light chain CDR1 amino acid sequence substantially the same as, or identical to, SEQ ID NO: 58, a light chain CDR2 amino acid sequence substantially the same as, or identical to, SEQ ID NO: 142, a light chain CDR3 amino acid sequence substantially the same as, or identical to, SEQ ID NO: 141, a heavy chain CDR1 amino acid sequence substantially the same as, or identical to, SEQ ID NO: 148, a heavy chain CDR2 amino acid sequence substantially the same as, or identical to, SEQ ID NO: 149, and a heavy chain CDR3 amino acid sequence substantially the same as, or identical to, SEQ ID NO: 150, wherein the CDRs are defined according to the KABAT method.

Also disclosed are antibodies or antigen-binding fragments comprising a light chain variable region amino acid sequence that is at least 90% identical to the amino acid sequence of SEQ ID NO: 166 and a heavy chain variable region amino acid sequence that is at least 90% identical to the amino acid sequence of SEQ ID NO: 174 where the antibodies or antigen-binding fragments include a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 168, a heavy chain CDR2 amino acid sequence substantially the same as, or identical to, SEQ ID NO: 169, and a heavy chain CDR3 amino acid sequence substantially the same as, or identical to, SEQ ID NO: 170, wherein the CDRs are defined according to the IMGT method.

Also disclosed are antibodies or antigen-binding fragments comprising a light chain variable region amino acid sequence that is at least 90% identical to the amino acid sequence of SEQ ID NO: 166, and a heavy chain variable region amino acid sequence that is at least 90% identical to the amino acid sequence of SEQ ID NO: 174 where the antibodies or antigen-binding fragments include a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 171, a heavy chain CDR2 amino acid sequence substantially the same as, or identical to, SEQ ID NO: 172, and a heavy chain CDR3 amino acid sequence substantially the same as, or identical to, SEQ ID NO: 173, wherein the CDRs are defined according to the KABAT method.

Also disclosed are antibodies or antigen-binding fragments comprising a light chain variable region amino acid sequence that is at least 90% identical to the amino acid sequence of SEQ ID NO: 192 and a heavy chain variable region amino acid sequence that is at least 90% identical to the amino acid sequence of SEQ ID NO: 200 where the antibodies or antigen-binding fragments include a light chain CDR1 amino acid sequence substantially the same as, or identical to, SEQ ID NO: 187, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 196, wherein the CDRs are defined according to the IMGT method.

Also disclosed are antibodies or antigen-binding fragments comprising a light chain variable region amino acid sequence that is at least 90% identical to the amino acid sequence of SEQ ID NO: 192, and a heavy chain variable region amino acid sequence that is at least 90% identical to the amino acid sequence of SEQ ID NO: 200 where the antibodies or antigen-binding fragments include a light chain CDR1 amino acid sequence substantially the same as, or identical to, SEQ ID NO: 190, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 198, and a heavy chain CDR3 amino acid sequence substantially the same as, or identical to, SEQ ID NO: 199, wherein the CDRs are defined according to the KABAT method.

Also disclosed are antibodies or antigen-binding fragments comprising a light chain variable region amino acid sequence that is at least 90% identical to the amino acid sequence of SEQ ID NO: 219 and a heavy chain variable region amino acid sequence that is at least 90% identical to the amino acid sequence of SEQ ID NO: 223 where the antibodies or antigen-binding fragments include a light chain CDR1 amino acid sequence substantially the same as, or identical to, SEQ ID NO: 217, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 221, and a heavy chain CDR3 amino acid sequence substantially the same as, or identical to, SEQ ID NO: 196, wherein the CDRs are defined according to the IMGT method.

Also disclosed are antibodies or antigen-binding fragments comprising a light chain variable region amino acid sequence that is at least 90% identical to the amino acid sequence of SEQ ID NO: 219, and a heavy chain variable region amino acid sequence that is at least 90% identical to the amino acid sequence of SEQ ID NO: 223 where the antibodies or antigen-binding fragments include a light chain CDR1 amino acid sequence substantially the same as, or identical to, SEQ ID NO: 218, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 222, and a heavy chain CDR3 amino acid sequence substantially the same as, or identical to, SEQ ID NO: 199, wherein the CDRs are defined according to the KABAT method.

Also disclosed are antibodies or antigen-binding fragments comprising a light chain variable region amino acid sequence that is at least 90% identical to the amino acid sequence of SEQ ID NO: 238 and a heavy chain variable region amino acid sequence that is at least 90% identical to the amino acid sequence of SEQ ID NO: 243 where the antibodies or antigen-binding fragments include a light chain CDR1 amino acid sequence substantially the same as, or identical to, SEQ ID NO: 233, a light chain CDR2 amino acid sequence substantially the same as, or identical to, SEQ ID NO: 234, a light chain CDR3 amino acid sequence substantially the same as, or identical to, SEQ ID NO: 235, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 240, wherein the CDRs are defined according to the IMGT method.

Also disclosed are antibodies or antigen-binding fragments comprising a light chain variable region amino acid sequence that is at least 90% identical to the amino acid sequence of SEQ ID NO: 238, and a heavy chain variable region amino acid sequence that is at least 90% identical to the amino acid sequence of SEQ ID NO: 243 where the antibodies or antigen-binding fragments include a light chain CDR1 amino acid sequence substantially the same as, or identical to, SEQ ID NO: 236, a light chain CDR2 amino acid sequence substantially the same as, or identical to, SEQ ID NO: 237, a light chain CDR3 amino acid sequence substantially the same as, or identical to, SEQ ID NO: 235, a heavy chain CDR1 amino acid sequence substantially the same as, or identical to, SEQ ID NO: 241, a heavy chain CDR2 amino acid sequence substantially the same as, or identical to, SEQ ID NO: 198, and a heavy chain CDR3 amino acid sequence substantially the same as, or identical to, SEQ ID NO: 242, wherein the CDRs are defined according to the KABAT method.

Also disclosed are antibodies or antigen-binding fragments comprising a light chain variable region amino acid sequence that is at least 90% identical to the amino acid sequence of SEQ ID NO: 260 and a heavy chain variable region amino acid sequence that is at least 90% identical to the amino acid sequence of SEQ ID NO: 267 where the antibodies or antigen-binding fragments include a light chain CDR1 amino acid sequence substantially the same as, or identical to, SEQ ID NO: 257, a light chain CDR2 amino acid sequence substantially the same as, or identical to, SEQ ID NO: 188, a light chain CDR3 amino acid sequence substantially the same as, or identical to, SEQ ID NO: 258, a heavy chain CDR1 amino acid sequence substantially the same as, or identical to, SEQ ID NO: 8, a heavy chain CDR2 amino acid sequence substantially the same as, or identical to, SEQ ID NO: 262, and a heavy chain CDR3 amino acid sequence substantially the same as, or identical to, SEQ ID NO: 263, wherein the CDRs are defined according to the IMGT method.

Also disclosed are antibodies or antigen-binding fragments comprising a light chain variable region amino acid sequence that is at least 90% identical to the amino acid sequence of SEQ ID NO: 260, and a heavy chain variable region amino acid sequence that is at least 90% identical to the amino acid sequence of SEQ ID NO: 267 where the antibodies or antigen-binding fragments include a light chain CDR1 amino acid sequence substantially the same as, or identical to, SEQ ID NO: 259, a light chain CDR2 amino acid sequence substantially the same as, or identical to, SEQ ID NO: 191, a light chain CDR3 amino acid sequence substantially the same as, or identical to, SEQ ID NO: 258, a heavy chain CDR1 amino acid sequence substantially the same as, or identical to, SEQ ID NO: 264, a heavy chain CDR2 amino acid sequence substantially the same as, or identical to, SEQ ID NO: 265, and a heavy chain CDR3 amino acid sequence substantially the same as, or identical to, SEQ ID NO: 266, wherein the CDRs are defined according to the KABAT method.

Also disclosed are antibodies or antigen-binding fragments comprising a light chain variable region amino acid sequence that is at least 90% identical to the amino acid sequence of SEQ ID NO: 282 and a heavy chain variable region amino acid sequence that is at least 90% identical to the amino acid sequence of SEQ ID NO: 284 where the antibodies or antigen-binding fragments include a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method.

Also disclosed are antibodies or antigen-binding fragments comprising a light chain variable region amino acid sequence that is at least 90% identical to the amino acid sequence of SEQ ID NO: 282, and a heavy chain variable region amino acid sequence that is at least 90% identical to the amino acid sequence of SEQ ID NO: 284 where the antibodies or antigen-binding fragments include a light chain CDR1 amino acid sequence substantially the same as, or identical to, SEQ ID NO: 4, a light chain CDR2 amino acid sequence substantially the same as, or identical to, SEQ ID NO: 115, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method.

Also disclosed are isolated antibodies or antigen-binding fragments specific for FRα which include a light chain variable region amino acid sequence substantially the same as, or identical to, SEQ ID NO: 6. In some embodiments, the isolated antibody or antigen-binding fragment includes a heavy chain variable region amino acid sequence substantially the same as, or identical to, SEQ ID NO: 14. In some embodiments, the isolated antibody or antigen-binding fragment includes a light chain variable region amino acid sequence substantially the same as, or identical to, SEQ ID NO: 6 and a heavy chain variable region amino acid sequence substantially the same as, or identical to, SEQ ID NO: 14.

Also disclosed are isolated antibodies or antigen-binding fragments specific for FRα which include a light chain amino acid sequence substantially the same as, or identical to, SEQ ID NO: 7. In some embodiments, the isolated antibody or antigen-binding fragment includes a heavy chain amino acid sequence substantially the same as, or identical to, SEQ ID NO: 15. In some embodiments, the isolated antibody or antigen-binding fragment includes a light chain amino acid sequence substantially the same as, or identical to, SEQ ID NO: 7 and a heavy chain amino acid sequence substantially the same as, or identical to, SEQ ID NO: 15.

Also disclosed are isolated antibodies or antigen-binding fragments specific for FRα which include a light chain variable region amino acid sequence substantially the same as, or identical to, SEQ ID NO: 47. In some embodiments, the isolated antibody or antigen-binding fragment includes a heavy chain variable region amino acid sequence substantially the same as, or identical to, SEQ ID NO: 49. In some embodiments, the isolated antibody or antigen-binding fragment includes a light chain variable region amino acid sequence substantially the same as, or identical to, SEQ ID NO: 47 and a heavy chain variable region amino acid sequence substantially the same as, or identical to, SEQ ID NO: 49.

Also disclosed are isolated antibodies or antigen-binding fragments specific for FRα which include a light chain amino acid sequence substantially the same as, or identical to, SEQ ID NO: 48. In some embodiments, the isolated antibody or antigen-binding fragment includes a heavy chain amino acid sequence substantially the same as, or identical to, SEQ ID NO: 50. In some embodiments, the isolated antibody or antigen-binding fragment includes a light chain amino acid sequence substantially the same as, or identical to, SEQ ID NO: 48 and a heavy chain amino acid sequence substantially the same as, or identical to, SEQ ID NO: 50.

Also disclosed are isolated antibodies or antigen-binding fragments specific for FRα which include a light chain variable region amino acid sequence substantially the same as, or identical to, SEQ ID NO: 60. In some embodiments, the isolated antibody or antigen-binding fragment includes a heavy chain variable region amino acid sequence substantially the same as, or identical to, SEQ ID NO: 67. In some embodiments, the isolated antibody or antigen-binding fragment includes a light chain variable region amino acid sequence substantially the same as, or identical to, SEQ ID NO: 60 and a heavy chain variable region amino acid sequence substantially the same as, or identical to, SEQ ID NO: 67.

Also disclosed are isolated antibodies or antigen-binding fragments specific for FRα which include a light chain amino acid sequence substantially the same as, or identical to, SEQ ID NO: 61. In some embodiments, the isolated antibody or antigen-binding fragment includes a heavy chain amino acid sequence substantially the same as, or identical to, SEQ ID NO: 68. In some embodiments, the isolated antibodies or antigen-binding fragments include a light chain amino acid sequence substantially the same as, or identical to, SEQ ID NO: 61 and a heavy chain amino acid sequence substantially the same as, or identical to, SEQ ID NO: 68.

Also disclosed are isolated antibodies or antigen-binding fragments specific for FRα which include a light chain variable region amino acid sequence substantially the same as, or identical to, SEQ ID NO: 88. In some embodiments, the isolated antibody or antigen-binding fragment includes a heavy chain variable region amino acid sequence substantially the same as, or identical to, SEQ ID NO: 96. In some embodiments, the isolated antibody or antigen-binding fragment includes a light chain variable region amino acid sequence substantially the same as, or identical to, SEQ ID NO: 88 and a heavy chain variable region amino acid sequence substantially the same as, or identical to, SEQ ID NO: 96.

Also disclosed are isolated antibodies or antigen-binding fragments specific for FRα which include a light chain amino acid sequence substantially the same as, or identical to, SEQ ID NO: 89. In some embodiments, the isolated antibody or antigen-binding fragment includes a heavy chain amino acid sequence substantially the same as, or identical to, SEQ ID NO: 97. In some embodiments, the isolated antibody or antigen-binding fragment includes a light chain amino acid sequence substantially the same as, or identical to, SEQ ID NO: 89 and a heavy chain amino acid sequence substantially the same as, or identical to, SEQ ID NO: 97.

Also disclosed are isolated antibodies or antigen-binding fragments specific for FRα which include a light chain variable region amino acid sequence substantially the same as, or identical to, SEQ ID NO: 116. In some embodiments, the isolated antibody or antigen-binding fragment includes a heavy chain variable region amino acid sequence substantially the same as, or identical to, SEQ ID NO: 124. In some embodiments, the isolated antibody or antigen-binding fragment includes a light chain variable region amino acid sequence substantially the same as, or identical to, SEQ ID NO: 116 and a heavy chain variable region amino acid sequence substantially the same as, or identical to, SEQ ID NO: 124.

Also disclosed are isolated antibodies or antigen-binding fragments specific for FRα which include a light chain amino acid sequence substantially the same as, or identical to, SEQ ID NO: 117. In some embodiments, the isolated antibody or antigen-binding fragment includes a heavy chain amino acid sequence substantially the same as, or identical to, SEQ ID NO: 125. In some embodiments, the isolated antibody or antigen-binding fragment includes a light chain amino acid sequence substantially the same as, or identical to, SEQ ID NO: 117 and a heavy chain amino acid sequence substantially the same as, or identical to, SEQ ID NO: 125.

Also disclosed are isolated antibodies or antigen-binding fragments specific for FRα which include a light chain variable region amino acid sequence substantially the same as, or identical to, SEQ ID NO: 143. In some embodiments, the isolated antibody or antigen-binding fragment includes a heavy chain variable region amino acid sequence substantially the same as, or identical to, SEQ ID NO: 151. In some embodiments, the isolated antibody or antigen-binding fragment includes a light chain variable region amino acid sequence substantially the same as, or identical to, SEQ ID NO: 143 and a heavy chain variable region amino acid sequence substantially the same as, or identical to, SEQ ID NO: 151.

Also disclosed are isolated antibodies or antigen-binding fragments specific for FRα which include a light chain amino acid sequence substantially the same as, or identical to, SEQ ID NO: 144. In some embodiments, the isolated antibody or antigen-binding fragment includes a heavy chain amino acid sequence substantially the same as, or identical to, SEQ ID NO: 152. In some embodiments, the isolated antibody or antigen-binding fragment includes a light chain amino acid sequence substantially the same as, or identical to, SEQ ID NO: 144 and a heavy chain amino acid sequence substantially the same as, or identical to, SEQ ID NO: 152.

Also disclosed are isolated antibodies or antigen-binding fragments specific for FRα which include a light chain variable region amino acid sequence substantially the same as, or identical to, SEQ ID NO: 166. In some embodiments, the isolated antibody or antigen-binding fragment includes a heavy chain variable region amino acid sequence substantially the same as, or identical to, SEQ ID NO: 174. In some embodiments, the isolated antibody or antigen-binding fragment includes a light chain variable region amino acid sequence substantially the same as, or identical to, SEQ ID NO: 166 and a heavy chain variable region amino acid sequence substantially the same as, or identical to, SEQ ID NO: 174.

Also disclosed are isolated antibodies or antigen-binding fragments specific for FRα may include a light chain amino acid sequence substantially the same as, or identical to, SEQ ID NO: 167. In some embodiments, the isolated antibody or antigen-binding fragment includes a heavy chain amino acid sequence substantially the same as, or identical to, SEQ ID NO: 175. In some embodiments, the isolated antibody or antigen-binding fragment includes a light chain amino acid sequence substantially the same as, or identical to, SEQ ID NO: 167 and a heavy chain amino acid sequence substantially the same as, or identical to, SEQ ID NO: 175.

Also disclosed are isolated antibodies or antigen-binding fragments specific for FRα which include a light chain variable region amino acid sequence substantially the same as, or identical to, SEQ ID NO: 192. In some embodiments, the isolated antibody or antigen-binding fragment includes a heavy chain variable region amino acid sequence substantially the same as, or identical to, SEQ ID NO: 200. In some embodiments, the isolated antibody or antigen-binding fragment includes a light chain variable region amino acid sequence substantially the same as, or identical to, SEQ ID NO: 192 and a heavy chain variable region amino acid sequence substantially the same as, or identical to, SEQ ID NO: 200.

Also disclosed are isolated antibodies or antigen-binding fragments specific for FRα which include a light chain amino acid sequence substantially the same as, or identical to, SEQ ID NO: 193. In some embodiments, the isolated antibody or antigen-binding fragment includes a heavy chain amino acid sequence substantially the same as, or identical to, SEQ ID NO: 201. In some embodiments, the isolated antibody or antigen-binding fragment includes a light chain amino acid sequence substantially the same as, or identical to, SEQ ID NO: 193 and a heavy chain amino acid sequence substantially the same as, or identical to, SEQ ID NO: 201.

Also disclosed are isolated antibodies or antigen-binding fragments specific for FRα which include a light chain variable region amino acid sequence substantially the same as, or identical to, SEQ ID NO: 219. In some embodiments, the isolated antibody or antigen-binding fragment includes a heavy chain variable region amino acid sequence substantially the same as, or identical to, SEQ ID NO: 223. In some embodiments, the isolated antibody or antigen-binding fragment includes a light chain variable region amino acid sequence substantially the same as, or identical to, SEQ ID NO: 219 and a heavy chain variable region amino acid sequence substantially the same as, or identical to, SEQ ID NO: 223.

Also disclosed are isolated antibodies or antigen-binding fragments specific for FRα which include a light chain amino acid sequence substantially the same as, or identical to, SEQ ID NO: 220. In some embodiments, the isolated antibody or antigen-binding fragment includes a heavy chain amino acid sequence substantially the same as, or identical to, SEQ ID NO: 224. In some embodiments, the isolated antibody or antigen-binding fragment includes a light chain amino acid sequence substantially the same as, or identical to, SEQ ID NO: 220 and a heavy chain amino acid sequence substantially the same as, or identical to, SEQ ID NO: 224.

Also disclosed are isolated antibodies or antigen-binding fragments specific for FRα which include a light chain variable region amino acid sequence substantially the same as, or identical to, SEQ ID NO: 238. In some embodiments, the isolated antibody or antigen-binding fragment includes a heavy chain variable region amino acid sequence substantially the same as, or identical to, SEQ ID NO: 243. In some embodiments, the isolated antibody or antigen-binding fragment includes a light chain variable region amino acid sequence substantially the same as, or identical to, SEQ ID NO: 238 and a heavy chain variable region amino acid sequence substantially the same as, or identical to, SEQ ID NO: 243.

Also disclosed are isolated antibodies or antigen-binding fragments specific for FRα which include a light chain amino acid sequence substantially the same as, or identical to, SEQ ID NO: 239. In some embodiments, the isolated antibody or antigen-binding fragment includes a heavy chain amino acid sequence substantially the same as, or identical to, SEQ ID NO: 244. In some embodiments, the isolated antibody or antigen-binding fragment includes a light chain amino acid sequence substantially the same as, or identical to, SEQ ID NO: 239 and a heavy chain amino acid sequence substantially the same as, or identical to, SEQ ID NO: 244.

Also disclosed are isolated antibodies or antigen-binding fragments specific for FRα which include a light chain variable region amino acid sequence substantially the same as, or identical to, SEQ ID NO: 260. In some embodiments, the isolated antibody or antigen-binding fragment includes a heavy chain variable region amino acid sequence substantially the same as, or identical to, SEQ ID NO: 267. In some embodiments, the isolated antibody or antigen-binding fragment includes a light chain variable region amino acid sequence substantially the same as, or identical to, SEQ ID NO: 260 and a heavy chain variable region amino acid sequence substantially the same as, or identical to, SEQ ID NO: 267.

Also disclosed are isolated antibodies or antigen-binding fragments specific for FRα which include a light chain amino acid sequence substantially the same as, or identical to, SEQ ID NO: 261. In some embodiments, the isolated antibody or antigen-binding fragment includes a heavy chain amino acid sequence substantially the same as, or identical to, SEQ ID NO: 268. In some embodiments, the isolated antibody or antigen-binding fragment includes a light chain amino acid sequence substantially the same as, or identical to, SEQ ID NO: 261 and a heavy chain amino acid sequence substantially the same as, or identical to, SEQ ID NO: 268.

Also disclosed are isolated antibodies or antigen-binding fragments specific for FRα which include a light chain variable region amino acid sequence substantially the same as, or identical to, SEQ ID NO: 282. In some embodiments, the isolated antibody or antigen-binding fragment includes a heavy chain variable region amino acid sequence substantially the same as, or identical to, SEQ ID NO: 284. In some embodiments, the isolated antibody or antigen-binding fragment includes a light chain variable region amino acid sequence substantially the same as, or identical to, SEQ ID NO: 282 and a heavy chain variable region amino acid sequence substantially the same as, or identical to, SEQ ID NO: 284.

Also disclosed are isolated antibodies or antigen-binding fragments specific for FRα which include a light chain amino acid sequence substantially the same as, or identical to, SEQ ID NO: 283. In some embodiments, the isolated antibody or antigen-binding fragment includes a heavy chain amino acid sequence substantially the same as, or identical to, SEQ ID NO: 285. In some embodiments, the isolated antibody or antigen-binding fragment includes a light chain amino acid sequence substantially the same as, or identical to, SEQ ID NO: 283 and a heavy chain amino acid sequence substantially the same as, or identical to, SEQ ID NO: 285.

In some embodiments, the FRα antibody is produced by antibody-producing cells deposited with the American Type Culture Collection (10801 University Blvd., Manassas, Va. 20110-2209) on May 5, 2016 and assigned Accession No. PTA-123090. In some embodiments, the FRα antibody is produced by antibody-producing cells deposited with the American Type Culture Collection (10801 University Blvd., Manassas, Va. 20110-2209) on May 4, 2016 and assigned Accession No. PTA-123097. In some embodiments, the FRα antibody is produced by antibody-producing cells deposited with the American Type Culture Collection (10801 University Blvd., Manassas, Va. 20110-2209) on May 4, 2016 and assigned Accession No. PTA-123091. In some embodiments, the FRα antibody is produced by antibody-producing cells deposited with the American Type Culture Collection (10801 University Blvd., Manassas, Va. 20110-2209) on May 4, 2016 and assigned Accession No. PTA-123098. In some embodiments, the FRα antibody is produced by antibody-producing cells deposited with the American Type Culture Collection (10801 University Blvd., Manassas, Va. 20110-2209) on May 4, 2016 and assigned Accession No. PTA-123093. In some embodiments, the FRα antibody is produced by antibody-producing cells deposited with the American Type Culture Collection (10801 University Blvd., Manassas, Va. 20110-2209) on May 4, 2016 and assigned Accession No. PTA-123094. In some embodiments, the FRα antibody is produced by antibody-producing cells deposited with the American Type Culture Collection (10801 University Blvd., Manassas, Va. 20110-2209) on May 4, 2016 and assigned Accession No. PTA-123092. In some embodiments, the FRα antibody is produced by antibody-producing cells deposited with the American Type Culture Collection (10801 University Blvd., Manassas, Va. 20110-2209) on May 4, 2016 and assigned Accession No. PTA-123098. In some embodiments, the FRα antibody is produced by antibody-producing cells deposited with the American Type Culture Collection (10801 University Blvd., Manassas, Va. 20110-2209) on May 4, 2016 and assigned Accession No. PTA-123095. In some embodiments, the FRα antibody is produced by antibody-producing cells deposited with the American Type Culture Collection (10801 University Blvd., Manassas, Va. 20110-2209) on May 4, 2016 and assigned Accession No. PTA-123101. In some embodiments, the FRα antibody is produced by antibody-producing cells deposited with the American Type Culture Collection (10801 University Blvd., Manassas, Va. 20110-2209) on May 4, 2016 and assigned Accession No. PTA-123096. In some embodiments, the FRα antibody is produced by antibody-producing cells deposited with the American Type Culture Collection (10801 University Blvd., Manassas, Va. 20110-2209) on May 4, 2016 and assigned Accession No. PTA-123100. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides which have a nucleotide sequence substantially the same as, or identical to, SEQ ID NO: 21. In some embodiments, the isolated polynucleotides have a nucleotide sequence substantially the same as, or identical to, SEQ ID NO: 29. In some embodiments, the isolated polynucleotides have a nucleotide sequence substantially the same as, or identical to, SEQ ID NO: 21 and a nucleotide sequence substantially the same as, or identical to, SEQ ID NO: 29.

Also disclosed are isolated polynucleotides which have a nucleotide sequence substantially the same as, or identical to, SEQ ID NO: 22. In some embodiments, the isolated polynucleotides have a nucleotide sequence substantially the same as, or identical to, SEQ ID NO: 30. In some embodiments, the isolated polynucleotides have a nucleotide sequence substantially the same as, or identical to, SEQ ID NO: 22 and a nucleotide sequence substantially the same as, or identical to, SEQ ID NO: 30.

Also disclosed are isolated polynucleotides which have a nucleotide sequence substantially the same as, or identical to, SEQ ID NO: 51. In some embodiments, the isolated polynucleotides have a nucleotide sequence substantially the same as, or identical to, SEQ ID NO: 53. In some embodiments, the isolated polynucleotides have a nucleotide sequence substantially the same as, or identical to, SEQ ID NO: 51 and a nucleotide sequence substantially the same as, or identical to, SEQ ID NO: 53.

Also disclosed are isolated polynucleotides which have a nucleotide sequence substantially the same as, or identical to, SEQ ID NO: 52. In some embodiments, the isolated polynucleotides have a nucleotide sequence substantially the same as, or identical to, SEQ ID NO: 54. In some embodiments, the isolated polynucleotides have a nucleotide sequence substantially the same as, or identical to, SEQ ID NO: 52 and a nucleotide sequence substantially the same as, or identical to, SEQ ID NO: 54.

Also disclosed are isolated polynucleotides which have a nucleotide sequence substantially the same as, or identical to, SEQ ID NO: 74. In some embodiments, the isolated polynucleotides have a nucleotide sequence substantially the same as, or identical to, SEQ ID NO: 82. In some embodiments, the isolated polynucleotides have a nucleotide sequence substantially the same as, or identical to, SEQ ID NO: 74 and a nucleotide sequence substantially the same as, or identical to, SEQ ID NO: 82.

Also disclosed are isolated polynucleotides which have a nucleotide sequence substantially the same as, or identical to, SEQ ID NO: 75. In some embodiments, the isolated polynucleotides have a nucleotide sequence substantially the same as, or identical to, SEQ ID NO: 83. In some embodiments, the isolated polynucleotides have a nucleotide sequence substantially the same as, or identical to, SEQ ID NO: 75 and a nucleotide sequence substantially the same as, or identical to, SEQ ID NO: 83.

Also disclosed are isolated polynucleotides which have a nucleotide sequence substantially the same as, or identical to, SEQ ID NO: 102. In some embodiments, the isolated polynucleotides have a nucleotide sequence substantially the same as, or identical to, SEQ ID NO: 110. In some embodiments, the isolated polynucleotides have a nucleotide sequence substantially the same as, or identical to, SEQ ID NO: 102 and a nucleotide sequence substantially the same as, or identical to, SEQ ID NO: 110.

Also disclosed are isolated polynucleotides which have a nucleotide sequence substantially the same as, or identical to, SEQ ID NO: 103. In some embodiments, the isolated polynucleotides have a nucleotide sequence substantially the same as, or identical to, SEQ ID NO: 111. In some embodiments, the isolated polynucleotides have a nucleotide sequence substantially the same as, or identical to, SEQ ID NO: 103 and a nucleotide sequence substantially the same as, or identical to, SEQ ID NO: 111.

Also disclosed are isolated polynucleotides which have a nucleotide sequence substantially the same as, or identical to, SEQ ID NO: 130. In some embodiments, the isolated polynucleotides have a nucleotide sequence substantially the same as, or identical to, SEQ ID NO: 138. In some embodiments, the isolated polynucleotides have a nucleotide sequence substantially the same as, or identical to, SEQ ID NO: 130 and a nucleotide sequence substantially the same as, or identical to, SEQ ID NO: 138.

Also disclosed are isolated polynucleotides which have a nucleotide sequence substantially the same as, or identical to, SEQ ID NO: 131. In some embodiments, the isolated polynucleotides have a nucleotide sequence substantially the same as, or identical to, SEQ ID NO: 139. In some embodiments, the isolated polynucleotides have a nucleotide sequence substantially the same as, or identical to, SEQ ID NO: 131 and a nucleotide sequence substantially the same as, or identical to, SEQ ID NO: 139.

Also disclosed are isolated polynucleotides which have a nucleotide sequence substantially the same as, or identical to, SEQ ID NO: 156. In some embodiments, the isolated polynucleotides have a nucleotide sequence substantially the same as, or identical to, SEQ ID NO: 164. In some embodiments, the isolated polynucleotides have a nucleotide sequence substantially the same as, or identical to, SEQ ID NO: 156 and a nucleotide sequence substantially the same as, or identical to, SEQ ID NO: 164.

Also disclosed are isolated polynucleotides which have a nucleotide sequence substantially the same as, or identical to, SEQ ID NO: 157. In some embodiments, the isolated polynucleotides have a nucleotide sequence substantially the same as, or identical to, SEQ ID NO: 165. In some embodiments, the isolated polynucleotides have a nucleotide sequence substantially the same as, or identical to, SEQ ID NO: 157 and a nucleotide sequence substantially the same as, or identical to, SEQ ID NO: 165.

Also disclosed are isolated polynucleotides which have a nucleotide sequence substantially the same as, or identical to, SEQ ID NO: 177. In some embodiments, the isolated polynucleotides have a nucleotide sequence substantially the same as, or identical to, SEQ ID NO: 185. In some embodiments, the isolated polynucleotides have a nucleotide sequence substantially the same as, or identical to, SEQ ID NO: 177 and a nucleotide sequence substantially the same as, or identical to, SEQ ID NO: 185.

Also disclosed are isolated polynucleotides which have a nucleotide sequence substantially the same as, or identical to, SEQ ID NO: 178. In some embodiments, the isolated polynucleotides have a nucleotide sequence substantially the same as, or identical to, SEQ ID NO: 186. In some embodiments, the isolated polynucleotides have a nucleotide sequence substantially the same as, or identical to, SEQ ID NO: 178 and a nucleotide sequence substantially the same as, or identical to, SEQ ID NO: 186.

Also disclosed are isolated polynucleotides which have a nucleotide sequence substantially the same as, or identical to, SEQ ID NO: 207. In some embodiments, the isolated polynucleotides have a nucleotide sequence substantially the same as, or identical to, SEQ ID NO: 215. In some embodiments, the isolated polynucleotides have a nucleotide sequence substantially the same as, or identical to, SEQ ID NO: 207 and a nucleotide sequence substantially the same as, or identical to, SEQ ID NO: 215.

Also disclosed are isolated polynucleotides which have a nucleotide sequence substantially the same as, or identical to, SEQ ID NO: 208. In some embodiments, the isolated polynucleotides have a nucleotide sequence substantially the same as, or identical to, SEQ ID NO: 216. In some embodiments, the isolated polynucleotides have a nucleotide sequence substantially the same as, or identical to, SEQ ID NO: 208 and a nucleotide sequence substantially the same as, or identical to, SEQ ID NO: 216.

Also disclosed are isolated polynucleotides which have a nucleotide sequence substantially the same as, or identical to, SEQ ID NO: 227. In some embodiments, the isolated polynucleotides have a nucleotide sequence substantially the same as, or identical to, SEQ ID NO: 231. In some embodiments, the isolated polynucleotides have a nucleotide sequence substantially the same as, or identical to, SEQ ID NO: 227 and a nucleotide sequence substantially the same as, or identical to, SEQ ID NO: 231.

Also disclosed are isolated polynucleotides which have a nucleotide sequence substantially the same as, or identical to, SEQ ID NO: 228. In some embodiments, the isolated polynucleotides have a nucleotide sequence substantially the same as, or identical to, SEQ ID NO: 232. In some embodiments, the isolated polynucleotides have a nucleotide sequence substantially the same as, or identical to, SEQ ID NO: 228 and a nucleotide sequence substantially the same as, or identical to, SEQ ID NO: 232.

Also disclosed are isolated polynucleotides which have a nucleotide sequence substantially the same as, or identical to, SEQ ID NO: 250. In some embodiments, the isolated polynucleotides have a nucleotide sequence substantially the same as, or identical to, SEQ ID NO: 255. In some embodiments, the isolated polynucleotides have a nucleotide sequence substantially the same as, or identical to, SEQ ID NO: 250 and a nucleotide sequence substantially the same as, or identical to, SEQ ID NO: 255.

Also disclosed are isolated polynucleotides which have a nucleotide sequence substantially the same as, or identical to, SEQ ID NO: 251. In some embodiments, the isolated polynucleotides have a nucleotide sequence substantially the same as, or identical to, SEQ ID NO: 256. In some embodiments, the isolated polynucleotides have a nucleotide sequence substantially the same as, or identical to, SEQ ID NO: 251 and a nucleotide sequence substantially the same as, or identical to, SEQ ID NO: 256.

Also disclosed are isolated polynucleotides which have a nucleotide sequence substantially the same as, or identical to, SEQ ID NO: 272. In some embodiments, the isolated polynucleotides have a nucleotide sequence substantially the same as, or identical to, SEQ ID NO: 280. In some embodiments, the isolated polynucleotides have a nucleotide sequence substantially the same as, or identical to, SEQ ID NO: 272 and a nucleotide sequence substantially the same as, or identical to, SEQ ID NO: 280.

Also disclosed are isolated polynucleotides which have a nucleotide sequence substantially the same as, or identical to, SEQ ID NO: 273. In some embodiments, the isolated polynucleotides have a nucleotide sequence substantially the same as, or identical to, SEQ ID NO: 281. In some embodiments, the isolated polynucleotides have a nucleotide sequence substantially the same as, or identical to, SEQ ID NO: 273 and a nucleotide sequence substantially the same as, or identical to, SEQ ID NO: 281.

Also disclosed are isolated polynucleotides which have a nucleotide sequence substantially the same as, or identical to, SEQ ID NO: 286. In some embodiments, the isolated polynucleotides have a nucleotide sequence substantially the same as, or identical to, SEQ ID NO: 291. In some embodiments, the isolated polynucleotides have a nucleotide sequence substantially the same as, or identical to, SEQ ID NO: 286 and a nucleotide sequence substantially the same as, or identical to, SEQ ID NO: 291.

Also disclosed are isolated polynucleotides which have a nucleotide sequence substantially the same as, or identical to, SEQ ID NO: 287. In some embodiments, the isolated polynucleotides have a nucleotide sequence substantially the same as, or identical to, SEQ ID NO: 292. In some embodiments, the isolated polynucleotides have a nucleotide sequence substantially the same as, or identical to, SEQ ID NO: 287 and a nucleotide sequence substantially the same as, or identical to, SEQ ID NO: 292.

Also disclosed are isolated polynucleotides that encode an antibody or antigen-binding fragment comprising a light chain variable region, wherein the light chain variable region amino acid sequence is substantially the same as, or identical to, SEQ ID NO: 6. In some embodiments, the isolated polynucleotides encode an antibody or antigen-binding fragment comprising a heavy chain variable region, wherein the heavy chain variable region amino acid sequence is substantially the same as, or identical to, SEQ ID NO: 14. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 6 and the heavy chain variable region amino acid sequence is substantially the same as, or identical to, SEQ ID NO: 14.

Also disclosed are isolated polynucleotides that encode an antibody comprising a light chain, wherein the light chain amino acid sequence is substantially the same as, or identical to, SEQ ID NO: 7. In some embodiments, the isolated polynucleotides encode an antibody comprising a heavy chain, wherein the heavy chain amino acid sequence is substantially the same as, or identical to, SEQ ID NO: 15. In some embodiments, the isolated polynucleotides encode an antibody or antigen-binding fragment comprising a light chain and a heavy chain, wherein the light chain amino acid sequence is substantially the same as, or identical to, SEQ ID NO: 7 and the heavy chain amino acid sequence is substantially the same as, or identical to, SEQ ID NO: 15.

Also disclosed are isolated polynucleotides that encode an antibody or antigen-binding fragment comprising a light chain variable region, wherein the light chain variable region amino acid sequence is substantially the same as, or identical to, SEQ ID NO: 47. In some embodiments, the isolated polynucleotides encode an antibody or antigen-binding fragment comprising a heavy chain variable region, wherein the heavy chain variable region amino acid sequence is substantially the same as, or identical to, SEQ ID NO: 49. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 47 and the heavy chain variable region amino acid sequence is substantially the same as, or identical to, SEQ ID NO: 49.

Also disclosed are isolated polynucleotides that encode an antibody comprising a light chain, wherein the light chain amino acid sequence is substantially the same as, or identical to, SEQ ID NO: 48. In some embodiments, the isolated polynucleotides encode an antibody comprising a heavy chain, wherein the heavy chain amino acid sequence is substantially the same as, or identical to, SEQ ID NO: 50. In some embodiments, the isolated polynucleotides encode an antibody comprising a light chain and a heavy chain, wherein the light chain amino acid sequence substantially the same as, or identical to, SEQ ID NO: 48 and a heavy chain amino acid sequence substantially the same as, or identical to, SEQ ID NO: 50.

Also disclosed are isolated polynucleotides that encode an antibody or antigen-binding fragment comprising a light chain variable region, wherein the light chain variable region amino acid sequence is substantially the same as, or identical to, SEQ ID NO: 60. In some embodiments, the isolated polynucleotides encode an antibody or antigen-binding fragment comprising a heavy chain variable region, wherein the heavy chain variable region amino acid sequence is substantially the same as, or identical to, SEQ ID NO: 67. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 60 and the heavy chain variable region amino acid sequence is substantially the same as, or identical to, SEQ ID NO: 67.

Also disclosed are isolated polynucleotides that encode an antibody comprising a light chain, wherein the light chain amino acid sequence is substantially the same as, or identical to, SEQ ID NO: 61. In some embodiments, the isolated polynucleotides encode an antibody comprising a heavy chain, wherein the heavy chain amino acid sequence is substantially the same as, or identical to, SEQ ID NO: 68. In some embodiments, the isolated polynucleotides encode an antibody comprising a light chain and a heavy chain, wherein the light chain amino acid sequence substantially the same as, or identical to, SEQ ID NO: 61 and a heavy chain amino acid sequence substantially the same as, or identical to, SEQ ID NO: 68.

Also disclosed are isolated polynucleotides that encode an antibody or antigen-binding fragment comprising a light chain variable region, wherein the light chain variable region amino acid sequence is substantially the same as, or identical to, SEQ ID NO: 88. In some embodiments, the isolated polynucleotides encode an antibody or antigen-binding fragment comprising a heavy chain variable region, wherein the heavy chain variable region amino acid sequence is substantially the same as, or identical to, SEQ ID NO: 96. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 88 and the heavy chain variable region amino acid sequence is substantially the same as, or identical to, SEQ ID NO: 96.

Also disclosed are isolated polynucleotides that encode an antibody comprising a light chain, wherein the light chain amino acid sequence is substantially the same as, or identical to, SEQ ID NO: 89. In some embodiments, the isolated polynucleotides encode an antibody comprising a heavy chain, wherein the heavy chain amino acid sequence is substantially the same as, or identical to, SEQ ID NO: 97. In some embodiments, the isolated polynucleotides encode an antibody comprising a light chain and a heavy chain, wherein the light chain amino acid sequence substantially the same as, or identical to, SEQ ID NO: 89 and a heavy chain amino acid sequence substantially the same as, or identical to, SEQ ID NO: 97.

Also disclosed are isolated polynucleotides that encode an antibody or antigen-binding fragment comprising a light chain variable region, wherein the light chain variable region amino acid sequence is substantially the same as, or identical to, SEQ ID NO: 116. In some embodiments, the isolated polynucleotides encode an antibody or antigen-binding fragment comprising a heavy chain variable region, wherein the heavy chain variable region amino acid sequence is substantially the same as, or identical to, SEQ ID NO: 124. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 116 and the heavy chain variable region amino acid sequence is substantially the same as, or identical to, SEQ ID NO: 124.

Also disclosed are isolated polynucleotides that encode an antibody comprising a light chain, wherein the light chain amino acid sequence is substantially the same as, or identical to, SEQ ID NO: 117. In some embodiments, the isolated polynucleotides encode an antibody comprising a heavy chain, wherein the heavy chain amino acid sequence is substantially the same as, or identical to, SEQ ID NO: 125. In some embodiments, the isolated polynucleotides encode an antibody comprising a light chain and a heavy chain, wherein the light chain amino acid sequence substantially the same as, or identical to, SEQ ID NO: 117 and a heavy chain amino acid sequence substantially the same as, or identical to, SEQ ID NO: 125.

Also disclosed are isolated polynucleotides that encode an antibody or antigen-binding fragment comprising a light chain variable region, wherein the light chain variable region amino acid sequence is substantially the same as, or identical to, SEQ ID NO: 143. In some embodiments, the isolated polynucleotides encode an antibody or antigen-binding fragment comprising a heavy chain variable region, wherein the heavy chain variable region amino acid sequence is substantially the same as, or identical to, SEQ ID NO: 151. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 143 and the heavy chain variable region amino acid sequence is substantially the same as, or identical to, SEQ ID NO: 151.

Also disclosed are isolated polynucleotides that encode an antibody comprising a light chain, wherein the light chain amino acid sequence is substantially the same as, or identical to, SEQ ID NO: 144. In some embodiments, the isolated polynucleotides encode an antibody comprising a heavy chain, wherein the heavy chain amino acid sequence is substantially the same as, or identical to, SEQ ID NO: 152. In some embodiments, the isolated polynucleotides encode an antibody comprising a light chain and a heavy chain, wherein the light chain amino acid sequence substantially the same as, or identical to, SEQ ID NO: 144 and a heavy chain amino acid sequence substantially the same as, or identical to, SEQ ID NO: 152.

Also disclosed are isolated polynucleotides that encode an antibody or antigen-binding fragment comprising a light chain variable region, wherein the light chain variable region amino acid sequence is substantially the same as, or identical to, SEQ ID NO: 166. In some embodiments, the isolated polynucleotides encode an antibody or antigen-binding fragment comprising a heavy chain variable region, wherein the heavy chain variable region amino acid sequence is substantially the same as, or identical to, SEQ ID NO: 174. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 166 and the heavy chain variable region amino acid sequence is substantially the same as, or identical to, SEQ ID NO: 174.

Also disclosed are isolated polynucleotides that encode an antibody comprising a light chain, wherein the light chain amino acid sequence is substantially the same as, or identical to, SEQ ID NO: 167. In some embodiments, the isolated polynucleotides encode an antibody comprising a heavy chain, wherein the heavy chain amino acid sequence is substantially the same as, or identical to, SEQ ID NO: 175. In some embodiments, the isolated polynucleotides encode an antibody comprising a light chain and a heavy chain, wherein the light chain amino acid sequence substantially the same as, or identical to, SEQ ID NO: 167 and a heavy chain amino acid sequence substantially the same as, or identical to, SEQ ID NO: 175.

Also disclosed are isolated polynucleotides that encode an antibody or antigen-binding fragment comprising a light chain variable region, wherein the light chain variable region amino acid sequence is substantially the same as, or identical to, SEQ ID NO: 192. In some embodiments, the isolated polynucleotides encode an antibody or antigen-binding fragment comprising a heavy chain variable region, wherein the heavy chain variable region amino acid sequence is substantially the same as, or identical to, SEQ ID NO: 200. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 192 and the heavy chain variable region amino acid sequence is substantially the same as, or identical to, SEQ ID NO: 200.

Also disclosed are isolated polynucleotides that encode an antibody comprising a light chain, wherein the light chain amino acid sequence is substantially the same as, or identical to, SEQ ID NO: 193. In some embodiments, the isolated polynucleotides encode an antibody comprising a heavy chain, wherein the heavy chain amino acid sequence is substantially the same as, or identical to, SEQ ID NO: 201. In some embodiments, the isolated polynucleotides encode an antibody comprising a light chain and a heavy chain, wherein the light chain amino acid sequence substantially the same as, or identical to, SEQ ID NO: 193 and a heavy chain amino acid sequence substantially the same as, or identical to, SEQ ID NO: 201.

Also disclosed are isolated polynucleotides that encode an antibody or antigen-binding fragment comprising a light chain variable region, wherein the light chain variable region amino acid sequence is substantially the same as, or identical to, SEQ ID NO: 219. In some embodiments, the isolated polynucleotides encode an antibody or antigen-binding fragment comprising a heavy chain variable region, wherein the heavy chain variable region amino acid sequence is substantially the same as, or identical to, SEQ ID NO: 223. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 219 and the heavy chain variable region amino acid sequence is substantially the same as, or identical to, SEQ ID NO: 223.

Also disclosed are isolated polynucleotides that encode an antibody comprising a light chain, wherein the light chain amino acid sequence is substantially the same as, or identical to, SEQ ID NO: 220. In some embodiments, the isolated polynucleotides encode an antibody comprising a heavy chain, wherein the heavy chain amino acid sequence is substantially the same as, or identical to, SEQ ID NO: 224. In some embodiments, the isolated polynucleotides encode an antibody comprising a light chain and a heavy chain, wherein the light chain amino acid sequence substantially the same as, or identical to, SEQ ID NO: 220 and a heavy chain amino acid sequence substantially the same as, or identical to, SEQ ID NO: 224.

Also disclosed are isolated polynucleotides that encode an antibody or antigen-binding fragment comprising a light chain variable region, wherein the light chain variable region amino acid sequence is substantially the same as, or identical to, SEQ ID NO: 238. In some embodiments, the isolated polynucleotides encode an antibody or antigen-binding fragment comprising a heavy chain variable region, wherein the heavy chain variable region amino acid sequence is substantially the same as, or identical to, SEQ ID NO: 243. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 238 and the heavy chain variable region amino acid sequence is substantially the same as, or identical to, SEQ ID NO: 243.

Also disclosed are isolated polynucleotides that encode an antibody comprising a light chain, wherein the light chain amino acid sequence is substantially the same as, or identical to, SEQ ID NO: 239. In some embodiments, the isolated polynucleotides encode an antibody comprising a heavy chain, wherein the heavy chain amino acid sequence is substantially the same as, or identical to, SEQ ID NO: 244. In some embodiments, the isolated polynucleotides encode antibody comprising a light chain and a heavy chain, wherein the light chain amino acid sequence substantially the same as, or identical to, SEQ ID NO: 239 and a heavy chain amino acid sequence substantially the same as, or identical to, SEQ ID NO: 244.

Also disclosed are isolated polynucleotides that encode an antibody or antigen-binding fragment comprising a light chain variable region, wherein the light chain variable region amino acid sequence is substantially the same as, or identical to, SEQ ID NO: 260. In some embodiments, the isolated polynucleotides encode an antibody or antigen-binding fragment comprising a heavy chain variable region, wherein the heavy chain variable region amino acid sequence is substantially the same as, or identical to, SEQ ID NO: 267. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 260 and the heavy chain variable region amino acid sequence is substantially the same as, or identical to, SEQ ID NO: 267.

Also disclosed are isolated polynucleotides that encode an antibody comprising a light chain, wherein the light chain amino acid sequence is substantially the same as, or identical to, SEQ ID NO: 261. In some embodiments, the isolated polynucleotides encode an antibody comprising a heavy chain, wherein the heavy chain amino acid sequence is substantially the same as, or identical to, SEQ ID NO: 268. In some embodiments, the isolated polynucleotides encode an antibody comprising a light chain and a heavy chain, wherein the light chain amino acid sequence substantially the same as, or identical to, SEQ ID NO: 261 and a heavy chain amino acid sequence substantially the same as, or identical to, SEQ ID NO: 268.

Also disclosed are isolated polynucleotides that encode an antibody or antigen-binding fragment comprising a light chain variable region, wherein the light chain variable region amino acid sequence is substantially the same as, or identical to, SEQ ID NO: 282. In some embodiments, the isolated polynucleotides encode an antibody or antigen-binding fragment comprising a heavy chain variable region, wherein the heavy chain variable region amino acid sequence is substantially the same as, or identical to, SEQ ID NO: 284. In some embodiments, the isolated polynucleotides encode an antibody or antigen-binding fragment comprising a light chain variable region and a heavy chain variable region, wherein the light chain variable region amino acid sequence is substantially the same as, or identical to, SEQ ID NO: 282 and the heavy chain variable region amino acid sequence is substantially the same as, or identical to, SEQ ID NO: 284.

Also disclosed are isolated polynucleotides that encode an antibody comprising a light chain, wherein the light chain amino acid sequence is substantially the same as, or identical to, SEQ ID NO: 283. In some embodiments, the isolated polynucleotides encode an antibody comprising a heavy chain, wherein the heavy chain amino acid sequence is substantially the same as, or identical to, SEQ ID NO: 285. In some embodiments, the isolated polynucleotides encode an antibody comprising a light chain and a heavy chain, wherein the light chain amino acid sequence substantially the same as, or identical to, SEQ ID NO: 283 and a heavy chain amino acid sequence substantially the same as, or identical to, SEQ ID NO: 285.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 1, a light chain CDR2 of the encoded antibody is substantially the same as, or identical to, the amino acid sequence of SEQ ID NO: 2, a light chain CDR3 of the encoded antibody is substantially the same as, or identical to, the amino acid sequence of SEQ ID NO: 3, a heavy chain CDR1 of the encoded antibody is substantially the same as, or identical to, the amino acid sequence of SEQ ID NO: 8, a heavy chain CDR2 of the encoded antibody is substantially the same as, or identical to, the amino acid sequence of SEQ ID NO: 9, and a heavy chain CDR3 of the encoded antibody is substantially the same as, or identical to, the amino acid sequence of SEQ ID NO: 10, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 1, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 9, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 10, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 4, a light chain CDR2 of the encoded antibody is substantially the same as, or identical to, the amino acid sequence of SEQ ID NO: 5, a light chain CDR3 of the encoded antibody is substantially the same as, or identical to, the amino acid sequence of SEQ ID NO: 3, a heavy chain CDR1 of the encoded antibody is substantially the same as, or identical to, the amino acid sequence of SEQ ID NO: 11, a heavy chain CDR2 of the encoded antibody is substantially the same as, or identical to, the amino acid sequence of SEQ ID NO: 12, and a heavy chain CDR3 of the encoded antibody is substantially the same as, or identical to, the amino acid sequence of SEQ ID NO: 13, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 4, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 5, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 11, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 12, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 13, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 55, a light chain CDR2 of the encoded antibody is substantially the same as, or identical to, the amino acid sequence of SEQ ID NO: 56, a light chain CDR3 of the encoded antibody is substantially the same as, or identical to, the amino acid sequence of SEQ ID NO: 57, a heavy chain CDR1 of the encoded antibody is substantially the same as, or identical to, the amino acid sequence of SEQ ID NO: 62, a heavy chain CDR2 of the encoded antibody is substantially the same as, or identical to, the amino acid sequence of SEQ ID NO: 63, and a heavy chain CDR3 of the encoded antibody is substantially the same as, or identical to, the amino acid sequence of SEQ ID NO: 64, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 55, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 56, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 62, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 63, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 64, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 58, a light chain CDR2 of the encoded antibody is substantially the same as, or identical to, the amino acid sequence of SEQ ID NO: 59, a light chain CDR3 of the encoded antibody is substantially the same as, or identical to, the amino acid sequence of SEQ ID NO: 57, a heavy chain CDR1 of the encoded antibody is substantially the same as, or identical to, the amino acid sequence of SEQ ID NO: 65, a heavy chain CDR2 of the encoded antibody is substantially the same as, or identical to, the amino acid sequence of SEQ ID NO: 66, and a heavy chain CDR3 of the encoded antibody is substantially the same as, or identical to, the amino acid sequence of SEQ ID NO: 64, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 58, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 59, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 65, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 66, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 64, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 84, a light chain CDR2 of the encoded antibody is substantially the same as, or identical to, the amino acid sequence of SEQ ID NO: 85, a light chain CDR3 of the encoded antibody is substantially the same as, or identical to, the amino acid sequence of SEQ ID NO: 86, a heavy chain CDR1 of the encoded antibody is substantially the same as, or identical to, the amino acid sequence of SEQ ID NO: 90, a heavy chain CDR2 of the encoded antibody is substantially the same as, or identical to, the amino acid sequence of SEQ ID NO: 91, and a heavy chain CDR3 of the encoded antibody is substantially the same as, or identical to, the amino acid sequence of SEQ ID NO: 92, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 84, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 85, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 86, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 90, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 91, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 92, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 87, a light chain CDR2 of the encoded antibody is substantially the same as, or identical to, the amino acid sequence of SEQ ID NO: 32, a light chain CDR3 of the encoded antibody is substantially the same as, or identical to, the amino acid sequence of SEQ ID NO: 86, a heavy chain CDR1 of the encoded antibody is substantially the same as, or identical to, the amino acid sequence of SEQ ID NO: 93, a heavy chain CDR2 of the encoded antibody is substantially the same as, or identical to, the amino acid sequence of SEQ ID NO: 94, and a heavy chain CDR3 of the encoded antibody is substantially the same as, or identical to, the amino acid sequence of SEQ ID NO: 95, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 87, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 32, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 86, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 93, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 94, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 95, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 112, a light chain CDR2 of the encoded antibody is substantially the same as, or identical to, the amino acid sequence of SEQ ID NO: 2, a light chain CDR3 of the encoded antibody is substantially the same as, or identical to, the amino acid sequence of SEQ ID NO: 113, a heavy chain CDR1 of the encoded antibody is substantially the same as, or identical to, the amino acid sequence of SEQ ID NO: 118, a heavy chain CDR2 of the encoded antibody is substantially the same as, or identical to, the amino acid sequence of SEQ ID NO: 119, and a heavy chain CDR3 of the encoded antibody is substantially the same as, or identical to, the amino acid sequence of SEQ ID NO: 120, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 112, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 113, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 118, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 119, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 120, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 114, a light chain CDR2 of the encoded antibody is substantially the same as, or identical to, the amino acid sequence of SEQ ID NO: 115, a light chain CDR3 of the encoded antibody is substantially the same as, or identical to, the amino acid sequence of SEQ ID NO: 113, a heavy chain CDR1 of the encoded antibody is substantially the same as, or identical to, the amino acid sequence of SEQ ID NO: 121, a heavy chain CDR2 of the encoded antibody is substantially the same as, or identical to, the amino acid sequence of SEQ ID NO: 122, and a heavy chain CDR3 of the encoded antibody is substantially the same as, or identical to, the amino acid sequence of SEQ ID NO: 123, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 114, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 115, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 113, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 121, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 122, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 123, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 55, a light chain CDR2 of the encoded antibody is substantially the same as, or identical to, the amino acid sequence of SEQ ID NO: 140, a light chain CDR3 of the encoded antibody is substantially the same as, or identical to, the amino acid sequence of SEQ ID NO: 141, a heavy chain CDR1 of the encoded antibody is substantially the same as, or identical to, the amino acid sequence of SEQ ID NO: 145, a heavy chain CDR2 of the encoded antibody is substantially the same as, or identical to, the amino acid sequence of SEQ ID NO: 146, and a heavy chain CDR3 of the encoded antibody is substantially the same as, or identical to, the amino acid sequence of SEQ ID NO: 147, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 55, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 140, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 141, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 145, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 146, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 147, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 58, a light chain CDR2 of the encoded antibody is substantially the same as, or identical to, the amino acid sequence of SEQ ID NO: 142, a light chain CDR3 of the encoded antibody is substantially the same as, or identical to, the amino acid sequence of SEQ ID NO: 141, a heavy chain CDR1 of the encoded antibody is substantially the same as, or identical to, the amino acid sequence of SEQ ID NO: 148, a heavy chain CDR2 of the encoded antibody is substantially the same as, or identical to, the amino acid sequence of SEQ ID NO: 149, and a heavy chain CDR3 of the encoded antibody is substantially the same as, or identical to, the amino acid sequence of SEQ ID NO: 150, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 58, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 142, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 141, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 148, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 149, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 150, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 55, a light chain CDR2 of the encoded antibody is substantially the same as, or identical to, the amino acid sequence of SEQ ID NO: 56, a light chain CDR3 of the encoded antibody is substantially the same as, or identical to, the amino acid sequence of SEQ ID NO: 57, a heavy chain CDR1 of the encoded antibody is substantially the same as, or identical to, the amino acid sequence of SEQ ID NO: 168, a heavy chain CDR2 of the encoded antibody is substantially the same as, or identical to, the amino acid sequence of SEQ ID NO: 169, and a heavy chain CDR3 of the encoded antibody is substantially the same as, or identical to, the amino acid sequence of SEQ ID NO: 170, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 55, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 56, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 168, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 169, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 170, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 58, a light chain CDR2 of the encoded antibody is substantially the same as, or identical to, the amino acid sequence of SEQ ID NO: 59, a light chain CDR3 of the encoded antibody is substantially the same as, or identical to, the amino acid sequence of SEQ ID NO: 57, a heavy chain CDR1 of the encoded antibody is substantially the same as, or identical to, the amino acid sequence of SEQ ID NO: 171, a heavy chain CDR2 of the encoded antibody is substantially the same as, or identical to, the amino acid sequence of SEQ ID NO: 172, and a heavy chain CDR3 of the encoded antibody is substantially the same as, or identical to, the amino acid sequence of SEQ ID NO: 173, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 58, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 59, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 171, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 172, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 173, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 187, a light chain CDR2 of the encoded antibody is substantially the same as, or identical to, the amino acid sequence of SEQ ID NO: 188, a light chain CDR3 of the encoded antibody is substantially the same as, or identical to, the amino acid sequence of SEQ ID NO: 189, a heavy chain CDR1 of the encoded antibody is substantially the same as, or identical to, the amino acid sequence of SEQ ID NO: 194, a heavy chain CDR2 of the encoded antibody is substantially the same as, or identical to, the amino acid sequence of SEQ ID NO: 195, and a heavy chain CDR3 of the encoded antibody is substantially the same as, or identical to, the amino acid sequence of SEQ ID NO: 196, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 187, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 188, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 194, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 195, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 196, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 190, a light chain CDR2 of the encoded antibody is substantially the same as, or identical to, the amino acid sequence of SEQ ID NO: 191, a light chain CDR3 of the encoded antibody is substantially the same as, or identical to, the amino acid sequence of SEQ ID NO: 189, a heavy chain CDR1 of the encoded antibody is substantially the same as, or identical to, the amino acid sequence of SEQ ID NO: 197, a heavy chain CDR2 of the encoded antibody is substantially the same as, or identical to, the amino acid sequence of SEQ ID NO: 198, and a heavy chain CDR3 of the encoded antibody is substantially the same as, or identical to, the amino acid sequence of SEQ ID NO: 199, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 190, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 191, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 197, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 198, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 199, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 217, a light chain CDR2 of the encoded antibody is substantially the same as, or identical to, the amino acid sequence of SEQ ID NO: 188, a light chain CDR3 of the encoded antibody is substantially the same as, or identical to, the amino acid sequence of SEQ ID NO: 189, a heavy chain CDR1 of the encoded antibody is substantially the same as, or identical to, the amino acid sequence of SEQ ID NO: 194, a heavy chain CDR2 of the encoded antibody is substantially the same as, or identical to, the amino acid sequence of SEQ ID NO: 221, and a heavy chain CDR3 of the encoded antibody is substantially the same as, or identical to, the amino acid sequence of SEQ ID NO: 196, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 217, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 188, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 194, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 221, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 196, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 218, a light chain CDR2 of the encoded antibody is substantially the same as, or identical to, the amino acid sequence of SEQ ID NO: 191, a light chain CDR3 of the encoded antibody is substantially the same as, or identical to, the amino acid sequence of SEQ ID NO: 189, a heavy chain CDR1 of the encoded antibody is substantially the same as, or identical to, the amino acid sequence of SEQ ID NO: 197, a heavy chain CDR2 of the encoded antibody is substantially the same as, or identical to, the amino acid sequence of SEQ ID NO: 222, and a heavy chain CDR3 of the encoded antibody is substantially the same as, or identical to, the amino acid sequence of SEQ ID NO: 199, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 218, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 191, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 197, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 222, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 199, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 233, a light chain CDR2 of the encoded antibody is substantially the same as, or identical to, the amino acid sequence of SEQ ID NO: 234, a light chain CDR3 of the encoded antibody is substantially the same as, or identical to, the amino acid sequence of SEQ ID NO: 235, a heavy chain CDR1 of the encoded antibody is substantially the same as, or identical to, the amino acid sequence of SEQ ID NO: 194, a heavy chain CDR2 of the encoded antibody is substantially the same as, or identical to, the amino acid sequence of SEQ ID NO: 195, and a heavy chain CDR3 of the encoded antibody is substantially the same as, or identical to, the amino acid sequence of SEQ ID NO: 240, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 233, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 234, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 235, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 194, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 195, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 240, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 236, a light chain CDR2 of the encoded antibody is substantially the same as, or identical to, the amino acid sequence of SEQ ID NO: 237, a light chain CDR3 of the encoded antibody is substantially the same as, or identical to, the amino acid sequence of SEQ ID NO: 235, a heavy chain CDR1 of the encoded antibody is substantially the same as, or identical to, the amino acid sequence of SEQ ID NO: 241, a heavy chain CDR2 of the encoded antibody is substantially the same as, or identical to, the amino acid sequence of SEQ ID NO: 198, and a heavy chain CDR3 of the encoded antibody is substantially the same as, or identical to, the amino acid sequence of SEQ ID NO: 242, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 236, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 237, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 235, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 241, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 198, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 242, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 257, a light chain CDR2 of the encoded antibody is substantially the same as, or identical to, the amino acid sequence of SEQ ID NO: 188, a light chain CDR3 of the encoded antibody is substantially the same as, or identical to, the amino acid sequence of SEQ ID NO: 258, a heavy chain CDR1 of the encoded antibody is substantially the same as, or identical to, the amino acid sequence of SEQ ID NO: 8, a heavy chain CDR2 of the encoded antibody is substantially the same as, or identical to, the amino acid sequence of SEQ ID NO: 262, and a heavy chain CDR3 of the encoded antibody is substantially the same as, or identical to, the amino acid sequence of SEQ ID NO: 263, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 257, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 188, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 258, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 262, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 263, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 259, a light chain CDR2 of the encoded antibody is substantially the same as, or identical to, the amino acid sequence of SEQ ID NO: 191, a light chain CDR3 of the encoded antibody is substantially the same as, or identical to, the amino acid sequence of SEQ ID NO: 258, a heavy chain CDR1 of the encoded antibody is substantially the same as, or identical to, the amino acid sequence of SEQ ID NO: 264, a heavy chain CDR2 of the encoded antibody is substantially the same as, or identical to, the amino acid sequence of SEQ ID NO: 265, and a heavy chain CDR3 of the encoded antibody is substantially the same as, or identical to, the amino acid sequence of SEQ ID NO: 266, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 259, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 191, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 258, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 264, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 265, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 266, wherein the CDR is defined according to the KABAT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 1, a light chain CDR2 of the encoded antibody is substantially the same as, or identical to, the amino acid sequence of SEQ ID NO: 2, a light chain CDR3 of the encoded antibody is substantially the same as, or identical to, the amino acid sequence of SEQ ID NO: 3, a heavy chain CDR1 of the encoded antibody is substantially the same as, or identical to, the amino acid sequence of SEQ ID NO: 8, a heavy chain CDR2 of the encoded antibody is substantially the same as, or identical to, the amino acid sequence of SEQ ID NO: 9, and a heavy chain CDR3 of the encoded antibody is substantially the same as, or identical to, the amino acid sequence of SEQ ID NO: 10, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 1, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 9, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 10, wherein the CDR is defined according to the IMGT method.

Described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 4, a light chain CDR2 of the encoded antibody is substantially the same as, or identical to, the amino acid sequence of SEQ ID NO: 115, a light chain CDR3 of the encoded antibody is substantially the same as, or identical to, the amino acid sequence of SEQ ID NO: 3, a heavy chain CDR1 of the encoded antibody is substantially the same as, or identical to, the amino acid sequence of SEQ ID NO: 11, a heavy chain CDR2 of the encoded antibody is substantially the same as, or identical to, the amino acid sequence of SEQ ID NO: 12, and a heavy chain CDR3 of the encoded antibody is substantially the same as, or identical to, the amino acid sequence of SEQ ID NO: 13, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 4, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 115, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the KABAT method. In some embodiments, the isolated polynucleotides encode an antibody or antigen-binding fragment that includes a heavy chain CDR1 substantially the same as, or identical to, the amino acid sequence of SEQ ID NO: 11, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 12, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 13, wherein the CDR is defined according to the KABAT method.

Described herein are isolated polynucleotide nucleotide sequences substantially similar to, or the same as, SEQ ID NO: 16, SEQ ID NO: 17, SEQ ID NO: 18, SEQ ID NO: 23, SEQ ID NO: 24, and SEQ ID NO 25. In other embodiments, the isolated polynucleotides are substantially similar to, or the same as, SEQ ID NO: 19, SEQ ID NO: 20, SEQ ID NO: 18, SEQ ID NO: 26, SEQ ID NO: 27, and SEQ ID NO 28.

Described herein are isolated polynucleotide nucleotide sequences substantially similar to, or the same as, SEQ ID NO: 69, SEQ ID NO: 70, SEQ ID NO: 71, SEQ ID NO: 76, SEQ ID NO: 77, and SEQ ID NO 78. In other embodiments, the isolated polynucleotides are substantially similar to, or the same as, SEQ ID NO: 72, SEQ ID NO: 73, SEQ ID NO: 71, SEQ ID NO: 79, SEQ ID NO: 80, and SEQ ID NO 81.

Described herein are isolated polynucleotide nucleotide sequences substantially similar to, or the same as, SEQ ID NO: 98, SEQ ID NO: 99, SEQ ID NO: 100, SEQ ID NO: 104, SEQ ID NO: 105, and SEQ ID NO 106. In other embodiments, the isolated polynucleotides are substantially similar to, or the same as, SEQ ID NO: 101, SEQ ID NO: 40, SEQ ID NO: 100, SEQ ID NO: 107, SEQ ID NO: 108, and SEQ ID NO 109.

Described herein are isolated polynucleotide nucleotide sequences substantially similar to, or the same as, SEQ ID NO: 126, SEQ ID NO: 17, SEQ ID NO: 127, SEQ ID NO: 132, SEQ ID NO: 133, and SEQ ID NO 134. In other embodiments, the isolated polynucleotides are substantially similar to, or the same as, SEQ ID NO: 128, SEQ ID NO: 129, SEQ ID NO: 127, SEQ ID NO: 135, SEQ ID NO: 136, and SEQ ID NO 137.

Described herein are isolated polynucleotide nucleotide sequences substantially similar to, or the same as, SEQ ID NO: 69, SEQ ID NO: 153, SEQ ID NO: 154, SEQ ID NO: 158, SEQ ID NO: 159, and SEQ ID NO 160. In other embodiments, the isolated polynucleotides are substantially similar to, or the same as, SEQ ID NO: 72, SEQ ID NO: 155, SEQ ID NO: 154, SEQ ID NO: 161, SEQ ID NO: 162, and SEQ ID NO 163.

Described herein are isolated polynucleotide nucleotide sequences substantially similar to, or the same as, SEQ ID NO: 69, SEQ ID NO: 70, SEQ ID NO: 71, SEQ ID NO: 179, SEQ ID NO: 180, and SEQ ID NO 181. In other embodiments, the isolated polynucleotides are substantially similar to, or the same as, SEQ ID NO: 72, SEQ ID NO: 73, SEQ ID NO: 176, SEQ ID NO: 182, SEQ ID NO: 183, and SEQ ID NO 184.

Described herein are isolated polynucleotide nucleotide sequences substantially similar to, or the same as, SEQ ID NO: 202, SEQ ID NO: 203, SEQ ID NO: 204, SEQ ID NO: 209, SEQ ID NO: 210, and SEQ ID NO 211. In other embodiments, the isolated polynucleotides are substantially similar to, or the same as, SEQ ID NO: 205, SEQ ID NO: 206, SEQ ID NO: 204, SEQ ID NO: 212, SEQ ID NO: 213, and SEQ ID NO 214.

Described herein are isolated polynucleotide nucleotide sequences substantially similar to, or the same as, SEQ ID NO: 225, SEQ ID NO: 203, SEQ ID NO: 204, SEQ ID NO: 209, SEQ ID NO: 229, and SEQ ID NO 211. In other embodiments, the isolated polynucleotides are substantially similar to, or the same as, SEQ ID NO: 226, SEQ ID NO: 206, SEQ ID NO: 204, SEQ ID NO: 212. SEQ ID NO: 230, and SEQ ID NO 214.

Described herein are isolated polynucleotide nucleotide sequences substantially similar to, or the same as, SEQ ID NO: 245, SEQ ID NO: 246, SEQ ID NO: 247, SEQ ID NO: 209, SEQ ID NO: 210, and SEQ ID NO 252. In other embodiments, the isolated polynucleotides are substantially similar to, or the same as, SEQ ID NO: 248, SEQ ID NO: 249, SEQ ID NO: 247, SEQ ID NO: 253, SEQ ID NO: 213, and SEQ ID NO 254.

Described herein are isolated polynucleotide nucleotide sequences substantially similar to, or the same as, SEQ ID NO: 269, SEQ ID NO: 203, SEQ ID NO: 270, SEQ ID NO: 274, SEQ ID NO: 275, and SEQ ID NO 276. In other embodiments, the isolated polynucleotides are substantially similar to, or the same as, SEQ ID NO: 271, SEQ ID NO: 206, SEQ ID NO: 270, SEQ ID NO: 277, SEQ ID NO: 278, and SEQ ID NO 279.

Described herein are isolated polynucleotide nucleotide sequences substantially similar to, or the same as, SEQ ID NO: 16, SEQ ID NO: 17, SEQ ID NO: 18, SEQ ID NO: 288, SEQ ID NO: 24, and SEQ ID NO 25. In other embodiments, the isolated polynucleotides are substantially similar to, or the same as, SEQ ID NO: 19, SEQ ID NO: 129, SEQ ID NO: 18, SEQ ID NO: 289, SEQ ID NO: 290, and SEQ ID NO 28.

Also described herein are isolated polynucleotides that encode an antibody or antigen-binding fragment specific for folate receptor alpha (FRα) wherein the light chain CDR1 of the encoded antibody is substantially the same as, or identical to, the amino acid sequence of SEQ ID NO: 1, the light chain CDR2 of the encoded antibody is substantially the same as, or identical to, the amino acid sequence of SEQ ID NO: 2, and the light chain CDR3 of the encoded antibody is substantially the same as, or identical to, the amino acid sequence SEQ ID NO: 3, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 1, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the IMGT method.

Also described herein are isolated polynucleotides that encode an antibody or antigen-binding fragment specific for folate receptor alpha (FRα) wherein the light chain CDR1 of the encoded antibody is substantially the same as, or identical to, the amino acid sequence of SEQ ID NO: 4, the light chain CDR2 of the encoded antibody is substantially the same as, or identical to, the amino acid sequence of SEQ ID NO: 5, and the light chain CDR3 of the encoded antibody is substantially the same as, or identical to, the amino acid sequence SEQ ID NO: 3, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 4, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 5, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the KABAT method.

Also described herein are isolated polynucleotides that encode an antibody or antigen-binding fragment specific for folate receptor alpha (FRα) wherein the heavy chain CDR1 of the encoded antibody is substantially the same as, or identical to, the amino acid sequence of SEQ ID NO: 8, the heavy chain CDR2 of the encoded antibody is substantially the same as, or identical to, the amino acid sequence of SEQ ID NO: 9, and the heavy chain CDR3 of the encoded antibody is substantially the same as, or identical to, the amino acid sequence SEQ ID NO: 10, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 9, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 10, wherein the CDR is defined according to the IMGT method.

Also described herein are isolated polynucleotides that encode an antibody or antigen-binding fragment specific for folate receptor alpha (FRα) wherein the heavy chain CDR1 of the encoded antibody is substantially the same as, or identical to, the amino acid sequence of SEQ ID NO: 11, the heavy chain CDR2 of the encoded antibody is substantially the same as, or identical to, the amino acid sequence of SEQ ID NO: 12, and the heavy chain CDR3 of the encoded antibody is substantially the same as, or identical to, the amino acid sequence SEQ ID NO: 13, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 11, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 12, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 13, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 55, a light chain CDR2 of the encoded antibody is substantially the same as, or identical to, the amino acid sequence of SEQ ID NO: 56, and a light chain CDR3 of the encoded antibody is substantially the same as, or identical to, the amino acid sequence of SEQ ID NO: 57, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 55, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 56, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 58, a light chain CDR2 of the encoded antibody is substantially the same as, or identical to, the amino acid sequence of SEQ ID NO: 59, a light chain CDR3 of the encoded antibody is substantially the same as, or identical to, the amino acid sequence of SEQ ID NO: 57, wherein the CDR is defined according to the KABAT method. In some embodiments, the isolated polynucleotides encode an antibody or antigen-binding fragment that includes a light chain CDR1 substantially the same as, or identical to, the amino acid sequence of SEQ ID NO: 58, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 59, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 62, a heavy chain CDR2 of the encoded antibody is substantially the same as, or identical to, the amino acid sequence of SEQ ID NO: 63, and a heavy chain CDR3 of the encoded antibody is substantially the same as, or identical to, the amino acid sequence of SEQ ID NO: 64, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 62, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 63, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 64, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 65, a heavy chain CDR2 of the encoded antibody is substantially the same as, or identical to, the amino acid sequence of SEQ ID NO: 66, and a heavy chain CDR3 of the encoded antibody is substantially the same as, or identical to, the amino acid sequence of SEQ ID NO: 64, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 65, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 66, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 64, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 84, a light chain CDR2 of the encoded antibody is substantially the same as, or identical to, the amino acid sequence of SEQ ID NO: 85, and a light chain CDR3 of the encoded antibody is substantially the same as, or identical to, the amino acid sequence of SEQ ID NO: 86, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 84, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 85, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 86, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 87, a light chain CDR2 of the encoded antibody is substantially the same as, or identical to, the amino acid sequence of SEQ ID NO: 32, and a light chain CDR3 of the encoded antibody is substantially the same as, or identical to, the amino acid sequence of SEQ ID NO: 86, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 87, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 32, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 86, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 90, a heavy chain CDR2 of the encoded antibody is substantially the same as, or identical to, the amino acid sequence of SEQ ID NO: 91, and a heavy chain CDR3 of the encoded antibody is substantially the same as, or identical to, the amino acid sequence of SEQ ID NO: 92, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 90, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 91, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 92, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 93, a heavy chain CDR2 of the encoded antibody is substantially the same as, or identical to, the amino acid sequence of SEQ ID NO: 94, and a heavy chain CDR3 of the encoded antibody is substantially the same as, or identical to, the amino acid sequence of SEQ ID NO: 95, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 93, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 94, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 95, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 112, a light chain CDR2 of the encoded antibody is substantially the same as, or identical to, the amino acid sequence of SEQ ID NO: 2, and a light chain CDR3 of the encoded antibody is substantially the same as, or identical to, the amino acid sequence of SEQ ID NO: 113, In some embodiments, the isolated polynucleotides encode an antibody or antigen-binding fragment that includes a light chain CDR1 substantially the same as, or identical to, the amino acid sequence of SEQ ID NO: 112, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO:

2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 113, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 114, a light chain CDR2 of the encoded antibody is substantially the same as, or identical to, the amino acid sequence of SEQ ID NO: 115, and a light chain CDR3 of the encoded antibody is substantially the same as, or identical to, the amino acid sequence of SEQ ID NO: 113, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 114, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 115, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 113, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 118, a heavy chain CDR2 of the encoded antibody is substantially the same as, or identical to, the amino acid sequence of SEQ ID NO: 119, and a heavy chain CDR3 of the encoded antibody is substantially the same as, or identical to, the amino acid sequence of SEQ ID NO: 120, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 118, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 119, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 120, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 121, a heavy chain CDR2 of the encoded antibody is substantially the same as, or identical to, the amino acid sequence of SEQ ID NO: 122, and a heavy chain CDR3 of the encoded antibody is substantially the same as, or identical to, the amino acid sequence of SEQ ID NO: 123, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 121, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 122, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 123, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 55, a light chain CDR2 of the encoded antibody is substantially the same as, or identical to, the amino acid sequence of SEQ ID NO: 140, and a light chain CDR3 of the encoded antibody is substantially the same as, or identical to, the amino acid sequence of SEQ ID NO: 141, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 55, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 140, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 141, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 58, a light chain CDR2 of the encoded antibody is substantially the same as, or identical to, the amino acid sequence of SEQ ID NO: 142, and a light chain CDR3 of the encoded antibody is substantially the same as, or identical to, the amino acid sequence of SEQ ID NO: 141, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 58, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 142, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 141, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 145, a heavy chain CDR2 of the encoded antibody is substantially the same as, or identical to, the amino acid sequence of SEQ ID NO: 146, and a heavy chain CDR3 of the encoded antibody is substantially the same as, or identical to, the amino acid sequence of SEQ ID NO: 147, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 145, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 146, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 147, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 148, a heavy chain CDR2 of the encoded antibody is substantially the same as, or identical to, the amino acid sequence of SEQ ID NO: 149, and a heavy chain CDR3 of the encoded antibody is substantially the same as, or identical to, the amino acid sequence of SEQ ID NO: 150, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 148, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 149, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 150, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 55, a light chain CDR2 of the encoded antibody is substantially the same as, or identical to, the amino acid sequence of SEQ ID NO: 56, and a light chain CDR3 of the encoded antibody is substantially the same as, or identical to, the amino acid sequence of SEQ ID NO: 57, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 55, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 56, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 58, a light chain CDR2 of the encoded antibody is substantially the same as, or identical to, the amino acid sequence of SEQ ID NO: 59, and a light chain CDR3 of the encoded antibody is substantially the same as, or identical to, the amino acid sequence of SEQ ID NO: 57, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 58, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 59, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 57, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 168, a heavy chain CDR2 of the encoded antibody is substantially the same as, or identical to, the amino acid sequence of SEQ ID NO: 169, and a heavy chain CDR3 of the encoded antibody is substantially the same as, or identical to, the amino acid sequence of SEQ ID NO: 170, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 168, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 169, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 170, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 171, a heavy chain CDR2 of the encoded antibody is substantially the same as, or identical to, the amino acid sequence of SEQ ID NO: 172, and a heavy chain CDR3 of the encoded antibody is substantially the same as, or identical to, the amino acid sequence of SEQ ID NO: 173, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 171, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 172, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 173, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 187, a light chain CDR2 of the encoded antibody is substantially the same as, or identical to, the amino acid sequence of SEQ ID NO: 188, and a light chain CDR3 of the encoded antibody is substantially the same as, or identical to, the amino acid sequence of SEQ ID NO: 189, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 187, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 188, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 190, a light chain CDR2 of the encoded antibody is substantially the same as, or identical to, the amino acid sequence of SEQ ID NO: 191, and a light chain CDR3 of the encoded antibody is substantially the same as, or identical to, the amino acid sequence of SEQ ID NO: 189, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 190, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 191, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 194, a heavy chain CDR2 of the encoded antibody is substantially the same as, or identical to, the amino acid sequence of SEQ ID NO: 195, and a heavy chain CDR3 of the encoded antibody is substantially the same as, or identical to, the amino acid sequence of SEQ ID NO: 196, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 194, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 195, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 196, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 197, a heavy chain CDR2 of the encoded antibody is substantially the same as, or identical to, the amino acid sequence of SEQ ID NO: 198, and a heavy chain CDR3 of the encoded antibody is substantially the same as, or identical to, the amino acid sequence of SEQ ID NO: 199, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 197, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 198, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 199, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 217, a light chain CDR2 of the encoded antibody is substantially the same as, or identical to, the amino acid sequence of SEQ ID NO: 188, and a light chain CDR3 of the encoded antibody is substantially the same as, or identical to, the amino acid sequence of SEQ ID NO: 189, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 217, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 188, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 218, a light chain CDR2 of the encoded antibody is substantially the same as, or identical to, the amino acid sequence of SEQ ID NO: 191, and a light chain CDR3 of the encoded antibody is substantially the same as, or identical to, the amino acid sequence of SEQ ID NO: 189, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 218, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 191, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 189, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 194, a heavy chain CDR2 of the encoded antibody is substantially the same as, or identical to, the amino acid sequence of SEQ ID NO: 221, and a heavy chain CDR3 of the encoded antibody is substantially the same as, or identical to, the amino acid sequence of SEQ ID NO: 196, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 194, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 221, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 196, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 197, a heavy chain CDR2 of the encoded antibody is substantially the same as, or identical to, the amino acid sequence of SEQ ID NO: 222, and a heavy chain CDR3 of the encoded antibody is substantially the same as, or identical to, the amino acid sequence of SEQ ID NO: 199, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 197, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 222, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 199, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 233, a light chain CDR2 of the encoded antibody is substantially the same as, or identical to, the amino acid sequence of SEQ ID NO: 234, and a light chain CDR3 of the encoded antibody is substantially the same as, or identical to, the amino acid sequence of SEQ ID NO: 235, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 233, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 24, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 235, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 236, a light chain CDR2 of the encoded antibody is substantially the same as, or identical to, the amino acid sequence of SEQ ID NO: 237, and a light chain CDR3 of the encoded antibody is substantially the same as, or identical to, the amino acid sequence of SEQ ID NO: 235, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 236, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 237, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 235, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 194, a heavy chain CDR2 of the encoded antibody is substantially the same as, or identical to, the amino acid sequence of SEQ ID NO: 195, and a heavy chain CDR3 of the encoded antibody is substantially the same as, or identical to, the amino acid sequence of SEQ ID NO: 240, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 194, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 195, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 240, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 241, a heavy chain CDR2 of the encoded antibody is substantially the same as, or identical to, the amino acid sequence of SEQ ID NO: 198, and a heavy chain CDR3 of the encoded antibody is substantially the same as, or identical to, the amino acid sequence of SEQ ID NO: 242, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 241, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 198, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 242, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 257, a light chain CDR2 of the encoded antibody is substantially the same as, or identical to, the amino acid sequence of SEQ ID NO: 188, and a light chain CDR3 of the encoded antibody is substantially the same as, or identical to, the amino acid sequence of SEQ ID NO: 258, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 257, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 188, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 258, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 259, a light chain CDR2 of the encoded antibody is substantially the same as, or identical to, the amino acid sequence of SEQ ID NO: 191, and a light chain CDR3 of the encoded antibody is substantially the same as, or identical to, the amino acid sequence of SEQ ID NO: 258, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 259, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 191, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 258, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 8, a heavy chain CDR2 of the encoded antibody is substantially the same as, or identical to, the amino acid sequence of SEQ ID NO: 262, and a heavy chain CDR3 of the encoded antibody is substantially the same as, or identical to, the amino acid sequence of SEQ ID NO: 263, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 262, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 263, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 264, a heavy chain CDR2 of the encoded antibody is substantially the same as, or identical to, the amino acid sequence of SEQ ID NO: 265, and a heavy chain CDR3 of the encoded antibody is substantially the same as, or identical to, the amino acid sequence of SEQ ID NO: 266, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 264, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 265, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 266, wherein the CDR is defined according to the KABAT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 1, a light chain CDR2 of the encoded antibody is substantially the same as, or identical to, the amino acid sequence of SEQ ID NO: 2, and a light chain CDR3 of the encoded antibody is substantially the same as, or identical to, the amino acid sequence of SEQ ID NO: 3, wherein the CDRs are defined according to the IMGT method. In some embodiments, the isolated polynucleotides encode an antibody or antigen-binding fragment that includes a light chain CDR1 substantially the same as, or identical to, the amino acid sequence of SEQ ID NO: 1, wherein the CDR is defined according to the IMGT method. In some embodiments, the isolated polynucleotides encode an antibody or antigen-binding fragment that includes a light chain CDR2 substantially the same as, or identical to, the amino acid sequence of SEQ ID NO: 2, wherein the CDR is defined according to the IMGT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the IMGT method.

Also described herein are isolated polynucleotides that encode an antibody or antigen-binding fragment specific for folate receptor alpha (FRα) wherein a light chain CDR1 of the encoded antibody is substantially the same as, or identical to, the amino acid sequence of SEQ ID NO: 4, a light chain CDR2 of the encoded antibody is substantially the same as, or identical to, the amino acid sequence of SEQ ID NO: 115, and a light chain CDR3 of the encoded antibody is substantially the same as, or identical to, the amino acid sequence of SEQ ID NO: 3, wherein the CDRs are defined according to the KABAT method. In some embodiments, the isolated polynucleotides encode an antibody or antigen-binding fragment that includes a light chain CDR1 substantially the same as, or identical to, the amino acid sequence of SEQ ID NO: 4, wherein the CDR is defined according to the KABAT method. In some embodiments, the isolated polynucleotides encode an antibody or antigen-binding fragment that includes a light chain CDR2 substantially the same as, or identical to, the amino acid sequence of SEQ ID NO: 115, wherein the CDR is defined according to the KABAT method. In some embodiments, the isolated polynucleotides encode an antibody or antigen-binding fragment that includes a light chain CDR3 substantially the same as, or identical to, the amino acid sequence of SEQ ID NO: 3, wherein the CDR is defined according to the KABAT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 8, a heavy chain CDR2 of the encoded antibody is substantially the same as, or identical to, the amino acid sequence of SEQ ID NO: 9, and a heavy chain CDR3 of the encoded antibody is substantially the same as, or identical to, the amino acid sequence of SEQ ID NO: 10, wherein the CDRs are defined according to the IMGT method. In some embodiments, the isolated polynucleotides encode an antibody or antigen-binding fragment that includes a heavy chain CDR1 substantially the same as, or identical to, the amino acid sequence of SEQ ID NO: 8, wherein the CDR is defined according to the IMGT method. In some embodiments, the isolated polynucleotides encode an antibody or antigen-binding fragment that includes a heavy chain CDR2 substantially the same as, or identical to, the amino acid sequence of SEQ ID NO: 9, wherein the CDR is defined according to the IMGT method. In some embodiments, the isolated polynucleotides encode an antibody or antigen-binding fragment that includes a heavy chain CDR3 substantially the same as, or identical to, the amino acid sequence of SEQ ID NO: 10, wherein the CDR is defined according to the IMGT method.

Also described herein are isolated polynucleotides that encode an antibody or antigen-binding fragment specific for folate receptor alpha (FRα) wherein a heavy chain CDR1 of the encoded antibody is substantially the same as, or identical to, the amino acid sequence of SEQ ID NO: 11, a heavy chain CDR2 of the encoded antibody is substantially the same as, or identical to, the amino acid sequence of SEQ ID NO: 12, and a heavy chain CDR3 of the encoded antibody is substantially the same as, or identical to, the amino acid sequence of SEQ ID NO: 13, wherein the CDRs are defined according to the KABAT method. In some embodiments, the isolated polynucleotides encode an antibody or antigen-binding fragment that includes a heavy chain CDR1 substantially the same as, or identical to, the amino acid sequence of SEQ ID NO: 11, wherein the CDR is defined according to the KABAT method. In some embodiments, the isolated polynucleotides encode an antibody or antigen-binding fragment that includes a heavy chain CDR2 substantially the same as, or identical to, the amino acid sequence of SEQ ID NO: 12, wherein the CDR is defined according to the KABAT method. In some embodiments, the isolated polynucleotides encode an antibody or antigen-binding fragment that includes a heavy chain CDR3 substantially the same as, or identical to, the amino acid sequence of SEQ ID NO: 13, wherein the CDR is defined according to the KABAT method.

Polynucleotides encoding engineered antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The antibodies or antigen-binding fragments described herein include variants having single or multiple amino acid substitutions, deletions, or additions that retain the biological properties (e.g., binding affinity or immune effector activity) of the described antibodies or antigen-binding fragments. The skilled person may produce variants having single or multiple amino acid substitutions, deletions, or additions. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

The antibodies or antigen-binding fragments described herein may embody several antibody isotypes, such as IgM, IgD, IgG, IgA and IgE. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments In some embodiments the isolated polynucleotides capable of encoding the domains provided herein may be included on the same, or different, vectors to produce an antibody or antigen-binding fragment. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody- or antigen-binding fragment-encoding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate antibody or antigen-binding fragment-producing cells. Thus, another aspect features host cells transformed with vectors comprising a nucleic acid sequence encoding an antibody or antigen-binding fragment thereof that specifically binds FRα, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Also provided are cells capable of expressing the described vectors. The cells may be eukaryotic cells, yeast cells, plant cells or bacteria. Cells suitable for use in the expression of the antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. In preferred embodiments, the eukaryotic cell is a CHO cell. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods for Detecting FRα in a Biological Sample

Provided herein are methods for detecting folate receptor alpha (FRα) in a biological sample. In some embodiments, the method involves exposing the sample to any one of the antibodies or antigen-binding fragments described herein and detecting FRα. In some embodiments, the biological sample is derived from urine, blood, serum, plasma, saliva, ascites, circulating cells, circulating tumor cells, cells that are not tissue associated, tissues, surgically resected tumor tissue, biopsies, fine needle aspiration samples, or histological preparations. In some embodiments, the biological sample is derived from a human or nonhuman primate. In some embodiments, the antibody is labeled. In some embodiments, the label is a radiolabel, an epitope tag, biotin, a chromophore label, a fluorophore label, an electrochemiluminescence (ECL) label, or an enzyme. In preferred embodiments, the electrochemiluminescence (ECL) label is a sulfo-tag. In some embodiments, the method further involves exposing the sample to a second antibody or antigen-binding fragment of any one of the described antibodies. In some embodiments, the second antibody or antigen-binding fragment is immobilized to a solid support. In preferred embodiments, the second antibody or antigen-binding fragment is biotinylated and the solid support is coated with streptavidin, and the isolated antibody or antigen-binding fragment is immobilized to the solid support by the binding of biotin to streptavidin. In some embodiments, the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA. In some embodiments, the sample is diluted prior to detecting folate receptor alpha (FRα) in the sample. In some embodiments, the sample is centrifuged, vortexed, or both, prior to detecting folate receptor alpha (FRα) in the sample. In some embodiments, the level of folate receptor alpha (FRα) in the sample is quantified. In some embodiments, the sample is exposed to MORAb-003 prior to detecting folate receptor alpha (FRα) in the sample.

Various combinations of the antibodies, or antigen-binding fragments thereof, may be used to detect FRα in a sample, as depicted in Table 2.

TABLE 2

Antibody combinations for detecting FRα in a sample

| Detection mAbs | Capture mAbs | | | | | | |
|---|---|---|---|---|---|---|---|
| | 24H8.D3 | 19D4.B7 | 24H8.F3 | 1C6.E12.G8 | 1D2.D8.G10 | 6A2.G7 | 19D2.G9 |
| 24H8.D3 | | X | X | X | X | X | X |
| 19D4.B7 | X | | X | X | X | X | X |
| 24H8.F3 | X | X | | X | X | X | X |
| 1C6.E12.G8 | X | X | X | | | X | X |
| 1D2.D8.G10 | X | X | X | X | | X | X |
| 6A2.G7 | X | X | X | X | X | | X |
| 19D2.G9 | X | X | X | X | X | X | |

TABLE 2-continued

Antibody combinations for detecting FRα in a sample

| | | | | | | | |
|---|---|---|---|---|---|---|---|
| 26A9.C4 | X | X | X | X | X | X | X |
| 2F11.F8 | X | X | X | X | X | X | X |
| 5C12.H8 | X | X | X | X | X | X | X |
| 28H12.G9 | X | X | X | X | X | X | X |
| 30G6.G6.G4.E9 | X | X | X | X | X | X | X |
| 1A8.G11.E7 | X | X | X | X | X | X | X |

| Detection | Capture mAbs | | | | | |
|---|---|---|---|---|---|---|
| mAbs | 26A9.C4 | 2F11.F8 | 5C12.H8 | 28H12.G9 | 30G6.G6.G4.E9 | 1A8.G11.E7 |
| 24H8.D3 | X | X | X | X | X | X |
| 19D4.B7 | X | X | X | X | X | X |
| 24H8.F3 | X | X | X | X | X | X |
| 1C6.E12.G8 | X | X | X | X | X | X |
| 1D2.D8.G10 | X | X | X | X | X | X |
| 6A2.G7 | X | X | X | X | X | X |
| 19D2.G9 | X | X | X | X | X | X |
| 26A9.C4 | | X | X | X | X | X |
| 2F11.F8 | X | | X | X | X | X |
| 5C12.H8 | X | X | | X | X | X |
| 28H12.G9 | X | X | X | | X | X |
| 30G6.G6.G4.E9 | X | X | X | X | | X |
| 1A8.G11.E7 | X | X | X | X | X | X |

In some embodiments, the method involves exposing the sample to a first isolated antibody or antigen-binding fragment comprising a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a first isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 5, 2016 that has been assigned Accession No. PTA-123090 and a second isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or the isolated antibody that is produced by antibody-producing cells deposited with the American Type Culture Collection (10801 University Blvd., Manassas, Va. 20110-2209) on May 19, 2011 that has been assigned Accession No. PTA-11884, wherein the first isolated antibody or antigen-binding fragment is immobilized to a solid support and the second isolated antibody or antigen-binding fragment is labeled.

In other embodiments, the method involves exposing the sample to a first isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or the isolated antibody that is produced by antibody-producing cells deposited with the American Type Culture Collection (10801 University Blvd., Manassas, Va. 20110-2209) on May 19, 2011 that has been assigned Accession No. PTA-11884 and a second isolated antibody or antigen-binding fragment comprising a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a second isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the second isolated antibody that is produced by antibody-producing cells deposited with the American Type Culture Collection (10801 University Blvd., Manassas, Va. 20110-2209) on May 5, 2016 that has been assigned Accession No. PTA-123090, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 5, 2016 that has been assigned Accession No. PTA-123090.

In other embodiments, the first isolated antibody or antigen-binding fragment or the second isolated antibody or antigen-binding fragment comprises the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or the isolated antibody that is produced by antibody-producing cells deposited with the American Type Culture Collection (10801 University Blvd., Manassas, Va. 20110-2209) on May 19, 2011 that has been assigned Accession No. PTA-11884.

In other embodiments, the first isolated antibody or antigen-binding fragment or the second isolated antibody or antigen-binding fragment comprises a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123097.

In other embodiments, the first isolated antibody or antigen-binding fragment or the second isolated antibody or antigen-binding fragment comprises a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 62, a heavy chain CDR2 amino acid sequence substantially the same as, or identical to, SEQ ID NO: 63, and a heavy chain CDR3 amino acid sequence substantially the same as, or identical to, SEQ ID NO: 64, wherein the CDRs are defined according to the IMGT method, or an isolated antibody or antigen-binding fragment comprising a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 65, a heavy chain CDR2 amino acid sequence substantially the same as, or identical to, SEQ ID NO: 66, and a heavy chain CDR3 amino acid sequence substantially the same as, or identical to, SEQ ID NO: 64, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123091, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises a light chain CDR1 amino acid sequence substantially the same as, or identical to, SEQ ID NO: 84, a light chain CDR2 amino acid sequence substantially the same as, or identical to SEQ ID NO: 85, a light chain CDR3 amino acid sequence substantially the same as, or identical to, SEQ ID NO: 86, a heavy chain CDR1 amino acid sequence substantially the same as, or identical to, SEQ ID NO: 90, a heavy chain CDR2 amino acid sequence substantially the same as, or identical to, SEQ ID NO: 91, and a heavy chain CDR3 amino acid sequence substantially the same as, or identical to, SEQ ID NO: 92, wherein the CDRs are defined according to the IMGT method, or a isolated antibody or antigen-binding fragment comprising a light chain an isolated antibody or antigen-binding fragment comprising a light chain CDR1 amino acid sequence substantially the same as, or identical to, SEQ ID NO: 87, a light chain CDR2 amino acid sequence substantially the same as, or identical to, SEQ ID NO: 32, a light chain CDR3 amino acid sequence substantially the same as, or identical to, SEQ ID NO: 86, a heavy chain CDR1 amino acid sequence substantially the same as, or identical to, SEQ ID NO: 93, a heavy chain CDR2 amino acid sequence substantially the same as, or identical to, SEQ ID NO: 94, and a heavy chain CDR3 amino acid sequence substantially the same as, or identical to, SEQ ID NO: 95, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123098, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 112, a light chain CDR2 amino acid sequence substantially the same as, or identical to, SEQ ID NO: 2, a light chain CDR3 amino acid sequence substantially the same as, or identical to, SEQ ID NO: 113, a heavy chain CDR1 amino acid sequence substantially the same as, or identical to, SEQ ID NO: 118, a heavy chain CDR2 amino acid sequence substantially the same as, or identical to, SEQ ID NO: 119, and a heavy chain CDR3 amino acid sequence substantially the same as, or identical to, SEQ ID NO: 120, wherein the CDRs are defined according to the IMGT method, or a isolated antibody or antigen-binding fragment comprising a light chain CDR1 amino acid sequence substantially the same as, or identical to, SEQ ID NO: 114, a light chain CDR2 amino acid sequence substantially the same as, or identical to, SEQ ID NO: 115, a light chain CDR3 amino acid sequence substantially the same as, or identical to, SEQ ID NO: 113, a heavy chain CDR1 amino acid sequence substantially the same as, or identical to, SEQ ID NO: 121, a heavy chain CDR2 amino acid sequence substantially the same as, or identical to, SEQ ID NO: 122, and a heavy chain CDR3 amino acid sequence substantially the same as, or identical to, SEQ ID NO: 123, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123093, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 55, a light chain CDR2 amino acid sequence substantially the same as, or identical to, SEQ ID NO: 140, a light chain CDR3 amino acid sequence substantially the same as, or identical to, SEQ ID NO: 141, a heavy chain CDR1 amino acid sequence substantially the same as, or identical to, SEQ ID NO: 145, a heavy chain CDR2 amino acid sequence substantially the same as, or identical to, SEQ ID NO: 146, and a heavy chain CDR3 amino acid sequence substantially the same as, or identical to, SEQ ID NO: 147, wherein the CDRs are defined according to the IMGT method, or an isolated antibody or antigen-binding fragment comprising a light chain CDR1 amino acid sequence substantially the same as, or identical to, SEQ ID NO: 58, a light chain CDR2 amino acid sequence substantially the same as, or identical to, SEQ ID NO: 142, a light chain CDR3 amino acid sequence substantially the same as, or identical to, SEQ ID NO: 141, a heavy chain CDR1 amino acid sequence substantially the same as, or identical to, SEQ ID NO: 148, a heavy chain CDR2 amino acid sequence substantially the same as, or identical to, SEQ ID NO: 149, and a heavy chain CDR3 amino acid sequence substantially the same as, or identical to, SEQ ID NO: 150, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123094, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 168, a heavy chain CDR2 amino acid sequence substantially the same as, or identical to, SEQ ID NO: 169, and a heavy chain CDR3 amino acid sequence substantially the same as, or identical to, SEQ ID NO: 170, wherein the CDRs are defined according to the IMGT method, or an isolated antibody or antigen-binding fragment comprising a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 171, a heavy chain CDR2 amino acid sequence substantially the same as, or identical to, SEQ ID NO: 172, and a heavy chain CDR3 amino acid sequence substantially the same as, or identical to, SEQ ID NO: 173, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123092, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 187, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 196, wherein the CDRs are defined according to the IMGT method, or a second isolated antibody or antigen-binding fragment comprising a light chain CDR1 amino acid sequence substantially the same as, or identical to SEQ ID NO: 190, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 198, and a heavy chain CDR3 amino acid sequence substantially the same as, or identical to, SEQ ID NO: 199, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123098, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 217, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 221, and a heavy chain CDR3 amino acid sequence substantially the same as, or identical to, SEQ ID NO: 196, wherein the CDRs are defined according to the IMGT method, or an isolated antibody or antigen-binding fragment comprising a light chain CDR1 amino acid sequence substantially the same as, or identical to, SEQ ID NO: 218, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 222, and a heavy chain CDR3 amino acid sequence substantially the same as, or identical to, SEQ ID NO: 199, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123095, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 233, a light chain CDR2 amino acid sequence substantially the same as, or identical to, SEQ ID NO: 234, a light chain CDR3 amino acid sequence substantially the same as, or identical to, SEQ ID NO: 235, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 240, wherein the CDRs are defined according to the IMGT method, or a isolated antibody or antigen-binding fragment comprising a light chain CDR1 amino acid sequence substantially the same as, or identical to, SEQ ID NO: 236, a light chain CDR2 amino acid sequence substantially the same as, or identical to, SEQ ID NO: 237, a light chain CDR3 amino acid sequence substantially the same as, or identical to, SEQ ID NO: 235, a heavy chain CDR1 amino acid sequence substantially the same as, or identical to, SEQ ID NO: 241, a heavy chain CDR2 amino acid sequence substantially the same as, or identical to, SEQ ID NO: 198, and a heavy chain CDR3 amino acid sequence substantially the same as, or identical to, SEQ ID NO: 242, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123101, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 257, a light chain CDR2 amino acid sequence substantially the same as, or identical to, SEQ ID NO: 188, a light chain CDR3 amino acid sequence substantially the same as, or identical to, SEQ ID NO: 258, a heavy chain CDR1 amino acid sequence substantially the same as, or identical to, SEQ ID NO: 8, a heavy chain CDR2 amino acid sequence substantially the same as, or identical to, SEQ ID NO: 262, and a heavy chain CDR3 amino acid sequence substantially the same as, or identical to, SEQ ID NO: 263, wherein the CDRs are defined according to the IMGT method, or an isolated antibody or antigen-binding fragment comprising a light chain CDR1 amino acid sequence substantially the same as, or identical to, SEQ ID NO: 259, a light chain CDR2 amino acid sequence substantially the same as, or identical to, SEQ ID NO: 191, a light chain CDR3 amino acid sequence substantially the same as, or identical to, SEQ ID NO: 258, a heavy chain CDR1 amino acid sequence substantially the same as, or identical to, SEQ ID NO: 264, a heavy chain CDR2 amino acid sequence substantially the same as, or identical to, SEQ ID NO: 265, and a heavy chain CDR3 amino acid sequence substantially the same as, or identical to, SEQ ID NO: 266, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123096, wherein the first isolated antibody or antigen-binding fragment is immobilized to a solid support and the second isolated antibody or antigen-binding fragment is labeled.

In other embodiments, the first isolated antibody or antigen-binding fragment or the second isolated antibody or antigen-binding fragment comprises an isolated antibody or antigen-binding fragment comprising a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or an isolated antibody or antigen-binding fragment comprising SEQ ID NO: 4, a light chain CDR2 amino acid sequence substantially the same as, or identical to, SEQ ID NO: 115, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123100, wherein the first isolated antibody or antigen-binding fragment is immobilized to a solid support and the second isolated antibody or antigen-binding fragment is labeled.

Various combinations of the antibodies, or antigen-binding fragments thereof, may be used to detect FRα in a sample. For example, any first isolated antibody or antibody fragment described herein may be paired with any second isolated antibody or antibody fragment described herein. In preferred embodiments, the first isolated antibody or antigen-binding fragment and the second isolated antibody or antigen-binding fragment are different.

In some embodiments, the biological sample is derived from urine, blood, serum, plasma, saliva, ascites, circulating cells, circulating tumor cells, cells that are not tissue associated, tissues, surgically resected tumor tissue, biopsies, fine needle aspiration samples, or histological preparations. In some embodiments, the biological sample is derived from a human or nonhuman primate. In some embodiments, the antibody is labeled. The described antibodies and antigen-binding fragments may be detectably labeled. In some embodiments labeled antibodies and antigen-binding fragments may facilitate the detection FRα via the methods described herein. Many such labels are readily known to those skilled in the art. For example, suitable labels include, but should not be considered limited to, radiolabels, fluorescent labels (such as DyLight® 649), epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like. In some embodiments, the label is a radiolabel, an epitope tag, biotin, a chromophore label, a fluorophore label, an electrochemiluminescence (ECL) label, or an enzyme. In preferred embodiments, the electrochemiluminescence (ECL) label is a sulfo-tag.

In some embodiments, the first isolated antibody or antigen-binding fragment is biotinylated and the solid support is coated with streptavidin, and the isolated antibody or antigen-binding fragment is immobilized to the solid support by the binding of biotin to streptavidin. In some embodiments, the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA. In some embodiments, the level of FRα in the sample is quantified.

In some embodiments described herein detection of FRα-expressing cancer cells in a subject may be used to determine that the subject may be treated with a therapeutic agent directed against FRα. In some embodiments the therapeutic agent directed against FRα may be an antibody, such as farletuzumab (MORAb-003). In some embodiments, the sample is exposed to MORAb-003 prior to detecting FRα in the sample.

Methods for Diagnosing, Monitoring and Treating Folate Receptor Alpha (FRα)-Expressing Cancer Provided herein are methods for diagnosing a folate receptor alpha (FRα)-expressing cancer in a subject. FRα-expressing cancers include ovarian, breast, thyroid, colorectal, endometrial, fallopian tube, or lung cancer of epithelial origin in a subject. In some embodiments, as described above, detecting FRα in a sample, such as a histological sample, a fine needle aspirate sample, resected tumor tissue, circulating cells, circulating tumor cells, and the like, provides the ability to diagnose cancer in the subject from whom the sample was obtained. In some embodiments, it may already be known that the subject from whom the sample was obtained has cancer, but the type of cancer afflicting the subject may not yet have been diagnosed or a preliminary diagnosis may be unclear, thus detecting FRα in a sample obtained from the subject can allow for, or clarify, diagnosis of the cancer.

In some embodiments, the described methods involve exposing the biological sample of the subject to any one of the antibodies or antigen-binding fragments described herein. In some embodiments, the described methods involve exposing the biological sample of the subject to an antibody or antigen-binding fragment capable of binding the epitope of FRα that is bound by any one of the antibodies or antigen binding fragments described herein. In some embodiments, the described methods involve quantifying the amount of FRα present in the sample that is bound by the antibody or antigen-binding fragment. In some embodiments, the described methods involve comparing the amount of FRα present in the sample to a known standard. In some embodiments, the described methods involve determining whether the subject's FRα levels fall within the levels of FRα associated with cancer.

Also described herein are methods for monitoring a folate receptor alpha (FRα)-expressing cancer in a subject. In some embodiments, the described methods involve exposing the biological sample of the subject to any one of the antibodies or antigen-binding fragments described herein. In some embodiments, the described methods involve exposing the biological sample of the subject to an antibody or antigen-binding fragment capable of binding the epitope of FRα that is bound by the antibody or antigen binding fragment of any one of the antibodies or antigen-binding fragments described herein. In some embodiments, the described methods involve quantifying the amount of FRα present in the sample that is bound by the antibody or antigen-binding fragment. In some embodiments, the described methods involve comparing the amount of FRα present in the sample to a known standard. In some embodiments, the described methods involve comparing the amount of FRα present in the sample to a biological sample obtained from the subject at an earlier point in time. In some embodiments, the described methods involve determining whether the subject's FRα levels are indicative of cancer progression, regression or stable disease.

Also provided herein are methods for treating a folate receptor alpha (FRα)-expressing cancer in a subject. In some embodiments, the described methods involve exposing the biological sample of the subject to any one of the antibodies or antigen-binding fragments described herein. In some embodiments, the described methods involve exposing the biological sample of the subject to an antibody or antigen-binding fragment capable of binding the epitope of FRα that is bound by the antibody or antigen binding fragment of any one of the antibodies or antigen-binding fragments described herein. In some embodiments, the described methods involve quantifying the amount of FRα present in the sample that is bound by the antibody or antigen-binding fragment. In some embodiments, the described methods involve comparing the amount of FRα present in the sample to a known standard. In some embodiments, the described methods involve determining whether the subject's FRα levels fall within the levels of FRα associated with cancer. In some embodiments, the described methods involve administering to the subject, or prescribing, a treatment for the cancer.

In some embodiments of the described methods, the antibody or antigen-binding fragment of any one of the antibodies or antigen-binding fragments described herein is labeled. In some embodiments, the label is a radiolabel, an epitope tag, biotin, a chromophore label, a fluorophore label, an electrochemiluminescence (ECL) label, or an enzyme. In preferred embodiments, the electrochemiluminescence (ECL) label is a sulfo-tag.

In some embodiments of the methods described herein, the step of exposing a biological sample of the subject to the antibody or antigen-binding fragment of any one of the antibodies or antigen-binding fragments described herein or an antibody or antigen-binding fragment capable of binding the epitope of folate receptor alpha (FRα) that is bound by the antibody or antigen binding fragment of any one of the antibodies or antigen-binding fragments described herein further comprises exposing the biological sample of the subject to a second antibody or antigen-binding fragment capable of binding FRα.

In some embodiments of the methods described herein, the antibody or antigen-binding fragment or the second antibody or antigen-binding fragment is the isolated antibody or antigen-binding fragment which includes a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method. In some embodiments of the methods described herein, the antibody or antigen-binding fragment is the isolated antibody or antigen-binding fragment which includes a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method. In some embodiments of the methods described herein, the antibody or antigen-binding fragment is the isolated antibody or antigen-binding fragment that is produced by antibody-producing cells deposited with the American Type Culture Collection (10801 University Blvd., Manassas, Va. 20110-2209) on May 5, 2016 that has been assigned Accession No. PTA-123090.

In some embodiments of the methods described herein, the antibody or antigen-binding fragment or the second antibody or antigen-binding fragment is the isolated antibody or antigen-binding fragment with a light chain CDR1 amino acid sequence substantially the same as, or identical to, SEQ ID NO: 31, a light chain CDR2 amino acid sequence substantially the same as, or identical to, SEQ ID NO: 32, a light chain CDR3 amino acid sequence substantially the same as, or identical to, SEQ ID NO: 33, a heavy chain CDR1 amino acid sequence substantially the same as, or identical to SEQ ID NO: 35, a heavy chain CDR2 amino acid sequence substantially the same as, or identical to, SEQ ID NO: 36, and a heavy chain CDR3 amino acid sequence substantially the same as, or identical to, SEQ ID NO: 37 or the isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-1884.

In other embodiments, the antibody or antigen-binding fragment or the second antibody or antigen-binding fragment comprises a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or a isolated antibody or antigen-binding fragment comprising a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123097.

In other embodiments, the antibody or antigen-binding fragment or the second antibody or antigen-binding fragment comprises a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 62, a heavy chain CDR2 amino acid sequence substantially the same as, or identical to, SEQ ID NO: 63, and a heavy chain CDR3 amino acid sequence substantially the same as, or identical to, SEQ ID NO: 64, wherein the CDRs are defined according to the IMGT method, or an isolated antibody or antigen-binding fragment comprising a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 65, a heavy chain CDR2 amino acid sequence substantially the same as, or identical to, SEQ ID NO: 66, and a heavy chain CDR3 amino acid sequence substantially the same as, or identical to, SEQ ID NO: 64, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123091, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises a light chain CDR1 amino acid sequence substantially the same as, or identical to, SEQ ID NO: 84, a light chain CDR3 amino acid sequence substantially the same as, or identical to, SEQ ID NO: 85, a light chain CDR3 amino acid sequence substantially the same as, or identical to, SEQ ID NO: 86, a heavy chain CDR1 amino acid sequence substantially the same as, or identical to, SEQ ID NO: 90, a heavy chain CDR2 amino acid sequence substantially the same as, or identical to, SEQ ID NO: 91, and a heavy chain CDR3 amino acid sequence substantially the same as, or identical to, SEQ ID NO: 92, wherein the CDRs are defined according to the IMGT method, or a isolated antibody or antigen-binding fragment comprising a light chain CDR1 amino acid sequence substantially the same as, or identical to, SEQ ID NO: 87, a light chain CDR2 amino acid sequence substantially the same as, or identical to, SEQ ID NO: 32, a light chain CDR3 amino acid sequence substantially the same as, or identical to, SEQ ID NO: 86, a heavy chain CDR1 amino acid sequence substantially the same as, or identical to, SEQ ID NO: 93, a heavy chain CDR2 amino acid sequence substantially the same as, or identical to, SEQ ID NO: 94, and a heavy chain CDR3 amino acid sequence substantially the same as, or identical to, SEQ ID NO: 95, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123098, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR1 amino acid sequence substantially the same as, or identical to, SEQ ID NO: 112, a light chain CDR2 amino acid sequence substantially the same as, or identical to, SEQ ID NO: 2, a light chain CDR3 amino acid sequence substantially the same as, or identical to, SEQ ID NO: 113, a heavy chain CDR1 amino acid sequence substantially the same as, or identical to, SEQ ID NO: 118, a heavy chain CDR2 amino acid sequence substantially the same as, or identical to, SEQ ID NO: 119, and a heavy chain CDR3 amino acid sequence substantially the same as, or identical to, SEQ ID NO: 120, wherein the CDRs are defined according to the IMGT method, or an isolated antibody or antigen-binding fragment comprising a light chain CDR1 amino acid sequence substantially the same as, or identical to, SEQ ID NO: 114, a light chain CDR2 amino acid sequence substantially the same as, or identical to, SEQ ID NO: 115, a light chain CDR3 amino acid sequence substantially the same as, or identical to, SEQ ID NO: 113, a heavy chain CDR1 amino acid sequence substantially the same as, or identical to, SEQ ID NO: 121, a heavy chain CDR2 amino acid sequence substantially the same as, or identical to, SEQ ID NO: 122, and a heavy chain CDR3 amino acid sequence substantially the same as, or identical to, SEQ ID NO: 123, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123093, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR1 amino acid sequence substantially the same as, or identical to, SEQ ID NO: 55, a light chain CDR2 amino acid sequence substantially the same as, or identical to, SEQ ID NO: 140, a light chain CDR3 amino acid sequence substantially the same as, or identical to, SEQ ID NO: 141, a heavy chain CDR1 amino acid sequence substantially the same as, or identical to, SEQ ID NO: 145, a heavy chain CDR2 amino acid sequence substantially the same as, or identical to, SEQ ID NO: 146, and a heavy chain CDR3 amino acid sequence substantially the same as, or identical to, SEQ ID NO: 147, wherein the CDRs are defined according to the IMGT method, or an isolated antibody or antigen-binding fragment comprising a light chain CDR1 amino acid sequence substantially the same as, or identical to, SEQ ID NO: 58, a light chain CDR2 amino acid sequence substantially the same as, or identical to, SEQ ID NO: 142, a light chain CDR3 amino acid sequence substantially the same as, or identical to, SEQ ID NO: 141, a heavy chain CDR1 amino acid sequence substantially the same as, or identical to, SEQ ID NO: 148, a heavy chain CDR2 amino acid sequence substantially the same as, or identical to, SEQ ID NO: 149, and a heavy chain CDR3 amino acid sequence substantially the same as, or identical to, SEQ ID NO: 150, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123094, wherein the first isolated antibody or antigen-binding fragment is immobilized to a solid support and the second isolated antibody or antigen-binding fragment is labeled.

In other embodiments, the antibody or antigen-binding fragment or the isolated antibody or antigen-binding fragment comprises an isolated antibody or antigen-binding fragment comprising a light chain CDR1 amino acid sequence substantially the same as, or identical to, SEQ ID NO: 55, a light chain CDR2 amino acid sequence substantially the same as, or identical to, SEQ ID NO: 56, a light chain CDR3 amino acid sequence substantially the same as, or identical to, SEQ ID NO: 57, a heavy chain CDR1 amino acid sequence substantially the same as, or identical to, SEQ ID NO: 168, a heavy chain CDR2 amino acid sequence substantially the same as, or identical to, SEQ ID NO: 169, and a heavy chain CDR3 amino acid sequence substantially the same as, or identical to, SEQ ID NO: 170, wherein the CDRs are defined according to the IMGT method, or an isolated antibody or antigen-binding fragment comprising a light chain CDR1 amino acid sequence substantially the same as, or identical to, SEQ ID NO: 58, a light chain CDR2 amino acid sequence substantially the same as, or identical to, SEQ ID NO: 59, a light chain CDR3 amino acid sequence substantially the same as, or identical to, SEQ ID NO: 57, a heavy chain CDR1 amino acid sequence substantially the same as, or identical to, SEQ ID NO: 171, a heavy chain CDR2 amino acid sequence substantially the same as, or identical to, SEQ ID NO: 172, and a heavy chain CDR3 amino acid sequence substantially the same as, or identical to, SEQ ID NO: 173, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123092, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR3 amino acid sequence substantially the same as, or identical to, SEQ ID NO: 187, a light chain CDR3 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 196, wherein the CDRs are defined according to the IMGT method, or a second isolated antibody or antigen-binding fragment comprising a light chain CDR1 amino acid sequence substantially the same as, or identical to, SEQ ID NO: 190, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 198, and a heavy chain CDR3 amino acid sequence substantially the same as, or identical to, SEQ ID NO: 199, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123098, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR1 amino acid sequence substantially the same as, or identical to, SEQ ID NO: 217, a light chain CDR2 amino acid sequence substantially the same as, or identical to, SEQ ID NO: 188, a light chain CDR3 amino acid sequence substantially the same as, or identical to, SEQ ID NO: 189, a heavy chain CDR1 amino acid sequence substantially the same as, or identical to, SEQ ID NO: 194, a heavy chain CDR2 amino acid sequence substantially the same as, or identical to, SEQ ID NO: 221, and a heavy chain CDR3 amino acid sequence substantially the same as, or identical to, SEQ ID NO: 196, wherein the CDRs are defined according to the IMGT method, or an isolated antibody or antigen-binding fragment comprising a light chain CDR1 amino acid sequence substantially the same as, or identical to SEQ ID NO: 218, a light chain CDR2 amino acid sequence substantially the same as, or identical to, SEQ ID NO: 191, a light chain CDR3 amino acid sequence substantially the same as, or identical to, SEQ ID NO: 189, a heavy chain CDR1 amino acid sequence substantially the same as, or identical to, SEQ ID NO: 197, a heavy chain CDR2 amino acid sequence substantially the same as, or identical to, SEQ ID NO: 222, and a heavy chain CDR3 amino acid sequence substantially the same as, or identical to, SEQ ID NO: 199, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123095, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR1 amino acid sequence substantially the same as, or identical to, SEQ ID NO: 233, a light chain CDR2 amino acid sequence substantially the same as, or identical to, SEQ ID NO: 234, a light chain CDR3 amino acid sequence substantially the same as, or identical to, SEQ ID NO: 235, a heavy chain CDR1 amino acid sequence substantially the same as, or identical to, SEQ ID NO: 194, a heavy chain CDR2 amino acid sequence substantially the same as, or identical to, SEQ ID NO: 195, and a heavy chain CDR3 amino acid sequence substantially the same as, or identical to, SEQ ID NO: 240, wherein the CDRs are defined according to the IMGT method, or a isolated antibody or antigen-binding fragment comprising a light chain CDR1 amino acid sequence substantially the same as, or identical to, SEQ ID NO: 236, a light chain CDR2 amino acid sequence substantially the same as, or identical to, SEQ ID NO: 237, a light chain CDR3 amino acid sequence substantially the same as, or identical to, SEQ ID NO: 235, a heavy chain CDR1 amino acid sequence substantially the same as, or identical to, SEQ ID NO: 241, a heavy chain CDR2 amino acid sequence substantially the same as, or identical to, SEQ ID NO: 198, and a heavy chain CDR3 amino acid sequence substantially the same as, or identical to, SEQ ID NO: 242, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123101, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR1 amino acid sequence substantially the same as, or identical to, SEQ ID NO: 257, a light chain CDR2 amino acid sequence substantially the same as, or identical to, SEQ ID NO: 188, a light chain CDR3 amino acid sequence substantially the same as, or identical to, SEQ ID NO: 258, a heavy chain CDR1 amino acid sequence substantially the same as, or identical to, SEQ ID NO: 8, a heavy chain CDR2 amino acid sequence substantially the same as, or identical to, SEQ ID NO: 262, and a heavy chain CDR3 amino acid sequence substantially the same as, or identical to, SEQ ID NO: 263, wherein the CDRs are defined according to the IMGT method, or an isolated antibody or antigen-binding fragment comprising a light chain CDR1 amino acid sequence substantially the same as, or identical to SEQ ID NO: 259, a light chain CDR2 amino acid sequence substantially the same as, or identical to, SEQ ID NO: 191, a light chain CDR3 amino acid sequence substantially the same as, or identical to, SEQ ID NO: 258, a heavy chain CDR1 amino acid sequence substantially the same as, or identical to, SEQ ID NO: 264, a heavy chain CDR2 amino acid sequence substantially the same as, or identical to, SEQ ID NO: 265, and a heavy chain CDR3 amino acid sequence substantially the same as, or identical to, SEQ ID NO: 266, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123096, wherein the first isolated antibody or antigen-binding fragment is immobilized to a solid support and the second isolated antibody or antigen-binding fragment is labeled.

In other embodiments, the antibody or antigen-binding fragment or the second antibody or antigen-binding fragment comprises an isolated antibody or antigen-binding fragment comprising a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, or an isolated antibody or antigen-binding fragment with a light chain CDR1 amino acid sequence substantially the same as, or identical to, SEQ ID NO: 4, a light chain CDR2 amino acid sequence substantially the same as, or identical to, SEQ ID NO: 115, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the isolated antibody that is produced by antibody-producing cells deposited with the American Type Culture Collection (10801 University Blvd., Manassas, Va. 20110-2209) on May 4, 2016 that has been assigned Accession No. PTA-123100, wherein the first isolated antibody or antigen-binding fragment is immobilized to a solid support and the second isolated antibody or antigen-binding fragment is labeled.

In some embodiments, the antibody or antigen-binding fragment is the isolated antibody or antigen-binding fragment with a light chain CDR1 amino acid sequence substantially the same as, or identical to, SEQ ID NO: 31, a light chain CDR2 amino acid sequence substantially the same as, or identical to, SEQ ID NO: 32, a light chain CDR3 amino acid sequence substantially the same as, or identical to, SEQ ID NO: 33, a heavy chain CDR1 amino acid sequence substantially the same as, or identical to SEQ ID NO: 35, a heavy chain CDR2 amino acid sequence substantially the same as, or identical to, SEQ ID NO: 36, and a heavy chain CDR3 amino acid sequence substantially the same as, or identical to, SEQ ID NO: 37 or the isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884 and the second antibody or antigen-binding fragment is the isolated antibody or antigen-binding fragment with a light chain CDR1 amino acid sequence substantially the same as, or identical to, SEQ ID NO: 1, a light chain CDR2 amino acid sequence substantially the same as, or identical to, SEQ ID NO: 2, a light chain CDR3 amino acid sequence substantially the same as, or identical to, SEQ ID NO: 3, a heavy chain CDR1 amino acid sequence substantially the same as, or identical to, SEQ ID NO: 8, a heavy chain CDR2 amino acid sequence substantially the same as, or identical to, SEQ ID NO: 9, and a heavy chain CDR3 amino acid sequence substantially the same as, or identical to, SEQ ID NO: 10, wherein the CDRs are defined according to the IMGT method, the isolated antibodies or antigen-binding fragment with a light chain CDR1 amino acid sequence substantially the same as, or identical to, SEQ ID NO: 4, a light chain CDR2 amino acid sequence substantially the same as, or identical to, SEQ ID NO: 5, a light chain CDR3 amino acid sequence substantially the same as, or identical to, SEQ ID NO: 3, a heavy chain CDR1 amino acid sequence substantially the same as, or identical to, SEQ ID NO: 11, a heavy chain CDR2 amino acid sequence substantially the same as, or identical to, SEQ ID NO: 12, and a heavy chain CDR3 amino acid sequence substantially the same as, or identical to, SEQ ID NO: 13, wherein the CDRs are defined according to the KABAT method, or the antigen-binding fragment is the isolated antibody or antigen-binding fragment that is produced by antibody-producing cells deposited with the American Type Culture Collection (10801 University Blvd., Manassas, Va. 20110-2209) on May 5, 2016 that has been assigned Accession No. PTA-123090.

Various combinations of the antibodies, or antigen-binding fragments thereof, may be used to quantify the amount of FRα in a sample. For example, any isolated antibody or antibody fragment described herein may be paired with any second isolated antibody or antibody fragment in paragraphs described herein. In preferred embodiments, the isolated antibody or antigen-binding fragment and the second isolated antibody or antigen-binding fragment are different.

In some embodiments, the second antibody or antigen-binding fragment is immobilized to a solid support. In some embodiments, the second antibody or antigen-binding fragment is biotinylated and the solid support is coated with streptavidin, and the isolated antibody or antigen-binding fragment is immobilized to the solid support by the binding of biotin to streptavidin. In some embodiments, the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA. In some embodiments, the FRα-expressing cancer is ovarian cancer. In some embodiments, the method is conducted following treatment of the subject for cancer with MORAb-003.

In various embodiments of the described diagnostic methods a control sample is used. The control sample may be a positive or negative assay control that ensures the assay used is working properly; for example, an assay control of this nature might be commonly used for immunohistochemistry assays. Alternatively, the control sample may be a standardized control amount of FRα in a healthy subject. In some embodiments, the observed FRα levels of the tested subject may be compared with FRα levels observed in samples from control subjects known to have FRα-expressing cancer.

The diagnostic methods provided herein also provide a basis upon which it may be possible to predict whether a subject has a relatively higher or lower likelihood of surviving 5 years following diagnosis. In some embodiments, the described method may be used to predict a favorable outcome for a subject having adenocarcinoma, wherein a favorable outcome is defined as having an increased 5-year survival rate. As data provided herein indicate, subjects determined to have stage I or stage II adenocarcinoma that does not express FRα are about 2 times more likely to die within five years than subjects determined to have stage I or stage II adenocarcinoma that does express FRα. Accordingly, the diagnostic methods described herein may be combined with this knowledge to allow for a method of predicting 5-year survivorship likelihood for subjects determined to have cancer. In some embodiments the method is used to predict the 5-year survivorship likelihood for subjects determined to have adenocarcinoma.

In some embodiments the described prognostic method will involve: contacting a biological sample of a subject with an FRα-specific antibody, or antigen-binding fragment thereof (such as those derivable from the antibodies and fragments provided in Table 1), quantifying the amount of FRα present in the sample that is bound by the antibody or antigen-binding fragment thereof, comparing the amount of FRα present in the sample to a known standard; and determining whether the subject's FRα levels indicate the presence of a FRα expressing cancer, thereby allowing for a prediction to be made as to the likelihood the subject will survive five years after being diagnosed with cancer. In some embodiments the subject is known to have or determined to have adenocarcinoma. In some embodiments the subject is a human.

In some embodiments the described methods involve assessing whether FRα-expressing cancer is progressing, regressing, or remaining stable by determining the amount of FRα-associated with a cell or tissue that is present in a test sample derived from the subject; and comparing the observed amount of FRα with the amount of FRα in a sample obtained from the subject, in a similar manner, at an earlier point in time, wherein a difference between the amount of FRα in the test sample and the earlier sample provides an indication of whether the cancer is progressing, regressing, or remaining stable. In this regard, a test sample with an increased amount of FRα, relative to the amount observed for the earlier sample, may indicate progression of a FRα-expressing cancer. Conversely, a test sample with a decreased amount of FRα, relative to the amount observed for the earlier sample, may indicate regression of a FRα-expressing cancer. Accordingly, a test sample with an insignificant difference in the amount of FRα, relative to the amount observed for the earlier sample, may indicate a state of stable disease for a FRα-expressing cancer. In some embodiments the amount of FRα in a sample derived from the subject is assessed by contacting the sample with an antibody that binds FRα such as the antibodies described herein. The sample assessed for the presence of FRα may be circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether FRα-expressing cancer is progressing, regressing, or remaining stable by determining the amount of FRα not associated with a cell or tissue that is present in a test sample derived from the subject; and comparing the observed amount of FRα with the amount of FRα in a sample obtained from the subject, in a similar manner, at an earlier point in time, wherein a difference between the amount of FRα in the test sample and the earlier sample provides an indication of whether the cancer is progressing, regressing, or remaining stable. In this regard, a test sample with an increased amount of FRα relative to the amount observed for the earlier sample, may indicate progression of a FRα-expressing cancer. Conversely, a test sample with a decreased amount of FRα relative to the amount observed for the earlier sample, may indicate regression of a FRα-expressing cancer. Accordingly, a test sample with an insignificant difference in the amount of FRα relative to the amount observed for the earlier sample, may indicate a state of stable disease for a FRα-expressing cancer. In some embodiments the amount of FRα in a sample derived from the subject is assessed by contacting the sample with an antibody that binds FRα, such as the antibodies described herein. The sample assessed for the presence of FRα may be urine, blood, serum, plasma, saliva, ascites, histological preparations, and the like.

Kits of the Invention

Provided herein are kits for detecting the presence of folate receptor alpha (FRα) in a biological sample. In some embodiments, the kit may contain the antibody or antigen-binding fragment of any one of the antibodies or antigen-binding fragments described herein. In some embodiments, the kit may contain an antibody or antigen-binding fragment capable of binding the epitope of FRα that is bound by the antibody or antigen binding fragment of any one of the antibodies or antigen-binding fragments described herein. In some embodiments, the kit may contain an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody or antigen-binding fragment that is produced by antibody-producing cells deposited with the American Type Culture Collection (10801 University Blvd., Manassas, Va. 20110-2209) on May 19, 2011 that has been assigned Accession No. PTA-11884. In some embodiments, the kit may contain a vessel for containing the antibody, when not in use, and instructions for use of the antibody.

Also provided herein are kits for detecting the presence of folate receptor alpha (FRα) in a biological sample. In some embodiments, the kit may contain the antibody or antigen-binding fragment of any one of the antibodies or antigen-binding fragments described herein, wherein the antibody or antigen-binding fragment is affixed to a solid support. In some embodiments, the kit may contain an antibody or antigen-binding fragment capable of binding the epitope of FRα that is bound by the antibody or antigen binding fragment of any one of the antibodies or antigen-binding fragments described herein wherein the antibody or antigen-binding fragment is affixed to a solid support. For example, the kit may contain the antibody or antigen-binding fragment described herein.

Also provided herein are kits for detecting the presence of folate receptor alpha (FRα) in a biological sample. In some embodiments, the kit may contain the antibody or antigen-binding fragment of any one of the antibodies or antigen-binding fragments described herein, wherein the antibody or antigen-binding fragment is affixed to a solid support. In some embodiments, the kit may contain an antibody or antigen-binding fragment capable of binding the epitope of FRα that is bound by the antibody or antigen binding fragment of any one of the antibodies or antigen-binding fragments described herein wherein the antibody or antigen-binding fragment is affixed to a solid support. For example, the kit may contain the antibody or antigen-binding fragment described herein.

Also described herein are kits for detecting the presence of folate receptor alpha (FRα) in a biological sample. In some embodiments, the kit may contain the antibody or antigen-binding fragment of any one of the antibodies or antigen-binding fragments described herein, wherein the antigen-binding fragment is detectably labeled. In some embodiments, the kit may contain an antibody or antigen-binding fragment capable of binding the epitope of FRα that is bound by the antibody or antigen binding fragment of any one of the antibodies or antigen-binding fragments described herein, wherein the antigen-binding fragment is detectably labeled. For example, the kit may contain the antibody or antigen-binding fragment described in paragraphs herein.

The provided antibody, or antigen-binding fragment, may be in solution; lyophilized; affixed to a substrate, carrier, or plate; or conjugated to a detectable label.

The described kits may also include additional components useful for performing the methods described herein. By way of example, the kits may comprise means for obtaining a sample from a subject, a control sample, e.g., a sample from a subject having slowly progressing cancer and/or a subject not having cancer, one or more sample compartments, and/or instructional material which describes performance of a method of the invention and tissue specific controls/standards.

The means for determining the level of FRα, can further include, for example, buffers or other reagents for use in an assay for determining the level of FRα. The instructions can be, for example, printed instructions for performing the assay and/or instructions for evaluating the level of expression of FRα.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

The described kits may also include a blocking reagent that can be applied to a sample to decrease nonspecific binding of a primary or secondary antibody. An example of a blocking reagent is bovine serum albumin (BSA), which may be diluted in a buffer prior to use. Other commercial blocking reagents, such as Block Ace and ELISA Synblock (AbD serotec), Background Punisher (BIOCARE MEDICAL), and StartingBlock (Thermo Fisher Scientific) are known in the art. The described kits may also include a negative control primary antibody that does not bind to FRα sufficiently to yield a positive result in an antibody-based detection assay. In addition, the described kits may include a secondary antibody capable of binding to a FRα primary antibody, such antibody 24H8.D3, antibody 19D4.B7, antibody 24H8.F3, or antibody 1C6.E12.G8. In some embodiments the secondary antibody may be conjugated to a detectable label, such as horse radish peroxidase (HRP) or a fluorophore, to allow for detection of the primary antibody bound to a sample. The described kits may also include a colorimetric or chemiluminescent substrate that allows the presence of a bound secondary antibody to be detected on a sample. In some embodiments the colorimetric or chemiluminescent substrate may be 2,2'-azino-bis(3-ethylbenzothiazoline-6-sulphonic acid) (ABTS); 3,3',5,5'-Tetramethylbenzidine (TMB); 3,3'-Diaminobenzidine (DAB); SuperSignal (Thermo Fisher Scientific); ECL reagent (Thermo Fisher Scientific) or other such reagents known to those of ordinary skill in the art.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within the and can be made without departing from the true scope of the invention.

Example 1—Expression and Purification of Recombinant, Human Folate Receptor Alpha To conduct the experiments associated with the studies described herein, several folate receptor alpha ("FRα" or "FOLR1")-expressing cell systems or lines were created to generate FRα-expressing cell substrates or to generate purified recombinant human FRα protein. One expression system used was a Sf9 insect cell line that expressed recombinant human FRα via baculovirus. This system was prepared using a human FRα sequence, containing a leader sequence optimized for insect cell expression, an N-terminal 6× histidine (6×his) epitope tag (SEQ ID NO: 294), and the native GPI attachment site intact. The cells were then incubated in a 1 L shake flask and log-phase cultures of Sf9 insect cells were infected with the recombinant baculovirus at a multiplicity of infection (MOI) of <1. Cells from 30 L of culture were harvested, lysed and extracted 2× with 1× phosphate-buffered saline (PBS) containing 10 mM 3-[(3-cholamidopropyl)dimethylammonio]-1-propanesulfonate (CHAPS). The NaCl concentration was adjusted to 300 mM and filtered through a 0.2 μm membrane. The clarified supernatant was purified by affinity chromatography, using 1×PBS with 2M NaCl, 1 mM CHAPS, pH 7.4 as wash buffer, followed by elution with 10 mM 3-(N-morpholino) propanesulfonic acid (MOPS), 3M $MgCl_2$, 1 mM CHAPS, pH 6.8. Peak fractions were dialyzed extensively against IX PBS, pH 7.4, analyzed for purity by SDS-PAGE, quantitated by bicinchoninic acid assay (BCA) assay, aliquoted and stored at −80° Celsius.

A Chinese hamster ovary (CHO) cell line stably expressing and secreting human FRα was produced using a human folate receptor alpha (FRα) sequence, containing a human immunoglobulin kappa leader sequence and a C-terminal 6×his epitope tag (SEQ ID NO: 294) replacing the GPI attachment site. Once produced, the FRα-expressing CHO cells were grown at 25 L-scale in wave bags. To purify the secreted FRα protein, cell supernatant was cleared of cellular debris by depth filtration and then concentrated 10-fold by tangential flow filtration and diafiltered into 50 mM sodium phosphate, 300 mM NaCl, 1 mM imidazole, pH 8.0. This was loaded onto a pre-packed Talon® IMAC column using an FPLC. Unbound material was washed out using 50 mM sodium phosphate, 300 mM NaCl, 5 mM imidazole, pH 8.0 and bound protein was eluted using a linear gradient of 5 mM-100 mM imidazole in 50 mM sodium phosphate, 300 mM NaCl, pH 8.0. Peak fractions were dialyzed extensively against 1×PBS, pH 7.4, analyzed for purity by SDS-PAGE, quantitated by BCA assay, aliquoted and stored at −80° Celsius.

A similar cell system was also produced for human folate receptor beta (FRβ), human folate receptor gamma (FRγ), and human folate receptor delta (FRδ). Briefly, constructs of either FRβ, FRγ, or FRδ containing a human immunoglobulin kappa leader sequence and a C-terminal 6×his epitope tag (SEQ ID NO: 294) replacing the GPI attachment site, were used to transiently transfect 1 L cultures of 293F cells. Recombinant FR proteins were purified as described above for human FRα.

A Chinese hamster ovary (CHO) cell line stably expressing and secreting a human mesothelin sequence, containing a human immunoglobulin kappa leader sequence and a C-terminal 6×his epitope tag (SEQ ID NO: 294) replacing the GPI attachment site, was also prepared, as mesothelin served as a negative control for many studies. Human mesothelin-expressing CHO cells were grown at 25 L-scale in wave bags. To purify the secreted mesothelin protein, cell supernatant was cleared of debris by hollow-fiber filtration and clarified supernatant was concentrated 10-fold by tangential flow filtration. Supernatant NaCl concentration was adjusted to 300 mM NaCl and 0.5 mM imidazole. This was loaded onto a pre-packed Talon® IMAC column using an FPLC. Unbound material was washed out using 50 mM sodium phosphate, 300 mM NaCl, 3 mM imidazole, pH 8.0 and bound protein was eluted using 50 mM sodium phosphate, 300 mM NaCl, 150 mM imidazole, and pH 8.0. Peak fractions were dialyzed extensively against 50 mM potassium phosphate, pH 7.5. Ammonium sulfate was added to a final concentration of 1M, and final purification was then done on a pre-packed phenyl sepharose column using a step gradient of 1M-0M ammonium sulfate in 50 mM potassium phosphate, pH 7.5. Peak fractions were dialyzed extensively against 1×PBS, pH 7.4, analyzed for purity by SDS-PAGE, quantitated by BCA assay, aliquoted and stored at −80° Celsius.

Example 2—Production of Purified Reduced and Alkylated FRα

Efforts were undertaken to produce a reduced and alkylated antigenic form of FRα. To reduce the protein, purified FRα was concentrated to 2 mg/mL in phosphate buffered saline (pH 7.4) using centrifugal filters (Amicon Ultra, 3 kDa MW limit). The protein concentration was determined using a BCA assay (Thermo Scientific). The resultant FRα was diluted 1:1 in 8M urea/PBS to generate a final concentration of 1 mg/mL FRα in PBS containing 4M urea. Dithiothreitol solution (500 mM in PBS) was added to a final concentration of 10 mM. The solution was incubated at 65° Celsius for one hour, and cooled to room temperature.

Next 1M of iodoacetamide solution in phosphate buffer saline was added into the reduced folate receptor solution to a final concentration of 10 mM, and the reaction was kept in dark at room temperature for 30 minutes. The protein remained soluble under these conditions. The final reduced FRα to be used for immunization was stored in phosphate buffer saline containing 4M of urea, 10 mM of DTT, and 10 mM of iodoacetamide.

FIG. 1 shows the differential migration of native FRα protein and a reduced and alkylated form of the protein analyzed by SDS-PAGE under non-reducing conditions.

Example 3—Production of Hybridomas to FRα

Eight week old female Balb/c mice were immunized with hexa-histidine (SEQ ID NO: 294) tagged FRα protein (n=5) or reduced and alkylated FRα protein (n=5). Initial intraperitoneal immunizations administered on day 0 comprised 50 μg of the respective immunogen mixed 1:1 (v:v) with complete Freund's adjuvant (Rockland, Cat # D614-0050). Mice were then boosted with 50 μg immunogen mixed 1:1 (v:v) with incomplete Freund's adjuvant (Rockland, Cat # D615-0050) administered intraperitoneally 14 days later and every 21 days thereafter. Blood samples were collected from immunized mice 24 days after the initial immunization and every 21 days thereafter.

Collected blood samples were analyzed by direct enzyme-linked immunoassay (EIA) against FRα. Plates were coated with FRα protein (100 μl of a 1 μg/mL solution in PBS, 0.02 M potassium phosphate, 0.15 M Sodium Chloride, pH 7.2) and incubated overnight at 4° C., washed with PBS containing 0.2% Tween®-20 (PBST; Rockland, Cat # MB-075-1000) and blocked with 3% fish gel (Sigma) for 1 hr at room temperature. A 3-fold dilution series of individual mouse serum samples were allowed to bind for 1 hr at room temperature, plates were then washed 3 times with PBST and subsequently probed with an HRP-conjugated rabbit-anti-mouse antibody (Rockland, Cat #610-4320) at 1:2500 for 30 minutes at 37° C. TMB substrate (Rockland, Cat # TMBE-100) was added and the reaction was stopped after 30 minutes by addition of 100 mL of 1M HCl prior to absorbance reading at 450 nm (Microplate Reader "Benchmark"; Biorad). All samples were counter-screened against hexa-histidine tagged (SEQ ID NO: 294) recombinant mesothelin (mesothelin-His$_6$ ("His$_6$" disclosed as SEQ ID NO: 294)) protein as a negative control.

Spleens from mice showing the highest antigen-specific titers were harvested and hybridomas were prepared by electrofusion (Hybrimune™ Model CEEF-50B Waveform Generator; Cellectis, Romainville, France) of splenocytes with Sp2/0 Ag14 myeloma cells (ATTC CRL1581). Subsequently, hybridoma supernatants were screened by ELISA against FRα and recombinant Mesothelin-His$_6$ ("His$_6$" disclosed as SEQ ID NO: 294) as described above to select positive parental fusion cell lines.

Selected parental cell lines determined to produce antibodies reactive to recombinant human FRα (rhFRα) were then subcloned by limiting dilution. The antibodies produced by these cells were then retested for FRα binding and isotyped using the Clonetyping™ System (SouthernBiotech, Birmingham, Ala.). Supernatants from these clones were further screened by direct ELISA against three additional isoforms of the human folate receptor (FRβ, FRγ and FRδ) to determine receptor specificity. Plates were coated overnight with 100 μL of a 1 μg/mL solution of the respective FR isoform at 4° C., washed with PBS containing 0.2% Tween®-20 (Rockland, Cat # MB-075-1000) and blocked with 3% fish gel (Sigma). A 3-fold dilution series of culture supernatants was allowed to bind for 1 hr at room temperature, before plates were washed and probed with an HRP-conjugated anti-mouse antibody as described above. Clones producing antibodies reactive to FRβ, FRγ or FRδ were not selected for further analysis.

Hybridoma clones 24H8.D3, 1C6.E12.G8, 1D2.D8.G0, 6A2.G7, 19D2.G9, 26A9.C4, 2F11.F8, 5C12.H8, 24H8.F3, 28H12.G9, 30G6.G6.G4.E9, and 1A8.G11.E7, generated from the mice immunized with either native/non-reduced or reduced/alkylated folate receptor alpha as listed in Table 3, were selected for further analysis. On May 4, 2016, the clones were deposited with the American Type Culture Collection (10801 University Blvd. Manassas, Va. 20110-2209) and were assigned the following ATCC accession numbers: 24H8.D3 (PTA-123090), 1C6.E12.G8 (PTA-123091), 1D2.D8.G10 (PTA-123098), 6A2.G7 (PTA-123093), 19D2.G9 (PTA-123094), 26A9.C4 (PTA-123092), 2F11.F8 (PTA-123098), 5C12.H8 (PTA-123095), 24H8.F3 (PTA-123097), 28H12.G9 (PTA-123101), 30G6.G6.G4.E9 (PTA-123096), and 1A8.G11.E7 (PTA-123100).

Example 4—Production of Purified Monoclonal Antibodies

Selected cell lines were tested for mycoplasma using a mycoplasma test kit (Rockland, Cat # MAB-012) before seeding into 1 L roller bottles containing serum free medium (Invitrogen, Cat #12045-076) and 5% low IgG FBS (0.1 μg/ml) (Gibco, Cat #16250-078) at $0.5 \times 10^5$ cells/mL. Cultures were allowed to grow at 37° C. for either 14 or 21 days, after which supernatant was harvested and concentrated approximately 10-fold through a 50 kDa filtration membrane (Spectrum Labs, Rancho Dominguez Calif.) and then purified using protein A chromatography (Rockland, Cat # PA50-00-0025). Bound antibody was eluted with 0.1M sodium citrate, pH 3.5/4.5 depending on antibody isotype, and buffer was exchanged against PBS by dialysis using a 12-14 kDa membranous tubing (Spectrum Labs, Rancho Dominguez Calif.). Purified antibody was sterile filtered using a 0.22 μm Express™ PLUS Stericups (Millipore, Billerica Mass.) and stored at 4° C. for further testing.

Efforts were undertaken to sequence the heavy and light chains of the hybridoma clones. First, total RNA was isolated from the hybridoma cell line (cell pellets of $1 \times 10^3$ to $1 \times 10^5$ cells each) using the RNAqueous® kit (Ambion) according to the manufacturer's protocol. RNA was quantified using a NanoDrop™ 8000 spectrophotometer (Thermo Scientific).

Isolated RNA was then amplified via multiplex RT-PCR, performed in triplicate for each hybridoma with a Mastercycler® EP Gradient Thermocycler (Eppendorf). First, two separate gene-specific cDNA amplifications were performed for each hybridoma (≤1 μg RNA/reaction) to determine which Ig heavy and light chain genes were used during Ig rearrangement. Each cocktail consisted of unique family-specific primers designed to anneal to any of the potential murine Ig V gene families (IgHv, IgKv) and Ig constant region genes (IgHc$_{Gamma}$, IgKc). cDNA generation and amplification was performed using SuperScript® III One-Step RT-PCR System with Platinum® Taq High Fidelity (Invitrogen) under the following conditions: 55° C. for 30 minutes and 95° C. for 2 minutes, followed by 40 cycles of 95° C. for 1 minute, 55° C. for 1 minute, 68° C. for 1 minute, and a final 68° C. for 10 minutes completion step. DNA products were electrophoresed on a 2% agarose gel. Appropriate bands were excised and gel purified using the QIA-

TABLE 3

Characterization of hybridoma clones selected for further analysis

| Folate Receptor alpha Cell line | IgG Subtype (Will be verified again on CofAs) | FOLR-1 Immunogen: Antigen-Reduced/ Native | BIAcore affinity KD (M) (D.O. Data) | ATCC accession number |
|---|---|---|---|---|
| 24H8.D3 | IgG1 K | Reduced/Alkylated FOLR-1 | — | PTA-123090 |
| 1C6.E12.G8 | IgG1 K | Native/Non-reduced FOLR-1 | 9.76E−09 | PTA-123091 |
| 1D2.D8.G10 | IgG1 K | Native/Non-reduced FOLR-1 | 6.88E−09 | PTA-123098 |
| 6A2.G7 | IgG1 K | Native/Non-reduced FOLR-1 | 1.50E−08 | PTA-123093 |
| 19D2.G9 | IgG1 K | Native/Non-reduced FOLR-1 | 2.85E−09 | PTA-123094 |
| 26A9.C4 | IgG1 K | Native/Non-reduced FOLR-1 | — | PTA-123092 |
| 2F11.F8 | IgG1 K | Reduced/Alkylated FOLR-1 | — | PTA-123098 |
| 5C12.H8 | IgG2b K | Reduced/Alkylated FOLR-1 -1 | 1.08E−08 | PTA-123095 |
| 24H8.F3 | IgG1 K | Reduced/Alkylated FOLR-1 | — | PTA-123097 |
| 28H12.G9 | IgG1 K | Reduced/Alkylated FOLR-1 | 9.92E−09 | PTA-123101 |
| 30G6.G6.G4.E9 | IgG1 K | Reduced/Alkylated FOLR-1 | — | PTA-123096 |
| 1A8.G11.E7 | IgG1 K | Reduced/Alkylated FOLR-1 | — | PTA-123100 | quick® Gel Extraction Kit (Qiagen) following the manufacturer's protocol. Purified DNA was submitted for sequencing (GENEWIZ, Inc., South Plainfield, N.J.) to determine the germline gene segments expressed by each hybridoma.

Further RT-PCR analysis suited to the particular genes identified for the hybridomas was then performed using the same RNA source as above and gene-specific primers (in contrast to family-specific primers used in the multiplex RT-PCR mixture). To facilitate cloning, amplified Ig cDNAs were placed into an In-Fusion (IF) expression vector, each gene-specific primer also contained vector-compatible linker sequences which would enable homologous crossover. All other reagents and thermocycler conditions are the same as those used for the multiplex RT-PCR experiments, described above.

Example 5—MORAb-003 Interference in the Control Folate Receptor Alpha Assay

The previously described ECL assay disclosed in U.S. Pat. No. 8,475,795 for the detection of folate receptor assay in serum, plasma and urine was demonstrated to be interfered with in the presence of the therapeutic monoclonal antibody farletuzumab (MORAb-003), thereby obviating its use to monitor therapeutic response, i.e. in the presence of therapeutic MORAb-003. Table 4 shows the pattern of interference by MORAb-003 at two concentrations, for the assay configured with MAb 9F3.H9.H3.H3.B5.G2 ("9F3") as capture and MAb 24F12.B1 ("24F12") as detection across the standard curve. As disclosed in U.S. Pat. No. 8,475,795, antibodies 9F3 and 24F12 were deposited with the American Type Culture Collection (10801 University Blvd., Manassas, Va. 20110-2209) on May 19, 2011 and were assigned ATCC accession numbers PTA-11887 and PTA-1886, respectively. The assay demonstrates a MORAb-003 concentration-dependent interference pattern. As such, additional MAbs were screened to identify a capture/detect combination insensitive to endogenous MORAb-003.

MSD were used. The serum samples were incubated with 10 µg/mL MORAb-003 overnight and tested at 1:20 dilution. Serum samples were incubated in diluent overnight as a control and tested at 1:20 and 1:80 dilutions. The calibrator was also treated with 10 µg/mL MORAb-003 overnight. 24H8.D3 was tested as both a capture and detection antibody, and was identified as promising due to high signal to background (S/B) levels.

FIG. 2A shows the light intensity count resulting from pairwise combinations of thirteen capture antibodies and thirteen detection antibodies. FIG. 2B shows the average signal to background (S/B) values resulting from the pairwise combinations of thirteen capture antibodies and thirteen detection antibodies.

The effect of MORAb-003 interference was assessed at 10 µg/mL. Antibody pairs were assessed to determine which antibody combination exhibited the least interference by MORAb-003 based on a low signal.

All combinations were masked where the specific signal was below 1000. MAb 30G6.G6.G4.E9 was not able to detect endogenous levels of antigen. Percent Drug Interference was calculated using the formula % Drug Interference= (Signal with Drug−Blank)/(Signal without Drug−Blank). FIG. 3A shows percent interference/drug suppression after adding 10 µg/mL MORAb-003 for the pairwise combinations of thirteen capture antibodies and thirteen detection antibodies in a control calibrator solution containing recombinant purified FRα at a concentration of 500 µg/mL. FIG. 3B shows percent interference/drug suppression after adding 10 µg/mL MORAb-003 for the pairwise combinations of thirteen capture antibodies and thirteen detection antibodies in serum samples. The positive control is located in the upper right corner for comparison. Percent interference= (Signal with MORAb-003−Blank)/(Signal without MORAb-003−Blank).

TABLE 4

MORAb-003 Interference in the Control folate receptor alpha assay
Previously Described Assay: 9F3 Capture/24F12 Detect

| [MORAb-003] µg/mL | STD01 | STD02 | STD03 | STD04 | STD05 | STD06 | STD07 | STD08 |
|---|---|---|---|---|---|---|---|---|
| 0 | 100% | 100% | 100% | 100% | 100% | 100% | 100% | 100% |
| 10 | 68% | 70% | 61% | 73% | 71% | 103% | 87% | 121% |
| 50 | 54% | 49% | 58% | 57% | 75% | 78% | 88% | 115% |

Example 6—Selecting MAb Pairs with the Least Interference from MORAb-003 Antibody Pair Screening Antibody pairs were assessed to determine which pair gave good assay performance and exhibited the least interference by MORAb-003. Screening was performed on thirteen monoclonal antibodies such that all antibodies were screened as capture and detection antibodies. An antibody pair disclosed in U.S. Pat. No. 8,475,795—26B3.F2 (capture) and 19D4.B7 (detection)—was used as a positive control. Antibodies 26B3.F2 and 19D4.B7 were previously deposited with the American Type Culture Collection (10801 University Blvd., Manassas, Va. 20110-2209) on May 19, 2011 and were assigned Accession Nos. PTA-11885 and PTA-11884, respectively. Serum samples provided by Example 7: Assessment and Screening of Antibody Pairs Based on Dilution Linearity of Two Serum Samples and Standard Curve Performance Dilution linearity profiles and standard curve performance of various antibody pairs listed below were assessed using two serum samples. The antibodies assessed were 1A8.G11.E7, 24H8.D3, 9F3, 19D4.B7 and 19D2.G9. FIG. 4 shows examples of dilution linearity when using 24H8.D3 and 19D4.B7 as both the capture and detection antibody as compared to other antibody pairs. Dilution adjusted concentrations were normalized to the concentration at 1:20 dilution and the grayed sections are antibody combinations not considered during the screening.

Figure 5A:
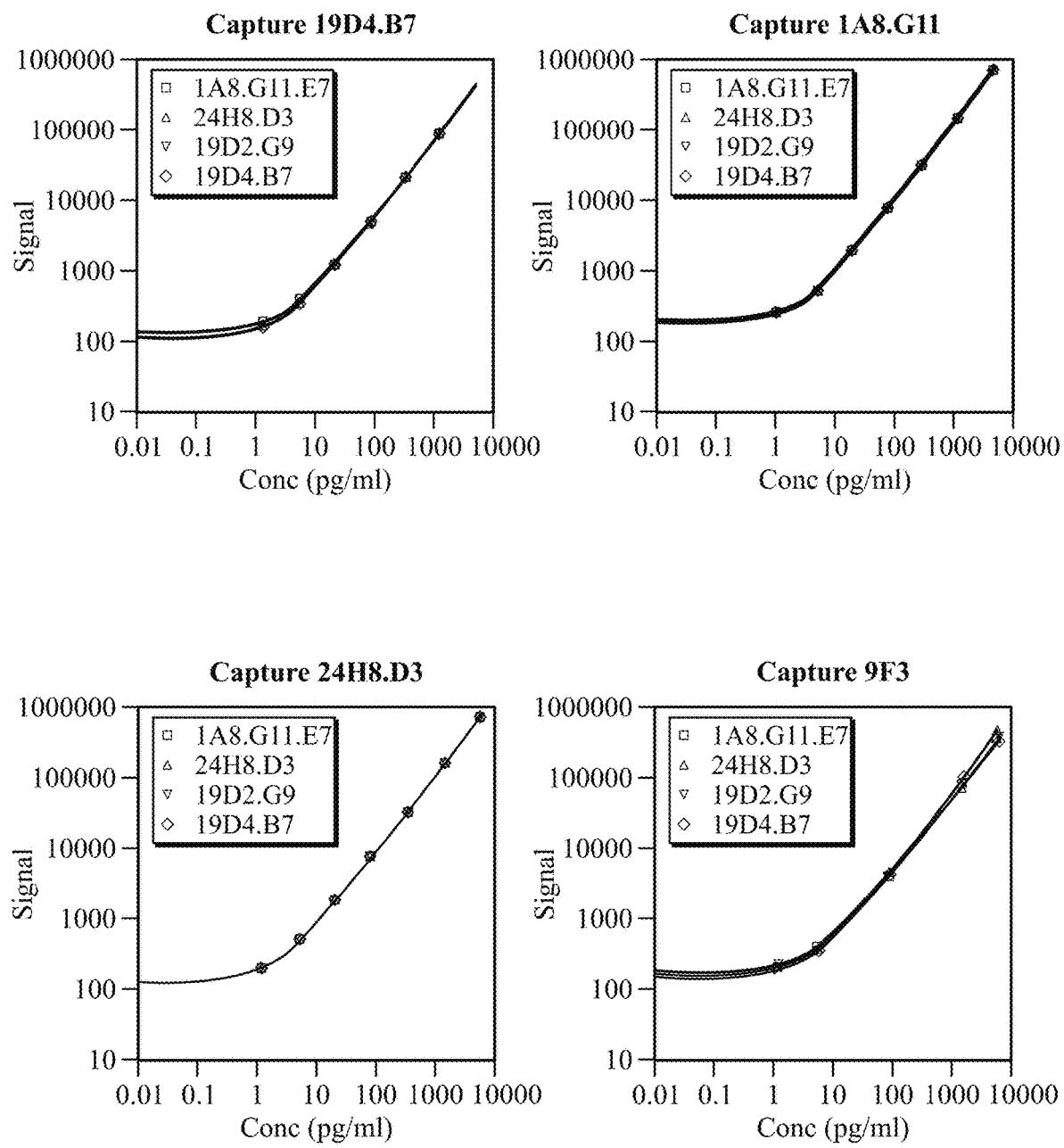

Next, the standard curve performance and slope were assessed for the selected antibody pairs. The final selected antibody pair and best configuration for the assay included 24H8.D3 as the capture antibody and 19D4.B7 as the detector based on the superior slope (1.09) as shown in FIG. 5A and FIG. 5B. 1A8.G11.E7 and 24H8.D3 likely recognize the same or similar epitope because they behave the same and do not work with one another. FIG. 5A depicts graphs of signal plotted against concentration for a defined capture antibody and paired with one of four detection antibodies. FIG. 5B shows the standard curve and hill slope data for the tested antibody pairs. 19D4.B7 worked better as a detector than when used as a capture.

Example 8: Final Folate Receptor Alpha Electrochemiluminescence (ECL) Assay Protocol/Configuration Small spot Streptavidin (ss-SAV) plates were blocked with 150 μL of Meso Scale Discovery® (MSD) Blocker A at room temperature with shaking for 30 minutes. Each well was coated with 25 μL of biotin-conjugated 24H8.D3 capture antibodies at 0.5 μg/mL. The plates were incubated at room temperature with shaking for 1 hour. The plates were washed three times with PBST. Next, 25 μL of the sample/calibrator was added to each well. The samples were incubated at room temperature with shaking for 2 hours. The plates were then washed three times with PBST. 25 μL of SULFO-TAG (from Meso Scale Diagnostics, LLC) conjugated 19D4.B7 detection antibody was added to each well at a concentration of 1 μg/mL. The plates were incubated at room temperature for 1 hour with shaking. The plates were washed three times with PBST. The plates were read with 2× Read Buffer T immediately. The standards were generated using recombinant purified FRα for a standard curve with a zero calibrator, as depicted in Table 5.

TABLE 5

FRα Calibrator Concentrations

| FRα Calibrator | Concentration (pg/mL) |
|---|---|
| STD01 | 5000 |
| STD02 | 1250 |
| STD03 | 313 |
| STD04 | 78.1 |
| STD05 | 19.5 |
| STD06 | 4.88 |
| STD07 | 1.22 |
| STD08 | 0 |

Example 9—Folate Receptor Alpha Assay Performance and Sample Matrix Assessments Reference Range 40 human patient samples (20 healthy normal patients and 20 ovarian cancer patients) were used to establish the reference ranges for the FRα ECL assay. Each patient provided four sample types (serum, plasma, first morning urine and spot urine) to assess performance and suitability of each sample type. Three patients did not have the spot urine sample available. Samples were spiked with 100 μg/mL MORAb-003. To control the study, samples were spiked with assay diluent and run in parallel with the MORAb-003 drug-treated samples.

Figure 6:
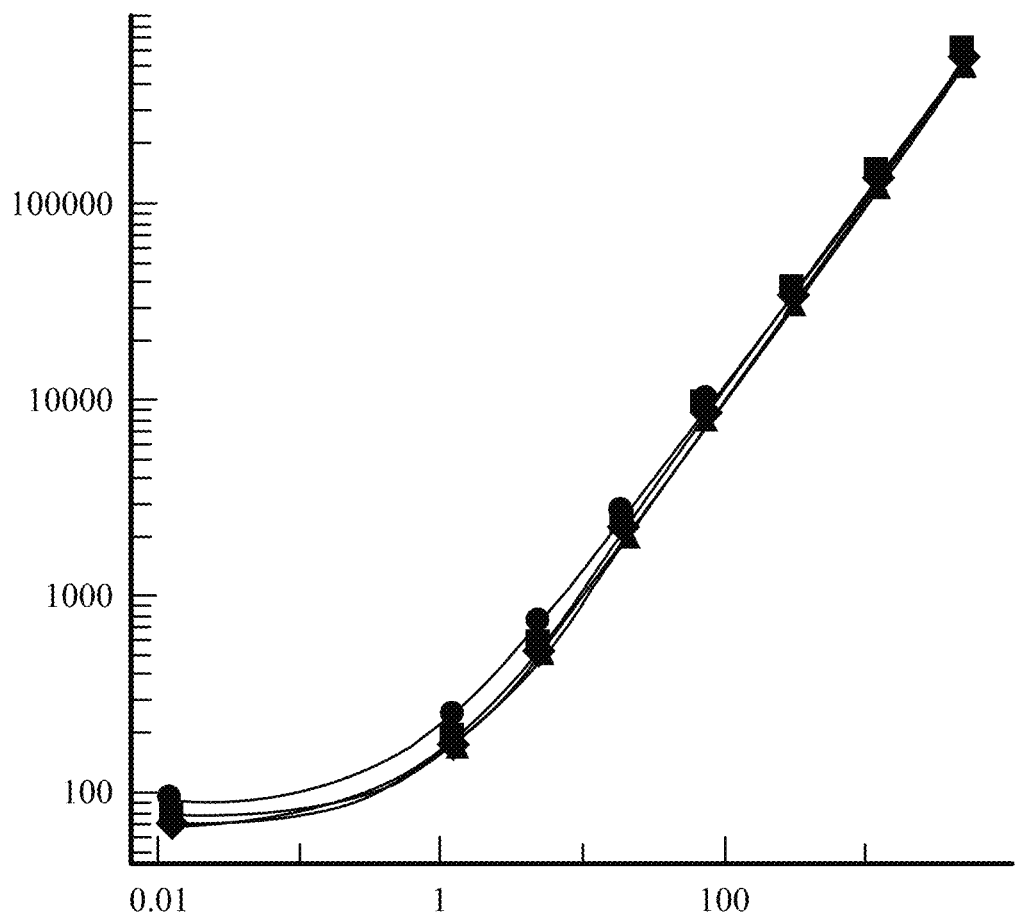
FIG. 6 shows a graph of light intensity counts of FRα standard samples across six consecutive runs plotted against the concentration (in pg/mL) of the standard samples.

Table 6 shows the light intensity counts of eight FRα standard samples with concentrations ranging from 0 μg/mL to 5000 μg/mL over six consecutive runs. The data, also depicted in graphical form in FIG. 6, demonstrates that the standard curve exhibited good reproducibility over the range of the curve for all six runs.

TABLE 6

FRα Standard Curve Reproducibility

| Concentration (pg/mL) | Run 1 | Run 2 | Run 3 | Run 4 | Run 5 | Run 6 |
|---|---|---|---|---|---|---|
| 5000 | 575,925 | 497,441 | 577,490 | 482,426 | 545,520 | 574,299 |
| 1250 | 144,897 | 128,264 | 141,966 | 139,753 | 136,379 | 142,468 |
| 313 | 39,318 | 30,733 | 34,432 | 34,586 | 31,829 | 33,302 |
| 78.1 | 10,071 | 8,381 | 8,611 | 8,347 | 7,654 | 7,633 |
| 19.5 | 2,739 | 2,085 | 2,121 | 2,107 | 1,925 | 2,000 |
| 4.88 | 739 | 546 | 569 | 566 | 518 | 522 |
| 1.22 | 256 | 206 | 192 | 188 | 179 | 184 |
| 0 | 95 | 79 | 73 | 70 | 78 | 79.1 |
| Hill slope | 0.98 | 1.00 | 1.02 | 1.02 | 1.04 | 1.04 |
| LLOD | 0.18 | 0.25 | 0.26 | 0.26 | 0.31 | 0.55 |

Figure 7A:
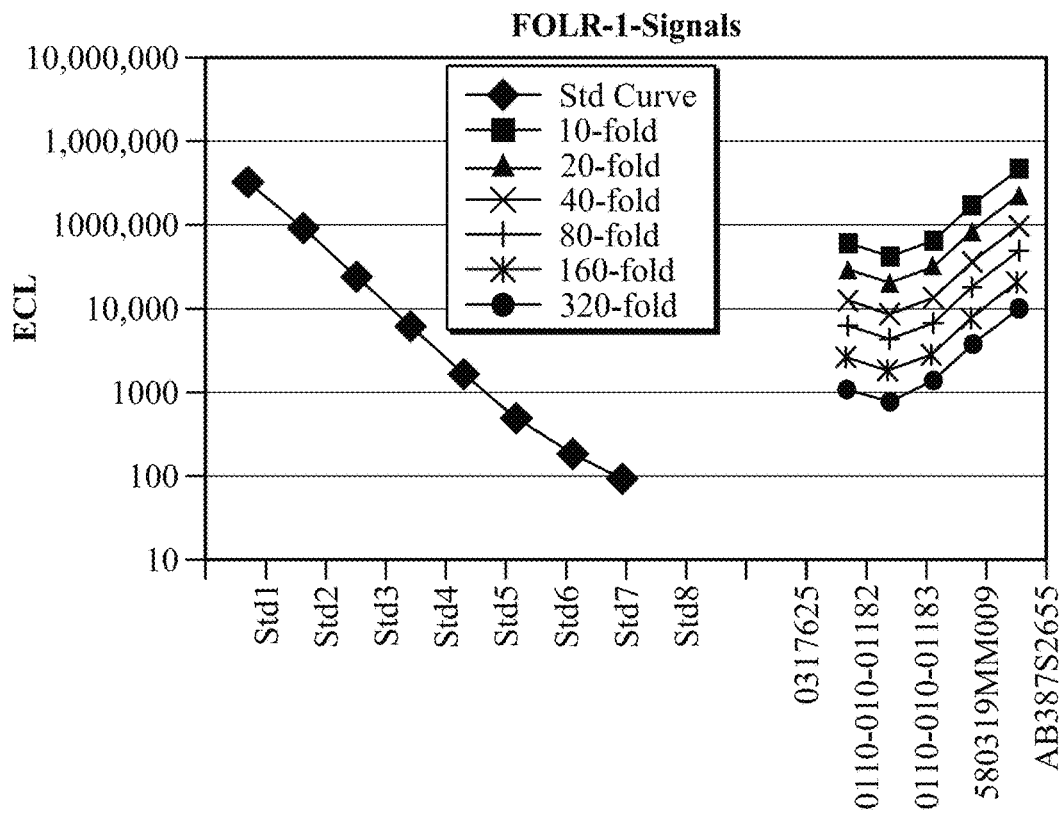
FIGS. 7A-7D illustrate the FRα signal and FRα dilution linearity curves for five serum and five urine samples.
Figure 7B:
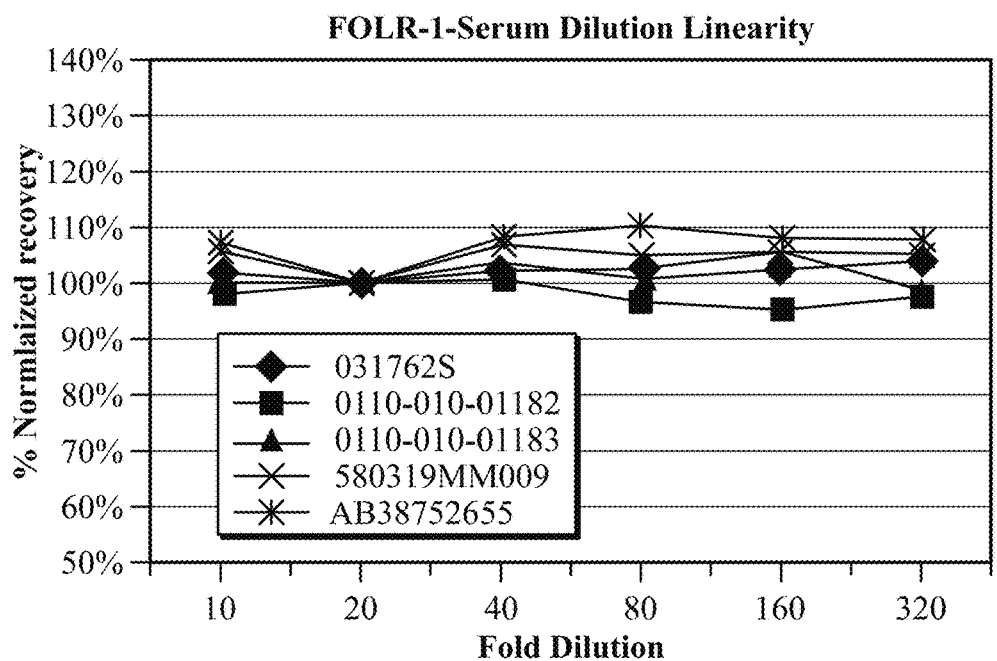
Figure 7C:
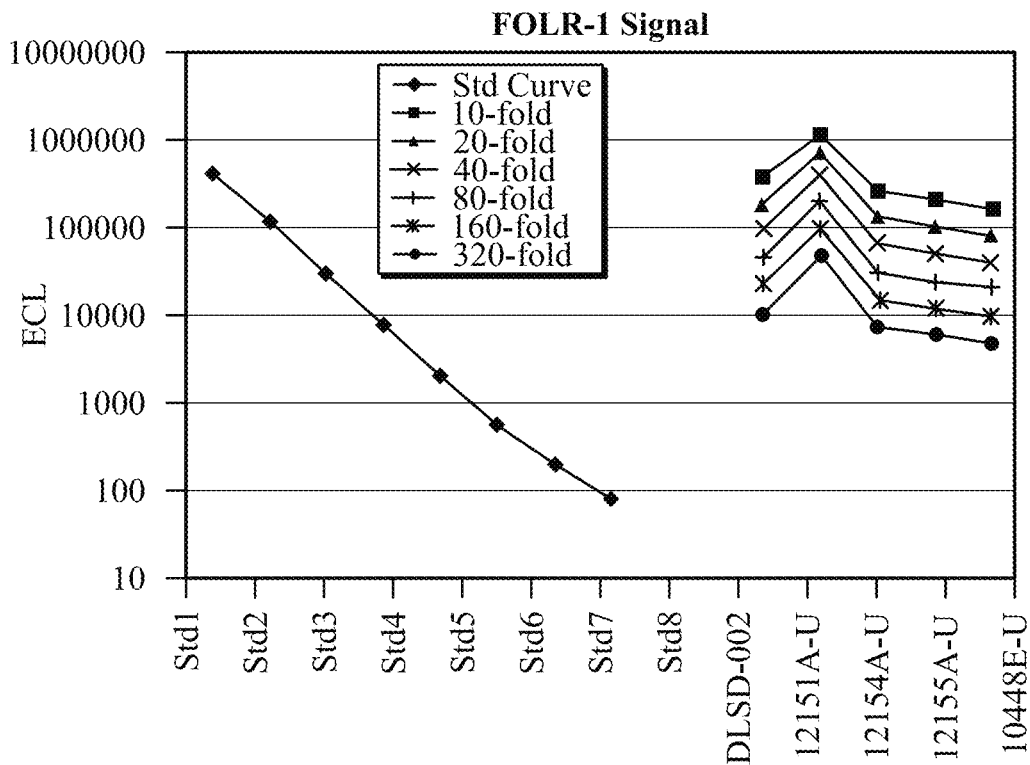
Figure 7D:
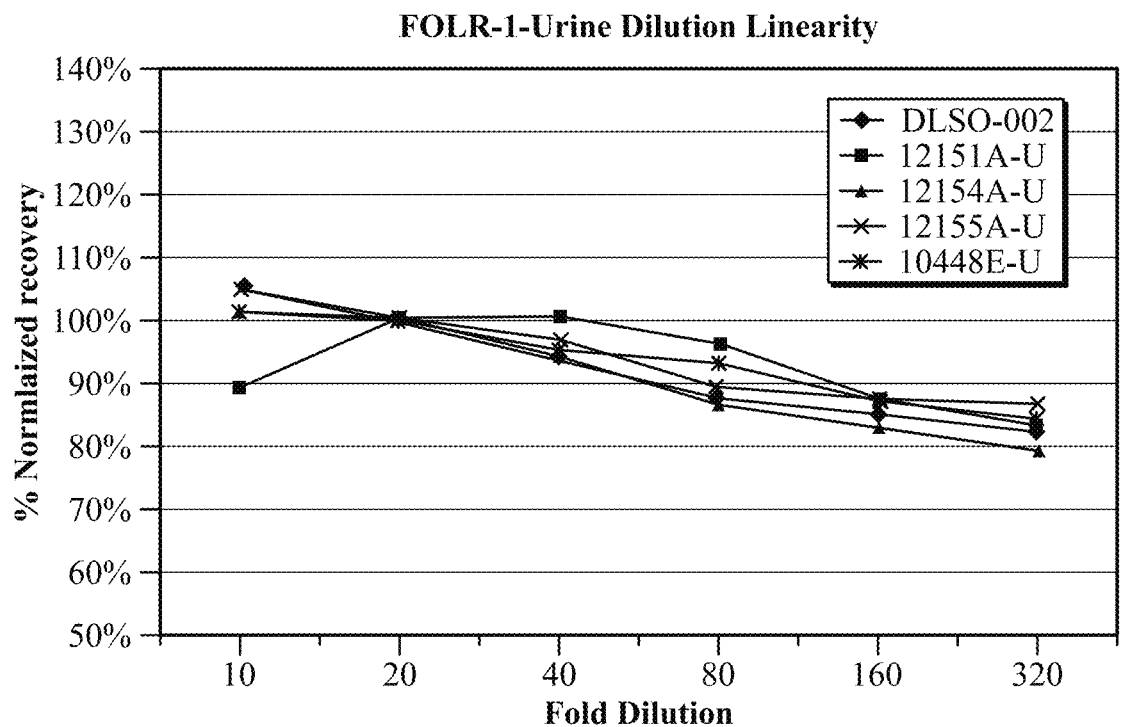

Dilution Linearity was assessed using serum and urine samples. Five serum and five urine samples were tested at six different dilutions. Serum samples fell within the range of the standard curve while urine samples displayed slightly higher FRα levels (FIG. 7A-7D). FIG. 7A shows a graph of the light intensity counts (y-axis) of eight standard FRα samples and five serum samples (x-axis) at 10, 20, 40, 80, 160 and 320-fold dilutions. FIG. 7B shows a graph of the percent normalized recovery (y-axis) plotted against the fold dilution for all five serum samples (x-axis) and demonstrates good dilution linearity with approximately 10% variance. FIG. 7C shows a graph of the light intensity counts (y-axis) of eight standard FRα samples and five urine samples (x-axis) at 10, 20, 40, 80, 160 and 320-fold dilutions. FIG. 7D shows a graph of the percent normalized recovery (y-axis) plotted against the fold dilution for all five urine samples (x-axis) and demonstrates acceptable dilution linearity (within approximately 20% variance).

Folate Receptor Alpha Spike Recovery

Figure 8A:
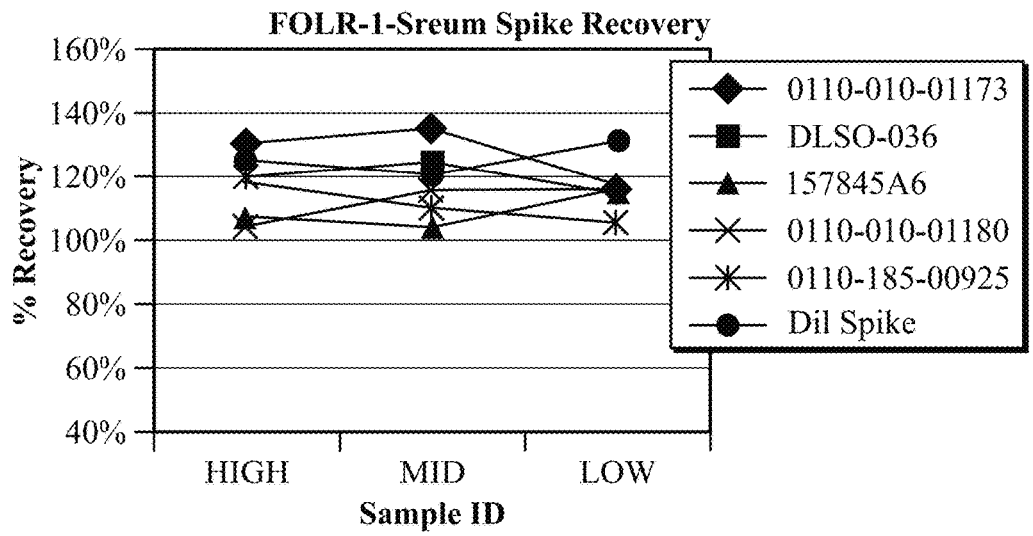
FIGS. 8A and 8B illustrate FRα serum and urine spike recovery values. Five serum samples and five urine samples were spiked with high (H), medium (M) and low (L) levels of FRα calibrator and run with a control diluent. The percent normalized recovery, as compared to expected recovery values, was plotted on the y-axis and spike levels were plotted on the x-axis.
Figure 8B:
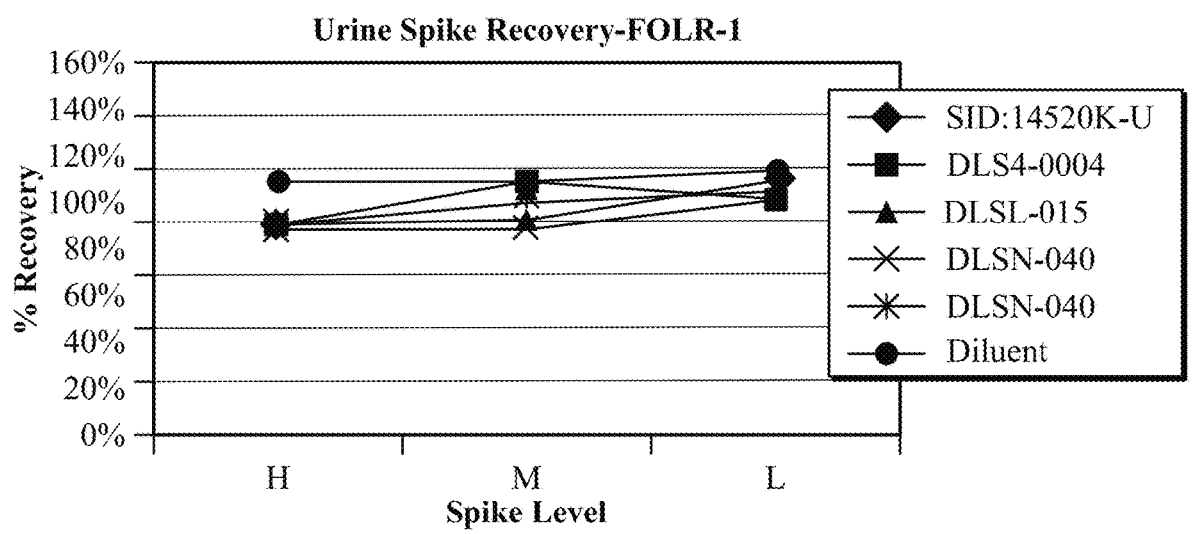

Five serum and five urine samples were spiked with high (H), medium (M) and low (L) levels of the FRα calibrator and run in comparison to diluent as a control. In FIG. 8A and FIG. 8B, the percent normalized recovery, as compared to expected recovery values, was plotted on the y-axis and spike levels were plotted on the x-axis. FIG. 8A shows the results from the five serum samples and FIG. 8B slows the results from the five urine samples. Slightly elevated but acceptable recovery values were seen in the serum samples.
Folate Receptor Alpha Assay Precision (% CV)

Figure 9:
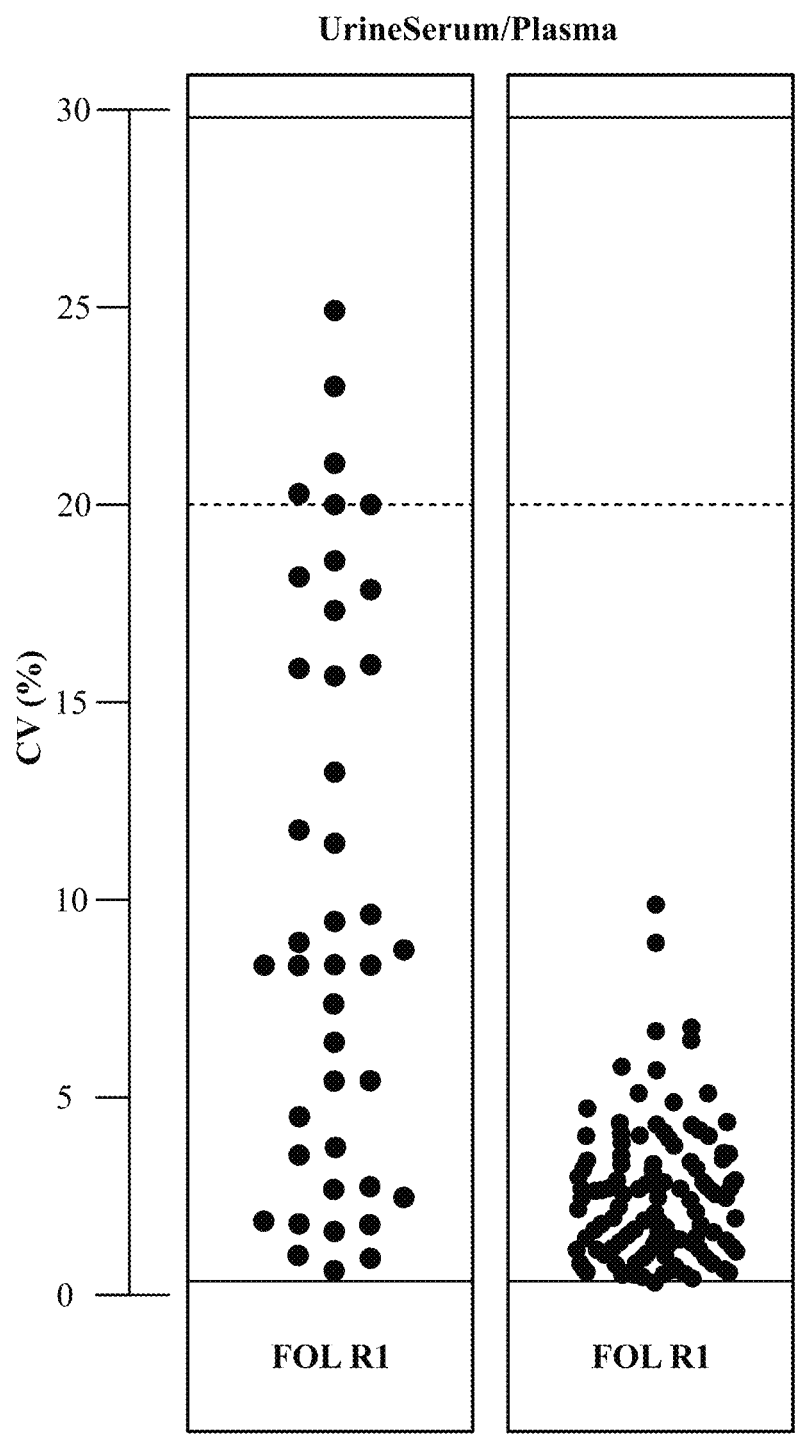
FIG. 9 depicts percent coefficient of variance (CV) values for urine and serum/plasma samples, in duplicate.

The precision or coefficient of variance was assessed by testing all serum, plasma and urine samples in duplicate. Serum and plasma results were consistent with CVs generally ≤5%. Urine CV % results were generally higher than serum and plasma and more varied across the detectable range of the curve, as depicted in FIG. 9.

Example 10—Folate Receptor Alpha ECL Assay Performance in the Presence of MORAb-003

Figure 10A:
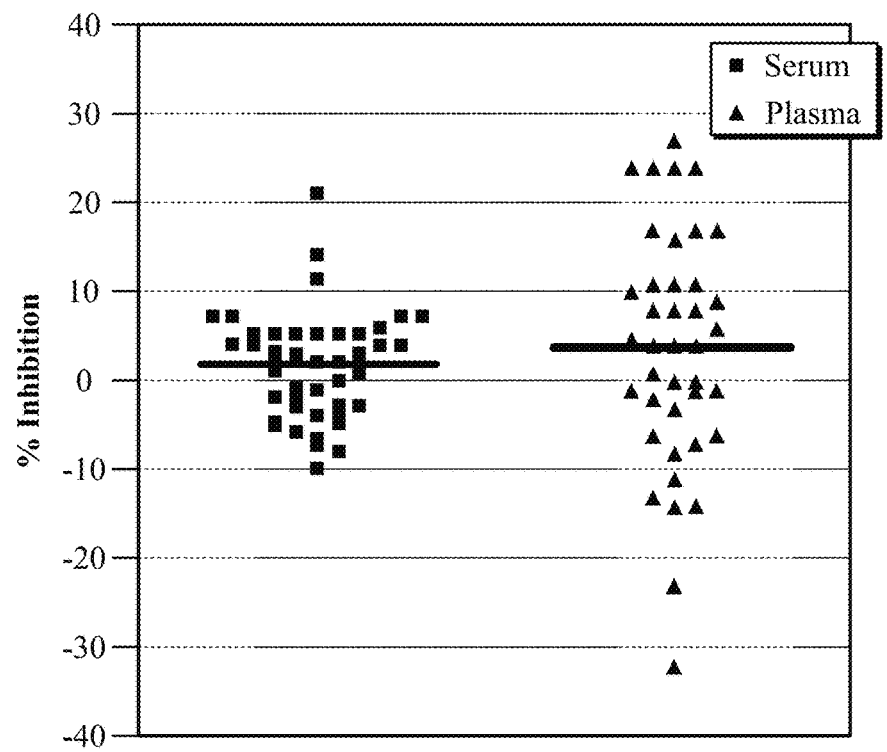
FIG. 10A illustrates the percent inhibition of FRα levels in plasma and serum samples with and without 100 μg/mL MORAb-003, where percent inhibition=(Diluent−MORAb-003)/Diluent.
Figure 10B:
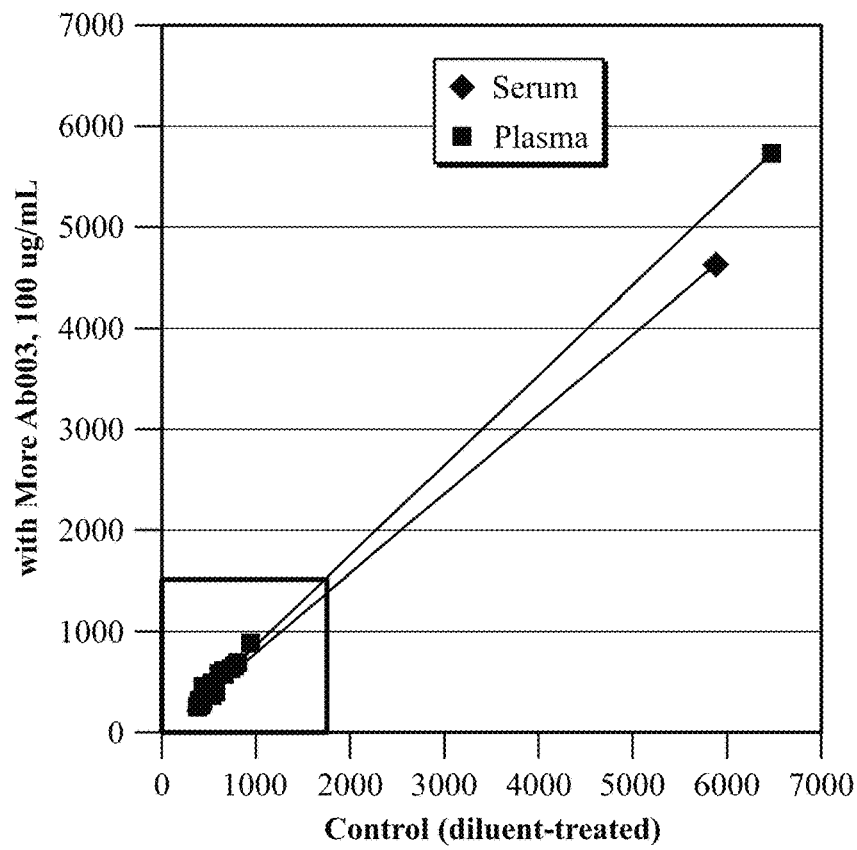
FIG. 10B is a plot of FRα levels in serum or plasma samples treated with 100 μg/mL MORAb-003 (y-axis) against FRα levels in control, diluent-treated, serum or plasma samples (x-axis)
Figure 10C:
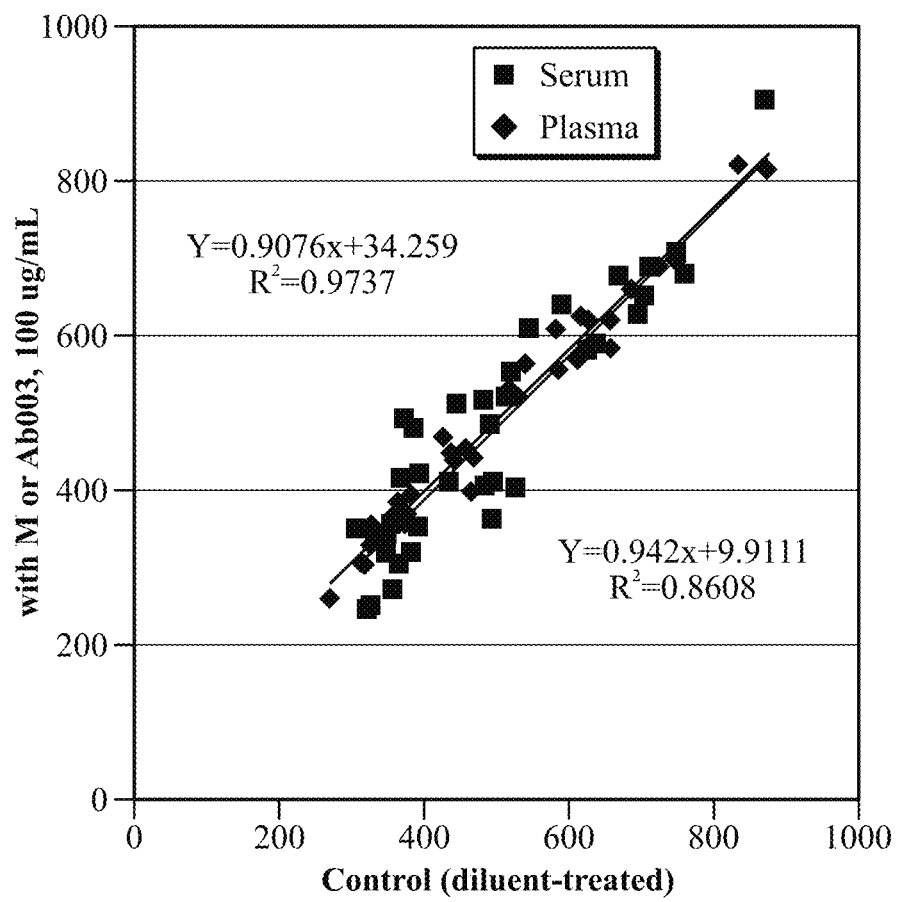
FIG. 10C is an expanded view of the low, boxed, end of the curve in FIG. 10B. $R^2$ values for serum and plasma are also provided in FIG. 10C.

The effect of MORAb-003 on the performance of the FRα ECL assay was assessed in serum and plasma. FRα levels were tested in samples with or without MORAb-003 spiked into patient samples at a level of 100 µg/mL, which is the approximate expected level in patients receiving treatment. The percent inhibition was calculated as % Inhibition= (Diluent/Drug)/Diluent where drug is MORAb-003. The assay exhibits minimal interference in serum and plasma samples with serum being the best sample matrix with less interference. As depicted in FIGS. 10A-10C, the percent inhibition median serum value was 3% with a range of −10% to 14%. The plasma median serum value was 4% with a range of −32% to 27%. Sample # DLSO-015 was omitted from the correlation analysis as inhibition in serum was 21% and inhibition in plasma was 10%. FIG. 10A illustrates the percent inhibition of FRα levels in plasma and serum samples with and without 100 µg/mL MORAb-003. FIG. 10B is a plot of FRα levels in serum or plasma samples treated with 100 µg/mL MORAb-003 (y-axis) against FRα levels in control, diluent-treated, serum or plasma samples (x-axis), and FIG. 10C is an expanded view of the low, boxed, end of the curve in FIG. 10B. $R^2$ values for serum and plasma are also provided in FIG. 10C.

Sample Matrix Testing and Performance with Addition of MORAb-003

To evaluate the performance of serum, plasma and urine in the FRα ECL assay, 40 human patient samples (20 healthy normal patients and 20 ovarian cancer patients) were identified. Each patient had four sample types assessed with the exception of three patients without spot urine samples (serum, plasma, first morning urine and spot urine). To assess performance and suitability of each sample type and the possible interference of MORAb-003 in serum and plasma samples, the serum and plasma samples were run with and without the addition of MORAb-003 along with the standard curve.

Figure 11:
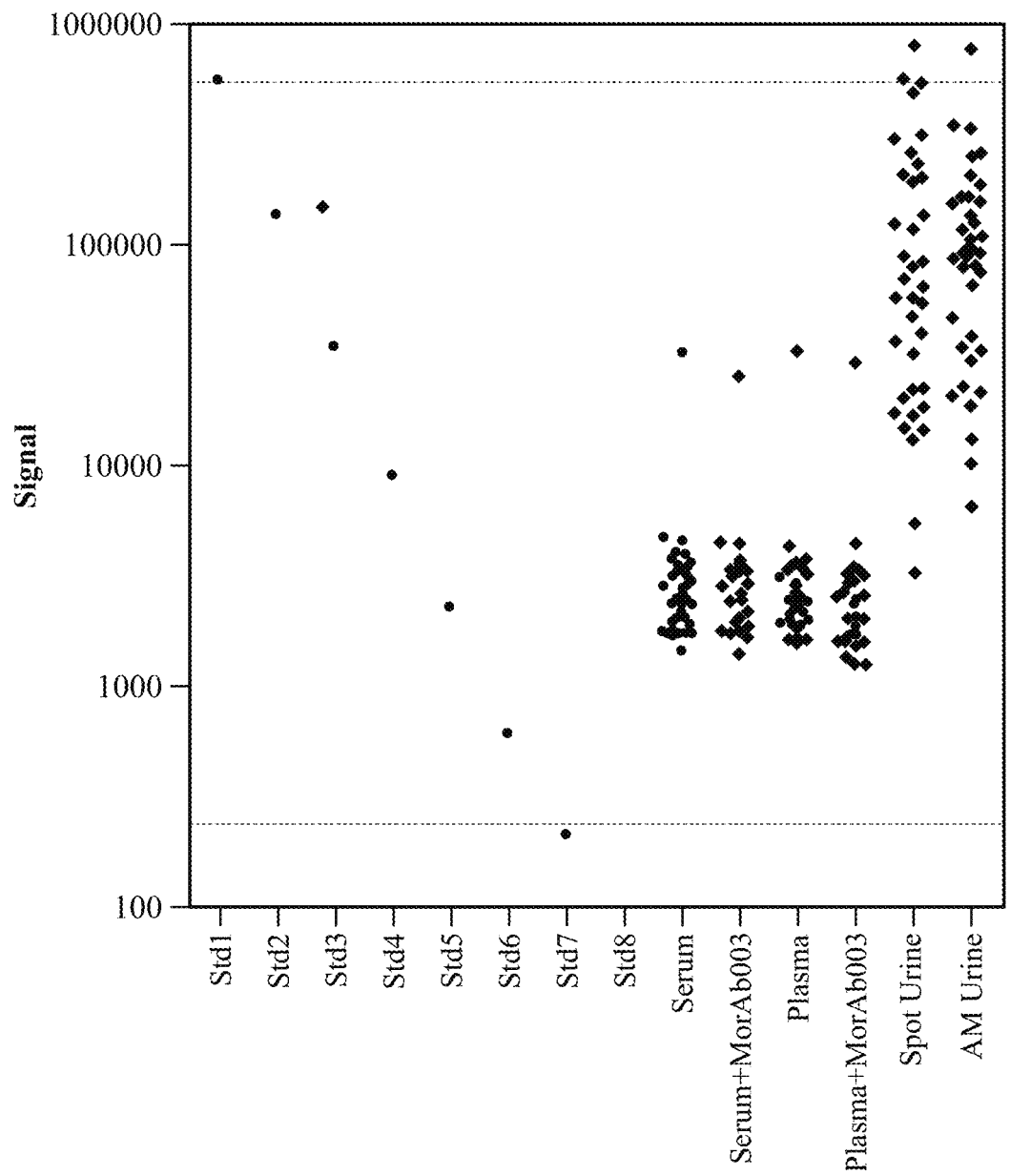
FIG. 11 shows a graph of the FRα light intensity count (y-axis) for eight standard samples, serum and plasma samples with and without MORAb-003, and spot and AM urine samples (x-axis).

The serum and plasma samples were detectable and in the range of the curve, however, urine results were generally higher than serum and plasma values and a few urine samples had values that were above the range of the curve at the dilution used in this assessment. Serum and plasma exhibited excellent concordance and little change in values with the addition of MORAb-003. The results of these analyses are depicted in Table 7 and graphically in FIG. 11. The graph in FIG. 11 plots light intensity count for eight standard samples, serum and plasma samples with and without MORAb-003, and spot and first morning (AM) urine samples.

TABLE 7

Serum and Plasma Concordance in the Presence of MORAb-003

| Sample Type | Sample Dilution Factor | Concentration (pg/mL) | | | Total # samples | # samples above TOC | # samples <3x background | % samples detected |
| --- | --- | --- | --- | --- | --- | --- | --- | --- |
| | | Median | Min | Max | | | | |
| Serum | 20 | 461 | 267 | 5,849 | 40 | 0 | 0 | 100 |
| Plasma | 20 | 463 | 308 | 6,398 | 40 | 0 | 0 | 100 |
| Spot Urine | 20 | 10,535 | 485 | >20,000 | 37 | 2 | 0 | 95 |
| AM Urine | 20 | 18,086 | 1,265 | >20,000 | 40 | 1 | 0 | 98 |

Example 11: Analytical Characterization of Assay Antibodies

Selection of antibodies used in assay development included an analysis of the physical properties of each antibody. The antibodies were processed to ensure they were in the optimal buffer for the intended use as either a capture or detection antibody before analysis. The antibodies were evaluated using the following methods: (1) capillary isoelectric focusing (cIEF) to establish the pI peak and range and the peak profile; (2) dynamic light scattering (DLS) to assess aggregation; (3) experion automated electrophoresis (reducing and non-reducing) to assess purity and establish a heavy to light chain ratio. The results from the analyses are depicted in FIG. 12A and FIG. 12B. L/P represents labels of biotin per protein.

What is claimed:

1. An isolated antibody, or antigen-binding fragment thereof, specific for folate receptor alpha (FRα) comprising:
   a. a light chain CDR1 comprising the amino acid sequence of SEQ ID NO: 1, a light chain CDR2 comprising the amino acid sequence of SEQ ID NO: 2, a light chain CDR3 comprising the amino acid sequence of SEQ ID NO: 3, a heavy chain CDR1 comprising the amino acid sequence of SEQ ID NO: 8, a heavy chain CDR2 comprising the amino acid sequence of SEQ ID NO: 9, and a heavy chain CDR3 comprising the amino acid sequence of SEQ ID NO: 10, wherein the CDRs are defined according to the IMGT method; or
   b. a light chain CDR1 comprising the amino acid sequence of SEQ ID NO: 4, a light chain CDR2 comprising the amino acid sequence of SEQ ID NO: 5, a light chain CDR3 comprising the amino acid sequence of SEQ ID NO: 3, a heavy chain CDR1 comprising the amino acid sequence of SEQ ID NO: 11, a heavy chain CDR2 comprising the amino acid sequence of SEQ ID NO: 12, and a heavy chain CDR3 comprising the amino acid sequence of SEQ ID NO: 13, wherein the CDRs are defined according to the KABAT method.

2. The isolated antibody or antigen-binding fragment of claim 1, wherein the antibody is a murine antibody.

3. The isolated antibody or antigen-binding fragment of claim 1, wherein the antibody isotype is IgG.

4. The isolated antibody or antigen-binding fragment of claim 1, wherein the antibody is chimeric.

5. The isolated antibody or antigen-binding fragment of claim 1, wherein the antibody is humanized.

6. The isolated antibody or antigen-binding fragment of claim 1, wherein:
   a. the antibody or antigen-binding fragment of (a) has a light chain variable region comprising an amino acid sequence that is at least 90% identical to the amino acid sequence of SEQ ID NO: 6 and a heavy chain variable region that is at least 90% identical to the amino acid sequence of SEQ ID NO: 14; or
   b. the antibody or antigen-binding fragment of (b) has a light chain variable region comprising an amino acid sequence that is at least 90% identical to the amino acid sequence of SEQ ID NO: 6 and a heavy chain variable region that is at least 90% identical to the amino acid sequence of SEQ ID NO: 14.

7. The isolated antibody or antigen-binding fragment of claim 6, wherein the light chain variable region has the amino acid sequence of SEQ ID NO: 6 and the heavy chain variable region has the amino acid sequence of SEQ ID NO: 14.

8. An isolated antibody, or antigen-binding fragment thereof, specific for folate receptor alpha (FRα) comprising a light chain variable region that has the amino acid sequence of SEQ ID NO: 6 and a heavy chain variable region that has the amino acid sequence of SEQ ID NO: 14.

9. An isolated antibody, or antigen-binding fragment thereof, specific for folate receptor alpha (FRα) comprising a light chain that has the amino acid sequence of SEQ ID NO: 7 and a heavy chain that has the amino acid sequence of SEQ ID NO: 15.

10. An isolated antibody specific for folate receptor alpha (FRα) comprising the amino acid sequence of an antibody produced by the cell line deposited with the ATCC having accession number PTA-123090.

11. An isolated polynucleotide comprising the nucleotide sequence of SEQ ID NO: 21 and SEQ ID NO: 29.

12. An isolated polynucleotide comprising the nucleotide sequence of SEQ ID NO: 22 and SEQ ID NO: 30.

13. An isolated polynucleotide encoding an antibody or antigen-binding fragment comprising a light chain variable region and a heavy chain variable region wherein the light chain variable region comprises the amino acid sequence of SEQ ID NO: 6 and the heavy chain variable region comprises the amino acid sequence of SEQ ID NO: 14.

14. An isolated polynucleotide encoding an antibody comprising a light chain and a heavy chain wherein the light chain comprises the amino acid sequence of SEQ ID NO: 7 and the heavy chain comprises the amino acid sequence of SEQ ID NO: 15.

15. An isolated polynucleotide sequence encoding an antibody or antigen-binding fragment specific for folate receptor alpha (FRα), wherein:
   a. a light chain CDR1 of the encoded antibody comprises the amino acid sequence of SEQ ID NO: 1, a light chain CDR2 of the encoded antibody comprises the amino acid sequence of SEQ ID NO: 2, a light chain CDR3 of the encoded antibody comprises the amino acid sequence of SEQ ID NO: 3, a heavy chain CDR1 of the encoded antibody comprises the amino acid sequence of SEQ ID NO: 8, a heavy chain CDR2 of the encoded antibody comprises the amino acid sequence of SEQ ID NO: 9, and a heavy chain CDR3 of the encoded antibody comprises the amino acid sequence of SEQ ID NO: 10, wherein the CDRs are defined according to the IMGT method; or
   b. a light chain CDR1 of the encoded antibody comprises the amino acid sequence of SEQ ID NO: 4, a light chain CDR2 of the encoded antibody comprises the amino acid sequence of SEQ ID NO: 5, a light chain CDR3 of the encoded antibody comprises the amino acid sequence of SEQ ID NO: 3, a heavy chain CDR1 of the encoded antibody comprises the amino acid sequence of SEQ ID NO: 11, a heavy chain CDR2 of the encoded antibody comprises the amino acid sequence of SEQ ID NO: 12, and a heavy chain CDR3 of the encoded antibody comprises the amino acid sequence of SEQ ID NO: 13, wherein the CDRs are defined according to the KABAT method.

16. An isolated polynucleotide comprising the nucleotide sequences of:
   a. SEQ ID NO: 16, SEQ ID NO: 17, SEQ ID NO: 18, SEQ ID NO: 23, SEQ ID NO: 24, and SEQ ID NO 25; or b. SEQ ID NO: 19, SEQ ID NO: 20, SEQ ID NO: 18, SEQ ID NO: 26, SEQ ID NO: 27, and SEQ ID NO 28.

17. An isolated polynucleotide sequence encoding an antibody light chain or antigen-binding fragment specific for folate receptor alpha (FRα), wherein:
   a. the light chain CDR1 of the encoded antibody comprises the amino acid sequence of SEQ ID NO: 1, the light chain CDR2 of the encoded antibody comprises the amino acid sequence of SEQ ID NO: 2, and the light chain CDR3 of the encoded antibody comprises the amino acid sequence SEQ ID NO: 3, wherein the CDRs are defined according to the IMGT method; or
   b. the light chain CDR1 of the encoded antibody comprises the amino acid sequence of SEQ ID NO: 4, the light chain CDR2 of the encoded antibody comprises the amino acid sequence of SEQ ID NO: 5, and the light chain CDR3 of the encoded antibody comprises the amino acid sequence SEQ ID NO: 3, wherein the CDRs are defined according to the KABAT method.

18. An isolated polynucleotide sequence encoding an antibody heavy chain or antigen-binding fragment specific for folate receptor alpha (FRα), wherein:
   a. the heavy chain CDR1 of the encoded antibody comprises the amino acid sequence of SEQ ID NO: 8, the heavy chain CDR2 of the encoded antibody comprises the amino acid sequence of SEQ ID NO: 9, and the heavy chain CDR3 of the encoded antibody comprises the amino acid sequence SEQ ID NO: 10, wherein the CDRs are defined according to the IMGT method; or
   b. the heavy chain CDR1 of the encoded antibody comprises the amino acid sequence of SEQ ID NO: 11, the heavy chain CDR2 of the encoded antibody comprises the amino acid sequence of SEQ ID NO: 12, and the heavy chain CDR3 of the encoded antibody comprises the amino acid sequence SEQ ID NO: 13, wherein the CDRs are defined according to the KABAT method.

19. A vector comprising the isolated polynucleotide of claim 16.

20. A recombinant cell comprising the vector of claim 19.

21. The recombinant cell of claim 20, wherein the cell is a eukaryotic cell, a yeast cell, a plant cell, or a bacterium.

22. The recombinant cell of claim 21, wherein the eukaryotic cell is a CHO cell.

23. A method of detecting folate receptor alpha (FRα) in a biological sample, comprising exposing the sample to the antibody or antigen-binding fragment of claim 1, and detecting FRα.

24. The method of claim 23, wherein the biological sample is derived from urine, blood, serum, plasma, saliva, ascites, circulating cells, circulating tumor cells, cells that are not tissue associated, tissues, surgically resected tumor tissue, biopsies, fine needle aspiration samples, or histological preparations.

25. The method of claim 23, wherein the biological sample is derived from a human or nonhuman primate.

26. The method of claim 23, wherein the antibody or antigen-binding fragment is labeled.

27. The method of claim 26, wherein the label is a radiolabel, an epitope tag, biotin, a chromophore label, a fluorophore label, an electrochemiluminescence (ECL) label, or an enzyme.

28. The method of claim 27, wherein the electrochemiluminescence (ECL) label is a sulfo-tag.

29. The method of claim 23, further comprising exposing the sample to a second antibody or antigen-binding fragment antigen-binding fragment thereof, specific for folate receptor alpha (FRα) comprising:
   a. a light chain CDR1 comprising the amino acid sequence of SEQ ID NO: 1, a light chain CDR2 comprising the amino acid sequence of SEQ ID NO: 2, a light chain CDR3 comprising the amino acid sequence of SEQ ID NO: 3, a heavy chain CDR1 comprising the amino acid sequence of SEQ ID NO: 8, a heavy chain CDR2 comprising the amino acid sequence of SEQ ID NO: 9, and a heavy chain CDR3 comprising the amino acid sequence of SEQ ID NO: 10, wherein the CDRs are defined according to the IMGT method; or
   b. a light chain CDR1 comprising the amino acid sequence of SEQ ID NO: 4, a light chain CDR2 comprising the amino acid sequence of SEQ ID NO: 5, a light chain CDR3 comprising the amino acid sequence of SEQ ID NO: 3, a heavy chain CDR1 comprising the amino acid sequence of SEQ ID NO: 11, a heavy chain CDR2 comprising the amino acid sequence of SEQ ID NO: 12, and a heavy chain CDR3 comprising the amino acid sequence of SEQ ID NO: 13, wherein the CDRs are defined according to the KABAT method.

30. The method of claim 29, wherein the second antibody or antigen-binding fragment is immobilized to a solid support.

31. The method of claim 30, wherein the second antibody or antigen-binding fragment is biotinylated and the solid support is coated with streptavidin, and the isolated antibody or antigen-binding fragment is immobilized to the solid support by the binding of biotin to streptavidin.

32. The method of claim 23, wherein the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA.

33. The method of claim 23, wherein the sample is diluted prior to detecting folate receptor alpha (FRα) in the sample.

34. The method of claim 23, wherein the sample is centrifuged, vortexed, or both, prior to detecting folate receptor alpha (FRα) in the sample.

35. The method of claim 23, wherein the level of folate receptor alpha (FRα) in the sample is quantified.

36. The method of claim 23, wherein the sample is exposed to MORAb-003 prior to detecting folate receptor alpha (FRα) in the sample.

37. A method of detecting folate receptor alpha (FRα) in a biological sample, comprising:
   a. exposing the sample to a first isolated antibody or antigen-binding fragment comprising the isolated antibody or antigen-binding fragment of claim 1 and a second isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody comprising the amino acid sequence of an antibody produced by the cell line deposited with the ATCC having the accession number PTA-11884, or
   b. exposing a first isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody comprising the amino acid sequence of an antibody produced by the cell line deposited with the ATCC having the accession number PTA-11884 and a second isolated antibody or antigen-binding fragment comprising the isolated antibody or antigen-binding fragment of claim 1;
wherein the first isolated antibody or antigen-binding fragment is immobilized to a solid support and the second isolated antibody or antigen-binding fragment is labeled.

38. The method of claim 37, wherein the biological sample is derived from urine, blood, serum, plasma, saliva, ascites, circulating cells, circulating tumor cells, cells that are not tissue associated, tissues, surgically resected tumor tissue, biopsies, fine needle aspiration samples, or histological preparations.

39. The method claim 37, wherein the biological sample is derived from a human or nonhuman primate.

40. The method of claim 37, wherein the sample is diluted prior to detecting FRα in the sample.

41. The method of claim 37, wherein the sample is centrifuged, vortexed, or both, prior to detecting FRα in the sample.

42. The method of claim 37, wherein the label is a radiolabel, an epitope tag, biotin, a chromophore label, a fluorophore label, an electrochemiluminescence (ECL) label, or an enzyme.

43. The method of claim 42, wherein the electrochemiluminescence (ECL) label is a sulfo-tag.

44. The method of claim 37, wherein the first isolated antibody or antigen-binding fragment is biotinylated and the solid support is coated with streptavidin, and the first isolated antibody or antigen-binding fragment is immobilized to the solid support by the binding of biotin to streptavidin.

45. The method of claim 37, wherein the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA.

46. The method of claim 37, wherein the level of FRα in the sample is quantified.

47. The method of claim 37, wherein the sample is exposed to MORAb-003 prior to detecting folate receptor alpha (FRα) in the sample.

48. A method of diagnosing a folate receptor alpha (FRα)-expressing cancer in a subject, comprising:
 a. exposing the biological sample of the subject to the antibody or antigen-binding fragment of claim 1,
 b. quantifying the amount of FRα present in the sample that is bound by the antibody or antigen-binding fragment;
 c. comparing the amount of FRα present in the sample to a known standard; and
 d. determining whether the subject's FRα levels fall within the levels of FRα associated with cancer.

49. A method of monitoring a folate receptor alpha (FRα)-expressing cancer in a subject, comprising:
 a. exposing the biological sample of the subject to: the antibody or antigen-binding fragment of claim 1,
 b. quantifying the amount of FRα present in the sample that is bound by the antibody or antigen-binding fragment;
 c. comparing the amount of FRα present in the sample to either
  i. a known standard, or
  ii. a biological sample obtained from the subject at an earlier point in time; and
 d. determining whether the subject's FRα levels are indicative of cancer progression, regression or stable disease.

50. A method of treating a folate receptor alpha (FRα)-expressing cancer in a subject, comprising:
 a. exposing the biological sample of the subject to: the antibody or antigen-binding fragment of claim 1,
 b. quantifying the amount of FRα present in the sample that is bound by the antibody or antigen-binding fragment;
 c. comparing the amount of FRα present in the sample to a known standard;
 d. determining whether the subject's FRα levels fall within the levels of FRα associated with cancer; and
 e. administering to the subject, or prescribing, a treatment for the cancer.

51. The method of claim 48, wherein the antibody or antigen-binding fragment is immobilized to a solid support.

52. The method of claim 48, wherein the antibody or antigen-binding fragment is biotinylated and the solid support is coated with streptavidin, and the isolated antibody or antigen-binding fragment is immobilized to the solid support by the binding of biotin to streptavidin.

53. The method of claim 48, wherein the step of exposing the biological sample of the subject to:
the antibody or antigen-binding fragment of claim 1,
further comprises exposing the biological sample of the subject to a second antibody or antigen-binding fragment.

54. The method of claim 53, wherein the second antibody or antigen-binding fragment comprises a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody comprising the amino acid sequence of an antibody produced by the cell line deposited with the ATCC having the accession number PTA-11884.

55. The method of claim 54, wherein the second antibody, or antigen-binding fragment is labeled.

56. The method of claim 55, wherein the label is a radiolabel, an epitope tag, biotin, a chromophore label, a fluorophore label, an electrochemiluminescence (ECL) label, or an enzyme.

57. The method of claim 56, wherein the electrochemiluminescence (ECL) label is a sulfo-tag.

58. The method of claim 45, wherein the presence of folate receptor alpha (FRα) in the sample is detected using western blot, immunohistochemistry, immunofluorescence, flow cytometry, radioimmunoassay, immunoprecipitation, electrochemiluminescence immunoassay (ECLIA), or ELISA.

59. The method of claim 48, wherein the FRα-expressing cancer is ovarian cancer.

60. The method of claim 48, wherein the method is conducted following treatment of the subject for cancer with MORAb-003.

61. A kit for detecting the presence of folate receptor alpha (FRα) in a biological sample, comprising:
   a. the antibody or antigen-binding fragment of claim 1, or
   b. an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody comprising the amino acid sequence of an antibody produced by the cell line deposited with the ATCC having the accession number PTA-11884; and
   a vessel for containing the antibody, when not in use, and instructions for use of the antibody.

62. A kit for detecting the presence of folate receptor alpha (FRα) in a biological sample, comprising:
   a. the antibody or antigen-binding fragment of claim 1, or
   b. an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody comprising the amino acid sequence of an antibody produced by the cell line deposited with the ATCC having the accession number PTA-11884,
   wherein the antibody or antigen-binding fragment is affixed to a solid support.

63. A kit for detecting the presence of folate receptor alpha (FRα) in a biological sample, comprising:
   a. the antibody or antigen-binding fragment of any claim 1, or
   b. an isolated antibody or antigen-binding fragment with a light chain CDR1 comprising the amino acid sequence of SEQ ID NO: 31, a light chain CDR2 comprising the amino acid sequence of SEQ ID NO: 32, a light chain CDR3 comprising the amino acid sequence of SEQ ID NO: 33, a heavy chain CDR1 comprising the amino acid sequence of SEQ ID NO: 35, a heavy chain CDR2 comprising the amino acid sequence of SEQ ID NO: 36, and a heavy chain CDR3 comprising the amino acid sequence of SEQ ID NO: 37 or an isolated antibody comprising the amino acid sequence of an antibody produced by the cell line deposited with the ATCC having the accession number PTA-11884,
   wherein the antigen-binding fragment is detectably labeled.

* * * * *

SEQUENCE LISTING

<160> NUMBER OF SEQ ID NOS: 294

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Asp Ile Ser Asn His
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Thr Ser
1

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Gly Asn Thr Leu Trp Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Asp Ile Ser Asn His Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Thr Ser Lys Leu His Ser
1               5

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic

```
                polypeptide

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30

Leu Asn Trp Tyr Gln Gln Lys Pro Asp Gly Thr Ile Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Trp Thr
                85                  90                  95

Phe Gly Gly Gly Thr Lys Leu Glu Ile Lys
            100                 105

<210> SEQ ID NO 7
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30

Leu Asn Trp Tyr Gln Gln Lys Pro Asp Gly Thr Ile Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Trp Thr
                85                  90                  95

Phe Gly Gly Gly Thr Lys Leu Glu Ile Lys Arg Ala Asp Ala Ala Pro
            100                 105                 110

Thr

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Ser Leu Thr Ser Tyr Gly
1               5

<210> SEQ ID NO 9
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 9

Ile Trp Gly Asp Gly Ser Thr
1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Lys Pro His Pro Ala Ala Thr Gly Ala Met Asp Tyr
1               5                  10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Tyr Gly Val Ser
1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Trp Gly Asp Gly Ser Thr Asn Tyr His Ser Thr Leu Ile Ser
1               5                  10                  15

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro His Pro Ala Ala Thr Gly Ala Met Asp Tyr
1               5                  10

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Lys Glu Ser Gly Pro Gly Leu Val Ala Pro Ser Gln
1               5                  10                  15

Ser Leu Ser Ile Thr Cys Thr Val Ser Gly Phe Ser Leu Thr Ser Tyr
```

```
                    20                  25                  30
Gly Val Ser Trp Val Arg Gln Pro Pro Gly Lys Gly Leu Glu Trp Leu
                35                  40                  45

Gly Val Ile Trp Gly Asp Gly Ser Thr Asn Tyr His Ser Thr Leu Ile
            50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Pro His Pro Ala Ala Thr Gly Ala Met Asp Tyr Trp Gly Gln Gly
                100                 105                 110

Thr Ser Val Thr Val Ser Ser
            115

<210> SEQ ID NO 15
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Ser Trp Val Arg Gln Pro Pro Gly Lys Gly Leu Glu Trp Leu
                35                  40                  45

Gly Val Ile Trp Gly Asp Gly Ser Thr Asn Tyr His Ser Thr Leu Ile
            50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Pro His Pro Ala Ala Thr Gly Ala Met Asp Tyr Trp Gly Gln Gly
                100                 105                 110

Thr Ser Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe
                165                 170

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caggacatta gcaatcat                                                   18

<210> SEQ ID NO 17
```

```
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 tacacatca                                                                 9

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caacagggta atacgctttg gacg                                               24

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agggcaagtc aggacattag caatcattta aac                                     33

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tacacatcaa aattacactc a                                                  21

<210> SEQ ID NO 21
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gatatccaga tgacacagac tacatcctcc ctgtctgcct ctctgggaga cagagtcacc        60
atcagttgca gggcaagtca ggacattagc aatcatttaa actggtatca acagaaacca      120
gatggaacta ttaaactcct gatctactac acatcaaaat tacactcagg agtcccatca      180
aggttcagtg gcagtgggtc tggaacagat tattctctca ccattagcaa cctggaacaa      240
gaagatattg ccacttactt ttgccaacag ggtaatacgc tttggacgtt cggtggaggc      300
accaagctgg aaatcaaa                                                   318

<210> SEQ ID NO 22
<211> LENGTH: 339
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 22
gatatccaga tgacacagac tacatcctcc ctgtctgcct ctctgggaga cagagtcacc    60
atcagttgca gggcaagtca ggacattagc aatcatttaa actggtatca acagaaacca   120
gatggaacta ttaaactcct gatctactac acatcaaaat tacactcagg agtcccatca   180
aggttcagtg gcagtgggtc tggaacagat tattctctca ccattagcaa cctggaacaa   240
gaagatattg ccacttactt ttgccaacag ggtaatacgc tttggacgtt cggtggaggc   300
accaagctgg aaatcaaacg ggctgatgct gcaccaact                          339

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
gggttctcat taaccagtta tggt                                           24

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
atatggggtg acgggagcac a                                              21

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
gccaaacctc atcctgcggc tactggcgct atggactac                           39

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
agttatggtg taagc                                                     15

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27

```
gtaatatggg gtgacgggag cacaaattat cattcaactc tcatatcc                48
```

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
cctcatcctg cggctactgg cgctatggac tac                                33
```

<210> SEQ ID NO 29
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
caggtgcagc tgaaggagtc aggacctggc ctggtggcgc cctcacagag cctgtccatc    60
acatgcactg tctcagggtt ctcattaacc agttatggtg taagctgggt tcgccagcct   120
ccaggaaagg gtctggagtg gctgggagta atatggggtg acgggagcac aaattatcat   180
tcaactctca tatccagact gagcatcagc aaggataact ccaagagcca gttttctta    240 aaactgaaca gtctgcaaac tgatgacaca gccacgtact actgtgccaa acctcatcct   300
gcggctactg gcgctatgga ctactggggt caaggaacct cagtcaccgt ctcctca      357
```

<210> SEQ ID NO 30
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
caggtgcagc tgaaggagtc aggacctggc ctggtggcgc cctcacagag cctgtccatc    60
acatgcactg tctcagggtt ctcattaacc agttatggtg taagctgggt tcgccagcct   120
ccaggaaagg gtctggagtg gctgggagta atatggggtg acgggagcac aaattatcat   180
tcaactctca tatccagact gagcatcagc aaggataact ccaagagcca gttttctta    240 aaactgaaca gtctgcaaac tgatgacaca gccacgtact actgtgccaa acctcatcct   300
gcggctactg gcgctatgga ctactggggt caaggaacct cagtcaccgt ctcctcagcc   360
aaaacgacac ccccatctgt ctatccactg gcccctggat ctgctgccca aactaactcc   420
atggtgaccc tgggatgcct ggtcaagggc tatttccctg agccagtgac agtgacctgg   480
aactctggat ccctgtccag cggtgtgcac accttc                             516
```

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Arg Ala Ser Glu Ser Val Asp Thr Tyr Gly Asn Asn Phe Ile His
1               5                   10                  15
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Leu Ala Ser Asn Leu Glu Ser
1               5
```

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Gln Gln Asn Asn Gly Asp Pro Trp Thr
1               5
```

<210> SEQ ID NO 34
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Pro Ala Ser Leu Ala Val Ser Leu Gly Gln Arg Ala Thr Ile Ser Cys
1               5                   10                  15

Arg Ala Ser Glu Ser Val Asp Thr Tyr Gly Asn Asn Phe Ile His Trp
            20                  25                  30

Tyr Gln Gln Lys Pro Gly Gln Pro Pro Lys Leu Leu Ile Tyr Leu Ala
        35                  40                  45

Ser Asn Leu Glu Ser Gly Val Pro Ala Arg Phe Ser Gly Ser Gly Ser
    50                  55                  60

Arg Thr Asp Phe Thr Leu Thr Ile Asp Pro Val Glu Ala Asp Asp Ala
65                  70                  75                  80

Ala Thr Tyr Tyr Cys Gln Gln Asn Asn Gly Asp Pro Trp Thr Phe Gly
                85                  90                  95

Gly Gly Thr Lys Leu Glu Ile Lys Arg Ala Asp Ala Ala Pro
            100                 105                 110
```

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
His Pro Tyr Met His
1               5
```

<210> SEQ ID NO 36

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ile Asp Pro Ala Asn Gly Asn Thr Lys Tyr Asp Pro Lys Phe Gln
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Glu Val Ala Asp Tyr Thr Met Asp Tyr
1               5                   10

<210> SEQ ID NO 38
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Ala Arg Glu Leu Val Lys Pro Gly Ala Ser Val Lys Leu Ser Cys
1               5                   10                  15

Thr Ala Ser Gly Phe Asn Ile Lys His Pro Tyr Met His Trp Val Lys
            20                  25                  30

Gln Arg Pro Asp Gln Gly Leu Glu Trp Ile Gly Arg Ile Asp Pro Ala
        35                  40                  45

Asn Gly Asn Thr Lys Tyr Asp Pro Lys Phe Gln Gly Lys Ala Thr Ile
    50                  55                  60

Thr Ala Asp Thr Ser Ser Asn Thr Ala Tyr Leu Gln Leu Ser Ser Leu
65                  70                  75                  80

Thr Ser Glu Asp Thr Ala Val Tyr Tyr Cys Gly Arg Glu Glu Val Ala
                85                  90                  95

Asp Tyr Thr Met Asp Tyr Trp Gly Gln Gly Thr Ser Val Thr Val Ser
            100                 105                 110

Ser Ala Lys Thr Thr Ala Pro Ser Val Tyr Pro Leu Ala Pro Val
        115                 120                 125

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agagccagtg aaagtgttga tacttatggc aataatttta tacac                      45

<210> SEQ ID NO 40
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cttgcatcca acctagaatc t                                              21

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cagcaaaata atggggatcc gtggacg                                        27

<210> SEQ ID NO 42
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
ccagcttctt tggctgtgtc tctagggcag agggccacca tatcctgcag agccagtgaa    60
agtgttgata cttatggcaa taattttata cactggtacc agcagaaacc aggacagcca   120
cccaaactcc tcatttatct tgcatccaac ctagaatctg gggtccctgc caggttcagt   180
ggcagtgggt ctaggacaga cttcaccctc accattgatc ctgtggaggc tgatgatgct   240
gcaacctatt actgtcagca aaataatggg gatccgtgga cgttcggtgg aggcaccaag   300
ctggagatca aacgggctga tgctgcacca a                                  331

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cacccctata tgcac                                                     15

<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aggattgatc ctgcgaatgg taatactaaa tatgacccga agttccaggg c              51

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 45
gaggaggtgg cggactatac tatggactac                                          30

<210> SEQ ID NO 46
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ggggcagagc ttgtgaagcc aggggcctca gtcaagttgt cctgcacagc ttctggcttc         60
aacattaaac accctatat gcactgggtg aagcagaggc ctgaccaggg cctggagtgg          120
attggaagga ttgatcctgc gaatggtaat actaaatatg acccgaagtt ccagggcaag         180
gccactataa cagcagacac atcctccaac acagcctacc tacagctcag cagcctgaca         240
tctgaggaca ctgccgtcta ttactgtggt agagaggagg tggcggacta ctatggac          300 tactggggtc aaggaacctc agtcaccgtc tcctcagcca aaacaacagc cccatcggtc         360
tatccactgg cccctgtgtg                                                    380

<210> SEQ ID NO 47
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Thr Thr Ser Ser Leu Ser Ala Ser Leu Gly Asp Arg Val Thr Ile Ser
1               5                   10                  15

Cys Arg Ala Ser Gln Asp Ile Ser Asn His Leu Asn Trp Tyr Gln Gln
            20                  25                  30

Lys Pro Asp Gly Thr Ile Lys Leu Leu Ile Tyr Tyr Thr Ser Lys Leu
        35                  40                  45

His Ser Gly Val Pro Ser Arg Phe Ser Gly Ser Gly Ser Gly Thr Asp
    50                  55                  60

Tyr Ser Leu Thr Ile Ser Asn Leu Glu Gln Glu Asp Ile Ala Thr Tyr
65                  70                  75                  80

Phe Cys Gln Gln Gly Asn Thr Leu Trp Thr Phe Gly Gly Gly Thr Lys
                85                  90                  95

Leu Glu Ile Lys
        100

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Thr Thr Ser Ser Leu Ser Ala Ser Leu Gly Asp Arg Val Thr Ile Ser
1               5                   10                  15

Cys Arg Ala Ser Gln Asp Ile Ser Asn His Leu Asn Trp Tyr Gln Gln
            20                  25                  30

```
Lys Pro Asp Gly Thr Ile Lys Leu Leu Ile Tyr Tyr Thr Ser Lys Leu
            35                  40                  45

His Ser Gly Val Pro Ser Arg Phe Ser Gly Ser Gly Ser Gly Thr Asp
 50                  55                  60

Tyr Ser Leu Thr Ile Ser Asn Leu Glu Gln Glu Asp Ile Ala Thr Tyr
 65                  70                  75                  80

Phe Cys Gln Gln Gly Asn Thr Leu Trp Thr Phe Gly Gly Gly Thr Lys
                85                  90                  95

Leu Glu Ile Lys Arg Ala Asp Ala Ala Pro Thr Val Ser Ile Phe Pro
            100                 105                 110

Pro Ser Ser Glu Gln Leu
            115

<210> SEQ ID NO 49
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Pro Gly Leu Val Ala Pro Ser Gln Ser Leu Ser Ile Thr Cys Thr
1               5                   10                  15

Val Ser Gly Phe Ser Leu Thr Ser Tyr Gly Val Ser Trp Val Arg Gln
            20                  25                  30

Pro Pro Gly Lys Gly Leu Glu Trp Leu Gly Val Ile Trp Gly Asp Gly
        35                  40                  45

Ser Thr Asn Tyr His Ser Thr Leu Ile Ser Arg Leu Ser Ile Ser Lys
 50                  55                  60

Asp Asn Ser Lys Ser Gln Val Phe Leu Lys Leu Asn Ser Leu Gln Thr
 65                  70                  75                  80

Asp Asp Thr Ala Thr Tyr Tyr Cys Ala Lys Pro His Pro Ala Ala Thr
                85                  90                  95

Gly Ala Met Asp Tyr Trp Gly Gln Gly Thr Ser Val Thr Val Ser Ser
            100                 105                 110

<210> SEQ ID NO 50
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Pro Gly Leu Val Ala Pro Ser Gln Ser Leu Ser Ile Thr Cys Thr
1               5                   10                  15

Val Ser Gly Phe Ser Leu Thr Ser Tyr Gly Val Ser Trp Val Arg Gln
            20                  25                  30

Pro Pro Gly Lys Gly Leu Glu Trp Leu Gly Val Ile Trp Gly Asp Gly
        35                  40                  45

Ser Thr Asn Tyr His Ser Thr Leu Ile Ser Arg Leu Ser Ile Ser Lys
 50                  55                  60

Asp Asn Ser Lys Ser Gln Val Phe Leu Lys Leu Asn Ser Leu Gln Thr
 65                  70                  75                  80

Asp Asp Thr Ala Thr Tyr Tyr Cys Ala Lys Pro His Pro Ala Ala Thr
                85                  90                  95
```

Gly Ala Met Asp Tyr Trp Gly Gln Gly Thr Ser Val Thr Val Ser Ser
             100                 105                 110

Ala Lys Thr Thr Pro Pro Ser Val Tyr Pro Leu Ala Pro Gly Ser Ala
         115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe
                165

<210> SEQ ID NO 51
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
actacatcct ccctgtctgc ctctctggga gacagagtca ccatcagttg cagggcaagt      60
caggacatta gcaatcattt aaactggtat caacagaaac cagatggaac tattaaactc     120
ctgatctact acacatcaaa attacactca ggagtcccat caaggttcag tggcagtggg     180
tctggaacag attattctct caccattagc aacctggaac aagaagatat tgccacttac     240
ttttgccaac agggtaatac gctttggacg ttcgtggag gcaccaagct ggaaatmaaa     300

<210> SEQ ID NO 52
<211> LENGTH: 353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
ctacatcctc cctgtctgcc tctctgggag acagagtcac catcagttgc agggcaagtc      60
aggacattag caatcattta aactggtatc aacagaaacc agatggaact attaaactcc    120
tgatctacta cacatcaaaa ttacactcag gagtcccatc aaggttcagt ggcagtgggt    180
ctggaacaga ttattctctc accattagca acctggaaca agaagatatt gccacttact    240
tttgccaaca gggtaatacg ctttggacgt tcggtggagg caccaagctg gaaatmaaac    300
gggctgatgc tgcaccaact gtatccatct tcccaccatc cagtgagcag tta           353

<210> SEQ ID NO 53
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ggacctggcc tggtggcgcc ctcacagagc ctgtccatca catgcactgt ctcaggttc       60 tcattaacca gttatggtgt aagctgggtt cgccagcctc aggaaaggg tctggagtgg     120 ctgggagtaa tatggggtga cgggagcaca aattatcatt caactctcat atccagactg    180
agcatcagca aggataactc caagagccaa gttttcttaa aactgaacag tctgcaaact    240

```
gatgacacag ccacgtacta ctgtgccaaa cctcatcctg cggctactgg cgctatggac    300
tactggggtc aaggaacctc agtcaccgtc tcctca                              336
```

<210> SEQ ID NO 54
<211> LENGTH: 496
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
ggacctggcc tggtggcgcc ctcacagagc ctgtccatca catgcactgt ctcaggttc      60 tcattaacca gttatggtgt aagctgggtt cgccagcctc caggaaaggg tctggagtgg   120
ctgggagtaa tatggggtga cgggagcaca aattatcatt caactctcat atccagactg   180
agcatcagca aggataactc caagagccaa gttttcttaa aactgaacag tctgcaaact   240
gatgacacag ccacgtacta ctgtgccaaa cctcatcctg cggctactgg cgctatggac   300
tactggggtc aaggaacctc agtcaccgtc tcctcagcca aaacgacacc cccatctgtc   360
tatccactgg ccctggatc tgctgcccaa actaactcca tggtgaccct gggatgcctg    420
gtcaagggct atttccctga gccagtgaca gtgacctgga actctggatc cctgtccagc   480
ggtgtgcaca ccttcc                                                    496
```

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Asn Ile His Asn Tyr
1               5

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ala Lys
1

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln His Phe Trp Ser Thr Pro Tyr Thr
1               5

<210> SEQ ID NO 58
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 58

Arg Ala Ser Gly Asn Ile His Asn Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Ala Lys Thr Leu Ala Asp
1               5

<210> SEQ ID NO 60
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Pro Ala Ser Leu Ser Ala Ser Val Gly Glu Thr Val Thr Ile
1               5                   10                  15

Thr Cys Arg Ala Ser Gly Asn Ile His Asn Tyr Leu Ala Trp Tyr Gln
                20                  25                  30

Gln Lys Gln Gly Lys Ser Pro Gln Leu Leu Val Tyr Asn Ala Lys Thr
            35                  40                  45

Leu Ala Asp Gly Val Pro Ser Arg Phe Ser Gly Ser Gly Ser Gly Thr
        50                  55                  60

Gln Tyr Ser Leu Lys Ile Asn Ser Leu Gln Pro Glu Asp Phe Gly Ser
65                  70                  75                  80

Tyr Tyr Cys Gln His Phe Trp Ser Thr Pro Tyr Thr Phe Gly Gly Gly
                85                  90                  95

Thr Lys Leu Glu Ile Lys
            100

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ser Pro Ala Ser Leu Ser Ala Ser Val Gly Glu Thr Val Thr Ile
1               5                   10                  15

Thr Cys Arg Ala Ser Gly Asn Ile His Asn Tyr Leu Ala Trp Tyr Gln
                20                  25                  30

Gln Lys Gln Gly Lys Ser Pro Gln Leu Leu Val Tyr Asn Ala Lys Thr
            35                  40                  45

Leu Ala Asp Gly Val Pro Ser Arg Phe Ser Gly Ser Gly Ser Gly Thr
        50                  55                  60
```

Gln Tyr Ser Leu Lys Ile Asn Ser Leu Gln Pro Glu Asp Phe Gly Ser
65                  70                  75                  80

Tyr Tyr Cys Gln His Phe Trp Ser Thr Pro Tyr Thr Phe Gly Gly Gly
                85                  90                  95

Thr Lys Leu Glu Ile Lys Arg Ala Asp Ala Ala Pro Thr Val Ser Ile
            100                 105                 110

Phe Pro Pro Ser Ser Glu Gln Leu
            115                 120

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Thr Phe Asn Ser Ser Tyr
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Tyr Ala Gly Asn Gly Gly Thr
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Thr Tyr Thr Asn Tyr Trp Tyr Phe Asp Val
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Ser Tyr Ile Thr
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Trp Ile Tyr Ala Gly Asn Gly Gly Thr Thr Tyr Asn Gln Lys Phe Thr
1               5                   10                  15

Gly
```

<210> SEQ ID NO 67
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Ser Gly Ala Arg Glu Leu Val Lys Pro Gly Ala Ser Val Lys Leu Ser
1               5                   10                  15

Cys Lys Thr Ser Gly Phe Thr Phe Asn Ser Ser Tyr Ile Thr Trp Leu
                20                  25                  30

Lys Gln Lys Pro Gly Gln Ser Leu Glu Trp Ile Ala Trp Ile Tyr Ala
            35                  40                  45

Gly Asn Gly Gly Thr Thr Tyr Asn Gln Lys Phe Thr Gly Lys Ala Gln
        50                  55                  60

Leu Thr Val Asp Thr Ser Ser Thr Ala Tyr Met Gln Phe Ser Ser
65                  70                  75                  80

Leu Thr Thr Glu Asp Ser Ala Ile Tyr Tyr Cys Ala Ser Glu Thr Tyr
                85                  90                  95

Thr Asn Tyr Trp Tyr Phe Asp Val Trp Gly Ser Gly Thr Thr Val Thr
                100                 105                 110

Val Ser Ser
        115
```

<210> SEQ ID NO 68
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Ser Gly Ala Arg Glu Leu Val Lys Pro Gly Ala Ser Val Lys Leu Ser
1               5                   10                  15

Cys Lys Thr Ser Gly Phe Thr Phe Asn Ser Ser Tyr Ile Thr Trp Leu
                20                  25                  30

Lys Gln Lys Pro Gly Gln Ser Leu Glu Trp Ile Ala Trp Ile Tyr Ala
            35                  40                  45

Gly Asn Gly Gly Thr Thr Tyr Asn Gln Lys Phe Thr Gly Lys Ala Gln
        50                  55                  60

Leu Thr Val Asp Thr Ser Ser Thr Ala Tyr Met Gln Phe Ser Ser
65                  70                  75                  80

Leu Thr Thr Glu Asp Ser Ala Ile Tyr Tyr Cys Ala Ser Glu Thr Tyr
                85                  90                  95

Thr Asn Tyr Trp Tyr Phe Asp Val Trp Gly Ser Gly Thr Thr Val Thr
                100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
        130                 135                 140

Lys Gly Tyr Phe Pro Glu Pro Val Thr Val Thr Trp Asn Ser Gly Ser
```

145            150            155            160
Leu Ser Ser Gly Val His Thr Phe
            165

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gggaatattc acaattat                                                18

<210> SEQ ID NO 70
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70 aatgcaaaa                                                           9

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caacattttt ggagtactcc gtacacg                                      27

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cgagcaagtg ggaatattca caattattta gca                               33

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aatgcaaaaa ccttagcaga t                                            21

<210> SEQ ID NO 74
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 74
cagtctccag cctccctatc tgcatctgtg ggagaaactg tcaccatcac atgtcgagca        60
agtgggaata ttcacaatta tttagcatgg tatcagcaga aacagggaaa atctcctcag       120
ctcctggtct ataatgcaaa aaccttagca gatggtgtgc catcaaggtt cagtggcagt       180
ggatcaggaa cacaatattc tctcaagatc aacagcctgc agcctgaaga ttttgggagt       240
tattactgtc aacattttg gagtactccg tacacgttcg gagggggac caagctggaa         300 ataaaa                                                                  306

<210> SEQ ID NO 75
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
cagtctccag cctccctatc tgcatctgtg ggagaaactg tcaccatcac atgtcgagca        60
agtgggaata ttcacaatta tttagcatgg tatcagcaga aacagggaaa atctcctcag       120
ctcctggtct ataatgcaaa aaccttagca gatggtgtgc catcaaggtt cagtggcagt       180
ggatcaggaa cacaatattc tctcaagatc aacagcctgc agcctgaaga ttttgggagt       240
tattactgtc aacattttg gagtactccg tacacgttcg gagggggac caagctggaa         300 ataaaacggg ctgatgctgc accaactgta tccatcttcc caccatccag tgagcagtta      360

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggcttcacct tcaacagtag ctat                                              24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atttatgctg gaaatggtgg tact                                              24

<210> SEQ ID NO 78
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcaagcgaga cgtatactaa ctactggtac ttcgatgtc                              39

<210> SEQ ID NO 79
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agtagctata taact                                                          15

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tggatttatg ctggaaatgg tggtactacc tataatcaga aattcacagg c                   51

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gagacgtata ctaactactg gtacttcgat gtc                                      33

<210> SEQ ID NO 82
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
tctggagctg agctggtgaa gcctgggggct tcagtgaagc tgtcctgcaa gacttctggc         60
ttcaccttca acagtagcta tataacttgg ttgaagcaaa agcctggaca gagtcttgag         120
tggattgcat ggatttatgc tggaaatggt ggtactacct ataatcagaa attcacaggc         180
aaggcccaat gactgtcga cacatcctcc agcacagcct acatgcagtt cagcagcctg         240
acaactgagg actctgccat ctattactgt gcaagcgaga cgtatactaa ctactggtac         300
ttcgatgtct ggggctcagg gaccacggtc accgtctcct ca                           342

<210> SEQ ID NO 83
<211> LENGTH: 502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
tctggagctg agctggtgaa gcctgggggct tcagtgaagc tgtcctgcaa gacttctggc         60
ttcaccttca acagtagcta tataacttgg ttgaagcaaa agcctggaca gagtcttgag         120
tggattgcat ggatttatgc tggaaatggt ggtactacct ataatcagaa attcacaggc         180
aaggcccaat gactgtcga cacatcctcc agcacagcct acatgcagtt cagcagcctg         240
acaactgagg actctgccat ctattactgt gcaagcgaga cgtatactaa ctactggtac         300
```

```
ttcgatgtct ggggctcagg gaccacggtc accgtctcct cagccaaaac gacacccca    360 tctgtctatc cactggcccc tggatctgct gcccaaacta actccatggt gaccctggga    420
tgcctggtca agggctattt ccctgagcca gtgacagtga cctggaactc tggatccctg    480
tccagcggtg tgcacacctt cc                                              502
```

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Ser Val Ser Thr Ser Gly Tyr Ser Tyr
1               5                   10

<210> SEQ ID NO 85
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Ala Ser
1

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Ser Arg Glu Leu Pro Pro Thr
1               5

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ala Ser Lys Ser Val Ser Thr Ser Gly Tyr Ser Tyr Met Tyr
1               5                   10                  15

<210> SEQ ID NO 88
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Ser Pro Ala Ser Leu Val Val Ser Leu Gly Gln Arg Ala Thr Ile
1               5                   10                  15

```
Ser Cys Arg Ala Ser Lys Ser Val Ser Thr Ser Gly Tyr Ser Tyr Met
             20                  25                  30

Tyr Trp Tyr Gln Gln Lys Ser Gly Gln Pro Pro Lys Leu Leu Ile Tyr
         35                  40                  45

Leu Ala Ser Asn Leu Glu Ser Gly Val Pro Ala Arg Phe Ser Gly Gly
     50                  55                  60

Gly Ser Gly Thr Asp Phe Thr Leu Asn Ile His Pro Val Glu Glu Glu
 65                  70                  75                  80

Asp Ala Ala Thr Tyr Tyr Cys Gln Gln Ser Arg Glu Leu Pro Pro Thr
                 85                  90                  95

Phe Gly Gly Gly Thr Lys Leu Glu Ile Lys
             100                 105
```

<210> SEQ ID NO 89
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Gln Ser Pro Ala Ser Leu Val Val Ser Leu Gly Gln Arg Ala Thr Ile
 1               5                  10                  15

Ser Cys Arg Ala Ser Lys Ser Val Ser Thr Ser Gly Tyr Ser Tyr Met
             20                  25                  30

Tyr Trp Tyr Gln Gln Lys Ser Gly Gln Pro Pro Lys Leu Leu Ile Tyr
         35                  40                  45

Leu Ala Ser Asn Leu Glu Ser Gly Val Pro Ala Arg Phe Ser Gly Gly
     50                  55                  60

Gly Ser Gly Thr Asp Phe Thr Leu Asn Ile His Pro Val Glu Glu Glu
 65                  70                  75                  80

Asp Ala Ala Thr Tyr Tyr Cys Gln Gln Ser Arg Glu Leu Pro Pro Thr
                 85                  90                  95

Phe Gly Gly Gly Thr Lys Leu Glu Ile Lys Arg Ala Asp Ala Ala Pro
             100                 105                 110

Thr Val Ser Ile Phe Pro Pro Ser Ser Glu Gln Leu
         115                 120
```

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Gly Tyr Ser Phe Thr Ser Asn Trp
 1               5
```

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Ile Tyr Pro Gly Asn Ser Asp Thr
```

```
<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Arg Gly Asp Gly Ser Ser Phe Trp Tyr Phe Asp Val
1               5                   10

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Asn Trp Met His
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ile Tyr Pro Gly Asn Ser Asp Thr Ser Tyr Asn Gln Lys Phe Lys
1               5                   10                  15

Gly

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Asp Gly Ser Ser Phe Trp Tyr Phe Asp Val
1               5                   10

<210> SEQ ID NO 96
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Ser Gly Thr Val Leu Ala Arg Pro Gly Ala Ser Val Lys Met Ser
1               5                   10                  15

Cys Lys Ala Ser Gly Tyr Ser Phe Thr Ser Asn Trp Met His Trp Ile
                20                  25                  30

Lys Gln Arg Pro Gly Gln Gly Leu Glu Trp Ile Gly Ala Ile Tyr Pro
            35                  40                  45
```

Gly Asn Ser Asp Thr Ser Tyr Asn Gln Lys Phe Lys Gly Lys Ala Lys
            50                  55                  60

Leu Thr Ala Val Thr Ser Ala Ser Thr Ala Tyr Met Glu Leu Ser Ser
 65                  70                  75                  80

Leu Thr Asn Glu Asp Ser Ala Val Tyr His Cys Thr Arg Gly Asp Gly
                    85                  90                  95

Ser Ser Phe Trp Tyr Phe Asp Val Trp Gly Ala Gly Thr Thr Val Thr
            100                 105                 110

Val Ser Ser
        115

<210> SEQ ID NO 97
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Ser Gly Thr Val Leu Ala Arg Pro Gly Ala Ser Val Lys Met Ser
 1               5                  10                  15

Cys Lys Ala Ser Gly Tyr Ser Phe Thr Ser Asn Trp Met His Trp Ile
            20                  25                  30

Lys Gln Arg Pro Gly Gln Gly Leu Glu Trp Ile Gly Ala Ile Tyr Pro
        35                  40                  45

Gly Asn Ser Asp Thr Ser Tyr Asn Gln Lys Phe Lys Gly Lys Ala Lys
    50                  55                  60

Leu Thr Ala Val Thr Ser Ala Ser Thr Ala Tyr Met Glu Leu Ser Ser
 65                  70                  75                  80

Leu Thr Asn Glu Asp Ser Ala Val Tyr His Cys Thr Arg Gly Asp Gly
                    85                  90                  95

Ser Ser Phe Trp Tyr Phe Asp Val Trp Gly Ala Gly Thr Thr Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe
                165

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aaaagtgtca gtacatctgg ctatagttat                                    30

<210> SEQ ID NO 99
<211> LENGTH: 9
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 99 cttgcatcc                                                              9

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cagcaaagta gggagcttcc tcccacg                                         27

<210> SEQ ID NO 101
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
agggccagta aaagtgtcag tacatctggc tatagttata tgtac                     45

<210> SEQ ID NO 102
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
cagtctcctg cttccttagt tgtatctctg gggcagaggg ccaccatctc atgcagggcc     60
agtaaaagtg tcagtacatc tggctatagt tatatgtact ggtaccaaca gaaatcagga    120
cagccaccca aactcctcat ctatcttgca tccaacctag aatctggggt ccctgccagg    180
ttcagtggcg gtgggtctgg gacagacttc accctcaaca tccatcctgt ggaggaggag    240
gatgctgcaa cctattactg tcagcaaagt agggagcttc ctcccacgtt cggagggggg    300
accaagctgg aaataaaa                                                 318

<210> SEQ ID NO 103
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
cagtctcctg cttccttagt tgtatctctg gggcagaggg ccaccatctc atgcagggcc     60
agtaaaagtg tcagtacatc tggctatagt tatatgtact ggtaccaaca gaaatcagga    120
cagccaccca aactcctcat ctatcttgca tccaacctag aatctggggt ccctgccagg    180
ttcagtggcg gtgggtctgg gacagacttc accctcaaca tccatcctgt ggaggaggag    240
gatgctgcaa cctattactg tcagcaaagt agggagcttc ctcccacgtt cggagggggg    300
accaagctgg aaataaaacg ggctgatgct gcaccaactg tatccatctt cccaccatcc    360
```
agtgagcagt ta                                                          372

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ggctacagct ttaccagcaa ctgg                                              24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atttatcctg gaaatagtga tact                                              24

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
acaagagggg acggtagtag tttctggtac ttcgatgtc                              39

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agcaactgga tgcac                                                        15

<210> SEQ ID NO 108
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gctatttatc ctggaaatag tgatactagt tacaaccaga agttcaaggg c                51

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggggacggta gtagtttctg gtacttcgat gtc                                    33

<210> SEQ ID NO 110
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
cagtctggga ctgtgctggc aaggcctggg gcttccgtga agatgtcctg caaggcttct    60
ggctacagct ttaccagcaa ctggatgcac tggataaaac agaggcctgg acagggtcta   120
gagtggattg gtgctattta tcctggaaat agtgatacta gttacaacca gaagttcaag   180
ggcaaggcca aactgactgc agtcacatcc gccagcactg cctacatgga gctcagcagc   240
ctgacaaatg aggactctgc ggtctatcac tgtacaagag gggacggtag tagtttctgg   300
tacttcgatg tctggggcgc agggaccacg gtcaccgtct cctca                   345

<210> SEQ ID NO 111
<211> LENGTH: 505
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
cagtctggga ctgtgctggc aaggcctggg gcttccgtga agatgtcctg caaggcttct    60
ggctacagct ttaccagcaa ctggatgcac tggataaaac agaggcctgg acagggtcta   120
gagtggattg gtgctattta tcctggaaat agtgatacta gttacaacca gaagttcaag   180
ggcaaggcca aactgactgc agtcacatcc gccagcactg cctacatgga gctcagcagc   240
ctgacaaatg aggactctgc ggtctatcac tgtacaagag gggacggtag tagtttctgg   300
tacttcgatg tctggggcgc agggaccacg gtcaccgtct cctcagccaa aacgacaccc   360
ccatctgtct atccactggc ccctggatct gctgcccaaa ctaactccat ggtgaccctg   420
ggatgcctgg tcaagggcta tttccctgag ccagtgacag tgacctggaa ctctggatcc   480
ctgtccagcg gtgtgcacac cttcc                                         505

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Asp Ile Ser Asn Tyr
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Gly Asn Thr Leu Pro Tyr Thr

-continued

```
<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Gln Asp Ile Ser Asn Tyr Leu Asn
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Thr Ser Arg Leu His Ser
1               5

<210> SEQ ID NO 116
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ser Ser Leu Ser Ala Ser Leu Gly Asp Arg Val Thr Ile Ser Cys Arg
1               5                   10                  15

Ala Ser Gln Asp Ile Ser Asn Tyr Leu Asn Trp Tyr Gln Gln Lys Pro
            20                  25                  30

Asp Gly Thr Val Lys Leu Leu Ile Tyr Tyr Thr Ser Arg Leu His Ser
        35                  40                  45

Gly Val Pro Ser Arg Phe Ser Gly Ser Gly Ser Gly Thr Asp Tyr Ser
    50                  55                  60

Leu Thr Ile Ser Asn Leu Glu Gln Glu Asp Ile Ala Thr Tyr Phe Cys
65                  70                  75                  80

Gln Gln Gly Asn Thr Leu Pro Tyr Thr Phe Gly Gly Gly Thr Lys Leu
                85                  90                  95

Glu Ile Lys

<210> SEQ ID NO 117
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ser Ser Leu Ser Ala Ser Leu Gly Asp Arg Val Thr Ile Ser Cys Arg
1               5                   10                  15

Ala Ser Gln Asp Ile Ser Asn Tyr Leu Asn Trp Tyr Gln Gln Lys Pro
            20                  25                  30

Asp Gly Thr Val Lys Leu Leu Ile Tyr Tyr Thr Ser Arg Leu His Ser
```

```
                35                  40                  45
Gly Val Pro Ser Arg Phe Ser Gly Ser Gly Thr Asp Tyr Ser
    50                  55                  60
Leu Thr Ile Ser Asn Leu Glu Gln Glu Asp Ile Ala Thr Tyr Phe Cys
65                  70                  75                  80
Gln Gln Gly Asn Thr Leu Pro Tyr Thr Phe Gly Gly Gly Thr Lys Leu
                85                  90                  95
Glu Ile Lys Arg Ala Asp Ala Ala Pro Thr Val Ser Ile Phe Pro Pro
            100                 105                 110
Ser Ser Glu Gln Leu
        115

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Tyr Thr Phe Ser Arg Tyr Asn
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Tyr Pro Gly Asn Gly Asp Thr
1               5

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Arg Asp Tyr Gly Ser Arg Tyr Ala Leu Asp Tyr
1               5                   10

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Tyr Asn Met His
1               5

<210> SEQ ID NO 122
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 122

Thr Ile Tyr Pro Gly Asn Gly Asp Thr Ser Tyr Asn Glu Lys Phe Lys
1               5                   10                  15

Gly

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Tyr Gly Ser Arg Tyr Ala Leu Asp Tyr
1               5                   10

<210> SEQ ID NO 124
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Ala Asp Leu Val Lys Pro Gly Ala Ser Val Lys Met Ser Cys Lys
1               5                   10                  15

Ala Ser Gly Tyr Thr Phe Ser Arg Tyr Asn Met His Trp Val Lys Gln
                20                  25                  30

Thr Pro Gly Gln Gly Leu Glu Trp Ile Gly Thr Ile Tyr Pro Gly Asn
            35                  40                  45

Gly Asp Thr Ser Tyr Asn Glu Lys Phe Lys Gly Lys Ala Thr Leu Thr
        50                  55                  60

Ala Asp Lys Ser Ser Ser Ile Val Tyr Met Gln Val Ser Ser Leu Thr
65                  70                  75                  80

Ser Glu Ala Ser Ala Val Tyr Tyr Cys Ala Arg Asp Tyr Gly Ser Arg
                85                  90                  95

Tyr Ala Leu Asp Tyr Trp Gly Gln Gly Thr Ser Val Thr Val Ser Ser
            100                 105                 110

<210> SEQ ID NO 125
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gly Ala Asp Leu Val Lys Pro Gly Ala Ser Val Lys Met Ser Cys Lys
1               5                   10                  15

Ala Ser Gly Tyr Thr Phe Ser Arg Tyr Asn Met His Trp Val Lys Gln
                20                  25                  30

Thr Pro Gly Gln Gly Leu Glu Trp Ile Gly Thr Ile Tyr Pro Gly Asn
            35                  40                  45

Gly Asp Thr Ser Tyr Asn Glu Lys Phe Lys Gly Lys Ala Thr Leu Thr
        50                  55                  60
```

```
Ala Asp Lys Ser Ser Ser Ile Val Tyr Met Gln Val Ser Ser Leu Thr
 65                  70                  75                  80

Ser Glu Ala Ser Ala Val Tyr Tyr Cys Ala Arg Asp Tyr Gly Ser Arg
                 85                  90                  95

Tyr Ala Leu Asp Tyr Trp Gly Gln Gly Thr Ser Val Thr Val Ser Ser
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe
                165
```

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
caggacatta gcaattat                                                     18

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
caacagggta atacgcttcc gtacacg                                            27

<210> SEQ ID NO 128
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agggcaagtc aggacattag caattattta aac                                     33

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tacacatcaa gattacactc a                                                  21

<210> SEQ ID NO 130
<211> LENGTH: 297
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 130
tcctccctgt ctgcctctct gggagacaga gtcaccatca gttgcagggc aagtcaggac    60
attagcaatt atttaaactg gtatcagcag aaaccagatg gaactgttaa actcctgatc   120
tactacacat caagattaca ctcaggagtc ccatcaaggt tcagtggcag tgggtctgga   180
acagattatt ctctcaccat tagcaacctg gagcaagaag atattgccac ttacttttgc   240
caacagggta atacgcttcc gtacacgttc ggaggggga ccaagctgga aataaaa      297

<210> SEQ ID NO 131
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
tcctccctgt ctgcctctct gggagacaga gtcaccatca gttgcagggc aagtcaggac    60
attagcaatt atttaaactg gtatcagcag aaaccagatg gaactgttaa actcctgatc   120
tactacacat caagattaca ctcaggagtc ccatcaaggt tcagtggcag tgggtctgga   180
acagattatt ctctcaccat tagcaacctg gagcaagaag atattgccac ttacttttgc   240
caacagggta atacgcttcc gtacacgttc ggaggggga ccaagctgga aataaaacgg   300
gctgatgctg caccaactgt atccatcttc ccaccatcca gtgagcagtt a           351

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggctacacat ttagccgtta caat                                           24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
atttatccag gaaatggtga tact                                           24

<210> SEQ ID NO 134
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcaagagact acggtagtcg gtatgctttg gactac                              36

<210> SEQ ID NO 135

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cgttacaata tgcac                                                     15

<210> SEQ ID NO 136
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
actatttatc caggaaatgg tgatacttcc tacaatgaga agttcaaagg c              51

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gactacggta gtcggtatgc tttggactac                                     30

<210> SEQ ID NO 138
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
ggggctgacc tggtgaagcc tggggcctca gtgaagatgt cctgcaaggc ttctggctac    60
acatttagcc gttacaatat gcactgggta aaacagacac ctggacaggg cctggaatgg   120
attggaacta tttatccagg aaatggtgat acttcctaca atgagaagtt caaaggcaag   180
gccacattga ctgcagacaa atcctccagt atagtctaca tgcaggtcag cagcctgaca   240
tctgaggcct ctgcggtcta ttactgtgca agagactacg gtagtcggta tgctttggac   300
tactggggtc aaggaacctc agtcaccgtc tcctca                             336

<210> SEQ ID NO 139
<211> LENGTH: 496
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
ggggctgacc tggtgaagcc tggggcctca gtgaagatgt cctgcaaggc ttctggctac    60
acatttagcc gttacaatat gcactgggta aaacagacac ctggacaggg cctggaatgg   120
attggaacta tttatccagg aaatggtgat acttcctaca atgagaagtt caaaggcaag   180
gccacattga ctgcagacaa atcctccagt atagtctaca tgcaggtcag cagcctgaca   240
```

```
tctgaggcct ctgcggtcta ttactgtgca agagactacg gtagtcggta tgctttggac    300
tactggggtc aaggaacctc agtcaccgtc tcctcagcca aaacgacacc cccatctgtc    360
tatccactgg ccctggatc tgctgcccaa actaactcca tggtgaccct gggatgcctg     420
gtcaagggct atttccctga gccagtgaca gtgacctgga actctggatc cctgtccagc    480
ggtgtgcaca ccttcc                                                    496
```

<210> SEQ ID NO 140
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

His Ala Lys
1

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Gln His Phe Trp Ser Thr Pro Pro Trp Thr
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

His Ala Lys Thr Leu Ala Arg Glu
1               5

<210> SEQ ID NO 143
<211> LENGTH: 104
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

Gln Ser Pro Ala Ser Leu Ser Ala Ser Val Gly Glu Thr Val Thr Ile
1               5                   10                  15

Thr Cys Arg Ala Ser Gly Asn Ile His Asn Tyr Leu Ala Trp Tyr Gln
                20                  25                  30

Gln Lys Gln Gly Lys Ser Pro Gln Leu Leu Val Asn His Ala Lys Thr
            35                  40                  45

Leu Ala Arg Glu Gly Val Pro Ser Arg Phe Ser Gly Ser Gly Ser Lys
        50                  55                  60

Thr Gln Tyr Ser Leu Lys Ile Thr Ser Leu Gln Pro Glu Asp Phe Gly
65                  70                  75                  80

Ser Tyr Tyr Cys Gln His Phe Trp Ser Thr Pro Pro Trp Thr Phe Gly

```
            85                  90                  95

Gly Gly Thr Lys Val Glu Ile Arg
        100

<210> SEQ ID NO 144
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Ser Pro Ala Ser Leu Ser Ala Ser Val Gly Glu Thr Val Thr Ile
1               5                   10                  15

Thr Cys Arg Ala Ser Gly Asn Ile His Asn Tyr Leu Ala Trp Tyr Gln
            20                  25                  30

Gln Lys Gln Gly Lys Ser Pro Gln Leu Leu Val Asn His Ala Lys Thr
        35                  40                  45

Leu Ala Arg Glu Gly Val Pro Ser Arg Phe Ser Gly Ser Gly Ser Lys
    50                  55                  60

Thr Gln Tyr Ser Leu Lys Ile Thr Ser Leu Gln Pro Glu Asp Phe Gly
65                  70                  75                  80

Ser Tyr Tyr Cys Gln His Phe Trp Ser Thr Pro Pro Trp Thr Phe Gly
                85                  90                  95

Gly Gly Thr Lys Val Glu Ile Arg Arg Ala Asp Ala Ala Pro Thr Val
            100                 105                 110

Ser Ile Phe Pro Pro Ser Ser Glu Gln Leu
        115                 120

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Phe Ser Leu Thr Thr Tyr Gly
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Trp Ser Gly Gly Ser Thr
1               5

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147
```

```
Val Arg Tyr Arg Tyr Asp Glu Gly Phe Thr Tyr
1               5                   10
```

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Thr Tyr Gly Val His
1               5
```

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Val Ile Trp Ser Gly Gly Ser Thr Glu Tyr Asn Ala Val Phe Ile Ser
1               5                   10                  15
```

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Tyr Arg Tyr Asp Glu Gly Phe Thr Tyr
1               5
```

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

```
Gly Pro Gly Leu Val Gln Pro Ser Gln Ser Leu Ser Ile Thr Cys Thr
1               5                   10                  15

Val Ser Gly Phe Ser Leu Thr Thr Tyr Gly Val His Trp Val Arg Gln
                20                  25                  30

Ser Pro Gly Lys Gly Leu Glu Trp Leu Gly Val Ile Trp Ser Gly Gly
            35                  40                  45

Ser Thr Glu Tyr Asn Ala Val Phe Ile Ser Arg Met Ser Ile Thr Lys
        50                  55                  60

Asp Asn Ser Lys Ser Gln Val Phe Phe Lys Met Asn Ser Leu Glu Ala
65                  70                  75                  80

Asn Asp Thr Ala Ile Tyr Tyr Cys Val Arg Tyr Arg Tyr Asp Glu Gly
                85                  90                  95

Phe Thr Tyr Trp Gly Gln Gly Ser Leu Val Thr Val Ser Ala
            100                 105                 110
```

<210> SEQ ID NO 152

<211> LENGTH: 163
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

```
Gly Pro Gly Leu Val Gln Pro Ser Gln Ser Leu Ser Ile Thr Cys Thr
1               5                   10                  15

Val Ser Gly Phe Ser Leu Thr Thr Tyr Gly Val His Trp Val Arg Gln
            20                  25                  30

Ser Pro Gly Lys Gly Leu Glu Trp Leu Gly Val Ile Trp Ser Gly Gly
        35                  40                  45

Ser Thr Glu Tyr Asn Ala Val Phe Ile Ser Arg Met Ser Ile Thr Lys
    50                  55                  60

Asp Asn Ser Lys Ser Gln Val Phe Phe Lys Met Asn Ser Leu Glu Ala
65                  70                  75                  80

Asn Asp Thr Ala Ile Tyr Tyr Cys Val Arg Tyr Arg Tyr Asp Glu Gly
                85                  90                  95

Phe Thr Tyr Trp Gly Gln Gly Ser Leu Val Thr Val Ser Ala Ala Lys
            100                 105                 110

Thr Thr Pro Pro Ser Val Tyr Pro Leu Ala Pro Gly Ser Ala Ala Gln
        115                 120                 125

Thr Asn Ser Met Val Thr Leu Gly Cys Leu Val Lys Gly Tyr Phe Pro
    130                 135                 140

Glu Pro Val Thr Val Thr Trp Asn Ser Gly Ser Leu Ser Ser Gly Val
145                 150                 155                 160

His Thr Phe
```

<210> SEQ ID NO 153
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153 catgcaaaa                                                                9

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
caacattttt ggagtactcc tccgtggacg                                         30

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
catgcaaaaa ccttagcaga a                                                  21

<210> SEQ ID NO 156
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
cagtctccag cctccctatc tgcatctgtg ggagaaactg tcaccatcac atgtcgagca      60
agtgggaata ttcacaatta tttagcatgg tatcagcaga aacagggaaa atctcctcag     120
ctcctggtca atcatgcaaa aaccttagca gaaggtgtgc catcaaggtt cagtggcagt     180
ggatcaaaaa cacaatattc tctcaagatc accagcctgc agcctgaaga ttttgggagt     240
tattactgtc aacatttttg gagtactcct ccgtggacgt tcggtggagg caccaaggtg     300
gaaatcaga                                                              309

<210> SEQ ID NO 157
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
cagtctccag cctccctatc tgcatctgtg ggagaaactg tcaccatcac atgtcgagca      60
agtgggaata ttcacaatta tttagcatgg tatcagcaga aacagggaaa atctcctcag     120
ctcctggtca atcatgcaaa aaccttagca gaaggtgtgc catcaaggtt cagtggcagt     180
ggatcaaaaa cacaatattc tctcaagatc accagcctgc agcctgaaga ttttgggagt     240
tattactgtc aacatttttg gagtactcct ccgtggacgt tcggtggagg caccaaggtg     300
gaaatcagac gggctgatgc tgcaccaact gtatccatct tcccaccatc cagtgagcag     360
tta                                                                    363

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggtttctcat taactaccta tggt                                              24

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
atatggagtg gtggaagcac a                                                 21

<210> SEQ ID NO 160
<211> LENGTH: 33
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 160
gtcaggtata ggtacgacga gggattcact tat                                33

<210> SEQ ID NO 161
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
acctatggtg tacac                                                    15

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gtgatatgga gtggtggaag cacagaatat aatgcagttt tcatctcc                48

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tataggtacg acgagggatt cacttat                                       27

<210> SEQ ID NO 164
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
ggacctggcc tagtgcagcc ctcacagagc ctgtccatca cctgcacagt ctctggtttc    60
tcattaacta cctatggtgt acactgggtt cgccagtctc caggaaaggg tctggagtgg   120
ctgggagtga tatggagtgg tggaagcaca gaatataatg cagttttcat ctccagaatg   180
agcatcacca aggacaattc caagagccaa gttttcttta aaatgaacag tctgaaagct   240
aatgacacag ccatatatta ctgtgtcagg tataggtacg acgagggatt cacttattgg   300
ggccaaggga gtctggtcac tgtctctgca                                   330

<210> SEQ ID NO 165
<211> LENGTH: 490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165

```
ggacctggcc tagtgcagcc ctcacagagc ctgtccatca cctgcacagt ctctggtttc    60
tcattaacta cctatggtgt acactgggtt cgccagtctc caggaaaggg tctggagtgg   120
ctgggagtga tatggagtgg tggaagcaca gaatataatg cagttttcat ctccagaatg   180
agcatcacca aggacaattc aagagccaa gttttcttta aaatgaacag tctggaagct   240
aatgacacag ccatatatta ctgtgtcagg tataggtacg acgagggatt cacttattgg   300
ggccaaggga gtctggtcac tgtctctgca gccaaaacga cacccccatc tgtctatcca   360
ctggcccctg gatctgctgc ccaaactaac tccatggtga ccctgggatg cctggtcaag   420
ggctatttcc ctgagccagt gacagtgacc tggaactctg gatccctgtc agcggtgtg    480 cacaccttcc                                                         490
```

<210> SEQ ID NO 166
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

```
Gln Ser Pro Ala Ser Leu Ser Ala Ser Val Gly Asp Thr Val Thr Ile
1               5                   10                  15

Thr Cys Arg Ala Ser Gly Asn Ile His Asn Tyr Leu Ala Trp Tyr Gln
            20                  25                  30

Gln Lys Gln Gly Lys Ser Pro Gln Leu Leu Val Tyr Asn Ala Lys Thr
        35                  40                  45

Leu Ala Asp Gly Val Pro Ser Arg Phe Ser Gly Ser Gly Ser Gly Thr
    50                  55                  60

Gln Tyr Ser Leu Lys Ile Asn Ser Leu Gln Pro Glu Asp Phe Gly Asn
65                  70                  75                  80

Tyr Tyr Cys Gln His Phe Trp Ser Thr Pro Tyr Thr Phe Gly Gly Gly
                85                  90                  95

Thr Lys Leu Glu Ile Lys
            100
```

<210> SEQ ID NO 167
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Gln Ser Pro Ala Ser Leu Ser Ala Ser Val Gly Asp Thr Val Thr Ile
1               5                   10                  15

Thr Cys Arg Ala Ser Gly Asn Ile His Asn Tyr Leu Ala Trp Tyr Gln
            20                  25                  30

Gln Lys Gln Gly Lys Ser Pro Gln Leu Leu Val Tyr Asn Ala Lys Thr
        35                  40                  45

Leu Ala Asp Gly Val Pro Ser Arg Phe Ser Gly Ser Gly Ser Gly Thr
    50                  55                  60

Gln Tyr Ser Leu Lys Ile Asn Ser Leu Gln Pro Glu Asp Phe Gly Asn
65                  70                  75                  80
```

```
Tyr Tyr Cys Gln His Phe Trp Ser Thr Pro Tyr Thr Phe Gly Gly Gly
            85                  90                  95

Thr Lys Leu Glu Ile Lys Arg Ala Asp Ala Ala Pro Thr Val Ser Ile
        100                 105                 110

Phe Pro Pro Ser Ser Glu Gln Leu
        115                 120
```

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

```
Gly Phe Thr Phe Ser Ser Ser Phe
1               5
```

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

```
Ile Tyr Gly Gly Asn Gly Gly Thr
1               5
```

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

```
Ala Ser Glu Thr Tyr Gly Asn Tyr Trp Tyr Phe Asp Val
1               5                   10
```

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

```
Ser Ser Phe Ile Ser
1               5
```

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

```
Trp Ile Tyr Gly Gly Asn Gly Gly Thr Ser Tyr Asn Gln Asn Phe Thr
1               5                   10                  15
```

Gly

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Glu Thr Tyr Gly Asn Tyr Trp Tyr Phe Asp Val
1               5                   10

<210> SEQ ID NO 174
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Ser Gly Ala Arg Glu Leu Val Lys Pro Gly Ala Ser Val Lys Leu Ser
1               5                   10                  15

Cys Lys Thr Ser Gly Phe Thr Phe Ser Ser Ser Phe Ile Ser Trp Leu
                20                  25                  30

Lys Gln Lys Pro Gly Gln Ser Leu Glu Trp Ile Ala Trp Ile Tyr Gly
            35                  40                  45

Gly Asn Gly Gly Thr Ser Tyr Asn Gln Asn Phe Thr Gly Lys Ala Gln
        50                  55                  60

Leu Thr Val Asp Thr Ser Ser Thr Ala Tyr Met Gln Phe Ser Ser
65                  70                  75                  80

Leu Thr Thr Glu Asp Ser Ala Val Tyr Tyr Cys Ala Ser Glu Thr Tyr
                85                  90                  95

Gly Asn Tyr Trp Tyr Phe Asp Val Trp Gly Ala Gly Thr Thr Val Thr
            100                 105                 110

Val Ser Ser
        115

<210> SEQ ID NO 175
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Ser Gly Ala Arg Glu Leu Val Lys Pro Gly Ala Ser Val Lys Leu Ser
1               5                   10                  15

Cys Lys Thr Ser Gly Phe Thr Phe Ser Ser Ser Phe Ile Ser Trp Leu
                20                  25                  30

Lys Gln Lys Pro Gly Gln Ser Leu Glu Trp Ile Ala Trp Ile Tyr Gly
            35                  40                  45

Gly Asn Gly Gly Thr Ser Tyr Asn Gln Asn Phe Thr Gly Lys Ala Gln
        50                  55                  60

Leu Thr Val Asp Thr Ser Ser Thr Ala Tyr Met Gln Phe Ser Ser
65                  70                  75                  80

Leu Thr Thr Glu Asp Ser Ala Val Tyr Tyr Cys Ala Ser Glu Thr Tyr
                85                  90                  95

Gly Asn Tyr Trp Tyr Phe Asp Val Trp Gly Ala Gly Thr Thr Val Thr
            100                 105                 110

Val Ser Ser Ala Lys Thr Thr Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe
                165

<210> SEQ ID NO 176
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aacatttttg gagtactccg tacacg                                         26

<210> SEQ ID NO 177
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
cagtctccag cctccctatc tgcatctgtg ggagacactg tcaccatcac atgtcgagca      60
agtgggaata ttcacaatta tttagcatgg tatcagcaga acagggaaa atctcctcag     120 ctcctggtct ataatgcaaa aaccttagca gatggtgtgc catcaaggtt cagtggcagt    180
ggatcaggaa cacaatattc tctcaagatc aacagcctgc agcctgaaga ttttgggaat    240
tattactgtc aacatttttg gagtactccg tacacgttcg gaggggggac caagctggaa    300
ataaaa                                                              306

<210> SEQ ID NO 178
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
cagtctccag cctccctatc tgcatctgtg ggagacactg tcaccatcac atgtcgagca      60
agtgggaata ttcacaatta tttagcatgg tatcagcaga acagggaaa atctcctcag     120 ctcctggtct ataatgcaaa aaccttagca gatggtgtgc catcaaggtt cagtggcagt    180
ggatcaggaa cacaatattc tctcaagatc aacagcctgc agcctgaaga ttttgggaat    240
tattactgtc aacatttttg gagtactccg tacacgttcg gaggggggac caagctggaa    300
ataaaacggg ctgatgctgc accaactgta tccatcttcc caccatccag tgagcagtta    360

<210> SEQ ID NO 179
<211> LENGTH: 24
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 179
ggcttcacct tcagcagtag tttt                                          24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
atttatggtg gaaatggtgg tact                                          24

<210> SEQ ID NO 181
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gcaagcgaga cgtatggtaa ctactggtac ttcgatgtc                          39

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182 agtagttttta taagt                                                   15

<210> SEQ ID NO 183
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tggatttatg gtggaaatgg tggtactagc tataatcaga acttcacagg c             51

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gagacgtatg gtaactactg gtacttcgat gtc                                33

<210> SEQ ID NO 185
<211> LENGTH: 342
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 185
tctggagctg aactggtgaa gcctggggct tcagtgaagc tgtcctgcaa gacttctggc      60
ttcaccttca gcagtagttt tataagttgg ttgaagcaaa agcctggaca gagtcttgag     120
tggattgcat ggatttatgg tggaaatggt ggtactagct ataatcagaa cttcacaggc     180
aaggcccaac tgactgtaga cacatcctcc agtacagcct acatgcaatt cagcagcctg     240
acaactgagg actctgccgt ctattactgt gcaagcgaga cgtatggtaa ctactggtac     300
ttcgatgtct ggggcgcagg gaccacggtc accgtctcct ca                        342

<210> SEQ ID NO 186
<211> LENGTH: 502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
tctggagctg aactggtgaa gcctggggct tcagtgaagc tgtcctgcaa gacttctggc      60
ttcaccttca gcagtagttt tataagttgg ttgaagcaaa agcctggaca gagtcttgag     120
tggattgcat ggatttatgg tggaaatggt ggtactagct ataatcagaa cttcacaggc     180
aaggcccaac tgactgtaga cacatcctcc agtacagcct acatgcaatt cagcagcctg     240
acaactgagg actctgccgt ctattactgt gcaagcgaga cgtatggtaa ctactggtac     300
ttcgatgtct ggggcgcagg gaccacggtc accgtctcct cagccaaaac gacaccccca     360
tctgtctatc cactggcccc tggatctgct gcccaaacta actccatggt gaccctggga     420
tgcctggtca aggctatttt ccctgagcca gtgacagtga cctggaactc tggatccctg     480
tccagcggtg tgcacacctt cc                                              502

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Glu Asn Val Asp Asn Tyr Gly Ile Ser Phe
1               5                   10

<210> SEQ ID NO 188
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ala Ser
1

<210> SEQ ID NO 189
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 189

Gln Gln Ser Lys Glu Val Pro Trp Thr
1               5

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Ala Ser Glu Asn Val Asp Asn Tyr Gly Ile Ser Phe Met Asn
1               5                   10                  15

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Ala Ser Asn Gln Gly Ser
1               5

<210> SEQ ID NO 192
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Pro Ala Ser Leu Ala Val Ser Leu Gly Gln Arg Ala Thr Ile Ser Cys
1               5                   10                  15

Arg Ala Ser Glu Asn Val Asp Asn Tyr Gly Ile Ser Phe Met Asn Trp
                20                  25                  30

Phe Gln Gln Lys Pro Gly Gln Pro Pro Lys Val Leu Ile Tyr Ala Ala
            35                  40                  45

Ser Asn Gln Gly Ser Gly Val Pro Ala Arg Phe Ser Gly Ser Gly Ser
    50                  55                  60

Gly Thr Asp Phe Ser Leu Asn Ile His Pro Met Glu Glu Asp Asp Thr
65                  70                  75                  80

Ala Met Tyr Phe Cys Gln Gln Ser Lys Glu Val Pro Trp Thr Phe Gly
                85                  90                  95

Gly Gly Thr Lys Leu Glu Ile Thr
            100

<210> SEQ ID NO 193
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Pro Ala Ser Leu Ala Val Ser Leu Gly Gln Arg Ala Thr Ile Ser Cys
1               5                   10                  15

Arg Ala Ser Glu Asn Val Asp Asn Tyr Gly Ile Ser Phe Met Asn Trp
            20                  25                  30

Phe Gln Gln Lys Pro Gly Gln Pro Lys Val Leu Ile Tyr Ala Ala
            35                  40                  45

Ser Asn Gln Gly Ser Gly Val Pro Ala Arg Phe Ser Gly Ser Gly Ser
        50                  55                  60

Gly Thr Asp Phe Ser Leu Asn Ile His Pro Met Glu Glu Asp Asp Thr
65                  70                  75                  80

Ala Met Tyr Phe Cys Gln Gln Ser Lys Glu Val Pro Trp Thr Phe Gly
                85                  90                  95

Gly Gly Thr Lys Leu Glu Ile Thr Arg Ala Asp Ala Ala Pro Thr Val
            100                 105                 110

Ser Ile Phe Pro Pro Ser Ser Glu Gln Leu
            115                 120

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Tyr Ser Ile Thr Ser Gly Tyr Tyr
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ile Asn Tyr Asp Gly Ser Asn
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Arg Gly Asn Tyr Tyr Ala Met Asp Tyr
1               5                   10

<210> SEQ ID NO 197
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Gly Tyr Tyr Trp Ile
1               5

<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Tyr Ile Asn Tyr Asp Gly Ser Asn Asn Tyr Asn Pro Ser Leu Lys Asn
1               5                   10                  15

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Asn Tyr Tyr Ala Met Asp Tyr
1               5

<210> SEQ ID NO 200
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Ser Gly Pro Gly Leu Val Lys Pro Ser Gln Ser Leu Ser Leu Thr
1               5                   10                  15

Cys Ser Val Thr Gly Tyr Ser Ile Thr Ser Gly Tyr Tyr Trp Ile Trp
                20                  25                  30

Ile Arg Gln Phe Pro Gly Asn Lys Leu Glu Trp Met Gly Tyr Ile Asn
        35                  40                  45

Tyr Asp Gly Ser Asn Asn Tyr Asn Pro Ser Leu Lys Asn Arg Ile Ser
    50                  55                  60

Ile Thr Arg Asp Thr Ser Lys Asn Gln Phe Phe Leu Lys Leu Asn Ser
65                  70                  75                  80

Val Thr Thr Glu Asp Thr Ala Thr Tyr Tyr Cys Ala Arg Gly Asn Tyr
                85                  90                  95

Tyr Ala Met Asp Tyr Trp Gly Gln Gly Thr Ser Val Thr Val Ser Ser
                100                 105                 110

<210> SEQ ID NO 201
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Ser Gly Pro Gly Leu Val Lys Pro Ser Gln Ser Leu Ser Leu Thr
1               5                   10                  15

Cys Ser Val Thr Gly Tyr Ser Ile Thr Ser Gly Tyr Tyr Trp Ile Trp
                20                  25                  30

```
Ile Arg Gln Phe Pro Gly Asn Lys Leu Glu Trp Met Gly Tyr Ile Asn
         35                  40                  45

Tyr Asp Gly Ser Asn Asn Tyr Asn Pro Ser Leu Lys Asn Arg Ile Ser
 50                  55                  60

Ile Thr Arg Asp Thr Ser Lys Asn Gln Phe Phe Leu Lys Leu Asn Ser
 65                  70                  75                  80

Val Thr Thr Glu Asp Thr Ala Thr Tyr Tyr Cys Ala Arg Gly Asn Tyr
                 85                  90                  95

Tyr Ala Met Asp Tyr Trp Gly Gln Gly Thr Ser Val Thr Val Ser Ser
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe
            165

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gaaaatgttg ataattatgg cattagtttt                                       30

<210> SEQ ID NO 203
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203 gctgcatcc                                                               9

<210> SEQ ID NO 204
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
cagcaaagta aggaggttcc gtggacg                                          27

<210> SEQ ID NO 205
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
agagccagcg aaaatgttga taattatggc attagtttta tgaac                     45
```

```
<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gctgcatcca accaaggatc c                                              21

<210> SEQ ID NO 207
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
ccagcttctt tggctgtgtc tctaggacag agggccacca tctcctgcag agccagcgaa     60
aatgttgata attatggcat tagttttatg aactggttcc aacagaaacc aggacagcca    120
cccaaagtcc tcatctatgc tgcatccaac caaggatccg ggtccctgc  caggtttagt    180 ggcagtgggt ctgggacaga cttcagcctc aacatccatc ctatggagga ggatgatact    240
gcaatgtatt tctgtcagca aagtaaggag gttccgtgga cgttcggtgg aggcaccaag    300
ctggaaatca ct                                                       312

<210> SEQ ID NO 208
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
ccagcttctt tggctgtgtc tctaggacag agggccacca tctcctgcag agccagcgaa     60
aatgttgata attatggcat tagttttatg aactggttcc aacagaaacc aggacagcca    120
cccaaagtcc tcatctatgc tgcatccaac caaggatccg ggtccctgc  caggtttagt    180 ggcagtgggt ctgggacaga cttcagcctc aacatccatc ctatggagga ggatgatact    240
gcaatgtatt tctgtcagca aagtaaggag gttccgtgga cgttcggtgg aggcaccaag    300
ctggaaatca ctcgggctga tgctgcacca actgtatcca tcttcccacc atccagtgag    360
cagtta                                                              366

<210> SEQ ID NO 209
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ggctactcca tcaccagtgg ttattac                                        27

<210> SEQ ID NO 210
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 210
ataaactacg acggtagcaa t                                              21

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gcaagaggga attactatgc tatggactac                                     30

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
agtggttatt actggatc                                                  18

<210> SEQ ID NO 213
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tacataaact acgacggtag caataactac aacccatctc tcaaaaat                 48

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gggaattact atgctatgga ctac                                           24

<210> SEQ ID NO 215
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
gagtcaggac ctggcctcgt gaaaccttct cagtctctgt ctctcacctg ctctgtcact    60
ggctactcca tcaccagtgg ttattactgg atctggatcc ggcagtttcc aggaaacaaa   120
ctggaatgga tgggctacat aaactacgac ggtagcaata actacaaccc atctctcaaa   180
aatcgaatct ccatcactcg tgacacatct aagaaccagt ttttcctgaa gttgaattct   240

```
gtgactactg aggacacagc tacatattac tgtgcaagag ggaattacta tgctatggac    300
tactggggtc aaggaacctc agtcaccgtc tcctca                              336
```

<210> SEQ ID NO 216
<211> LENGTH: 496
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216

```
gagtcaggac ctggcctcgt gaaaccttct cagtctctgt ctctcacctg ctctgtcact     60
ggctactcca tcaccagtgg ttattactgg atctggatcc ggcagtttcc aggaaacaaa    120
ctggaatgga tgggctacat aaactacgac ggtagcaata actacaaccc atctctcaaa    180
aatcgaatct ccatcactcg tgacacatct aagaaccagt ttttcctgaa gttgaattct    240
gtgactactg aggacacagc tacatattac tgtgcaagag ggaattacta tgctatggac    300
tactggggtc aaggaacctc agtcaccgtc tcctcagcca aaacgacacc cccatctgtc    360
tatccactgg cccctggatc tgctgcccaa actaactcca tggtgaccct gggatgcctg    420
gtcaagggct atttccctga gccagtgaca gtgacctgga actctggatc cctgtccagc    480
ggtgtgcaca ccttcc                                                    496
```

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Glu Ser Val Asp Asn Tyr Gly Ile Ser Phe
1               5                   10
```

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Arg Ala Ser Glu Ser Val Asp Asn Tyr Gly Ile Ser Phe Met Asn
1               5                   10                  15
```

<210> SEQ ID NO 219
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

```
Ser Pro Ala Ser Leu Ala Val Ser Leu Gly Gln Arg Ala Thr Ile Ser
1               5                   10                  15

Cys Arg Ala Ser Glu Ser Val Asp Asn Tyr Gly Ile Ser Phe Met Asn
            20                  25                  30
```

```
Trp Phe Gln Gln Lys Pro Gly Gln Pro Pro Lys Val Leu Ile Tyr Ala
             35                  40                  45

Ala Ser Asn Gln Gly Ser Gly Val Pro Ala Arg Phe Ser Gly Ser Gly
 50                  55                  60

Ser Gly Thr Asp Phe Ser Leu Asn Ile His Pro Met Glu Glu Asp Asp
 65                  70                  75                  80

Thr Ala Met Tyr Phe Cys Gln Gln Ser Lys Glu Val Pro Trp Thr Phe
                 85                  90                  95

Gly Gly Gly Thr Lys Leu Glu Ile Lys
            100                 105

<210> SEQ ID NO 220
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ser Pro Ala Ser Leu Ala Val Ser Leu Gly Gln Arg Ala Thr Ile Ser
 1               5                  10                  15

Cys Arg Ala Ser Glu Ser Val Asp Asn Tyr Gly Ile Ser Phe Met Asn
                 20                  25                  30

Trp Phe Gln Gln Lys Pro Gly Gln Pro Pro Lys Val Leu Ile Tyr Ala
             35                  40                  45

Ala Ser Asn Gln Gly Ser Gly Val Pro Ala Arg Phe Ser Gly Ser Gly
 50                  55                  60

Ser Gly Thr Asp Phe Ser Leu Asn Ile His Pro Met Glu Glu Asp Asp
 65                  70                  75                  80

Thr Ala Met Tyr Phe Cys Gln Gln Ser Lys Glu Val Pro Trp Thr Phe
                 85                  90                  95

Gly Gly Gly Thr Lys Leu Glu Ile Lys Arg Ala Asp Ala Ala Pro Thr
            100                 105                 110

Val Ser Ile Phe Pro Pro Ser Ser Glu Gln Leu
            115                 120

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ile Ser Tyr Asp Gly Ser Asn
 1               5

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Tyr Ile Ser Tyr Asp Gly Ser Asn Asn Tyr Asn Pro Ser Leu Lys Asn
 1               5                  10                  15
```

<210> SEQ ID NO 223
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gly Pro Gly Leu Val Lys Pro Ser Gln Ser Leu Ser Leu Thr Cys Ser
1               5                   10                  15

Val Thr Gly Tyr Ser Ile Thr Ser Gly Tyr Tyr Trp Ile Trp Ile Arg
                20                  25                  30

Gln Phe Pro Gly Asn Lys Leu Glu Trp Met Gly Tyr Ile Ser Tyr Asp
            35                  40                  45

Gly Ser Asn Asn Tyr Asn Pro Ser Leu Lys Asn Arg Ile Ser Ile Thr
        50                  55                  60

Arg Asp Thr Ser Lys Asn Gln Phe Phe Leu Lys Leu Asn Ser Val Thr
65                  70                  75                  80

Thr Glu Asp Thr Ala Thr Tyr Tyr Cys Ala Arg Gly Asn Tyr Tyr Ala
                85                  90                  95

Met Asp Tyr Trp Gly Gln Gly Thr Ser Val Thr Val Ser Ser
            100                 105                 110

<210> SEQ ID NO 224
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gly Pro Gly Leu Val Lys Pro Ser Gln Ser Leu Ser Leu Thr Cys Ser
1               5                   10                  15

Val Thr Gly Tyr Ser Ile Thr Ser Gly Tyr Tyr Trp Ile Trp Ile Arg
                20                  25                  30

Gln Phe Pro Gly Asn Lys Leu Glu Trp Met Gly Tyr Ile Ser Tyr Asp
            35                  40                  45

Gly Ser Asn Asn Tyr Asn Pro Ser Leu Lys Asn Arg Ile Ser Ile Thr
        50                  55                  60

Arg Asp Thr Ser Lys Asn Gln Phe Phe Leu Lys Leu Asn Ser Val Thr
65                  70                  75                  80

Thr Glu Asp Thr Ala Thr Tyr Tyr Cys Ala Arg Gly Asn Tyr Tyr Ala
                85                  90                  95

Met Asp Tyr Trp Gly Gln Gly Thr Ser Val Thr Val Ser Ser Ala Lys
            100                 105                 110

Thr Thr Pro Pro Ser Val Tyr Pro Leu Ala Pro Gly Cys Gly Asp Thr
        115                 120                 125

Thr Gly Ser Ser Val Thr Leu Gly Cys Leu Val Lys Gly Tyr Phe Pro
    130                 135                 140

Glu Ser Val Thr Val Thr Trp Asn Ser Gly Ser Leu Ser Ser Gly Val
145                 150                 155                 160

His Thr Phe

<210> SEQ ID NO 225
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 225
gaaagtgttg ataattatgg cattagtttt                                          30

<210> SEQ ID NO 226
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
agagccagcg aaagtgttga taattatggc attagtttta tgaac                         45

<210> SEQ ID NO 227
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
tctccagctt ctttggctgt gtctctaggg cagagggcca ccatctcctg cagagccagc         60
gaaagtgttg ataattatgg cattagtttt atgaactggt tccaacagaa accaggacag        120
ccacccaaag tcctcatcta tgctgcatcc aaccaaggat ccggggtccc tgccaggttt        180
agtggcagtg ggtctgggac agacttcagc ctcaacatcc atcctatgga ggaggatgat        240
actgcaatgt atttctgtca gcaaagtaag gaggttccgt ggacgttcgg tggaggcacc        300
aagctggaaa tcaaa                                                         315

<210> SEQ ID NO 228
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
tctccagctt ctttggctgt gtctctaggg cagagggcca ccatctcctg cagagccagc         60
gaaagtgttg ataattatgg cattagtttt atgaactggt tccaacagaa accaggacag        120
ccacccaaag tcctcatcta tgctgcatcc aaccaaggat ccggggtccc tgccaggttt        180
agtggcagtg ggtctgggac agacttcagc ctcaacatcc atcctatgga ggaggatgat        240
actgcaatgt atttctgtca gcaaagtaag gaggttccgt ggacgttcgg tggaggcacc        300
aagctggaaa tcaaacgggc tgatgctgca ccaactgtat ccatcttccc accatccagt        360
gagcagtta                                                                369

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
```
ataagctacg acggtagcaa t                                         21

<210> SEQ ID NO 230
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tacataagct acgacggtag caataactac aacccatctc tcaaaaat            48

<210> SEQ ID NO 231
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
ggacctggcc tcgtgaaacc ttctcagtct ctgtctctca cctgctctgt cactggctac    60
tccatcacca gtggttatta ctggatctgg atccggcagt tccaggaaa caaactggaa    120 tggatgggct acataagcta cgacggtagc aataactaca acccatctct caaaaatcga   180
atctccatca ctcgtgacac atctaagaac cagttttttcc tgaagttgaa ttctgtgact  240
actgaggaca cagctacata ttactgtgca agagggaatt actatgctat ggactactgg   300
ggtcaaggaa cctcagtcac cgtctcctca                                    330

<210> SEQ ID NO 232
<211> LENGTH: 490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
ggacctggcc tcgtgaaacc ttctcagtct ctgtctctca cctgctctgt cactggctac    60
tccatcacca gtggttatta ctggatctgg atccggcagt tccaggaaa caaactggaa    120 tggatgggct acataagcta cgacggtagc aataactaca acccatctct caaaaatcga   180
atctccatca ctcgtgacac atctaagaac cagttttttcc tgaagttgaa ttctgtgact  240
actgaggaca cagctacata ttactgtgca agagggaatt actatgctat ggactactgg   300
ggtcaaggaa cctcagtcac cgtctcctca gccaaaacaa cacccccatc agtctatcca   360
ctggcccctg ggtgtggaga tacaactggt tcctccgtga ctctgggatg cctggtcaag   420
ggctacttcc ctgagtcagt gactgtgact tggaactctg gatccctgtc agcggtgtg    480 cacaccttcc                                                          490

<210> SEQ ID NO 233
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

```
Gln Asp Val Ser Thr Ala
1               5

<210> SEQ ID NO 234
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Ala Ser
1

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Gln His Tyr Ser Thr Pro Leu Thr
1               5

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys Ala Ser Gln Asp Val Ser Thr Ala Val Ala
1               5                   10

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Ala Ser Tyr Arg Tyr Thr
1               5

<210> SEQ ID NO 238
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Ser His Lys Phe Met Ser Thr Ser Val Gly Asp Arg Val Ser Val
1               5                   10                  15

Thr Cys Lys Ala Ser Gln Asp Val Ser Thr Ala Val Ala Trp Tyr Gln
            20                  25                  30

Gln Lys Pro Gly Gln Ser Pro Lys Leu Leu Ile Phe Ser Ala Ser Tyr
        35                  40                  45
```

```
Arg Tyr Thr Gly Val Pro Asp Arg Phe Thr Gly Ser Gly Ser Gly Thr
 50                  55                  60

Asp Phe Thr Phe Thr Ile Ser Ser Val Gln Ala Arg Glu Asp Leu Ala
 65                  70                  75                  80

Val Tyr Tyr Cys Gln Gln His Tyr Ser Thr Pro Leu Thr Phe Gly Ala
                 85                  90                  95

Gly Thr Lys Leu Glu Leu Lys
            100
```

```
<210> SEQ ID NO 239
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239
```

```
Gln Ser His Lys Phe Met Ser Thr Ser Val Gly Asp Arg Val Ser Val
 1               5                  10                  15

Thr Cys Lys Ala Ser Gln Asp Val Ser Thr Ala Val Ala Trp Tyr Gln
             20                  25                  30

Gln Lys Pro Gly Gln Ser Pro Lys Leu Leu Ile Phe Ser Ala Ser Tyr
         35                  40                  45

Arg Tyr Thr Gly Val Pro Asp Arg Phe Thr Gly Ser Gly Ser Gly Thr
 50                  55                  60

Asp Phe Thr Phe Thr Ile Ser Ser Val Gln Ala Arg Glu Asp Leu Ala
 65                  70                  75                  80

Val Tyr Tyr Cys Gln Gln His Tyr Ser Thr Pro Leu Thr Phe Gly Ala
                 85                  90                  95

Gly Thr Lys Leu Glu Leu Lys Arg Ala Asp Ala Ala Pro Thr Val Ser
            100                 105                 110

Ile Phe Pro Pro Ser Ser Glu Gln Leu
        115                 120
```

```
<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240
```

```
Ala Arg Arg Asn Tyr Tyr Ala Val Asp Tyr
 1               5                  10
```

```
<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241
```

```
Ser Gly Tyr Tyr Trp Asn
 1               5
```

```
<210> SEQ ID NO 242
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 242

Arg Asn Tyr Tyr Ala Val Asp Tyr
1               5

<210> SEQ ID NO 243
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gly Pro Gly Leu Val Lys Pro Ser Gln Ser Leu Ser Leu Thr Cys Ser
1               5                   10                  15

Val Thr Gly Tyr Ser Ile Thr Ser Gly Tyr Tyr Trp Asn Trp Ile Arg
            20                  25                  30

Gln Phe Pro Gly Asn Lys Leu Glu Trp Met Gly Tyr Ile Asn Tyr Asp
        35                  40                  45

Gly Ser Asn Asn Tyr Asn Pro Ser Leu Lys Asn Arg Ile Ser Ile Thr
    50                  55                  60

Arg Asp Thr Ser Lys Asn Gln Phe Phe Leu Lys Leu Asn Ser Val Thr
65                  70                  75                  80

Thr Glu Asp Thr Ala Thr Tyr Tyr Cys Ala Arg Arg Asn Tyr Tyr Ala
                85                  90                  95

Val Asp Tyr Trp Gly Gln Gly Thr Ser Val Thr Val Ser Ser
            100                 105                 110

<210> SEQ ID NO 244
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gly Pro Gly Leu Val Lys Pro Ser Gln Ser Leu Ser Leu Thr Cys Ser
1               5                   10                  15

Val Thr Gly Tyr Ser Ile Thr Ser Gly Tyr Tyr Trp Asn Trp Ile Arg
            20                  25                  30

Gln Phe Pro Gly Asn Lys Leu Glu Trp Met Gly Tyr Ile Asn Tyr Asp
        35                  40                  45

Gly Ser Asn Asn Tyr Asn Pro Ser Leu Lys Asn Arg Ile Ser Ile Thr
    50                  55                  60

Arg Asp Thr Ser Lys Asn Gln Phe Phe Leu Lys Leu Asn Ser Val Thr
65                  70                  75                  80

Thr Glu Asp Thr Ala Thr Tyr Tyr Cys Ala Arg Arg Asn Tyr Tyr Ala
                85                  90                  95

Val Asp Tyr Trp Gly Gln Gly Thr Ser Val Thr Val Ser Ser Ala Lys
            100                 105                 110

Thr Thr Pro Pro Ser Val Tyr Pro Leu Ala Pro Gly Ser Ala Ala Gln
        115                 120                 125

Thr Asn Ser Met Val Thr Leu Gly Cys Leu Val Lys Gly Tyr Phe Pro
    130                 135                 140
```

```
Glu Pro Val Thr Val Thr Trp Asn Ser Gly Ser Leu Ser Ser Gly Val
145                 150                 155                 160

His Thr Phe
```

<210> SEQ ID NO 245
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
caggatgtga gtactgct                                                    18

<210> SEQ ID NO 246
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246 tcggcatcc                                                              9

<210> SEQ ID NO 247
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cagcaacatt atagtactcc gctcacg                                          27

<210> SEQ ID NO 248
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
aaggccagtc aggatgtgag tactgctgta gcc                                   33

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tcggcatcct accggtacac t                                                21

<210> SEQ ID NO 250
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250

```
cagtctcaca aattcatgtc cacatcagtg ggagacaggg tcagcgtcac ctgcaaggcc    60
agtcaggatg tgagtactgc tgtagcctgg tatcaacaga aaccaggaca atctcctaaa   120
ctgctgattt tctcggcatc ctaccggtac actggagtcc ctgatcgctt cactggcagt   180
ggatctggga cggatttcac tttcaccatc agcagtgtgc aggctgaaga cctggcagtt   240
tattactgtc agcaacatta tagtactccg ctcacgttcg gtgctgggac caagctggag   300
ctgaaa                                                              306
```

<210> SEQ ID NO 251
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251

```
cagtctcaca aattcatgtc cacatcagtg ggagacaggg tcagcgtcac ctgcaaggcc    60
agtcaggatg tgagtactgc tgtagcctgg tatcaacaga aaccaggaca atctcctaaa   120
ctgctgattt tctcggcatc ctaccggtac actggagtcc ctgatcgctt cactggcagt   180
ggatctggga cggatttcac tttcaccatc agcagtgtgc aggctgaaga cctggcagtt   240
tattactgtc agcaacatta tagtactccg ctcacgttcg gtgctgggac caagctggag   300
ctgaaacggg ctgatgctgc accaactgta tccatcttcc caccatccag tgagcagtta   360
```

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252

```
gcaagaagaa attactatgc tgtggactac                                     30
```

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253

```
agtggttatt actggaac                                                  18
```

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254

```
agaaattact atgctgtgga ctac                                           24
```

<210> SEQ ID NO 255

<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
ggacctggcc tcgtgaaacc ttctcagtct ctgtctctca cctgctctgt cactggctac    60
tccatcacca gtggttatta ctggaactgg atccggcagt ttccaggaaa caaactggaa   120
tggatgggct acataaacta cgacggtagc aataactaca acccatctct caaaaatcga   180
atctccatca ctcgtgacac atctaagaac cagttttttcc tgaagttgaa ttctgtgact   240
actgaggaca cagctacata ttactgtgca agaagaaatt actatgctgt ggactactgg   300
ggtcaaggaa cctcagtcac cgtctcctca                                    330

<210> SEQ ID NO 256
<211> LENGTH: 490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256
ggacctggcc tcgtgaaacc ttctcagtct ctgtctctca cctgctctgt cactggctac    60
tccatcacca gtggttatta ctggaactgg atccggcagt ttccaggaaa caaactggaa   120
tggatgggct acataaacta cgacggtagc aataactaca acccatctct caaaaatcga   180
atctccatca ctcgtgacac atctaagaac cagttttttcc tgaagttgaa ttctgtgact   240
actgaggaca cagctacata ttactgtgca agaagaaatt actatgctgt ggactactgg   300
ggtcaaggaa cctcagtcac cgtctcctca gccaaaacga cacccccatc tgtctatcca   360
ctggcccctg gatctgctgc ccaaactaac tccatggtga ccctgggatg cctggtcaag   420
ggctatttcc ctgagccagt gacagtgacc tggaactctg gatccctgtc agcggtgtg    480 cacaccttcc                                                          490

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Ser Val Asp Ile Tyr Gly Thr Ser Phe
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

His Gln Ser Lys Glu Val Pro Trp Thr
1               5

```
<210> SEQ ID NO 259
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Arg Ala Ser Glu Ser Val Asp Ile Tyr Gly Thr Ser Phe Met Asn
1               5                   10                  15

<210> SEQ ID NO 260
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Pro Ala Ser Leu Ala Val Ser Leu Gly Gln Arg Ala Thr Ile Ser Cys
1               5                   10                  15

Arg Ala Ser Glu Ser Val Asp Ile Tyr Gly Thr Ser Phe Met Asn Trp
            20                  25                  30

Phe Gln Gln Lys Pro Gly Gln Pro Pro Lys Leu Leu Ile Tyr Ala Ala
        35                  40                  45

Ser Asn Gln Gly Ser Gly Val Pro Ala Arg Phe Ser Gly Ser Gly Ser
    50                  55                  60

Gly Thr Glu Phe Ser Leu Asn Ile His Pro Met Glu Glu Asp Asp Thr
65                  70                  75                  80

Ala Met Tyr Phe Cys His Gln Ser Lys Glu Val Pro Trp Thr Phe Gly
                85                  90                  95

Gly Gly Thr Lys Leu Glu Ile Lys
            100

<210> SEQ ID NO 261
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Pro Ala Ser Leu Ala Val Ser Leu Gly Gln Arg Ala Thr Ile Ser Cys
1               5                   10                  15

Arg Ala Ser Glu Ser Val Asp Ile Tyr Gly Thr Ser Phe Met Asn Trp
            20                  25                  30

Phe Gln Gln Lys Pro Gly Gln Pro Pro Lys Leu Leu Ile Tyr Ala Ala
        35                  40                  45

Ser Asn Gln Gly Ser Gly Val Pro Ala Arg Phe Ser Gly Ser Gly Ser
    50                  55                  60

Gly Thr Glu Phe Ser Leu Asn Ile His Pro Met Glu Glu Asp Asp Thr
65                  70                  75                  80

Ala Met Tyr Phe Cys His Gln Ser Lys Glu Val Pro Trp Thr Phe Gly
                85                  90                  95

Gly Gly Thr Lys Leu Glu Ile Lys Arg Ala Asp Ala Ala Pro Thr Val
            100                 105                 110

Ser Ile Phe Pro Pro Ser Ser Glu Gln Leu
        115                 120
```

<210> SEQ ID NO 262
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ile Trp Ala Gly Gly Ile Thr
1               5

<210> SEQ ID NO 263
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ala Arg Ile Tyr Tyr Asp Tyr Asp Ala Trp Phe Ala Tyr
1               5                   10

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Tyr Gly Val His
1               5

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Val Ile Trp Ala Gly Gly Ile Thr Asn Tyr Asn Ser Ala Leu Met Ser
1               5                   10                  15

<210> SEQ ID NO 266
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ile Tyr Tyr Asp Tyr Asp Ala Trp Phe Ala Tyr
1               5                   10

<210> SEQ ID NO 267
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Pro Gly Leu Val Ala Pro Ser Gln Ser Leu Ser Ile Thr Cys Thr
1               5                   10                  15

Val Ser Gly Phe Ser Leu Thr Ser Tyr Gly Val His Trp Val Arg Gln
            20                  25                  30

Pro Pro Gly Lys Gly Leu Glu Trp Leu Gly Val Ile Trp Ala Gly Gly
        35                  40                  45

Ile Thr Asn Tyr Asn Ser Ala Leu Met Ser Arg Leu Ser Ile Ser Lys
50                  55                  60

Asp Asn Ser Lys Ser Gln Val Phe Leu Lys Met Asn Ser Leu Gln Thr
65                  70                  75                  80

Asp Asp Thr Ala Met Tyr Tyr Cys Ala Arg Ile Tyr Tyr Asp Tyr Asp
                85                  90                  95

Ala Trp Phe Ala Tyr Trp Gly Gln Gly Thr Leu Val Thr Val Ser Ala
            100                 105                 110

<210> SEQ ID NO 268
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gly Pro Gly Leu Val Ala Pro Ser Gln Ser Leu Ser Ile Thr Cys Thr
1               5                   10                  15

Val Ser Gly Phe Ser Leu Thr Ser Tyr Gly Val His Trp Val Arg Gln
            20                  25                  30

Pro Pro Gly Lys Gly Leu Glu Trp Leu Gly Val Ile Trp Ala Gly Gly
        35                  40                  45

Ile Thr Asn Tyr Asn Ser Ala Leu Met Ser Arg Leu Ser Ile Ser Lys
50                  55                  60

Asp Asn Ser Lys Ser Gln Val Phe Leu Lys Met Asn Ser Leu Gln Thr
65                  70                  75                  80

Asp Asp Thr Ala Met Tyr Tyr Cys Ala Arg Ile Tyr Tyr Asp Tyr Asp
                85                  90                  95

Ala Trp Phe Ala Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
130                 135                 140

Phe Pro Glu Pro Val Thr Val Thr Trp Asn Ser Gly Ser Leu Ser Ser
145                 150                 155                 160

Gly Val His Thr Phe
                165

<210> SEQ ID NO 269
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gaaagtgttg atatttatgg cactagtttt                                      30

<210> SEQ ID NO 270
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
caccaaagta aggaggttcc gtggacg                                         27

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
agagccagcg aaagtgttga tatttatggc actagtttta tgaac                     45

<210> SEQ ID NO 272
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272
ccagcttctt tggctgtgtc tctagggcag agggccacca tctcctgcag agccagcgaa     60
agtgttgata tttatggcac tagttttatg aactggttcc aacagaaacc aggacagcca    120
cccaaactcc tcatctatgc tgcatccaac caaggatccg gggtccctgc caggtttagt    180
ggcagtgggt ctgggacaga gttcagcctc aacatccatc ctatggagga ggatgatact    240
gcaatgtatt tctgtcacca aagtaaggag gttccgtgga cgttcggtgg aggcaccaag    300
ctggaaatca aa                                                       312

<210> SEQ ID NO 273
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
ccagcttctt tggctgtgtc tctagggcag agggccacca tctcctgcag agccagcgaa     60
agtgttgata tttatggcac tagttttatg aactggttcc aacagaaacc aggacagcca    120
cccaaactcc tcatctatgc tgcatccaac caaggatccg gggtccctgc caggtttagt    180
ggcagtgggt ctgggacaga gttcagcctc aacatccatc ctatggagga ggatgatact    240
gcaatgtatt tctgtcacca aagtaaggag gttccgtgga cgttcggtgg aggcaccaag    300
ctggaaatca aacgggctga tgctgcacca actgtatcca tcttcccacc atccagtgag    360
cagtta                                                              366

<210> SEQ ID NO 274
<211> LENGTH: 24

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gggttttcat taaccagcta tggt                                              24

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
atatgggccg gtggaatcac a                                                 21

<210> SEQ ID NO 276
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gccaggatct actatgatta cgacgcctgg tttgcttac                              39

<210> SEQ ID NO 277
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
agctatggtg tacac                                                        15

<210> SEQ ID NO 278
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gtaatatggg ccggtggaat cacaaattat aattcggctc tcatgtcc                    48

<210> SEQ ID NO 279
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
atctactatg attacgacgc ctggtttgct tac                                    33

<210> SEQ ID NO 280
<211> LENGTH: 336
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 280

```
ggacctggcc tggtggcgcc ctcacagagc ctgtccatca cttgcactgt ctctgggttt      60
tcattaacca gctatggtgt acactgggtt cgccagcctc caggaaaggg tctggagtgg     120
ctgggagtaa tatgggccgg tggaatcaca aattataatt cggctctcat gtccagactg     180
agcatcagca agacaactc caagagccaa gttttcttaa aaatgaacag tctgcaaact      240
gatgatacag ccatgtacta ctgtgccagg atctactatg attacgacgc tggtttgct      300 tactggggcc aagggactct ggtcactgtc tctgca                               336
```

<210> SEQ ID NO 281
<211> LENGTH: 496
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281

```
ggacctggcc tggtggcgcc ctcacagagc ctgtccatca cttgcactgt ctctgggttt      60
tcattaacca gctatggtgt acactgggtt cgccagcctc caggaaaggg tctggagtgg     120
ctgggagtaa tatgggccgg tggaatcaca aattataatt cggctctcat gtccagactg     180
agcatcagca agacaactc caagagccaa gttttcttaa aaatgaacag tctgcaaact      240
gatgatacag ccatgtacta ctgtgccagg atctactatg attacgacgc tggtttgct      300 tactggggcc aagggactct ggtcactgtc tctgcagcca aaacgacacc cccatctgtc     360
tatccactgg cccctggatc tgctgcccaa actaactcca tggtgaccct gggatgcctg     420
gtcaagggct atttccctga gccagtgaca gtgacctgga actctggatc cctgtccagc     480
ggtgtgcaca ccttcc                                                     496
```

<210> SEQ ID NO 282
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Thr Gln Thr Thr Ser Ser Leu Ser Ala Ser Leu Gly Asp Arg Val Thr
1               5                   10                  15

Ile Ser Cys Arg Ala Ser Gln Asp Ile Ser Asn His Leu Asn Trp Tyr
            20                  25                  30

Gln Gln Lys Pro Asp Gly Thr Val Lys Leu Leu Ile Tyr Tyr Thr Ser
        35                  40                  45

Arg Leu His Ser Gly Val Pro Ser Arg Phe Ser Gly Ser Gly Ser Gly
    50                  55                  60

Thr Asp Tyr Ser Leu Thr Ile Ser Asn Leu Glu Gln Glu Asp Ile Ala
65                  70                  75                  80

Thr Tyr Phe Cys Gln Gln Gly Asn Thr Leu Trp Thr Phe Gly Gly Gly
                85                  90                  95

Thr Lys Leu Glu Ile Lys
            100
```

<210> SEQ ID NO 283
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Thr Gln Thr Thr Ser Ser Leu Ser Ala Ser Leu Gly Asp Arg Val Thr
1               5                   10                  15

Ile Ser Cys Arg Ala Ser Gln Asp Ile Ser Asn His Leu Asn Trp Tyr
            20                  25                  30

Gln Gln Lys Pro Asp Gly Thr Val Lys Leu Leu Ile Tyr Tyr Thr Ser
        35                  40                  45

Arg Leu His Ser Gly Val Pro Ser Arg Phe Ser Gly Ser Gly Ser Gly
    50                  55                  60

Thr Asp Tyr Ser Leu Thr Ile Ser Asn Leu Glu Gln Glu Asp Ile Ala
65                  70                  75                  80

Thr Tyr Phe Cys Gln Gln Gly Asn Thr Leu Trp Thr Phe Gly Gly Gly
            85                  90                  95

Thr Lys Leu Glu Ile Lys Arg Ala Asp Ala Ala Pro Thr Val Ser Ile
        100                 105                 110

Phe Pro Pro Ser Ser Glu Gln Val
    115                 120

<210> SEQ ID NO 284
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Glu Ser Gly Pro Gly Leu Val Ala Pro Ser Gln Ser Leu Ser Ile Thr
1               5                   10                  15

Cys Thr Val Ser Gly Phe Ser Leu Thr Ser Tyr Gly Val Ser Trp Val
            20                  25                  30

Arg Gln Pro Pro Gly Lys Gly Leu Glu Trp Leu Gly Val Ile Trp Gly
        35                  40                  45

Asp Gly Ser Thr Asn Tyr His Ser Thr Leu Ile Ser Arg Leu Ser Ile
    50                  55                  60

Ser Lys Asp Asn Ser Lys Ser Gln Val Phe Leu Lys Leu Asn Ser Leu
65                  70                  75                  80

Gln Thr Asp Asp Thr Ala Thr Tyr Tyr Cys Ala Lys Pro His Pro Ala
            85                  90                  95

Ala Thr Gly Ala Met Asp Tyr Trp Gly Gln Gly Thr Ser Val Thr Val
        100                 105                 110

Ser Ser

<210> SEQ ID NO 285
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Glu Ser Gly Pro Gly Leu Val Ala Pro Ser Gln Ser Leu Ser Ile Thr
1               5                   10                  15

Cys Thr Val Ser Gly Phe Ser Leu Thr Ser Tyr Gly Val Ser Trp Val
            20                  25                  30

Arg Gln Pro Pro Gly Lys Gly Leu Glu Trp Leu Gly Val Ile Trp Gly
        35                  40                  45

Asp Gly Ser Thr Asn Tyr His Ser Thr Leu Ile Ser Arg Leu Ser Ile
    50                  55                  60

Ser Lys Asp Asn Ser Lys Ser Gln Val Phe Leu Lys Leu Asn Ser Leu
65                  70                  75                  80

Gln Thr Asp Asp Thr Ala Thr Tyr Tyr Cys Ala Lys Pro His Pro Ala
                85                  90                  95

Ala Thr Gly Ala Met Asp Tyr Trp Gly Gln Gly Thr Ser Val Thr Val
            100                 105                 110

Ser Ser Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe
                165

<210> SEQ ID NO 286
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286
acacagacta catcctccct gtctgcctct ctgggagaca gagtcaccat cagttgcagg      60
gcaagtcagg acattagcaa tcatttaaac tggtatcagc agaaaccaga tggaactgtt    120
aaactcctga tctactacac atcaagatta cactcaggag tcccatcaag gttcagtggc    180
agtgggtctg gaacagatta ttctctcacc attagcaacc tggagcaaga ggatattgcc    240
acttactttt gccaacaggg taatacgctt tggacgttcg gtggaggcac caagctggaa    300
atcaaa                                                               306

<210> SEQ ID NO 287
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 287
acacagacta catcctccct gtctgcctct ctgggagaca gagtcaccat cagttgcagg      60
gcaagtcagg acattagcaa tcatttaaac tggtatcagc agaaaccaga tggaactgtt    120
aaactcctga tctactacac atcaagatta cactcaggag tcccatcaag gttcagtggc    180
agtgggtctg gaacagatta ttctctcacc attagcaacc tggagcaaga ggatattgcc    240
acttactttt gccaacaggg taatacgctt tggacgttcg gtggaggcac caagctggaa    300

```
atcaaacggg ctgatgctgc accaactgta tccatcttcc caccatccag tgagcaggtt    360
```

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288

```
gggttctcat taaccagcta tggt                                            24
```

<210> SEQ ID NO 289
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289

```
agctatggtg taagc                                                      15
```

<210> SEQ ID NO 290
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290

```
gtaatatggg gtgacgggag cacaaattat cactcaactc tcatatcc                  48
```

<210> SEQ ID NO 291
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291

```
gagtcaggac ctggcctggt ggcgccctca cagagcctgt ccatcacatg cactgtctca    60
gggttctcat taaccagcta tggtgtaagc tgggttcgcc agcctccagg aaagggtctg   120
gagtggctgg gagtaatatg gggtgacggg agcacaaatt atcactcaac tctcatatcc   180
agactgagca tcagcaagga taactccaag agccaagttt tcttaaaact gaacagtctg   240
caaactgatg acacagccac gtactactgt gccaaacctc atcctgcggc tactggcgct   300
atggactact ggggtcaagg aacctcagtc accgtctcct ca                      342
```

<210> SEQ ID NO 292
<211> LENGTH: 502
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292

```
gagtcaggac ctggcctggt ggcgccctca cagagcctgt ccatcacatg cactgtctca    60
gggttctcat taaccagcta tggtgtaagc tgggttcgcc agcctccagg aaagggtctg   120
```

-continued

```
gagtggctgg gagtaatatg gggtgacggg agcacaaatt atcactcaac tctcatatcc    180
agactgagca tcagcaagga taactccaag agccaagttt tcttaaaact gaacagtctg    240
caaactgatg acacagccac gtactactgt gccaaacctc atcctgcggc tactggcgct    300
atggactact ggggtcaagg aacctcagtc accgtctcct cagccaaaac gacacccca    360 tctgtctatc cactggcccc tggatctgct gcccaaacta actccatggt gaccctggga    420
tgcctggtca agggctattt ccctgagcca gtgacagtga cctggaactc tggatccctg    480
tccagcggtg tgcacacctt cc    502
```

<210> SEQ ID NO 293
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 293

```
Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Gln Pro
                165                 170                 175

Phe His Phe Tyr Phe Pro Thr Pro Thr Val Leu Cys Asn Glu Ile Trp
            180                 185                 190

Thr His Ser Tyr Lys Val Ser Asn Tyr Ser Arg Gly Ser Gly Arg Cys
        195                 200                 205

Ile Gln Met Trp Phe Asp Pro Ala Gln Gly Asn Pro Asn Glu Glu Val
    210                 215                 220

Ala Arg Phe Tyr Ala Ala Ala Met Ser Gly Ala Gly Pro Trp Ala Ala
225                 230                 235                 240

Trp Pro Phe Leu Leu Ser Leu Ala Leu Met Leu Leu Trp Leu Leu Ser
                245                 250                 255
```

<210> SEQ ID NO 294
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6xHis tag

<400> SEQUENCE: 294

His His His His His His
1               5
```